US012649931B2

(12) United States Patent
Zhai et al.

(10) Patent No.: US 12,649,931 B2
(45) Date of Patent: Jun. 9, 2026

(54) SMARTBAC BACULOVIRUS EXPRESSION SYSTEM AND APPLICATION THEREOF

(71) Applicant: INSTITUTE OF BIOPHYSICS, CHINESE ACADEMY OF SCIENCES, Beijing (CN)

(72) Inventors: Yujia Zhai, Beijing (CN); Fei Sun, Beijing (CN)

(73) Assignee: INSTITUTE OF BIOPHYSICS, CHINESE PIE ACADEMY OF SCIENCES, Beijing (CN)

( * ) Notice: Subject to any disclaimer, the term of this patent is extended or adjusted under 35 U.S.C. 154(b) by 1310 days.

(21) Appl. No.: 16/960,227

(22) PCT Filed: Mar. 20, 2018

(86) PCT No.: PCT/CN2018/079510
     § 371 (c)(1),
     (2) Date: Jul. 6, 2020

(87) PCT Pub. No.: WO2019/136826
     PCT Pub. Date: Jul. 18, 2019

(65)          Prior Publication Data
     US 2021/0062219 A1     Mar. 4, 2021

(30)      Foreign Application Priority Data
     Jan. 12, 2018    (CN) .......................... 201810028508.0

(51) Int. Cl.
     *C12N 15/86*          (2006.01)
     *C07K 14/47*          (2006.01)
(52) U.S. Cl.
     CPC .............. *C12N 15/86* (2013.01); *C07K 14/47*
           (2013.01); *C12N 2710/14043* (2013.01);
           (Continued)

(58) Field of Classification Search
     CPC .......... C12N 15/86; C12N 2710/14043; C12N
           2800/106; C12N 2800/30; C12N 2820/00;
           (Continued)

(56)                References Cited

U.S. PATENT DOCUMENTS 6,277,600  B1     8/2001  Tomita et al.
     2007/0259414 A1*  11/2007  Butt ....................... C07K 14/00
                                                         435/243

FOREIGN PATENT DOCUMENTS

CN          101372685          2/2009
     CN          101372697          2/2009
                (Continued)

OTHER PUBLICATIONS

Berger I, Fitzgerald DJ, Richmond TJ. Baculovirus expression system for heterologous multiprotein complexes. Nat Biotechnol. Dec. 2004;22(12):1583-7. doi: 10.1038/nbt1036. Epub Nov. 28, 2004. PMID: 15568020. (Year: 2004).*

(Continued)

*Primary Examiner* — Brian Whiteman
*Assistant Examiner* — Amanda M Zahorik
(74) *Attorney, Agent, or Firm* — HAUPTMAN HAM, LLP

(57)              ABSTRACT

The present invention discloses a SmartBac baculovirus expression system and application thereof. The system can comprise a acceptor plasmid (containing fragment A or fragments B and C) and a donor plasmid (containing fragment D); the fragment A contains a promoter, a sequence encoding a protease, a protease cleavage site, an insertion region of a gene encoding a target object to be expressed and a termination sequence; the fragment B contains a promoter, a sequence encoding a protease and a termination sequence; the fragment C contains a promoter, an insertion region of a gene encoding a target object to be expressed and a termi- (Continued)

nation sequence; the fragment D contains a promoter, an insertion region of a gene encoding a target object to be expressed and a termination sequence. The present invention also provides three cloning strategies to achieve the expression of protein complexes with molecular weights of less than 600 kDa and the expression of protein complexes with molecular weights of no less than 600 kDa and efficient screening of a subunit most suitable for adding a purification tag. The present invention is of great significance for recombinantly expressing protein complexes with complex components and large molecular weights in insect cells.

15 Claims, 6 Drawing Sheets

Specification includes a Sequence Listing.

(52) U.S. Cl.
CPC .... *C12N 2800/106* (2013.01); *C12N 2800/30* (2013.01); *C12N 2820/00* (2013.01)

(58) Field of Classification Search
CPC ...... C12N 2710/14143; C12N 2800/40; C12N 15/65; C07K 14/47; C07K 2319/02; C07K 2319/21; C07K 2319/22; C07K 2319/42; C07K 2319/50
See application file for complete search history.

(56) References Cited

FOREIGN PATENT DOCUMENTS

| | | |
|---|---|---|
| CN | 107304432 | 10/2017 |
| WO | WO2005085456 | 9/2005 |

OTHER PUBLICATIONS

Sari D et al.The MultiBac Baculovirus/Insect Cell Expression Vector System for Producing Complex Protein Biologics. Adv Exp Med Biol. 2016;896:199-215. doi: 10. 1007/978-3-319-27216-0_13. PMID: 27165327; PMCID: PMC7122245. (Year: 2015).*

Borys Wróbel, Grzegorz Węgrzyn, Differential amplification efficiency of pMB1 and p15A (ColE1-type) replicons in *Escherichia coli* stringent and relaxed strains starved for particular amino acids, Microbiological Research, vol. 152, Issue 3, 1997, pp. 251-255, ISSN 0944-5013 (Year: 1997).*

Thomas G.M. Schmidt et al. Development of the Twin-Strep-tag® and its application for purification of recombinant proteins from cell culture supernatants, Protein Expression and Purification, vol. 92, Issue 1, 2013, pp. 54-61, ISSN 1046-5928, https://doi.org/10.1016/j.pep.2013.08.021. (Year: 2013).*

Zhao X, Li G, Liang S. Several affinity tags commonly used in chromatographic purification. J Anal Methods Chem. 2013;2013:581093. doi: 10.1155/2013/581093. Epub Dec. 26, 2013. PMID: 24490106; PMCID: PMC3893739. (Year: 2013).*

Large protein complex production using the SmartBac System—Strategies and Applications Yujia Zhai, Danyang Zhang, Leiye Yu, Fang Sun, Fei Sun bioRxiv 219246; doi: https://doi.org/10.1101/219246 (Year: 2017).*

Bleckmann M, Schürig M, Chen FF, Yen ZZ, Lindemann N, et al. (2016) Identification of Essential Genetic Baculoviral Elements for Recombinant Protein Expression by Transactivation in Sf21 Insect Cells. PLOS ONE 11(3): e0149424. (Year: 2016).*

Mansouri, M., Bellon-Echeverria, I., Rizk, A. et al. Highly efficient baculovirus-mediated multigene delivery in primary cells. Nat Commun 7, 11529 (2016). https://doi.org/10.1038/ncomms11529 (Year: 2016).*

Characterization of Alternative Promoters to Stagger and Control Multiple Gene Expression and Protein Production in the Baculovirus-Insect Cell System by Mohd Altamash Jauhar, A thesis presented to the University of Waterloo, 2014 (Year: 2014).*

Saarenpääet al. "Baculovirus-Mediated Expression of GPCRs in Insect Cells". Editor(s): Arun K. Shukla, Methods in Enzymology, Academic Press, vol. 556, 2015, pp. 185-218, ISSN 0076-6879, ISBN 9780128015216, DOI: 10.1016/bs.mie.2014.12.033 (Year: 2015).*

Stork How Many Species of Insects and Other Terrestrial Arthropods Are There on Earth? Annu. Rev. Entomol. 2018. 63:31-45. First published Sep. 22, 2017. (Year: 2017).*

Wu et al. Generating a host range-expanded recombinant baculovirus. Sci Rep 6, 28072 (2016). (Year: 2016).*

International search report dated Oct. 15, 2018 from corresponding application No. PCT/CN2018/079510.

Wei et al., "Advances in Research and Application of Baculovirus Expression System", Biotechnology Bulletin, No. 10. Oct. 31, 2010 (Oct. 31, 2010), pp. 1-7.

The Office Action dated Sep. 9, 2019 and English translation from corresponding application No. CN 201810028508.0.

\* cited by examiner

SEQUENCE LISTING

```
<160> NUMBER OF SEQ ID NOS: 56

<210> SEQ ID NO 1
<211> LENGTH: 7187
<212> TYPE: DNA
<213> ORGANISM: Artificial Sequence
<220> FEATURE:
<223> OTHER INFORMATION: Synthesized

<400> SEQUENCE: 1
gatgccctgc gtaagcgggt gtgggcggac aataaagtct taaactgaac aaaatagatc      60
taaactatga caataaagtc ttaaactaga cagaatagtt gtaaactgaa atcagtccag     120
ttatgctgtg aaaaagcata ctggactttt gttatggcta aagcaaactc ttcattttct     180
gaagtgcaaa ttgcccgtcg tattaaagag gggcgtggcc aagggcatgt aaagactata     240
ttcgcggcgt tgtgacaatt taccgaacaa ctccgcggcc gggaagccga tctcggcttg     300
aacgaattgt taggtggcgg tacttgggtc gatatcaaag tgcatcactt cttcccgtat     360
gcccaacttt gtatagagag ccactgcggg atcgtcaccg taatctgctt gcacgtagat     420
cacataagca ccaagcgcgt tggcctcatg cttgaggaga ttgatgagcg cggtggcaat     480
gccctgcctc cggtgctcgc cggagactgc gagatcatag atatagatct cactacgcgg     540
ctgctcaaac ttgggcagaa cgtaagccgc gagagcgcca acaaccgctt cttggtcgaa     600
```

-continued

```
ggcagcaagc gcgatgaatg tcttactacg gagcaagttc ccgaggtaat cggagtccgg      660
ctgatgttgg gagtaggtgg ctacgtctcc gaactcacga ccgaaaagat caagagcagc      720
ccgcatggat ttgacttggt cagggccgag cctacatgtg cgaatgatgc ccatacttga      780
gccacctaac tttgtttttag ggcgactgcc ctgctgcgta acatcgttgc tgctgcgtaa     840
catcgttgct gctccataac atcaaacatc gacccacggc gtaacgcgct tgctgcttgg      900
atgcccgagg catagactgt acaaaaaaac agtcataaca agccatgaaa accgccactg      960
cgccgttacc accgctgcgt tcggtcaagg ttctggacca gttgcgtgag cgcatacgct     1020
acttgcatta cagtttacga accgaacagg cttatgtcaa ctgggttcgt gccttcatcc     1080
gtttccacgg tgtgcgtcac ccggcaacct tgggcagcag cgaagtcgcc ataacttcgt     1140
atagcataca ttatacgaag ttatctgtaa ctataacggt cctaaggtag cgagtttaaa     1200
cactagttcg cgacctactc cggaatatta ataggttgct gatatcggga gttcagtcgt     1260
cgaatgcaaa gcgtaaaaaa tattaataag gtaaaaatta cagctacata aattacacaa     1320
tttaaacgga tcgatcatat ggcttatcct tacgacgtgc ctgactacgc cggagagagc     1380
ttgtttaagg ggccgcgtga ttacaaccct atatcgagca ccatttgtca tttgacgaat     1440
gaatctgatg ggcacacaac atcgttgtat ggtattggat ttggtccctt catcattaca     1500
aacaagcact tgtttagaag aaataatgga acactgttgg tccaatcact acatggtgta     1560
ttcaaggtca agaacaccac gactttgcaa caacacctca ttgatgggag ggacatgata     1620
attattcgca tgcctaagga tttcccacca tttcctcaaa agctgaaatt tagagagcca     1680
caaagggaag agagaatatg tcttgtgaca accaacttcc aaactaagag catgtctagc     1740
atggtgtcag acacttcttg cacattccct tcatctgatg gcatattctg gaagcattgg     1800
attcaaacca aggatgggca gtgtggcagt ccattagtat caactagaga tgggttcatt     1860
gttggtatac actcagcatc gaatttcacc aacacaaaca attatttcac aagcgtgccg     1920
aaaaacttca tggaattgtt gacaaatcag gaggcgcagc agtgggttag tggttggcga     1980
ttaaatgctg actcagtatt gtggggggc cataaagttt tcatggtgaa acctgaagag     2040
ccttttcagc cagttaagga agcgactcaa ctcatgaatg aattggtgta ctcgcaagaa     2100
aacctgtact tccagtcagc ctggagccat ccgcaatttg aaaaaggtgg cgggtccggc     2160
ggaggtagcg gcggaggttc ttggtctcac cctcagttcg agaaggatga cgatgataaa     2220
accatgggat ccctaggtac cgcggccgcg cgcgttggcc gattcattaa tgcagctggc     2280
acgacaggtt ccccgactgg aaagcgggca gtgagcgcaa cgcaattaat gtgagttagc     2340
tcactcatta ggcaccccag gctttacact ttatgcttcc ggctcgtatg ttgtgtggaa     2400
ttgtgagcgg ataacaattt cacacaggaa acagctatga ccatgattac gccaagctat     2460
ttaggtgacg cgttagaata ctcaagctat gcatcatctt tggttccgtc atcggaccca     2520
ttagtaacgg ccgccagtgt gctggagttt tgtagatacc catcacactg cgtccactg     2580 gaacatgcaa gtagagggcc caattcgccc tatagtgagt cgtattacaa ttcactggcc     2640
gtcgttttac aacgtcgtga ctgggaaaac cctggcgtta cccaacttaa tcgccttgca     2700
gcacatcccc ctttcgccag ctggcgtaat agcgaagagg cccgcaccga tcgcccttcc     2760
caacagttgc gcagcctata cgtacggtaa ctgactaaga attccgatta caaagacgat     2820
gacgacaagg gctcgagtga aaatttgtat tttcaaagct cgtcgacggt gagcaagggc     2880
gaggagctgt tcaccggggt ggtgcccatc ctggtcgagc tggacggcga cgtaaacggc     2940
cacaagttca gcgtgtccgg cgagggcgag ggcgatgcca cctacggcaa gctgaccctg     3000
```

-continued

```
aagttcatct gcaccaccgg caagctgccc gtgccctggc ccaccctcgt gaccaccctg   3060
acctacggcg tgcagtgctt cagccgctac cccgaccaca tgaagcagca cgacttcttc   3120
aagtccgcca tgcccgaagg ctacgtccag gagcgcacca tcttcttcaa ggacgacggc   3180
aactacaaga cccgcgccga ggtgaagttc gagggcgaca ccctggtgaa ccgcatcgag   3240
ctgaagggca tcgacttcaa ggaggacggc aacatcctgg gcacaagct ggagtacaac   3300 tacaacagcc acaacgtcta tatcatggcc gacaagcaga gaacggcat caaggtgaac   3360 ttcaagatcc gccacaacat cgaggacggc agcgtgcagc tcgccgacca ctaccagcag   3420 aacacccca tcggcgacgg ccccgtgctg ctgcccgaca ccactacct gagcacccag   3480 tccgccctga gcaaagaccc caacgagaag cgcgatcaca tggtcctgct ggagttcgtg   3540
accgccgccg ggatcactct cggcatggac gagctgtaca gtaactgac taaaagcttc   3600 gaaaggaagc tgagttggct gctgccaccg ctgagcaata actagcataa cccttgggg   3660 cctctaaacg ggtcttgagg ggttttttgc tgaaaggagg aactatcctc agggtcgaga   3720
agtactagag gatcataatc agccatacca catttgtaga ggttttactt gctttaaaaa   3780
acctcccaca cctcccctg aacctgaaac ataaaatgaa tgcaattgtt gttgttaact   3840
tgtttattgc agcttataat ggttacaaat aaagcaatag catcacaaat ttcacaaata   3900
aagcattttt ttcactgcat ctagttgtg gtttgtccaa actcatcaat gtatcttatc   3960
atgtctggat ctgatcactg cttgagccta ggagatccga accagataag tgaaatctag   4020
ttccaaacta ttttgtcatt tttaattttc gtattagctt acgacgctac acccagttcc   4080
catctatttt gtcactcttc cctaaataat ccttaaaaac tccatttcca ccctcccag   4140 ttcccaacta ttttgtccgc ccacagcggg gcattttct tcctgttatg ttttttaatca   4200 aacatcctgc caactccatg tgacaaaccg tcatcttcgg ctacttttc tctgtcacag   4260 aatgaaaatt tttctgtcat ctcttcgtta ttaatgtttg taattgactg aatatcaacg   4320
cttatttgca gcctgaatgg cgaatgggac gcgccctgta gcggcgcatt aagcgcggcg   4380
ggtgtggtgg ttacgcgcag cgtgaccgct acacttgcca gcgccctagc gcccgctcct   4440
ttcgctttct tcccttcctt tctcgccacg ttcgccggct ttccccgtca agctctaaat   4500 cggggctcc ctttagggtt ccgatttagt gctttacggc acctcgaccc caaaaaactt   4560
gattagggtg atggttcacg tagtgggcca tcgccctgat agacggtttt tcgcctttg   4620 acgttggagt ccacgttctt taatagtgga ctcttgttcc aaactggaac aacactcaac   4680
cctatctcgg tctattcttt tgatttataa gggattttgc cgatttcggc ctattggtta   4740
aaaaatgagc tgatttaaca aaaatttaac gcgaatttta acaaaatatt aacgtttaca   4800
atttcaggtg gcacttttcg gggaaatgtg cgcggaaccc ctatttgttt attttttctaa   4860 atacattcaa atatgtatcc gctcatgaga caataaccct gataaatgct tcaataatat   4920
tgaaaaagga agagtatgag tattcaacat ttccgtgtcg cccttattcc cttttttgcg   4980
gcattttgcc ttcctgtttt tgctcaccca gaaacgctgg tgaaagtaaa agatgctgaa   5040
gatcagttgg gtgcacgagt gggttacatc gaactggatc tcaacagcgg taagatcctt   5100
gagagttttc gccccgaaga acgttttcca atgatgagca cttttaaagt tctgctatgt   5160
ggcgcggtat tatcccgtat tgacgccggg caagagcaac tcggtcgccg catacactat   5220
tctcagaatg acttggttga gtactcacca gtcacagaaa agcatcttac ggatggcatg   5280
acagtaagag aattatgcag tgctgccata accatgagtg ataacactgc ggccaactta   5340
```

```
cttctgacaa cgatcggagg accgaaggag ctaaccgctt ttttgcacaa catgggggat     5400
catgtaactc gccttgatcg ttgggaaccg gagctgaatg aagccatacc aaacgacgag     5460
cgtgacacca cgatgcctgt agcaatggca acaacgttgc gcaaactatt aactggcgaa     5520
ctacttactc tagcttcccg gcaacaatta atagactgga tggaggcgga taaagttgca     5580
ggaccacttc tgcgctcggc ccttccggct ggctggttta ttgctgataa atctggagcc     5640
ggtgagcgtg ggtctcgcgg tatcattgca gcactggggc cagatggtaa gccctcccgt     5700
atcgtagtta tctacacgac ggggagtcag gcaactatgg atgaacgaaa tagacagatc     5760
gctgagatag gtgcctcact gattaagcat tggtaactgt cagaccaagt ttactcatat     5820
atactttaga ttgatttaaa acttcatttt taatttaaaa ggatctaggt gaagatcctt     5880
tttgataatc tcatgaccaa atcccttaa cgtgagtttt cgttccactg agcgtcagac      5940
cgcggggcat gactaacatg agaattacaa cttatatcgt atggggctga cttcaggtgc     6000
tacatttgaa gagataaatt gcactgaaat ctagaaatat tttatctgat taataagatg     6060
atcttcttga gatcgttttg gtctgcgcgt aatctcttgc tctgaaaacg gaaaaaaccg     6120
ccttgcaggg cggttttttcg aaggttctct gagctaccaa ctctttgaac cgaggtaact     6180
ggcttggagg agcgcagtca ccaaaacttg tcctttcagt ttagccttaa ccggcgcatg     6240
acttcaagac taactcctct aaatcaatta ccagtggctg ctgccagtgg tgcttttgca     6300
tgtctttccg ggttggactc aagacgatag ttaccggata aggcgcagcg tcggactga     6360 acggggggtt cgtgcataca gtccagcttg gagcgaactg cctacccgga actgagtgtc     6420
aggcgtggaa tgagacaaac gcggccataa cagcggaatg acaccggtaa accgaaaggc     6480
aggaacagga gagcgcacga gggagccgcc aggggaaacg cctggtatct ttatagtcct     6540
gtcgggtttc gccaccactg atttgagcgt cagatttcgt gatgcttgtc aggggggcgg     6600
agcctatgga aaaacggctt tgccgcggcc ctctcacttc cctgttaagt atcttcctgg     6660
catcttccag gaaatctccg ccccgttcgt aagccatttc cgctcgccgc agtcgaacga     6720
ccgagcgtag cgagtcagtg agcgaggaag cggaatatat cctgtatcac atattctgct     6780
gacgcaccgt tgcagccttt tttctcctgc cacatgaagc acttcactga caccctcatc     6840
agtgccaaca tagtaagcca gtatacactc cgctagcgct gatgtccggc ggtgcttttg     6900
ccgttacgca ccaccccgtc agtagctgaa caggagggac agctgataga aacagaagcc     6960
agttctttcc tgcgttatcc cctgattctg tggataaccg tattaccgcc tttgagtgag     7020
ctgataccgc tcgccgcagc cgaacgaccg agcgcagcga gtcagtgagc gaggaagcgg     7080
aagagcgcct gatgcggtat tttctcctta cgcatctgtg cggtatttca caccgcatag     7140
accagccgcg taacctggca aaatcggtta cggttgagta ataaatg                   7187
```

<210> SEQ ID NO 2
<211> LENGTH: 7187
<212> TYPE: DNA
<213> ORGANISM: Artificial Sequence
<220> FEATURE:
<223> OTHER INFORMATION: Synthesized

<400> SEQUENCE: 2

```
gatgccctgc gtaagcgggt gtgggcggac aataaagtct taaactgaac aaaatagatc       60
taaactatga caataaagtc ttaaactaga cagaatagtt gtaaactgaa atcagtccag       120
ttatgctgtg aaaaagcata ctggactttt gttatggcta agcaaactc ttcattttct        180 gaagtgcaaa ttgcccgtcg tattaaagag gggcgtggcc aagggcatgt aaagactata       240
```

-continued

```
ttcgcggcgt tgtgacaatt taccgaacaa ctccgcggcc gggaagccga tctcggcttg      300
aacgaattgt taggtggcgg tacttgggtc gatatcaaag tgcatcactt cttcccgtat      360
gcccaacttt gtatagagag ccactgcggg atcgtcaccg taatctgctt gcacgtagat      420
cacataagca ccaagcgcgt tggcctcatg cttgaggaga ttgatgagcg cggtggcaat      480
gccctgcctc cggtgctcgc cggagactgc gagatcatag atatagatct cactacgcgg      540
ctgctcaaac ttgggcagaa cgtaagccgc gagagcgcca acaaccgctt cttggtcgaa      600
ggcagcaagc gcgatgaatg tcttactacg gagcaagttc ccgaggtaat cggagtccgg      660
ctgatgttgg gagtaggtgg ctacgtctcc gaactcacga ccgaaaagat caagagcagc      720
ccgcatggat ttgacttggt cagggccgag cctacatgtg cgaatgatgc ccatacttga      780
gccacctaac tttgtttag ggcgactgcc ctgctgcgta acatcgttgc tgctgcgtaa      840
catcgttgct gctccataac atcaaacatc gacccacggc gtaacgcgct tgctgcttgg      900
atgcccgagg catagactgt acaaaaaaac agtcataaca agccatgaaa accgccactg      960
cgccgttacc accgctgcgt tcggtcaagg ttctggacca gttgcgtgag cgcatacgct     1020
acttgcatta cagtttacga accgaacagg cttatgtcaa ctgggttcgt gccttcatcc     1080
gtttccacgg tgtgcgtcac ccggcaacct tgggcagcag cgaagtcgcc ataacttcgt     1140
atagcataca ttatacgaag ttatctgtaa ctataacggt cctaaggtag cgagtttaaa     1200
cactagttcg cgacctactc cggaatatta ataggttgct gatatcggga gttcagtcgt     1260
cgaatgcaaa gcgtaaaaaa tattaataag gtaaaaatta cagctacata aattacacaa     1320
tttaaacgga tcgatcatat ggcttatcct tacgacgtgc ctgactacgc cggagagagc     1380
ttgtttaagg ggccgcgtga ttacaaccct atatcgagca ccatttgtca tttgacgaat     1440
gaatctgatg ggcacacaac atcgttgtat ggtattggat ttggtccctt catcattaca     1500
aacaagcact tgtttagaag aaataatgga acactgttgg tccaatcact acatggtgta     1560
ttcaaggtca agaacaccac gactttgcaa caacacctca ttgatgggag ggacatgata     1620
attattcgca tgcctaagga tttcccacca tttcctcaaa agctgaaatt tagagagcca     1680
caaagggaag agagaatatg tcttgtgaca accaacttcc aaactaagag catgtctagc     1740
atggtgtcag acacttcttg cacattccct tcatctgatg gcatattctg gaagcattgg     1800
attcaaacca aggatgggca gtgtggcagt ccattagtat caactagaga tgggttcatt     1860
gttggtatac actcagcatc gaatttcacc aacacaaaca attatttcac aagcgtgccg     1920
aaaaacttca tggaattgtt gacaaatcag gaggcgcagc agtgggttag tggttggcga     1980
ttaaatgctg actcagtatt gtgggggggc cataaagttt tcatggtgaa acctgaagag     2040 cctttttcagc cagttaagga agcgactcaa ctcatgaatg aattggtgta ctcgcaagaa     2100
aacctgtact tccagtcagc ctggagccat ccgcaatttg aaaaaggtgg cgggtccggc     2160
ggaggtagcg gcggaggttc ttggtctcac cctcagttcg agaaggatga cgatgataaa     2220
accatgggat ccctaggtac cgcggccgcg cgcgttggcc gattcattaa tgcagctggc     2280
acgacaggtt tcccgactgg aaagcgggca gtgagcgcaa cgcaattaat gtgagttagc     2340
tcactcatta ggcaccccag ctttacact ttatgcttcc ggctcgtatg ttgtgtggaa     2400
ttgtgagcgg ataacaattt cacacaggaa acagctatga ccatgattac gccaagctat     2460
ttaggtgacg cgttagaata ctcaagctat gcatcatctt tggttccgtc atcggaccca     2520
ttagtaacgg ccgccagtgt gctggagttt tgtagatacc catcacactg gcgtccactg     2580
```

-continued

```
gaacatgcaa gtagagggcc caattcgccc tatagtgagt cgtattacaa ttcactggcc    2640
gtcgttttac aacgtcgtga ctgggaaaac cctggcgtta cccaacttaa tcgccttgca    2700
gcacatcccc ctttcgccag ctggcgtaat agcgaagagg cccgcaccga tcgcccttcc    2760
caacagttgc gcagcctata cgtacggtaa ctgactaaga attccgagca aaagttgatt    2820
agcgaagaag acttaggctc gagtgaaaat ttgtattttc aaagctcgtc gacggtgtct    2880
aagggcgaag agctgattaa ggagaacatg cacatgaagc tgtacatgga gggcaccgtg    2940
aacaaccacc acttcaagtg cacatccgag ggcgaaggca gccctacga gggcacccag     3000 accatgagaa tcaaggtggt cgagggcggc cctctcccct tcgccttcga tatcctggct    3060
accagcttca tgtacggcag cagaaccttc atcaaccaca cccagggcat ccccgacttc    3120
tttaagcagt ccttccctga gggcttcaca tgggagagag tcaccacata cgaagacggg    3180
ggcgtgctga ccgctaccca ggacaccagc ctccaggacg gctgcctcat ctacaacgtc    3240
aagatcagag gggtgaactt cccatccaac ggccctgtga tgcagaagaa aacactcggc    3300
tgggaggcca acaccgagat gctgtacccc gctgacggcg cctggaagg cagaagcgac     3360 atggccctga gctcgtgggg cggggccac ctgatctgca acttcaagac cacatacaga     3420
tccaagaaac ccgctaagaa cctcaagatg cccggcgtct actatgtgga ccacagactg    3480
gaaagaatca aggaggccga caaagagacc tacgtcgagc agcacgaggt ggctgtggcc    3540
agatactgcg acctccctag caaactgggg cacaaactta attaactgac taaaagcttc    3600
gaaaggaagc tgagttggct gctgccaccg ctgagcaata actagcataa ccccttgggg    3660
cctctaaacg ggtcttgagg ggttttttgc tgaaaggagg aactatcctc agggtcgaga    3720
agtactagag gatcataatc agccatacca catttgtaga ggttttactt gctttaaaaa    3780
acctcccaca cctcccctg aacctgaaac ataaaatgaa tgcaattgtt gttgttaact     3840
tgtttattgc agcttataat ggttacaaat aaagcaatag catcacaaat ttcacaaata    3900
aagcattttt ttcactgcat tctagttgtg gtttgtccaa actcatcaat gtatcttatc    3960
atgtctggat ctgatcactg cttgagccta ggagatccga accagataag tgaaatctag    4020
ttccaaacta ttttgtcatt tttaattttc gtattagctt acgacgctac acccagttcc    4080
catctatttt gtcactcttc cctaaataat ccttaaaaac tccatttcca cccctcccag    4140
ttcccaacta ttttgtccgc ccacagcggg gcattttct tcctgttatg tttttaatca     4200
aacatcctgc caactccatg tgacaaaccg tcatcttcgg ctactttttc tctgtcacag    4260
aatgaaaatt tttctgtcat ctcttcgtta ttaatgtttg taattgactg aatatcaacg    4320
cttatttgca gcctgaatgg cgaatgggac gcgccctgta gcggcgcatt aagcgcggcg    4380
ggtgtggtgg ttacgcgcag cgtgaccgct acacttgcca gcgccctagc gcccgctcct    4440
ttcgctttct tcccttcctt tctcgccacg ttcgccggct ttccccgtca agctctaaat    4500 cggggggctcc ctttagggtt ccgatttagt gctttacggc acctcgaccc caaaaaactt    4560
gattagggtg atggttcacg tagtgggcca tcgccctgat agacggtttt tcgccctttg    4620
acgttggagt ccacgttctt taatagtgga ctcttgttcc aaactggaac aacactcaac    4680
cctatctcgg tctattcttt tgatttataa gggattttgc cgatttcggc ctattggtta    4740
aaaaatgagc tgatttaaca aaaatttaac gcgaattta acaaaatatt aacgtttaca     4800
atttcaggtg gcacttttcg gggaaatgtg cgcggaaccc ctatttgttt attttttctaa   4860 atacattcaa atatgtatcc gctcatgaga caataaccct gataaatgct tcaataatat    4920
tgaaaaagga agagtatgag tattcaacat ttccgtgtcg cccttattcc cttttttgcg    4980
```

```
gcattttgcc ttcctgtttt tgctcaccca gaaacgctgg tgaaagtaaa agatgctgaa      5040
gatcagttgg gtgcacgagt gggttacatc gaactggatc tcaacagcgg taagatcctt      5100
gagagttttc gccccgaaga acgtttttcca atgatgagca cttttaaagt tctgctatgt      5160
ggcgcggtat tatcccgtat tgacgccggg caagagcaac tcggtcgccg catacactat      5220
tctcagaatg acttggttga gtactcacca gtcacagaaa agcatcttac ggatggcatg      5280
acagtaagag aattatgcag tgctgccata accatgagtg ataacactgc ggccaactta      5340
cttctgacaa cgatcggagg accgaaggag ctaaccgctt ttttgcacaa catgggggat      5400
catgtaactc gccttgatcg ttgggaaccg gagctgaatg aagccatacc aaacgacgag      5460
cgtgacacca cgatgcctgt agcaatggca acaacgttgc gcaaactatt aactggcgaa      5520
ctacttactc tagcttcccg gcaacaatta atagactgga tggaggcgga taaagttgca      5580
ggaccacttc tgcgctcggc ccttccggct ggctggttta ttgctgataa atctggagcc      5640
ggtgagcgtg ggtctcgcgg tatcattgca gcactggggc cagatggtaa gccctcccgt      5700
atcgtagtta tctacacgac ggggagtcag gcaactatgg atgaacgaaa tagacagatc      5760
gctgagatag gtgcctcact gattaagcat tggtaactgt cagaccaagt ttactcatat      5820
atactttaga ttgatttaaa acttcatttt taatttaaaa ggatctaggt gaagatcctt      5880
tttgataatc tcatgaccaa aatcccttaa cgtgagtttt cgttccactg agcgtcagac      5940
cgcggggcat gactaacatg agaattacaa cttatatcgt atggggctga cttcaggtgc      6000
tacatttgaa gagataaatt gcactgaaat ctagaaatat tttatctgat taataagatg      6060
atcttcttga gatcgttttg gtctgcgcgt aatctcttgc tctgaaaacg gaaaaaccg      6120 ccttgcaggg cggtttttcg aaggttctct gagctaccaa ctctttgaac cgaggtaact      6180
ggcttggagg agcgcagtca ccaaaacttg tcctttcagt ttagccttaa ccggcgcatg      6240
acttcaagac taactcctct aaatcaatta ccagtggctg ctgccagtgg tgcttttgca      6300
tgtctttccg ggttggactc aagacgatag ttaccggata aggcgcagcg tcggactga      6360 acggggggtt cgtgcataca gtccagcttg gagcgaactg cctacccgga actgagtgtc      6420
aggcgtggaa tgagacaaac gcggccataa cagcggaatg acaccggtaa accgaaaggc      6480
aggaacagga gagcgcacga gggagccgcc aggggaaacg cctggtatct ttatagtcct      6540
gtcgggtttc gccaccactg atttgagcgt cagatttcgt gatgcttgtc agggggggcgg      6600 agcctatgga aaaacggctt tgccgcggcc ctctcacttc cctgttaagt atcttcctgg      6660
catcttccag gaaatctccg ccccgttcgt aagccatttc cgctcgccgc agtcgaacga      6720
ccgagcgtag cgagtcagtg agcgaggaag cggaatatat cctgtatcac atattctgct      6780
gacgcaccgt gcagccttt tttctcctgc cacatgaagc acttcactga caccctcatc      6840
agtgccaaca tagtaagcca gtatacactc cgctagcgct gatgtccggc ggtgcttttg      6900
ccgttacgca ccaccccgtc agtagctgaa caggagggac agctgataga aacagaagcc      6960
agttctttcc tgcgttatcc cctgattctg tggataaccg tattaccgcc tttgagtgag      7020
ctgataccgc tcgccgcagc cgaacgaccg agcgcagcga gtcagtgagc gaggaagcgg      7080
aagagcgcct gatgcggtat tttctcctta cgcatctgtg cggtatttca caccgcatag      7140
accagccgcg taacctggca aaatcggtta cggttgagta ataaatg      7187
```

<210> SEQ ID NO 3
<211> LENGTH: 7737
<212> TYPE: DNA

<213> ORGANISM: Artificial Sequence
<220> FEATURE:
<223> OTHER INFORMATION: Synthesized

<400> SEQUENCE: 3

```
gatgccctgc gtaagcgggt gtgggcggac aataaagtct taaactgaac aaaatagatc    60
taaactatga caataaagtc ttaaactaga cagaatagtt gtaaactgaa atcagtccag   120
ttatgctgtg aaaaagcata ctggactttt gttatggcta aagcaaactc ttcattttct   180
gaagtgcaaa ttgcccgtcg tattaaagag gggcgtggcc aagggcatgt aaagactata   240
ttcgcggcgt tgtgacaatt taccgaacaa ctccgcggcc gggaagccga tctcggcttg   300
aacgaattgt taggtggcgg tacttgggtc gatatcaaag tgcatcactt cttcccgtat   360
gcccaacttt gtatagagag ccactgcggg atcgtcaccg taatctgctt gcacgtagat   420
cacataagca ccaagcgcgt tggcctcatg cttgaggaga ttgatgagcg cggtggcaat   480
gccctgcctc cggtgctcgc cggagactgc gagatcatag atatagatct cactacgcgg   540
ctgctcaaac ttgggcagaa cgtaagccgc gagagcgcca acaaccgctt cttggtcgaa   600
ggcagcaagc gcgatgaatg tcttactacg gagcaagttc ccgaggtaat cggagtccgg   660
ctgatgttgg gagtaggtgg ctacgtctcc gaactcacga ccgaaaagat caagagcagc   720
ccgcatggat ttgacttggt cagggccgag cctacatgtg cgaatgatgc ccatacttga   780
gccacctaac tttgttttag ggcgactgcc ctgctgcgta acatcgttgc tgctgcgtaa   840
catcgttgct gctccataac atcaaacatc gacccacggc gtaacgcgct tgctgcttgg   900
atgcccgagg catagactgt acaaaaaaac agtcataaca agccatgaaa accgccactg   960
cgccgttacc accgctgcgt tcggtcaagg ttctggacca gttgcgtgag cgcatacgct  1020
acttgcatta cagtttacga accgaacagg cttatgtcaa ctgggttcgt gccttcatcc  1080
gtttccacgg tgtgcgtcac ccggcaacct tgggcagcag cgaagtcgcc ataacttcgt  1140
atagcataca ttatacgaag ttatctgtaa ctataacggt cctaaggtag cgagtttaaa  1200
cgacgtccta gattggttac tgggcgatga aggtttagtc ggcaaatcgt ccaacgttag  1260
tgacagcgtc agcggcaagt taatgcctat cattttgttg ataggcgcgg tcttgttttt  1320
aggtttaata ttttatttta tctacagata catgatgaaa ggagggaagg gaggtggtgt  1380
tggcgcagca acgtcgccaa ctcccattgt tatttctatg caaaaccca caccaacaac  1440 ggcccctcga taataaaaga caaaaataat ataaaatata tgtataatta attaaattca  1500
aaatatatgt ataaggccgg ccttagtcag ttacttgtac agctcgtcca tgccgagagt  1560
gatcccggcg gcggtcacga actccagcag gaccatgtga tcgcgcttct cgttggggtc  1620
tttgctcagg gcggactggg tgctcaggta gtggttgtcg ggcagcagca cggggccgtc  1680
gccgatgggg gtgttctgct ggtagtggtc ggcgagctgc acgctgccgt cctcgatgtt  1740
gtggcggatc ttgaagttca ccttgatgcc gttcttctgc ttgtcggcca tgatatagac  1800
gttgtggctg ttgtagttgt actccagctt gtgccccagg atgttgccgt cctccttgaa  1860
gtcgatgccc ttcagctcga tgcggttcac cagggtgtcg ccctcgaact tcacctcggc  1920
gcgggtcttg tagttgccgt cgtccttgaa gaagatggtg cgctcctgga cgtagccttc  1980
gggcatggcg gacttgaaga agtcgtgctg cttcatgtgg tcggggtagc ggctgaagca  2040
ctgcacgccg taggtcaggg tggtcacgag ggtgggccag ggcacgggca gcttgccggt  2100
ggtgcagatg aacttcaggg tcagcttgcc gtaggtggca tcgccctcgc cctcgccgga  2160
cacgctgaac ttgtggccgt ttacgtcgcc gtccagctcg accaggatgg gcaccacccc  2220
```

-continued

```
ggtgaacagc tcctcgccct tgctcatccc gggtgactgg aagtacaggt tttcttgcga   2280
gtacaccaat tcattcatga gttgagtcgc ttccttaact ggctgaaaag gctcttcagg   2340
tttcaccatg aaaactttat ggcccccca caatactgag tcagcattta atcgccaacc   2400
actaacccac tgctgcgcct cctgatttgt caacaattcc atgaagtttt tcggcacgct   2460
tgtgaaataa ttgtttgtgt tggtgaaatt cgatgctgag tgtataccaa caatgaaccc   2520
atctctagtt gatactaatg gactgccaca ctgcccatcc ttggtttgaa tccaatgctt   2580
ccagaatatg ccatcagatg aagggaatgt gcaagaagtg tctgacacca tgctagacat   2640
gctcttagtt tggaagttgg ttgtcacaag acatattctc tcttcccttt gtggctctct   2700
aaatttcagc ttttgaggaa atggtgggaa atccttaggc atgcgaataa ttatcatgtc   2760
cctcccatca atgaggtgtt gttgcaaagt cgtggtgttc ttgaccttga atacaccatg   2820
tagtgattgg accaacagtg ttccattatt tcttctaaac aagtgcttgt ttgtaatgat   2880
gaagggacca aatccaatac catacaacga tgttgtgtgc ccatcagatt cattcgtcaa   2940
atgacaaatg gtgctcgata tagggttgta atcacgcggc cccttaaaca agctctctcc   3000
ggcgtagtca ggcacgtcgt aaggataagc catatttaaa tatatgcttg cttgtgtgtt   3060
ccttattgaa gccttggtgt gactgattta ctagtagcgt tgaggcgtct tatataccccg  3120 accgttatct ggcctacgtg acacaaggca cgttgttaga ttaataatct tatcttttta   3180
tcttaattga taagattatt tttatctggc tgttataaaa acgggatcat gaacacggac   3240
gctcagtcga cagatctgtc gacggtttaa acactagttc gcgacctact ccggaatatt   3300
aataggttgc tgatatcggg agttcagtcg tcgaatgcaa agcgtaaaaa atattaataa   3360
ggtaaaaatt acagctacat aaattacaca atttaaacgg atcgatgagc tccatatggc   3420
ctggagccat ccgcaatttg aaaaaggtgg cgggtccggc ggaggtagcg gcggaggttc   3480
ttggtctcac cctcagttcg agaaggatga cgatgataaa accatgggat ccctaggtac   3540
cgcggccgcg cgcgttggcc gattcattaa tgcagctggc acgacaggtt tcccgactgg   3600
aaagcgggca gtgagcgcaa cgcaattaat gtgagttagc tcactcatta ggcaccccag   3660
gctttacact ttatgcttcc ggctcgtatg ttgtgtggaa ttgtgagcgg ataacaattt   3720
cacacaggaa acagctatga ccatgattac gccaagctat ttaggtgacg cgttagaata   3780
ctcaagctat gcatcatctt tggttccgtc atcggaccca ttagtaacgg ccgccagtgt   3840
gctggagttt tgtagatacc catcacactg gcgtccactg aacatgcaa gtagagggcc   3900 caattcgccc tatagtgagt cgtattacaa ttcactggcc gtcgttttac aacgtcgtga   3960
ctgggaaaac cctggcgtta cccaacttaa tcgccttgca gcacatcccc ctttcgccag   4020
ctggcgtaat agcgaagagg cccgcaccga tcgcccttcc caacagttgc gcagcctata   4080
cgtacggtaa ctgactaaga attccttaag cggaggcctg cagggctcga gttaactgac   4140
taaaagcttc gaaaggaagc tgagttggct gctgccaccg ctgagcaata actagcataa   4200 cccccttgggg cctctaaacg ggtcttgagg ggttttttgc tgaaaggagg aactatcctc   4260
agggtcgaga agtactagag gatcataatc agccatacca catttgtaga ggttttactt   4320
gctttaaaaa acctcccaca cctccccctg aacctgaaac ataaaatgaa tgcaattgtt   4380
gttgttaact tgtttattgc agcttataat ggttacaaat aaagcaatag catcacaaat   4440
ttcacaaata aagcattttt ttcactgcat tctagttgtg gtttgtccaa actcatcaat   4500
gtatcttatc atgtctggat ctgatcactg cttgagccta ggagatccga accagataag   4560
```

-continued

```
tgaaatctag ttccaaacta ttttgtcatt tttaattttc gtattagctt acgacgctac    4620
acccagttcc catctatttt gtcactcttc cctaaataat ccttaaaaac tccatttcca    4680
cccctcccag ttcccaacta ttttgtccgc ccacagcggg gcattttct tcctgttatg    4740 tttttaatca aacatcctgc caactccatg tgacaaaccg tcatcttcgg ctactttttc    4800
tctgtcacag aatgaaaatt tttctgtcat ctcttcgtta ttaatgtttg taattgactg    4860
aatatcaacg cttatttgca gcctgaatgg cgaatgggac gcgccctgta gcggcgcatt    4920
aagcgcggcg ggtgtggtgg ttacgcgcag cgtgaccgct acacttgcca gcgccctagc    4980
gcccgctcct ttcgctttct tcccttcctt tctcgccacg ttcgccggct ttccccgtca    5040
agctctaaat cggggctcc ctttagggtt ccgatttagt gctttacggc acctcgaccc    5100
caaaaaactt gattagggtg atggttcacg tagtgggcca tcgccctgat agacggtttt    5160
tcgccctttg acgttggagt ccacgttctt taatagtgga ctcttgttcc aaactggaac    5220
aacactcaac cctatctcgg tctattcttt tgatttataa gggattttgc cgatttcggc    5280
ctattggtta aaaaatgagc tgatttaaca aaaatttaac gcgaatttta acaaaatatt    5340
aacgtttaca atttcaggtg gcacttttcg gggaaatgtg cgcggaaccc ctatttgttt    5400
atttttctaa atacattcaa atatgtatcc gctcatgaga caataaccct gataaatgct    5460
tcaataatat tgaaaaagga agagtatgag tattcaacat ttccgtgtcg cccttattcc    5520
cttttttgcg gcattttgcc ttcctgtttt tgctcaccca gaaacgctgg tgaaagtaaa    5580
agatgctgaa gatcagttgg gtgcacgagt gggttacatc gaactggatc tcaacagcgg    5640
taagatcctt gagagttttc gccccgaaga acgttttcca atgatgagca cttttaaagt    5700
tctgctatgt ggcgcggtat tatcccgtat tgacgccggg caagagcaac tcggtcgccg    5760
catacactat tctcagaatg acttggttga gtactcacca gtcacagaaa agcatcttac    5820
ggatggcatg acagtaagag aattatgcag tgctgccata accatgagtg ataacactgc    5880
ggccaactta cttctgacaa cgatcggagg accgaaggag ctaaccgctt ttttgcacaa    5940
catgggggat catgtaactc gccttgatcg ttgggaaccg gagctgaatg aagccatacc    6000
aaacgacgag cgtgacacca cgatgcctgt agcaatggca acaacgttgc gcaaactatt    6060
aactggcgaa ctacttactc tagcttcccg gcaacaatta atagactgga tggaggcgga    6120
taaagttgca ggaccacttc tgcgctcggc ccttccggct ggctggttta ttgctgataa    6180
atctggagcc ggtgagcgtg ggtctcgcgg tatcattgca gcactggggc cagatggtaa    6240
gccctcccgt atcgtagtta tctacacgac ggggagtcag gcaactatgg atgaacgaaa    6300
tagacagatc gctgagatag gtgcctcact gattaagcat tggtaactgt cagaccaagt    6360
ttactcatat atactttaga ttgatttaaa acttcatttt taatttaaaa ggatctaggt    6420
gaagatcctt tttgataatc tcatgaccaa atcccttaa cgtgagtttt cgttccactg    6480
agcgtcagac cgcggggcat gactaacatg agaattacaa cttatatcgt atggggctga    6540
cttcaggtgc tacatttgaa gagataaatt gcactgaaat ctagaaatat tttatctgat    6600
taataagatg atcttcttga gatcgttttg gtctgcgcgt aatctcttgc tctgaaaacg    6660 gaaaaaccg ccttgcaggg cggttttcg aaggttctct gagctaccaa ctctttgaac    6720
cgaggtaact ggcttggagg agcgcagtca ccaaaacttg tcctttcagt ttagccttaa    6780
ccggcgcatg acttcaagac taactcctct aaatcaatta ccagtggctg ctgccagtgg    6840
tgcttttgca tgtctttccg ggttggactc aagacgatag ttaccggata aggcgcagcg    6900
gtcggactga acggggggtt cgtgcataca gtccagcttg gagcgaactg cctacccgga    6960
```

-continued

```
actgagtgtc aggcgtggaa tgagacaaac gcggccataa cagcggaatg acaccggtaa    7020
accgaaaggc aggaacagga gagcgcacga gggagccgcc aggggaaacg cctggtatct    7080
ttatagtcct gtcgggtttc gccaccactg atttgagcgt cagatttcgt gatgcttgtc    7140 agggggggcgg agcctatgga aaaacggctt tgccgcggcc ctctcacttc cctgttaagt    7200
atcttcctgg catcttccag gaaatctccg ccccgttcgt aagccatttc cgctcgccgc    7260
agtcgaacga ccgagcgtag cgagtcagtg agcgaggaag cggaatatat cctgtatcac    7320
atattctgct gacgcaccgg tgcagccttt tttctcctgc cacatgaagc acttcactga    7380
caccctcatc agtgccaaca tagtaagcca gtatacactc cgctagcgct gatgtccggc    7440
ggtgcttttg ccgttacgca ccaccccgtc agtagctgaa caggagggac agctgataga    7500
aacagaagcc agtctttcc tgcgttatcc cctgattctg tggataaccg tattaccgcc    7560
tttgagtgag ctgataccgc tcgccgcagc cgaacgaccg agcgcagcga gtcagtgagc    7620
gaggaagcgg aagagcgcct gatgcggtat tttctcctta cgcatctgtg cggtatttca    7680
caccgcatag accagccgcg taacctggca aaatcggtta cggttgagta ataaatg        7737
```

<210> SEQ ID NO 4
<211> LENGTH: 7734
<212> TYPE: DNA
<213> ORGANISM: Artificial Sequence
<220> FEATURE:
<223> OTHER INFORMATION: Synthesized

<400> SEQUENCE: 4

```
gatgccctgc gtaagcgggt gtgggcggac aataaagtct taaactgaac aaaatagatc      60
taaactatga caataaagtc ttaaactaga cagaatagtt gtaaactgaa atcagtccag     120
ttatgctgtg aaaaagcata ctggactttt gttatggcta aagcaaactc ttcattttct     180
gaagtgcaaa ttgcccgtcg tattaaagag gggcgtggcc aagggcatgt aaagactata     240
ttcgcggcgt tgtgacaatt taccgaacaa ctccgcggcc gggaagccga tctcggcttg     300
aacgaattgt taggtggcgg tacttgggtc gatatcaaag tgcatcactt cttcccgtat     360
gcccaacttt gtatagagag ccactgcggg atcgtcaccg taatctgctt gcacgtagat     420
cacataagca ccaagcgcgt tggcctcatg cttgaggaga ttgatgagcg cggtggcaat     480
gccctgcctc cggtgctcgc cggagactgc gagatcatag atatagatct cactacgcgg     540
ctgctcaaac ttgggcagaa cgtaagccgc gagagcgcca acaaccgctt cttggtcgaa     600
ggcagcaagc gcgatgaatg tcttactacg gagcaagttc ccgaggtaat cggagtccgg     660
ctgatgttgg gagtaggtgg ctacgtctcc gaactcacga ccgaaaagat caagagcagc     720
ccgcatggat ttgacttggt cagggccgag cctacatgtg cgaatgatgc ccatacttga     780
gccacctaac tttgttttag gcgactgccc ctgctgcgta acatcgttgc tgctgcgtaa     840
catcgttgct gctccataac atcaaacatc gacccacggc gtaacgcgct tgctgcttgg     900
atgcccgagg catagactgt acaaaaaaac agtcataaca agccatgaaa accgccactg     960
cgccgttacc accgctgcgt tcggtcaagg ttctggacca gttgcgtgag cgcatacgct    1020
acttgcatta cagtttacga accgaacagg cttatgtcaa ctgggttcgt gccttcatcc    1080
gtttccacgg tgtgcgtcac ccggcaacct tgggcagcag cgaagtcgcc ataacttcgt    1140
atagcataca ttatacgaag ttatctgtaa ctataacggt cctaaggtag cgagtttaaa    1200
cgacgtccta gattggttac tgggcgatga aggtttagtg ggcaaatcgt ccaacgttag    1260
```

-continued

```
tgacagcgtc agcggcaagt taatgcctat cattttgttg ataggcgcgg tcttgttttt    1320
aggtttaata ttttatttta tctacagata catgatgaaa ggagggaagg gaggtggtgt    1380
tggcgcagca acgtcgccaa ctcccattgt tatttctatg caaaacccca caccaacaac    1440
ggcccctcga taataaaaga caaaaataat ataaaatata tgtataatta attaaattca    1500
aaatatatgt ataaggccgg ccttagtcag ttaattaagt ttgtgcccca gtttgctagg    1560
gaggtcgcag tatctggcca cagccacctc gtgctgctcg acgtaggtct ctttgtcggc    1620
ctccttgatt ctttccagtc tgtggtccac atagtagacg ccgggcatct tgaggttctt    1680
agcgggtttc ttggatctgt atgtggtctt gaagttgcag atcaggtggc ccccgcccac    1740
gagcttcagg gccatgtcgc ttctgccttc caggccgccg tcagcggggt acagcatctc    1800
ggtgttggcc tcccagccga gtgttttctt ctgcatcaca gggccgttgg atgggaagtt    1860
cacccctctg atcttgacgt tgtagatgag gcagccgtcc tggaggctgg tgtcctgggt    1920
agcggtcagc acgcccccgt cttcgtatgt ggtgactctc tcccatgtga agccctcagg    1980
gaaggactgc ttaaagaagt cggggatgcc ctgggtgtgg ttgatgaagg ttctgctgcc    2040
gtacatgaag ctggtagcca ggatgtcgaa ggcgaagggg agagggccgc cctcgaccac    2100
cttgattctc atggtctggg tgccctcgta gggcttgcct tcgccctcgg atgtgcactt    2160
gaagtggtgg ttgttcacgg tgccctccat gtacagcttc atgtgcatgt tctccttaat    2220
cagctcttcg cccttagaca ccatcccggg tgactgaaag tacaggtttt cttgcgagta    2280
caccaattca ttcatgagtt gagtcgcttc cttaactggc tgaaaaggct cttcaggttt    2340
caccatgaaa actttatggc cccccacaa tactgagtca gcatttaatc gccaaccact    2400
aacccactgc tgcgcctcct gatttgtcaa caattccatg aagttttttcg gcacgcttgt    2460 gaaataattg tttgtgttgg tgaaattcga tgctgagtgt ataccaacaa tgaacccatc    2520
tctagttgat actaatggac tgccacactg cccatccttg gtttgaatcc aatgcttcca    2580
gaatatgcca tcagatgaag ggaatgtgca agaagtgtct gacaccatgc tagacatgct    2640
cttagtttgg aagttggttg tcacaagaca tattctctct tcccttgtg gctctctaaa    2700 tttcagcttt tgaggaaatg gtgggaaatc cttaggcatg cgaataatta tcatgtccct    2760
cccatcaatg aggtgttgtt gcaaagtcgt ggtgttcttg accttgaata caccatgtag    2820
tgattggacc aacagtgttc cattatttct tctaaacaag tgcttgtttg taatgatgaa    2880
gggaccaaat ccaataccat acaacgatgt tgtgtgccca tcagattcat tcgtcaaatg    2940
acaaatggtg ctcgatatag ggttgtaatc acgcggcccc ttaaacaagc tctctccggc    3000
gtagtcaggc acgtcgtaag gataagccat atttaaatat atgcttgctt gtgtgttcct    3060
tattgaagcc ttggtgtgac tgatttacta gtagcgttga ggcgtcttat atacccgacc    3120
gttatctggc ctacgtgaca caaggcacgt tgttagatta ataatcttat ctttttatct    3180
taattgataa gattattttt atctggctgt tataaaaacg ggatcatgaa cacggacgct    3240
cagtcgacag atctgtcgac ggtttaaaca ctagttcgcg acctactccg gaatattaat    3300
aggttgctga tatcgggagt tcagtcgtcg aatgcaaagc gtaaaaaata ttaataaggt    3360
aaaaattaca gctacataaa ttacacaatt taaacggatc gatgagctcc atatggcctg    3420
gagccatccg caatttgaaa aaggtggcgg gtccggcgga ggtagcggcg gaggttcttg    3480
gtctcaccct cagttcgaga aggatgacga tgataaaacc atgggatccc taggtaccgc    3540
ggccgcgcgc gttggccgat tcattaatgc agctggcacg acaggtttcc cgactggaaa    3600
gcgggcagtg agcgcaacgc aattaatgtg agttagctca ctcattaggc accccaggct    3660
```

-continued

```
ttacacttta tgcttccggc tcgtatgttg tgtggaattg tgagcggata acaatttcac   3720
acaggaaaca gctatgacca tgattacgcc aagctattta ggtgacgcgt tagaatactc   3780
aagctatgca tcatctttgg ttccgtcatc ggacccatta gtaacggccg ccagtgtgct   3840
ggagttttgt agatacccat cacactggcg tccactggaa catgcaagta gagggcccaa   3900
ttcgccctat agtgagtcgt attacaattc actggccgtc gttttacaac gtcgtgactg   3960
ggaaaaccct ggcgttaccc aacttaatcg ccttgcagca catccccctt cgccagctg    4020 gcgtaatagc gaagaggccc gcaccgatcg cccttccaa cagttgcgca gcctatacgt    4080
acggtaactg actaagaatt ccttaagcgg aggcctgcag ggctcgagtt aactgactaa   4140
aagcttcgaa aggaagctga gttggctgct gccaccgctg agcaataact agcataaccc   4200
cttggggcct ctaaacgggt cttgaggggg ttttttgctga aaggaggaac tatcctcagg   4260
gtcgagaagt actagaggat cataatcagc cataccacat ttgtagaggt tttacttgct   4320
ttaaaaaacc tcccacacct cccctgaac ctgaaacata aaatgaatgc aattgttgtt    4380
gttaacttgt ttattgcagc ttataatggt tacaaataaa gcaatagcat cacaaatttc   4440
acaaataaag catttttttc actgcattct agttgtggtt tgtccaaact catcaatgta   4500
tcttatcatg tctggatctg atcactgctt gagcctagga gatccgaacc agataagtga   4560
aatctagttc caaactattt tgtcatttt aatttttcgta ttagcttacg acgctacacc   4620
cagttcccat ctattttgtc actcttccct aaataatcct taaaaactcc atttccaccc   4680
ctcccagttc ccaactattt tgtccgccca cagcggggca ttttttcttcc tgttatgttt   4740 ttaatcaaac atcctgccaa ctccatgtga caaaccgtca tcttcggcta ctttttctct   4800
gtcacagaat gaaaattttt ctgtcatctc ttcgttatta atgtttgtaa ttgactgaat   4860
atcaacgctt atttgcagcc tgaatggcga atgggacgcg ccctgtagcg gcgcattaag   4920
cgcggcgggt gtggtggtta cgcgcagcgt gaccgctaca cttgccagcg ccctagcgcc   4980
cgctcctttc gctttcttcc cttcctttct cgccacgttc gccggctttc cccgtcaagc   5040
tctaaatcgg gggctccctt tagggttccg atttagtgct ttacggcacc tcgaccccaa   5100
aaaacttgat tagggtgatg gttcacgtag tgggccatcg ccctgataga cggttttttcg   5160 ccctttgacg ttggagtcca cgttctttaa tagtggactc ttgttccaaa ctggaacaac   5220
actcaaccct atctcggtct attcttttga tttataaggg attttgccga tttcggccta   5280
ttggttaaaa aatgagctga tttaacaaaa atttaacgcg aatttttaaca aaatattaac   5340 gtttacaatt tcaggtggca cttttcgggg aaatgtgcgc ggaacccta tttgtttatt    5400 tttctaaata cattcaaata tgtatccgct catgagacaa taaccctgat aaatgcttca   5460
ataatattga aaaaggaaga gtatgagtat tcaacatttc cgtgtcgccc ttattccctt   5520
ttttgcggca ttttgccttc ctgtttttgc tcacccagaa acgctggtga agtaaaaga    5580 tgctgaagat cagttgggtg cacgagtggg ttacatcgaa ctggatctca acagcggtaa   5640
gatccttgag agttttcgcc ccgaagaacg ttttccaatg atgagcactt ttaaagttct   5700
gctatgtggc gcggtattat cccgtattga cgccgggcaa gagcaactcg gtcgccgcat   5760
acactattct cagaatgact tggttgagta ctcaccagtc acagaaaagc atcttacgga   5820
tggcatgaca gtaagagaat tatgcagtgc tgccataacc atgagtgata acactgcggc   5880
caacttactt ctgacaacga tcggaggacc gaaggagcta accgcttttt tgcacaacat   5940
gggggatcat gtaactcgcc ttgatcgttg ggaaccggag ctgaatgaag ccataccaaa   6000
```

-continued

```
cgacgagcgt gacaccacga tgcctgtagc aatggcaaca acgttgcgca aactattaac    6060
tggcgaacta cttactctag cttcccggca acaattaata gactggatgg aggcggataa    6120
agttgcagga ccacttctgc gctcggccct tccggctggc tggtttattg ctgataaatc    6180
tggagccggt gagcgtgggt ctcgcggtat cattgcagca ctggggccag atggtaagcc    6240
ctcccgtatc gtagttatct acacgacggg gagtcaggca actatggatg aacgaaatag    6300
acagatcgct gagataggtg cctcactgat taagcattgg taactgtcag accaagttta    6360
ctcatatata ctttagattg atttaaaact tcatttttaa tttaaaagga tctaggtgaa    6420
gatccttttt gataatctca tgaccaaaat cccttaacgt gagttttcgt tccactgagc    6480
gtcagaccgc ggggcatgac taacatgaga attacaactt atatcgtatg gggctgactt    6540
caggtgctac atttgaagag ataaattgca ctgaaatcta gaaatatttt atctgattaa    6600
taagatgatc ttcttgagat cgttttggtc tgcgcgtaat ctcttgctct gaaaacggaa    6660
aaaaccgcct tgcagggcgg tttttcgaag gttctctgag ctaccaactc tttgaaccga    6720
ggtaactggc ttggaggagc gcagtcacca aaacttgtcc tttcagttta gccttaaccg    6780
gcgcatgact tcaagactaa ctcctctaaa tcaattacca gtggctgctg ccagtggtgc    6840
ttttgcatgt ctttccgggt tggactcaag acgatagtta ccggataagg cgcagcggtc    6900
ggactgaacg ggggggttcgt gcatacagtc cagcttggag cgaactgcct acccggaact    6960
gagtgtcagg cgtggaatga dacaaacgcg gccataacag cggaatgaca ccggtaaacc    7020
gaaaggcagg aacaggagag cgcacgaggg agccgccagg ggaaacgcct ggtatcttta    7080
tagtcctgtc gggtttcgcc accactgatt tgagcgtcag atttcgtgat gcttgtcagg    7140
ggggcggagc ctatggaaaa acggctttgc cgcggccctc tcacttccct gttaagtatc    7200
ttcctggcat cttccaggaa atctccgccc cgttcgtaag ccatttccgc tcgccgcagt    7260
cgaacgaccg agcgtagcga gtcagtgagc gaggaagcgg aatatatcct gtatcacata    7320
ttctgctgac gcaccggtgc agcctttttt ctcctgccac atgaagcact tcactgacac    7380
cctcatcagt gccaacatag taagccagta tacactccgc tagcgctgat gtccggcggt    7440
gcttttgccg ttacgcacca ccccgtcagt agctgaacag gagggacagc tgatagaaac    7500
agaagccagt tctttcctgc gttatcccct gattctgtgg ataaccgtat taccgccttt    7560
gagtgagctg ataccgctcg ccgcagccga acgaccgagc gcagcgagtc agtgagcgag    7620
gaagcggaag agcgcctgat gcggtatttt ctccttacgc atctgtgcgg tatttcacac    7680
cgcatagacc agccgcgtaa cctggcaaaa tcggttacgg ttgagtaata aatg          7734
```

<210> SEQ ID NO 5
<211> LENGTH: 4915
<212> TYPE: DNA
<213> ORGANISM: Artificial Sequence
<220> FEATURE:
<223> OTHER INFORMATION: Synthesized

<400> SEQUENCE: 5

```
cgcgccggta tgtacaggaa gaggtttata ctaaactgtt acattgcaaa cgtggtttcg     60
tgtgccaagt gtgaaaaccg atgtttaatc aaggctctga cgcatttcta caaccacgac    120
tccaagtgtg tgggtgaagt cagatgttta aacccatgtg cctggcagat aacttcgtat    180
aatgtatgct atacgaagtt atggtacgcg gccgcgtaga ggatctgttg atcagcagtt    240
caacctgttg ataatacgga cctttaattc aacccaacac aatatattat agttaaataa    300
gaattattat caaatcattt gtatattaat aaaaatacta tactgtaaat tacattttat    360
```

```
ttacaatcac tcgacaccgg tgatatccat atggcacatc accaccatca tcaccatcac    420
caccacggag gcagcgatga cgatgataaa accatgggat ccgctagctt aagctgtcag    480
accaagttta ctcatatata ctttagattg atttaaaact tcatttttaa tttaaaagga    540
tctaggtgaa gatccttttt gataatctca tgaccaaaat cccttaacgt gagttttcgt    600
tccactgagc gtcagacccc gtagaaaaga tcaaaggatc ttcttgagat ccttttttttc    660 tgcgcgtaat ctgctgcttg caaacaaaaa aaccaccgct accagcggtg gtttgtttgc    720
cggatcaaga gctaccaact ctttttccga aggtaactgg cttcagcaga gcgcagatac    780
caaatactgt tcttctagtg tagccgtagt taggccacca cttcaagaac tctgtagcac    840
cgcctacata cctcgctctg ctaatcctgt taccagtggc tgctgccagt ggcgataagt    900
cgtgtcttac cgggttggac tcaagacgat agttaccgga taaggcgcag cggtcgggct    960 gaacggggggg ttcgtgcaca gcccagct tggagcgaac gacctacacc gaactgagat    1020
acctacagcg tgagctatga gaaagcgcca cgcttcccga aggagaaag gcggacaggt    1080 atccggtaag cggcagggtc ggaacaggag agcgcacgag ggagcttcca gggggaaacg    1140
cctggtatct ttatagtcct gtcgggtttc gccacctctg acttgagcgt cgattttgt    1200 gatgctcgtc aggggggcgg agcctatgga aaaacgccag caacgcggcc tttttacggt    1260
tcctggcctt ttgctggcct tttgctcaca tgttctttcc tgcgttatcc cctgattctg    1320
tggataaccg tattaccgcc tttgagtgag ctgataccgc tcgccgcagc cgaacgaccg    1380
agcgcagcga gtcagtgagc gaggaagcgg aagagcgccc aatacgcaaa ccgcctctcc    1440
ccgcgcgttg gccgattcat taatgcagct ggcacgacag gtttcccgac tggaaagcgg    1500
gcagtgagcg caacgcaatt aatgtgagtt agctcactca ttaggcaccc caggctttac    1560
actttatgct tccggctcgt atgttgtgtg gaattgtgag cggataacaa tttcacacag    1620
gaaacagcta tgaccatgat tacgccaagc tatttaggtg acgcgttaga atactcaagc    1680
tatgcatcat ctttggttcc gtcatcggac ccattagtaa cggccgccag tgtgctggag    1740
ttttgtagat acccatcaca ctggcgtcca ctggaacatg caagtagagg gcccaattcg    1800
ccctatagtg agtcgtatta caattcactg gccgtcgttt tacaacgtcg tgactgggaa    1860
aaccctggcg ttacccaact taatcgcctt gcagcacatc ccccttttcgc cagctggcgt    1920 aatagcgaag aggcccgcac cgatcgccct tcccaacagt tgcgcagcct atacgtacgg    1980
taactgacta agaattccga ttacaaagac gatgacgaca agggctcgag tgaaaatttg    2040
tattttcaaa gcgggagctc tgtgagcaag gcggaggagc tgttcaccgg ggtggtgccc    2100
atcctggtcg agctggacgg cgacgtaaac ggccacaagt tcagcgtgtc cggcgagggc    2160
gagggcgatg ccacctacgg caagctgacc ctgaagttca tctgcaccac cggcaagctg    2220
cccgtgccct ggcccaccct cgtgaccacc ctgacctacg gcgtgcagtg cttcagccgc    2280
taccccgacc acatgaagca gcacgacttc ttcaagtccg ccatgcccga aggctacgtc    2340
caggagcgca ccatcttctt caaggacgac ggcaactaca agacccgcgc cgaggtgaag    2400
ttcgagggcg acaccctggt gaaccgcatc gagctgaagg gcatcgactt caaggaggac    2460
ggcaacatcc tggggcacaa gctggagtac aactacaaca gccacaacgt ctatatcatg    2520
gccgacaagc agaagaacgg catcaaggtg aacttcaaga tccgccacaa catcgaggac    2580
ggcagcgtgc agctcgccga ccactaccag cagaacaccc ccatcggcga cggccccgtg    2640
ctgctgcccg acaaccacta cctgagcacc cagtccgccc tgagcaaaga ccccaacgag    2700
```

-continued

```
aagcgcgatc acatggtcct gctggagttc gtgaccgccg ccgggatcac tctcggcatg    2760
gacgagctgt acaagtaact gactaaggta cccgaaagga agctgagttg gctgctgcca    2820
ccgctgagca ataactagca taacccttg gggcctctaa acgggtcttg aggggttttt     2880
tgctgaaagg aggaactatc ctcaggggga gatgggggag gctaactgaa acacggaagg    2940
agacaatacc ggaaggaacc cgcgctatga cggcaataaa aagacagaat aaaacgcacg    3000
ggtgttgggt cgtttgttca taaacgcggg gttcggtccc agggctggca ctctgtcgat    3060
accccaccga gaccccattg ggaccaatac gcccgcgttt cttccttttc cccacccaa     3120 cccccaagtt cgggtgaagg cccagggctc gcagccaacg tcggggcggc aagccctgcc    3180
atagccacta cgggtacgtc tgaaagcatg ccttttttgga atttacgtac taagctctca    3240
tgtttcacgt actaagctct catgtttaac gtactaagct ctcatgttta acgaactaaa    3300
ccctcatggc taacgtacta agctctcatg gctaacgtac taagctctca tgtttcacgt    3360
actaagctct catgtttgaa caataaaatt aatataaatc agcaacttaa atagcctcta    3420
aggttttaag ttttataaga aaaaaagaa tatataaggc ttttaaagct tttaaggttt     3480
aacggttgtg gacaacaagc cagggatgta acgcactgag aagcccttag agcctctcaa    3540
agcaattttc agtgacacag gaacacttaa cggctgacaa aattagcttc acgctgccgc    3600
aagcactcag ggcgcaaggg ctgctaaagg aagcggaaca cgtagaaagc cagtccgcag    3660
aaacggtgct gaccccggat gaatgtcagc tactgggcta tctggacaag ggaaaacgca    3720
agcgcaaaga gaaagcaggt agcttgcagt gggcttacat ggcgatagct agactgggcg    3780
gttttatgga cagcaagcga accggaattg ccagctgggg cgccctctgg taaggttggg    3840
aagccctgca aagtaaactg gatggctttc ttgccgccaa ggatctgatg gcgcagggga    3900
tcaagatctg atcaagagac aggatgagga tcgtttcgca tgattgaaca agatggattg    3960
cacgcaggtt ctccggccgc ttgggtggag aggctattcg gctatgactg gcacaacag    4020 acaatcggct gctctgatgc cgccgtgttc cggctgtcag cgcaggggcg cccggttctt    4080
tttgtcaaga ccgacctgtc cggtgccctg aatgaactgc aggacgaggc agcgcggcta    4140
tcgtggctgg ccacgacggg cgttccttgc gcagctgtgc tcgacgttgt cactgaagcg    4200
ggaagggact ggctgctatt gggcgaagtg ccggggcagg atctcctgtc atctcacctt    4260
gctcctgccg agaaagtatc catcatggct gatgcaatgc ggcggctgca tacgcttgat    4320
ccggctacct gcccattcga ccaccaagcg aaacatcgca tcgagcgagc acgtactcgg    4380
atggaagccg gtcttgtcga tcaggatgat ctggacgaag agcatcaggg gctcgcgcca    4440
gccgaactgt tcgccaggct caaggcgcgc atgcccgacg gcgaggatct cgtcgtgaca    4500
catggcgatg cctgcttgcc gaatatcatg gtggaaaatg gccgcttttc tggattcatc    4560
gactgtggcc ggctgggtgt ggcggaccgc tatcaggaca tagcgttggc tacccgtgat    4620
attgctgaag agcttggcgg cgaatgggct gaccgcttcc tcgtgcttta cggtatcgcc    4680
gctcccgatt cgcagcgcat cgccttctat cgccttcttg acgagttctt ctgagcggga    4740
ctctggggtt cgaaatgacc gaccaagcga cgcccaacct gccatcacga gatttcgatt    4800
ccaccgccgc cttctatgaa aggttgggct tcggaatcgt tttccgggac gccggctgga    4860
tgatcctcca gcgcggggat ctcatgctgg agttcttcgc ccacatcata tcgat        4915
```

<210> SEQ ID NO 6
<211> LENGTH: 4915
<212> TYPE: DNA
<213> ORGANISM: Artificial Sequence -continued

```
<220> FEATURE:
<223> OTHER INFORMATION: Synthesized

<400> SEQUENCE: 6
cgcgccggta tgtacaggaa gaggtttata ctaaactgtt acattgcaaa cgtggtttcg     60
tgtgccaagt gtgaaaaccg atgtttaatc aaggctctga cgcatttcta caaccacgac    120
tccaagtgtg tgggtgaagt cagatgttta aacccatgtg cctggcagat aacttcgtat    180
aatgtatgct atacgaagtt atggtacgcg gccgcgtaga ggatctgttg atcagcagtt    240
caacctgttg ataatacgga cctttaattc aacccaacac aatatattat agttaaataa    300
gaattattat caaatcattt gtatattaat taaaatacta tactgtaaat tacatttttat   360 ttacaatcac tcgacaccgg tgatatccat atggcacatc accaccatca tcaccatcac    420
caccacggag gcagcgatga cgatgataaa accatgggat ccgctagctt aagctgtcag    480 accaagtttta ctcatatata ctttagattg atttaaaact tcatttttaa tttaaaagga    540
tctaggtgaa gatcctttttt gataatctca tgaccaaaat cccttaacgt gagttttcgt    600
tccactgagc gtcagacccc gtagaaaaga tcaaaggatc ttcttgagat ccttttttttc   660 tgcgcgtaat ctgctgcttg caaacaaaaa aaccaccgct accagcggtg gtttgtttgc    720
cggatcaaga gctaccaact ctttttccga aggtaactgg cttcagcaga gcgcagatac    780
caaatactgt tcttctagtg tagccgtagt taggccacca cttcaagaac tctgtagcac    840
cgcctacata cctcgctctg ctaatcctgt taccagtggc tgctgccagt ggcgataagt    900
cgtgtcttac cgggttggac tcaagacgat agttaccgga taaggcgcag cggtcgggct    960 gaacggggggg ttcgtgcaca cagcccagct tggagcgaac gacctacacc gaactgagat   1020
acctacagcg tgagctatga aaagcgcca cgcttcccga agggagaaag gcggacaggt     1080
atccggtaag cggcagggtc ggaacaggag agcgcacgag ggagcttcca gggggaaacg    1140
cctggtatct ttatagtcct gtcgggtttc gccacctctg acttgagcgt cgattttttgt   1200 gatgctcgtc agggggggcgg agcctatgga aaaacgccag caacgcggcc ttttttacggt   1260 tcctggcctt ttgctggcct tttgctcaca tgttctttcc tgcgttatcc cctgattctg    1320
tggataaccg tattaccgcc tttgagtgag ctgataccgc tcgccgcagc cgaacgaccg    1380
agcgcagcga gtcagtgagc gaggaagcgg aagagcgccc aatacgcaaa ccgcctctcc    1440
ccgcgcgttg gccgattcat taatgcagct ggcacgacag gtttcccgac tggaaagcgg    1500
gcagtgagcg caacgcaatt aatgtgagtt agctcactca ttaggcaccc caggctttac    1560
actttatgct tccggctcgt atgttgtgtg gaattgtgag cggataacaa tttcacacag    1620
gaaacagcta tgaccatgat tacgccaagc tatttaggtg acgcgttaga atactcaagc    1680
tatgcatcat ctttggttcc gtcatcggac ccattagtaa cggccgccag tgtgctggag    1740
ttttgtagat acccatcaca ctggcgtcca ctggaacatg caagtagagg gcccaattcg    1800
ccctatagtg agtcgtatta caattcactg gccgtcgttt tacaacgtcg tgactgggaa    1860
aaccctggcg ttacccaact taatcgcctt gcagcacatc ccccttttcgc cagctggcgt   1920 aatagcgaag aggcccgcac cgatcgccct tcccaacagt tgcgcagcct atacgtacgg    1980
taactgacta agaattccga gcaaaagttg attagcgaag aagacttagg ctcgagtgaa    2040
aatttgtatt ttcaaagcgg gagctctgtg tctaagggcg aagagctgat taaggagaac    2100
atgcacatga agctgtacat ggagggcacc gtgaacaacc accacttcaa gtgcacatcc    2160
gagggcgaag gcaagcccta cgagggcacc cagaccatga gaatcaaggt ggtcgagggc    2220
```

-continued

```
ggccctctcc ccttcgcctt cgacatcctg gctaccagct tcatgtacgg cagcagaacc        2280
ttcatcaacc acacccaggg catccccgac ttctttaagc agtccttccc tgagggcttc        2340
acatgggaga gagtcaccac atacgaagac gggggcgtgc tgaccgctac ccaggacacc        2400
agcctccagg acggctgcct catctacaac gtcaagatca gaggggtgaa cttcccatcc        2460
aacggccctg tgatgcagaa gaaaacactc ggctgggagg ccaacaccga gatgctgtac        2520
cccgctgacg gcggcctgga aggcagaagc gacatggccc tgaagctcgt gggcgggggc        2580
cacctgatct gcaacttcaa gaccacatac agatccaaga aacccgctaa gaacctcaag        2640
atgcccggcg tctactatgt ggaccacaga ctggaaagaa tcaaggaggc cgacaaagag        2700
acctacgtcg agcagcacga ggtggctgtg gccagatact gcgacctccc tagcaaactg        2760
gggcacaaac ttaattaact gactaaggta cccgaaagga agctgagttg gctgctgcca        2820
ccgctgagca ataactagca taaccccttg gggcctctaa acgggtcttg aggggttttt        2880
tgctgaaagg aggaactatc ctcaggggga gatggggggag gctaactgaa acacggaagg        2940
agacaatacc ggaaggaacc cgcgctatga cggcaataaa aagacagaat aaaacgcacg        3000
ggtgttgggt cgtttgttca taaacgcggg gttcggtccc agggctggca ctctgtcgat        3060
accccaccga gaccccattg ggaccaatac gcccgcgttt cttccttttc cccaccccaa        3120
cccccaagtt cgggtgaagg cccagggctc gcagccaacg tcggggcggc aagccctgcc        3180
atagccacta cgggtacgtc tgaaagcatg ccttttttgga atttacgtac taagctctca        3240
tgtttcacgt actaagctct catgtttaac gtactaagct ctcatgttta acgaactaaa        3300
ccctcatggc taacgtacta agctctcatg gctaacgtac taagctctca tgtttcacgt        3360
actaagctct catgtttgaa caataaaatt aatataaatc agcaacttaa atagcctcta        3420
aggttttaag ttttataaga aaaaaaagaa tatataaggc ttttaaagct tttaaggttt        3480
aacggttgtg gacaacaagc cagggatgta acgcactgag aagcccttag agcctctcaa        3540
agcaattttc agtgacacag gaacacttaa cggctgacag aattagcttc acgctgccgc        3600
aagcactcag ggcgcaaggg ctgctaaagg aagcggaaca cgtagaaagc cagtccgcag        3660
aaacggtgct gacccggat gaatgtcagc tactgggcta tctggacaag ggaaaacgca        3720
agcgcaaaga gaaagcaggt agcttgcagt gggcttacat ggcgatagct agactgggcg        3780
gttttatgga cagcaagcga accggaattg ccagctgggg cgccctctgg taaggttggg        3840
aagccctgca aagtaaactg gatggctttc ttgccgccaa ggatctgatg gcgcagggga        3900
tcaagatctg atcaagagac aggatgagga tcgtttcgca tgattgaaca agatggattg        3960
cacgcaggtt ctccggccgc ttgggtggag aggctattcg gctatgactg gcacaacag        4020 acaatcggct gctctgatgc cgccgtgttc cggctgtcag cgcaggggcg cccggttctt        4080
tttgtcaaga ccgacctgtc cggtgccctg aatgaactgc aggacgaggc agcgcggcta        4140
tcgtggctgg ccacgacggg cgttccttgc gcagctgtgc tcgacgttgt cactgaagcg        4200
ggaagggact ggctgctatt gggcgaagtg ccggggcagg atctcctgtc atctcacctt        4260
gctcctgccg agaaagtatc catcatggct gatgcaatgc ggcggctgca tacgcttgat        4320
ccggctacct gcccattcga ccaccaagcg aaacatcgca tcgagcgagc acgtactcgg        4380
atggaagccg gtcttgtcga tcaggatgat ctggacgaag agcatcaggg gctcgcgcca        4440
gccgaactgt tcgccaggct caaggcgcgc atgcccgacg gcgaggatct cgtcgtgaca        4500
catggcgatg cctgcttgcc gaatatcatg gtggaaaatg gccgcttttc tggattcatc        4560
gactgtggcc ggctgggtgt ggcggaccgc tatcaggaca tagcgttggc tacccgtgat        4620
```

-continued

```
attgctgaag agcttggcgg cgaatgggct gaccgcttcc tcgtgcttta cggtatcgcc      4680
gctcccgatt cgcagcgcat cgccttctat cgccttcttg acgagttctt ctgagcggga      4740
ctctggggtt cgaaatgacc gaccaagcga cgcccaacct gccatcacga gatttcgatt      4800
ccaccgccgc cttctatgaa aggttgggct tcggaatcgt tttccgggac gccggctgga      4860
tgatcctcca gcgcggggat ctcatgctgg agttcttcgc ccacatcata tcgat          4915
```

<210> SEQ ID NO 7
<211> LENGTH: 9846
<212> TYPE: DNA
<213> ORGANISM: Artificial Sequence
<220> FEATURE:
<223> OTHER INFORMATION: Synthesized

<400> SEQUENCE: 7

```
gatgccctgc gtaagcgggt gtgggcggac aataaagtct taaactgaac aaaatagatc       60
taaactatga caataaagtc ttaaactaga cagaatagtt gtaaactgaa atcagtccag      120
ttatgctgtg aaaaagcata ctggactttt gttatggcta aagcaaactc ttcattttct      180
gaagtgcaaa ttgcccgtcg tattaaagag gggcgtggcc aagggcatgt aaagactata      240
ttcgcggcgt tgtgacaatt taccgaacaa ctccgcggcc gggaagccga tctcggcttg      300
aacgaattgt taggtggcgg tacttgggtc gatatcaaag tgcatcactt cttcccgtat      360
gcccaacttt gtatagagag ccactgcggg atcgtcaccg taatctgctt gcacgtagat      420
cacataagca ccaagcgcgt tggcctcatg cttgaggaga ttgatgagcg cggtggcaat      480
gccctgcctc cggtgctcgc cggagactgc gagatcatag atatagatct cactacgcgg      540
ctgctcaaac ttgggcagaa cgtaagccgc gagagcgcca acaaccgctt cttggtcgaa      600
ggcagcaagc gcgatgaatg tcttactacg gagcaagttc ccgaggtaat cggagtccgg      660
ctgatgttgg gagtaggtgg ctacgtctcc gaactcacga ccgaaaagat caagagcagc      720
ccgcatggat ttgacttggt cagggccgag cctacatgtg cgaatgatgc ccatacttga      780
gccacctaac tttgttttag ggcgactgcc ctgctgcgta acatcgttgc tgctgcgtaa      840
catcgttgct gctccataac atcaaacatc gacccacggc gtaacgcgct tgctgcttgg      900
atgcccgagg catagactgt acaaaaaaac agtcataaca agccatgaaa accgccactg      960
cgccgttacc accgctgcgt tcggtcaagg ttctggacca gttgcgtgag cgcatacgct     1020
acttgcatta cagtttacga accgaacagg cttatgtcaa ctgggttcgt gccttcatcc     1080
gtttccacgg tgtgcgtcac ccggcaacct tgggcagcag cgaagtcgcc ataacttcgt     1140
atagcataca ttatacgaag ttatctgtaa ctataacggt cctaaggtag cgagtttaaa     1200
cgacgtccta gattggttac tgggcgatga aggtttagtc ggcaaatcgt ccaacgttag     1260
tgacagcgtc agcggcaagt taatgcctat cattttgttg ataggcgcgg tcttgttttt     1320
aggtttaata ttttatttta tctacagata catgatgaaa ggagggaagg gaggtggtgt     1380
tggcgcagca acgtcgccaa ctcccattgt tatttctatg caaaacccca caccaacaac     1440
ggcccctcga taataaaaga caaaataat ataaaatata tgtataatta attaaattca      1500
aaatatatgt ataaggccgg ccttagtcag ttacttgtac agctcgtcca tgccgagagt     1560
gatcccggcg gcggtcacga actccagcag gaccatgtga tcgcgcttct cgttggggtc     1620
tttgctcagg gcggactggg tgctcaggta gtggttgtcg gcagcagca cggggccgtc     1680 gccgatgggg gtgttctgct ggtagtggtc ggcgagctgc acgctgccgt cctcgatgtt     1740
```

-continued

```
gtggcggatc ttgaagttca ccttgatgcc gttcttctgc ttgtcggcca tgatatagac   1800
gttgtggctg ttgtagttgt actccagctt gtgccccagg atgttgccgt cctccttgaa   1860
gtcgatgccc ttcagctcga tgcggttcac cagggtgtcg ccctcgaact tcacctcggc   1920
gcgggtcttg tagttgccgt cgtccttgaa gaagatggtg cgctcctgga cgtagccttc   1980
gggcatggcg gacttgaaga agtcgtgctg cttcatgtgg tcggggtagc ggctgaagca   2040
ctgcacgccg taggtcaggg tggtcacgag ggtgggccag ggcacgggca gcttgccggt   2100
ggtgcagatg aacttcaggg tcagcttgcc gtaggtggca tcgccctcgc cctcgccgga   2160
cacgctgaac ttgtggccgt ttacgtcgcc gtccagctcg accaggatgg gcaccacccc   2220
ggtgaacagc tcctcgccct tgctcatccc gggtgactgg aagtacaggt tttcttgcga   2280
gtacaccaat tcattcatga gttgagtcgc ttccttaact ggctgaaaag gctcttcagg   2340
tttcaccatg aaaactttat ggcccccccca caatactgag tcagcattta atcgccaacc   2400
actaacccac tgctgcgcct cctgatttgt caacaattcc atgaagtttt tcggcacgct   2460
tgtgaaataa ttgtttgtgt tggtgaaatt cgatgctgag tgtataccaa caatgaaccc   2520
atctctagtt gatactaatg gactgccaca ctgcccatcc ttggtttgaa tccaatgctt   2580
ccagaatatg ccatcagatg aagggaatgt gcaagaagtg tctgacacca tgctagacat   2640
gctcttagtt tggaagttgg ttgtcacaag acatattctc tcttcccttt gtggctctct   2700
aaatttcagc ttttgaggaa atggtgggaa atccttaggc atgcgaataa ttatcatgtc   2760
cctcccatca atgaggtgtt gttgcaaagt cgtggtgttc ttgaccttga atacaccatg   2820
tagtgattgg accaacagtg ttccattatt tcttctaaac aagtgcttgt ttgtaatgat   2880
gaagggacca aatccaatac catacaacga tgttgtgtgc ccatcagatt cattcgtcaa   2940
atgacaaatg gtgctcgata tagggttgta atcacgcggc cccttaaaca agctctctcc   3000
ggcgtagtca ggcacgtcgt aaggataagc catatttaaa tatatgcttg cttgtgtgtt   3060
ccttattgaa gccttggtgt gactgattta ctagtagcgt tgaggcgtct tatatacccg   3120
accgttatct ggcctacgtg acacaaggca cgttgttaga ttaataatct tatctttta   3180 tcttaattga taagattatt tttatctggc tgttataaaa acgggatcat gaacacggac   3240
gctcagtcga cagatctgtc gacggtttaa acactagttc gcgacctact ccggaatatt   3300
aataggttgc tgatatcggg agttcagtcg tcgaatgcaa agcgtaaaaa atattaataa   3360
ggtaaaaatt acagctacat aaattacaca atttaaacgg atcgatgagc tccatatggc   3420
ctggagccat ccgcaatttg aaaaaggtgg cgggtccggc ggaggtagcg gcggaggttc   3480
ttggtctcac cctcagttcg agaaggatga cgatgataaa accatgggat ccacagcaat   3540
caagcatgca ttacaaagag acatttttac accaaatgat gaacgcctgc tgagcattgt   3600
gaatgtctgc aaagcaggaa aaaagaaaaa gaactgtttt ttatgtgcca cagtgacaac   3660
tgaacgccct gtgcaggtta aggtggtcaa agtcaagaaa tccgataagg agatttctta   3720
caaaaggcag attgcatggg cccttcgaga tcttgctgtg gtagatgcca aagatgctat   3780
caaagaaaat cctgaatttg atttacactt tgaaaaaata tataaatggg ttgccagcag   3840
cactgctgaa aagaatgcat ttatttcatg catttggaaa ttgaatcagc gatatctccg   3900
gaagaaaatt gattttgtca atgttagctc acagcttttg gaagaactgc ctaaagttac   3960
agaagaatct gttccaagtg gagaaaaatca gagtgtgaca ggaggtgatg aagaagtagt   4020
agatgaatac caagagttaa atgcaagaga agaaacaggat atcgaaataa tgatggaagg   4080
ctgtgaatat gcaatctcga atgcggaagc ctttgcagaa aaattgtcca gagagctgca   4140
```

```
ggtgctagat ggggctaaca tccagtcaat catggcatct gaaaaacaag tcaacatcct   4200
gatgaaattg ctagatgagg ctctaaagga ggtagatcag attgaattga aactgagcag   4260
ttatgaggaa atgctccaaa gtgtaaaaga acaaatggat cagatctctg aaagcaacca   4320
cctaattcat cttagtaaca ctaataatgt aaaactccta tctgagatag agttccttgt   4380
gaaccacatg gacttggcca aaggtcatat aaaggccctt caggaaggag atcttgcttc   4440
ttccagaggc attgaggcct gcaccaatgc tgctgatgcc cttctgcagt gcatgaatgt   4500
agctcttcga ccaggccatg acttgcttct ggcagtcaaa cagcaacagc agcgattcag   4560
tgatttgcga gagctttttg cccggagact ggccagtcac ctcaacaatg tttttgttca   4620
acagggtcat gatcagagtt cgactcttgc ccaacactct gttgaactga ctttacccaa   4680
tcatcatcca tttcatagag atttgctccg atatgccaag ctgatggagt ggctaaagag   4740
tacagattat ggaaaatatg aaggactaac aaagaattac atggattatt tatcccgact   4800
atatgaaaga gaaatcaaag atttctttga agttgcaaag atcaagatga ctggcacaac   4860
taaagaaagc aagaagtttg ctacactgcc tcgaaaagaa agtgctgtca aacaggaaac   4920
agagagtctt catggaagtt cggggaaatt aactggatct acttctagtc taaataagct   4980
cagtgttcag agttcaggga atcgcagatc tcagtcatct tccctgttgg atatgggaaa   5040
catgtctgcc tctgatctcg atgttgctga caggaccaaa tttgataaga tctttgaaca   5100
ggtactaagt gaactggagc ccctatgtct ggcagaacag gacttcataa gtaaattttt   5160
caaactacag caacatcaaa gtatgcctgg aactatggct gaagcagagg acctggatgg   5220
aggaacatta tcacggcaac ataattgtgg cacaccactg cctgtttcat ctgagaaaga   5280
tatgatccgc caaatgatga ttaaaatatt tcgctgcatt gagccagagc tgaacaacct   5340
aattgcatta ggagacaaaa ttgatagctt taactctctt tatatgttag tcaaaatgag   5400
tcatcatgtg tggactgcac aaaatgtgga ccctgcttct ttcctaagta ctacattggg   5460
aaatgttttg gtgactgtca aaaggaactt tgacaaatgc attagtaacc aaataaggca   5520
aatggaagaa gtaaagatct caaaaaagag taaagttgga attcttccat ttgttgctga   5580
atttgaagaa tttgctggac ttgcagaatc aatcttcaaa aatgctgagc gtcgtggaga   5640
cctggataaa gcatacacca aacttatcag aggagtattt gttaatgtgg agaaagtagc   5700
aaatgaaagc cagaagaccc ccagggatgt ggttatgatg gaaaactttc accatatttt   5760
tgcaactctt tctcgattga aaatctcatg tctagaagca gaaaaaaaag aagccaaaca   5820
aaaatacaca gatcaccttc agtcttatgt catttactct ttaggacaac ctcttgaaaa   5880
actaaatcat ttctttgaag gtgttgaagc tcgcgtggca cagggcataa gggaggagga   5940
agtaagttac caacttgcat ttaacaaaca agaacttcgt aaagtcatta aggagtaccc   6000
tggaaaggaa gtaaaaaaag gtctagataa cctctacaag aaagttgata acatttatg    6060 tgaagagag aacttacttc aggtggtgtg gcactccatg caagatgaat ttatacgcca   6120
gtataagcac tttgaaggtt tgatagctcg ctgttatcct ggatctggtg ttacaatgga   6180
attcactatt caggacattc tggattattg ttccagcatt gcacagtccc acggctcgag   6240
ttaactgact aaaagcttcg aaaggaagct gagttggctg ctgccaccgc tgagcaataa   6300
ctagcataac cccttggggc ctctaaacgg gtcttgaggg gttttttgct gaaaggagga   6360
actatcctca gggtcgagaa gtactagagg atcataatca gccataccac atttgtagag   6420
gttttacttg ctttaaaaaa cctcccacac ctccccctga acctgaaaca taaaatgaat   6480
```

-continued

```
gcaattgttg ttgttaactt gtttattgca gcttataatg gttacaaata aagcaatagc   6540
atcacaaatt tcacaaataa agcatttttt tcactgcatt ctagttgtgg tttgtccaaa   6600
ctcatcaatg tatcttatca tgtctggatc tgatcactgc ttgagcctag gagatccgaa   6660
ccagataagt gaaatctagt tccaaactat tttgtcattt ttaattttcg tattagctta   6720
cgacgctaca cccagttccc atctattttg tcactcttcc ctaaataatc cttaaaaact   6780
ccatttccac ccctcccagt tcccaactat tttgtccgcc cacagcgggg cattttttctt  6840 cctgttatgt ttttaatcaa acatcctgcc aactccatgt gacaaaccgt catcttcggc   6900
tactttttct ctgtcacaga atgaaaattt ttctgtcatc tcttcgttat taatgtttgt   6960
aattgactga atatcaacgc ttatttgcag cctgaatggc gaatgggacg cgccctgtag   7020
cggcgcatta agcgcggcgg gtgtggtggt tacgcgcagc gtgaccgcta cacttgccag   7080
cgccctagcg cccgctcctt tcgctttctt cccttccttt ctcgccacgt tcgccggctt   7140
tccccgtcaa gctctaaatc gggggctccc tttagggttc cgatttagtg ctttacggca   7200
cctcgacccc aaaaaacttg attagggtga tggttcacgt agtgggccat cgccctgata   7260
gacggttttt cgccctttga cgttggagtc cacgttcttt aatagtggac tcttgttcca   7320
aactggaaca acactcaacc ctatctcggt ctattctttt gatttataag ggatttttgcc  7380 gatttcggcc tattggttaa aaaatgagct gatttaacaa aaatttaacg cgaattttaa   7440
caaaatatta acgtttacaa tttcaggtgg cacttttcgg ggaaatgtgc gcggaacccc   7500 tatttgtttta tttttctaaa tacattcaaa tatgtatccg ctcatgagac aataaccctg   7560
ataaatgctt caataatatt gaaaaaggaa gagtatgagt attcaacatt tccgtgtcgc   7620
ccttattccc ttttttgcgg cattttgcct tcctgttttt gctcacccag aaacgctggt   7680
gaaagtaaaa gatgctgaag atcagttggg tgcacgagtg ggttacatcg aactggatct   7740
caacagcggt aagatccttg agagttttcg ccccgaagaa cgttttccaa tgatgagcac   7800
ttttaaagtt ctgctatgtg gcgcggtatt atcccgtatt gacgccgggc aagagcaact   7860
cggtcgccgc atacactatt ctcagaatga cttggttgag tactcaccag tcacagaaaa   7920
gcatcttacg gatggcatga cagtaagaga attatgcagt gctgccataa ccatgagtga   7980
taacactgcg gccaacttac ttctgacaac gatcggagga ccgaaggagc taaccgcttt   8040
tttgcacaac atgggggatc atgtaactcg ccttgatcgt tgggaaccgg agctgaatga   8100
agccatacca aacgacgagc gtgacaccac gatgcctgta gcaatggcaa caacgttgcg   8160
caaactatta actggcgaac tacttactct agcttcccgg caacaattaa tagactggat   8220
ggaggcggat aaagttgcag gaccacttct gcgctcggcc cttccggctg gctggtttat   8280
tgctgataaa tctggagccg gtgagcgtgg gtctcgcggt atcattgcag cactggggcc   8340
agatggtaag ccctcccgta tcgtagttat ctacacgacg gggagtcagg caactatgga   8400
tgaacgaaat agacagatcg ctgagatagg tgcctcactg attaagcatt ggtaactgtc   8460
agaccaagtt tactcatata tactttagat tgatttaaaa cttcattttt aatttaaaag   8520
gatctaggtg aagatccttt ttgataatct catgaccaaa atcccttaac gtgagttttc   8580
gttccactga gcgtcagacc gcggggcatg actaacatga gaattacaac ttatatcgta   8640
tggggctgac ttcaggtgct acatttgaag agataaattg cactgaaatc tagaaatatt   8700
ttatctgatt aataagatga tcttcttgag atcgtttttgg tctgcgcgta atctcttgct   8760
ctgaaaacgg aaaaaaccgc cttgcagggc ggtttttcga aggttctctg agctaccaac   8820
tctttgaacc gaggtaactg gcttggagga gcgcagtcac caaaacttgt cctttcagtt   8880
```

-continued

```
tagccttaac cggcgcatga cttcaagact aactcctcta aatcaattac cagtggctgc      8940
tgccagtggt gctttttgcat gtctttccgg gttggactca agacgatagt taccggataa     9000
ggcgcagcgg tcggactgaa cgggggggttc gtgcatacag tccagcttgg agcgaactgc     9060
ctacccggaa ctgagtgtca ggcgtggaat gagacaaacg cggccataac agcggaatga     9120
caccggtaaa ccgaaaggca ggaacaggag agcgcacgag ggagccgcca ggggaaacgc     9180
ctggtatctt tatagtcctg tcgggtttcg ccaccactga tttgagcgtc agatttcgtg     9240
atgcttgtca gggggggcgga gcctatggaa aaacggcttt gccgcggccc tctcacttcc     9300
ctgttaagta tcttcctggc atcttccagg aaatctccgc cccgttcgta agccatttcc     9360
gctcgccgca gtcgaacgac cgagcgtagc gagtcagtga gcgaggaagc ggaatatatc     9420
ctgtatcaca tattctgctg acgcaccggt gcagcctttt ttctcctgcc acatgaagca     9480
cttcactgac accctcatca gtgccaacat agtaagccag tatacactcc gctagcgctg     9540
atgtccggcg gtgcttttgc cgttacgcac cacccccgtca gtagctgaac aggagggaca    9600
gctgatagaa acagaagcca gttctttcct gcgttatccc ctgattctgt ggataaccgt     9660
attaccgcct ttgagtgagc tgataccgct cgccgcagcc gaacgaccga gcgcagcgag     9720
tcagtgagcg aggaagcgga agagcgcctg atgcggtatt ttctccttac gcatctgtgc     9780
ggtatttcac accgcataga ccagccgcgt aacctggcaa aatcggttac ggttgagtaa     9840
taaatg                                                                9846

<210> SEQ ID NO 8
<211> LENGTH: 9933
<212> TYPE: DNA
<213> ORGANISM: Artificial Sequence
<220> FEATURE:
<223> OTHER INFORMATION: Synthesized

<400> SEQUENCE: 8
gatgccctgc gtaagcgggt gtgggcggac aataaagtct taaactgaac aaaatagatc        60
taaactatga caataaagtc ttaaactaga cagaatagtt gtaaactgaa atcagtccag       120
ttatgctgtg aaaaagcata ctggactttt gttatggcta aagcaaactc ttcattttct       180
gaagtgcaaa ttgcccgtcg tattaaagag gggcgtggcc aagggcatgt aaagactata       240
ttcgcggcgt tgtgacaatt taccgaacaa ctccgcggcc gggaagccga tctcggcttg       300
aacgaattgt taggtggcgg tacttgggtc gatatcaaag tgcatcactt cttcccgtat       360
gcccaacttt gtatagagag ccactgcggg atcgtcaccg taatctgctt gcacgtagat       420
cacataagca ccaagcgcgt tggcctcatg cttgaggaga ttgatgagcg cggtggcaat       480
gccctgcctc cggtgctcgc cggagactgc gagatcatag atatagatct cactacgcgg       540
ctgctcaaac ttgggcagaa cgtaagccgc gagagcgcca acaaccgctt cttggtcgaa       600
ggcagcaagc gcgatgaatg tcttactacg gagcaagttc ccgaggtaat cggagtccgg       660
ctgatgttgg gagtaggtgg ctacgtctcc gaactcacga ccgaaaagat caagagcagc       720
ccgcatggat ttgacttggt cagggccgag cctacatgtg cgaatgatgc ccatacttga       780
gccacctaac tttgttttag gcgactgccc tgctgcgta acatcgttgc tgctgcgtaa       840
catcgttgct gctccataac atcaaacatc gacccacggc gtaacgcgct tgctgcttgg       900
atgcccgagg catagactgt acaaaaaaac agtcataaca agccatgaaa accgccactg       960
cgccgttacc accgctgcgt tcggtcaagg ttctggacca gttgcgtgag cgcatacgct      1020
```

-continued

```
acttgcatta cagtttacga accgaacagg cttatgtcaa ctgggttcgt gccttcatcc   1080
gtttccacgg tgtgcgtcac ccggcaacct tgggcagcag cgaagtcgcc ataacttcgt   1140
atagcataca ttatacgaag ttatctgtaa ctataacggt cctaaggtag cgagtttaaa   1200
cgacgtccta gattggttac tgggcgatga aggtttagtc ggcaaatcgt ccaacgttag   1260
tgacagcgtc agcggcaagt taatgcctat cattttgttg ataggcgcgg tcttgttttt   1320
aggtttaata ttttatttta tctacagata catgatgaaa ggagggaagg gaggtggtgt   1380
tggcgcagca acgtcgccaa ctcccattgt tatttctatg caaaacccca caccaacaac   1440
ggcccctcga taataaaaga caaaaataat ataaaatata tgtataatta attaaattca   1500
aaatatatgt ataaggccgg ccttagtcag ttacttgtac agctcgtcca tgccgagagt   1560
gatcccggcg gcggtcacga actccagcag gaccatgtga tcgcgcttct cgttggggtc   1620
tttgctcagg gcggactggg tgctcaggta gtggttgtcg ggcagcagca cggggccgtc   1680
gccgatgggg gtgttctgct ggtagtggtc ggcgagctgc acgctgccgt cctcgatgtt   1740
gtggcggatc ttgaagttca ccttgatgcc gttcttctgc ttgtcggcca tgatatagac   1800
gttgtggctg ttgtagttgt actccagctt gtgccccagg atgttgccgt cctccttgaa   1860
gtcgatgccc ttcagctcga tgcggttcac cagggtgtcg ccctcgaact tcacctcggc   1920
gcgggtcttg tagttgccgt cgtccttgaa gaagatggtg cgctcctgga cgtagccttc   1980
gggcatggcg gacttgaaga agtcgtgctg cttcatgtgg tcggggtagc ggctgaagca   2040
ctgcacgccg taggtcaggg tggtcacgag ggtgggccag ggcacgggca gcttgccggt   2100
ggtgcagatg aacttcaggg tcagcttgcc gtaggtggca tcgccctcgc cctcgccgga   2160
cacgctgaac ttgtggccgt ttacgtcgcc gtccagctcg accaggatgg gcaccacccc   2220
ggtgaacagc tcctcgccct tgctcatccc gggtgactgg aagtacaggt tttcttgcga   2280
gtacaccaat tcattcatga gttgagtcgc ttccttaact ggctgaaaag gctcttcagg   2340
tttcaccatg aaaactttat ggcccccccca caatactgag tcagcattta atcgccaacc   2400
actaacccac tgctgcgcct cctgatttgt caacaattcc atgaagtttt tcggcacgct   2460
tgtgaaataa ttgtttgtgt tggtgaaatt cgatgctgag tgtataccaa caatgaaccc   2520
atctctagtt gatactaatg gactgccaca ctgcccatcc ttggtttgaa tccaatgctt   2580
ccagaatatg ccatcagatg aagggaatgt gcaagaagtg tctgacacca tgctagacat   2640
gctcttagtt tggaagttgg ttgtcacaag acatattctc tcttcccttt gtggctctct   2700
aaatttcagc ttttgaggaa atggtgggaa atccttaggc atgcgaataa ttatcatgtc   2760
cctcccatca atgaggtgtt gttgcaaagt cgtggtgttc ttgaccttga atacaccatg   2820
tagtgattgg accaacagtg ttccattatt tcttctaaac aagtgcttgt ttgtaatgat   2880
gaagggacca aatccaatac catacaacga tgttgtgtgc ccatcagatt cattcgtcaa   2940
atgacaaatg gtgctcgata tagggttgta atcacgcggc cccttaaaca agctctctcc   3000
ggcgtagtca ggcacgtcgt aaggataagc catatttaaa tatatgcttg cttgtgtgtt   3060
ccttattgaa gccttggtgt gactgattta ctagtagcgt tgaggcgtct tatatacccg   3120
accgttatct ggcctacgtg acacaaggca cgttgttaga ttaataatct tatctttta   3180 tcttaattga taagattatt tttatctggc tgttataaaa acgggatcat gaacacggac   3240
gctcagtcga cagatctgtc gacggtttaa acactagttc gcgacctact ccggaatatt   3300
aataggttgc tgatatcggg agttcagtcg tcgaatgcaa agcgtaaaaa atattaataa   3360
ggtaaaaatt acagctacat aaattacaca atttaaacgg atcgatgagc tccatatggc   3420
```

-continued

```
ctggagccat ccgcaatttg aaaaaggtgg cgggtccggc ggaggtagcg gcggaggttc      3480
ttggtctcac cctcagttcg agaaggatga cgatgataaa accatgggat ccctaggtac      3540
cgcggccgct agccgatcac gacaacccc ccttgtgacc ggcatctctc caaatgaagg       3600
gataccatgg acgaaggtca caatcagggg agaaaatctg gggactggcc ccaccgacct      3660
cataggcttg accatttgtg gacataattg cctcctgacg gcagaatgga tgtctgcaag      3720
taaaatagta tgtcgagtgg gacaagccaa aaatgacaaa ggagacatta ttgtcaccac      3780
taagtcaggt ggcagaggaa cctcaacagt ctctttcaag ctactcaaac ctgagaaaat      3840
aggcattttg gatcagtctg ctgtgtgggt tgatgaaatg aattattatg atatgcgcac      3900
tgacaggaac aaaggaattc cgcccttgtc cttacgtcct gctaacccgc ttggcattga      3960
gattgaaaaa agtaaatttt cgcagaagga cttagaaatg ctattccatg gaatgagtgc      4020
tgattttaca agtgagaatt tctcagcagc ctggtatctt atagagaatc actcaaacac      4080
cagttttgag cagctcaaaa tggcagtcac caacctaaag agacaggcta acaagaagag      4140
tgagggcagc ctggcctatg tgaaaggcgg tctcagtaca ttcttcgaag cacaggatgc      4200
cctctcagcc atccatcaaa aactagaagc agatggaacg gaaaaagtag aaggatccat      4260
gacgcagaaa ctggagaatg ttctgaacag agcaagtaat actgcagaca cattgtttca      4320
agaagtatta ggtcggaaag acaaggcaga ttccactaga aatgcactca atgtgcttca      4380
gcgatttaag tttctttca accttcctct aaatattgaa aggaatattc aaaagggtga      4440
ttatgatgtg gttattaatg attatgaaaa ggccaagtca ctttttggga aaacggaggt      4500
gcaagttttc aagaaatatt atgctgaagt agaaacaagg attgaagctt taagagaatt      4560
acttctggat aaaattgctt agacaccatc aactttacat gaccaaaaac gttacataag      4620
gtacctgtct gaccttcatg cgtctggtga ccctgcttgg caatgcattg gagcccaaca      4680
caagtggatc cttcagctca tgcacagttg caaagagggc tacgtgaaag atctgaaagg      4740
taacccaggc ctgcacagtc ccatgttgga tcttgataat gatacacgtc cctcagtgtt      4800
gggccatctc agtcagacag cgtccctgaa gaggggcagc agcttcagt ctggtcgaga       4860 cgacacgtgg agatacaaaa ctccccacag ggtggccttt gttgaaaaat tgacaaaact      4920
cgtcttgagc cagctgccta acttctggaa actctggatc tcctacgtta atggaagcct      4980
cttcagtgag actgctgaga gtcaggcca gattgaaaga tcaaagaatg taaggcaaag       5040
acaaaatgat tttaagaaaa tgattcagga agtaatgcac tccctggtga agcttacccg      5100
cggagccctg cttcccctca gcatccggga tggggaagcc aagcagtacg gaggctggga      5160
ggtgaagtgc gagctctccg gacagtggct cgctcacgcc atccagactg taagacttac      5220
tcacgaatcg ttgactgccc ttgaaattcc taatgacctg ttacagacta ccaggatct       5280 catcttggat ctccgagtac gttgcgtaat ggccacgttg cagcacacgg cggaagaaat      5340
aaagagatta gctgaaaaag aagactggat tgttgacaat gaaggactga cttctctacc      5400
atgtcagttt gaacagtgca tcgtgtgttc tctgcagtca ctgaaggggg ttctggagtg      5460
caagccggga gaggccagtg tcttccaaca acctaaaaca caggaggagg tttgccagct      5520
aagcatcaat ataatgcagg ttttttatata ctgtctggaa cagttgagca ccaagcctga      5580
tgcagatata gatactacac atctctctgt tgatgtttct tcccctgact tgtttggaag      5640
tatccatgaa gacttcagct tgacctcaga acagcgcctt ttgatagtcc taagtaattg      5700
ctgctatcta gaacgtcaca ccttcctaaa tatcgcagaa cattttgaaa agcacaactt      5760
```

-continued

```
ccagggaata gaaaaaatca cacaggttag catggcctca ttgaaagaac tagatcaaag    5820
actctttgaa aattacatcg agttgaaagc agatcccatc gttggctcct tagaacctgg    5880
aatttatgca ggatattttg attggaagga ctgcctgcct ccaacaggtg tcagaaacta    5940
tttaaaagaa gcactggtga atataattgc cgtgcatgca gaggtgttca ccatttccaa    6000
agaactggtc cctcgggtac tatccaaggt gatagaagca gtttctgaag agctcagtcg    6060
actgatgcag tgtgtttcat ccttcagcaa aaatggagct ttacaggcga gacttgaaat    6120
ctgtgctttg agggacactg tggctgttta cctgacaccc gaaagcaagt caagttttaa    6180
gcaggctttg gaagccctgc cccagctttc cagtggagca gataaaaagt tactggaaga    6240
gctcctgaac aagttcaaga gtagcatgca cttgcagctc acctgtttcc aagcagcttc    6300
ttcaaccatg atgaaaacag gctcgagtta actgactaaa agcttcgaaa ggaagctgag    6360
ttggctgctg ccaccgctga gcaataacta gcataacccc ttggggcctc taaacgggtc    6420
ttgaggggtt ttttgctgaa aggaggaact atcctcaggg tcgagaagta ctagaggatc    6480
ataatcagcc ataccacatt tgtagaggtt ttacttgctt taaaaaacct cccacacctc    6540
cccctgaacc tgaaacataa aatgaatgca attgttgttg ttaacttgtt tattgcagct    6600
tataatggtt acaaataaag caatagcatc acaaatttca caaataaagc atttttttca    6660
ctgcattcta gttgtggttt gtccaaactc atcaatgtat cttatcatgt ctggatctga    6720
tcactgcttg agcctaggag atccgaacca gataagtgaa atctagttcc aaactatttt    6780 gtcatttta attttcgtat tagcttacga cgctacaccc agttcccatc tattttgtca    6840
ctcttcccta aataatcctt aaaaactcca tttccacccc tcccagttcc caactatttt    6900
gtccgcccac agcggggcat ttttcttcct gttatgtttt taatcaaaca tcctgccaac    6960
tccatgtgac aaaccgtcat cttcggctac tttttctctg tcacagaatg aaaatttttc    7020
tgtcatctct tcgttattaa tgtttgtaat tgactgaata tcaacgctta tttgcagcct    7080
gaatggcgaa tgggacgcgc cctgtagcgg cgcattaagc gcggcgggtg tggtggttac    7140
gcgcagcgtg accgctacac ttgccagcgc cctagcgccc gctcctttcg ctttcttccc    7200
ttcctttctc gccacgttcg ccggctttcc ccgtcaagct ctaaatcggg ggctcccttt    7260
agggttccga tttagtgctt tacggcacct cgaccccaaa aaacttgatt agggtgatgg    7320
ttcacgtagt gggccatcgc cctgatagac ggttttttcgc cctttgacgt tggagtccac    7380
gttctttaat agtggactct tgttccaaac tggaacaaca ctcaacccta tctcggtcta    7440
ttcttttgat ttataaggga ttttgccgat ttcggcctat tggttaaaaa atgagctgat    7500
ttaacaaaaa tttaacgcga attttaacaa aatattaacg tttacaattt caggtggcac    7560
ttttcgggga aatgtgcgcg gaacccctat ttgtttattt ttctaaatac attcaaatat    7620
gtatccgctc atgagacaat aaccctgata aatgcttcaa taatattgaa aaaggaagag    7680
tatgagtatt caacatttcc gtgtcgccct tattcccttt tttgcggcat tttgccttcc    7740 tgttttttgct cacccagaaa cgctggtgaa agtaaaagat gctgaagatc agttgggtgc    7800
acgagtgggt tacatcgaac tggatctcaa cagcggtaag atccttgaga gttttcgccc    7860
cgaagaacgt tttccaatga tgagcacttt taaagttctg ctatgtggcg cggtattatc    7920
ccgtattgac gccgggcaag agcaactcgg tcgccgcata cactattctc agaatgactt    7980
ggttgagtac tcaccagtca cagaaaagca tcttacggat ggcatgacag taagagaatt    8040
atgcagtgct gccataacca tgagtgataa cactgcggcc aacttacttc tgacaacgat    8100
cggaggaccg aaggagctaa ccgcttttttt gcacaacatg ggggatcatg taactcgcct    8160
```

-continued

```
tgatcgttgg gaaccggagc tgaatgaagc cataccaaac gacgagcgtg acaccacgat    8220
gcctgtagca atggcaacaa cgttgcgcaa actattaact ggcgaactac ttactctagc    8280
ttcccggcaa caattaatag actggatgga ggcggataaa gttgcaggac cacttctgcg    8340
ctcggccctt ccggctggct ggtttattgc tgataaatct ggagccggtg agcgtgggtc    8400
tcgcggtatc attgcagcac tggggccaga tggtaagccc tcccgtatcg tagttatcta    8460
cacgacgggg agtcaggcaa ctatggatga acgaaataga cagatcgctg agataggtgc    8520
ctcactgatt aagcattggt aactgtcaga ccaagtttac tcatatatac tttagattga    8580
tttaaaactt catttttaat ttaaaaggat ctaggtgaag atcctttttg ataatctcat    8640
gaccaaaatc ccttaacgtg agttttcgtt ccactgagcg tcagaccgcg gggcatgact    8700
aacatgagaa ttacaactta tatcgtatgg ggctgacttc aggtgctaca tttgaagaga    8760
taaattgcac tgaaatctag aaatatttta tctgattaat aagatgatct tcttgagatc    8820
gttttggtct gcgcgtaatc tcttgctctg aaaacggaaa aaaccgcctt gcagggcggt    8880
ttttcgaagg ttctctgagc taccaactct ttgaaccgag gtaactggct tggaggagcg    8940
cagtcaccaa aacttgtcct ttcagtttag ccttaaccgg cgcatgactt caagactaac    9000
tcctctaaat caattaccag tggctgctgc cagtggtgct tttgcatgtc tttccgggtt    9060
ggactcaaga cgatagttac cggataaggc gcagcggtcg gactgaacgg ggggttcgtg    9120
catacagtcc agcttggagc gaactgccta cccggaactg agtgtcaggc gtggaatgag    9180
acaaacgcgg ccataacagc ggaatgacac cggtaaaccg aaaggcagga acaggagagc    9240
gcacgaggga gccgccaggg gaaacgcctg gtatctttat agtcctgtcg ggtttcgcca    9300
ccactgattt gagcgtcaga tttcgtgatg cttgtcaggg gggcggagcc tatggaaaaa    9360
cggctttgcc gcggccctct cacttccctg ttaagtatct tcctggcatc ttccaggaaa    9420
tctccgcccc gttcgtaagc catttccgct cgccgcagtc gaacgaccga gcgtagcgag    9480
tcagtgagcg aggaagcgga atatatcctg tatcacatat tctgctgacg caccggtgca    9540 gcctttttc tcctgccaca tgaagcactt cactgacacc ctcatcagtg ccaacatagt    9600
aagccagtat acactccgct agcgctgatg tccggcggtg cttttgccgt tacgcaccac    9660
cccgtcagta gctgaacagg agggacagct gatagaaaca gaagccagtt ctttcctgcg    9720
ttatcccctg attctgtgga taaccgtatt accgcctttg agtgagctga taccgctcgc    9780
cgcagccgaa cgaccgagcg cagcgagtca gtgagcgagg aagcggaaga gcgcctgatg    9840
cggtattttc tccttacgca tctgtgcggt atttcacacc gcatagacca gccgcgtaac    9900
ctggcaaaat cggttacggt tgagtaataa atg                                 9933
```

```
<210> SEQ ID NO 9
<211> LENGTH: 9400
<212> TYPE: DNA
<213> ORGANISM: Artificial Sequence
<220> FEATURE:
<223> OTHER INFORMATION: Synthesized

<400> SEQUENCE: 9
gatgccctgc gtaagcgggt gtgggcggac aataaagtct taaactgaac aaaatagatc      60
taaactatga caataaagtc ttaaactaga cagaatagtt gtaaactgaa atcagtccag     120
ttatgctgtg aaaaagcata ctggactttt gttatggcta agcaaactc ttcattttct     180 gaagtgcaaa ttgcccgtcg tattaaagag gggcgtggcc aagggcatgt aaagactata    240
```

```
ttcgcggcgt tgtgacaatt taccgaacaa ctccgcggcc gggaagccga tctcggcttg      300
aacgaattgt taggtggcgg tacttgggtc gatatcaaag tgcatcactt cttcccgtat      360
gcccaacttt gtatagagag ccactgcggg atcgtcaccg taatctgctt gcacgtagat      420
cacataagca ccaagcgcgt tggcctcatg cttgaggaga ttgatgagcg cggtggcaat      480
gccctgcctc cggtgctcgc cggagactgc gagatcatag atatagatct cactacgcgg      540
ctgctcaaac ttgggcagaa cgtaagccgc gagagcgcca acaaccgctt cttggtcgaa      600
ggcagcaagc gcgatgaatg tcttactacg gagcaagttc ccgaggtaat cggagtccgg      660
ctgatgttgg gagtaggtgg ctacgtctcc gaactcacga ccgaaaagat caagagcagc      720
ccgcatggat ttgacttggt cagggccgag cctacatgtg cgaatgatgc ccatacttga      780
gccacctaac tttgttttag ggcgactgcc ctgctgcgta acatcgttgc tgctgcgtaa      840
catcgttgct gctccataac atcaaacatc gacccacggc gtaacgcgct tgctgcttgg      900
atgcccgagg catagactgt acaaaaaaac agtcataaca agccatgaaa accgccactg      960
cgccgttacc accgctgcgt tcggtcaagg ttctggacca gttgcgtgag cgcatacgct     1020
acttgcatta cagtttacga accgaacagg cttatgtcaa ctgggttcgt gccttcatcc     1080
gtttccacgg tgtgcgtcac ccggcaacct tgggcagcag cgaagtcgcc ataacttcgt     1140
atagcataca ttatacgaag ttatctgtaa ctataacggt cctaaggtag cgagtttaaa     1200
cgacgtccta gattggttac tgggcgatga aggtttagtc ggcaaatcgt ccaacgttag     1260
tgacagcgtc agcggcaagt taatgcctat cattttgttg ataggcgcgg tcttgttttt     1320
aggtttaata ttttatttta tctacagata catgatgaaa ggagggaagg gaggtggtgt     1380
tggcgcagca acgtcgccaa ctcccattgt tatttctatg caaaacccca caccaacaac     1440
ggcccctcga taataaaaga caaaaataat ataaaatata tgtataatta attaaattca     1500
aaatatatgt ataaggccgg ccttagtcag ttacttgtac agctcgtcca tgccgagagt     1560
gatcccggcg gcggtcacga actccagcag gaccatgtga tcgcgcttct cgttggggtc     1620
tttgctcagg gcggactggg tgctcaggta gtggttgtcg ggcagcagca cggggccgtc     1680
gccgatgggg gtgttctgct ggtagtggtc ggcgagctgc acgctgccgt cctcgatgtt     1740
gtggcggatc ttgaagttca ccttgatgcc gttcttctgc ttgtcggcca tgatatagac     1800
gttgtggctg ttgtagttgt actccagctt gtgccccagg atgttgccgt cctccttgaa     1860
gtcgatgccc ttcagctcga tgcggttcac cagggtgtcg ccctcgaact tcacctcggc     1920
gcgggtcttg tagttgccgt cgtccttgaa gaagatggtg cgctcctgga cgtagccttc     1980
gggcatggcg gacttgaaga agtcgtgctg cttcatgtgg tcggggtagc ggctgaagca     2040
ctgcacgccg taggtcaggg tggtcacgag ggtgggccag ggcacgggca gcttgccggt     2100
ggtgcagatg aacttcaggg tcagcttgcc gtaggtggca tcgccctcgc cctcgccgga     2160
cacgctgaac ttgtggccgt ttacgtcgcc gtccagctcg accaggatgg gcaccacccc     2220
ggtgaacagc tcctcgccct tgctcatccc gggtgactgg aagtacaggt tttcttgcga     2280
gtacaccaat tcattcatga gttgagtcgc ttccttaact ggctgaaaag gctcttcagg     2340
tttcaccatg aaaactttat ggcccccca caatactgag tcagcattta atcgccaacc     2400
actaacccac tgctgcgcct cctgatttgt caacaattcc atgaagtttt tcggcacgct     2460
tgtgaaataa ttgtttgtgt tggtgaaatt cgatgctgag tgtataccaa caatgaaccc     2520
atctctagtt gatactaatg gactgccaca ctgcccatcc ttggtttgaa tccaatgctt     2580
ccagaatatg ccatcagatg aagggaatgt gcaagaagtg tctgacacca tgctagacat     2640
```

```
gctcttagtt tggaagttgg ttgtcacaag acatattctc tcttcccttt gtggctctct      2700
aaatttcagc tttttgaggaa atggtgggaa atccttaggc atgcgaataa ttatcatgtc      2760
cctcccatca atgaggtgtt gttgcaaagt cgtggtgttc ttgaccttga atacaccatg      2820
tagtgattgg accaacagtg ttccattatt tcttctaaac aagtgcttgt ttgtaatgat      2880
gaagggacca aatccaatac catacaacga tgttgtgtgc ccatcagatt cattcgtcaa      2940
atgacaaatg gtgctcgata tagggttgta atcacgcggc cccttaaaca agctctctcc      3000
ggcgtagtca ggcacgtcgt aaggataagc catatttaaa tatatgcttg cttgtgtgtt      3060
ccttattgaa gccttggtgt gactgattta ctagtagcgt tgaggcgtct tatatacccg      3120
accgttatct ggcctacgtg acacaaggca cgttgttaga ttaataatct tatcttttta      3180
tcttaattga taagattatt tttatctggc tgttataaaa acgggatcat gaacacggac      3240
gctcagtcga cagatctgtc gacggtttaa acactagttc gcgacctact ccggaatatt      3300
aataggttgc tgatatcggg agttcagtcg tcgaatgcaa agcgtaaaaa atattaataa      3360
ggtaaaaatt acagctacat aaattacaca atttaaacgg atcgatgagc tccatatggc      3420
ctggagccat ccgcaatttg aaaaaggtgg cgggtccggc ggaggtagcg gcggaggttc      3480
ttggtctcac cctcagttcg agaaggatga cgatgataaa accatgggat ccctaggtac      3540
cgcggccgcg atgaaggaga cagaccggga ggccgttgcg acagcagtgc aaagggttgc      3600
tgggatgctc cagcgcccgg accagctgga caaggtggag cagtatcgca ggagagaagc      3660
gcggaagaag gcctccgtgg aggccagatt gaaggccgcc atccagtcac agttggacgg      3720
ggtgcgcaca ggcctcagcc agctccacaa cgccctgaat gacgtcaaag acatccagca      3780
gtcgctggca gacgtcagca aggactggag gcagagcatc aacaccattg agagcctcaa      3840
ggacgtcaaa gacgccgtgg tgcagcacag ccagctcgcc gcagccgtgg agaacctcaa      3900
gaacatcttc tcagtgcctg agattgtgag ggagacccag gacctaattg aacaaggggc      3960
actcctgcaa gcccaccgga agctgatgga cctggaatgc tcccgggacg ggctgatgta      4020
cgagcagtac cgcatggaca gtgggaacac gcgtgacatg accctcatcc atggctactt      4080
tggcagcacg caggggctct ctgatgagct ggctaagcag ctgtggatgg tgctgcagag      4140
gtcactggtc actgtccgcc gtgaccccac cttgctggtc tcagttgtca ggatcattga      4200
aagggaagag aaaattgaca ggcgcatact tgaccggaaa aagcaaactg gctttgttcc      4260
tcctgggagg cccaagaatt ggaaggagaa aatgttcacc atcttggaga ggactgtgac      4320
caccagaatt gagggcacac aggcagatac cagagagtct gacaagatgt ggcttgtccg      4380
ccacctggaa attataagga agtacgtcct ggatgacctc attgtcgcca aaaacctgat      4440
ggttcagtgc tttcctcccc actatgagat ctttaagaac ctcctgaaca tgtaccacca      4500
agccctgagc acgcggatgc aggacctcgc atcggaagac ctggaagcca atgagatcgt      4560
gagcctcttg acgtgggtct aaacaccta cacaagtact gagatgatga ggaacgtgga      4620
gctggccccg gaagtggatg tcggcaccct ggagccattg ctttctccac acgtggtctc      4680
tgagctgctt gacacgtaca tgtccacgct cacttcaaac atcatcgcct ggctgcggaa      4740
agcgctggag acagacaaga aagactgggt caaagagaca gagccagaag ccgaccagga      4800
cgggtactac cagaccacac tccctgccat tgtcttccag atgtttgaac agaatcttca      4860
agttgctgct cagataagtg aagatttgaa aacaaaggta ctagttttat gtcttcagca      4920
gatgaattct ttcctaagca gatataaaga tgaagcgcag ctgtataaag aagagcacct      4980
```

-continued

```
gaggaatcgg cagcaccctc actgctacgt tcagtacatg atcgccatca tcaacaactg   5040
ccagaccttc aaggaatcca tagtcagttt aaaaagaaag tatttaaaga atgaagtgga   5100
agagggtgtg tctccgagcc agcccagcat ggacgggatt ttagacgcca tcgcgaagga   5160
gggctgcagc ggtttgctgg aggaggtctt cctggacctg gagcaacatc tgaatgaatt   5220
gatgacgaag aagtggctat tagggtcaaa cgctgtagac attatctgtg tcaccgtgga   5280
agactatttc aacgattttg ccaaaattaa aaagccgtat aagaagagga tgacggccga   5340
ggcgcaccgg cgcgtggtgg tggagtacct gcgggcggtc atgcagaagc gcatttcctt   5400
ccggagcccg gaggagcgca aggagggtgc cgagaagatg gttagggagg cagagcagct   5460
gcgcttcctg ttccggaagc tggcgtccgg tttcgggga gacgtggacg gatactgcga   5520
caccatcgtg gctgtggccg aagtgatcaa gctgacagac ccttctctgc tctacctgga   5580
ggtctccact ctggtcagca agtatccaga catcagggat gaccacatcg gtgcgctgct   5640
ggctgtgcgt ggggacgcca gccgtgacat gaagcagacc atcatggaga ccctggagca   5700
gggcccagca caggccagcc ccagctacgt gcccctcttc aaggacattg tggtgcccag   5760
cctgaacgtg gccaagctgc tcaagtaact cgagttaact gactaaaagc ttcgaaagga   5820
agctgagttg gctgctgcca ccgctgagca ataactagca taaccccttg gggcctctaa   5880
acgggtcttg aggggttttt tgctgaaagg aggaactatc ctcagggtcg agaagtacta   5940
gaggatcata atcagccata ccacatttgt agaggtttta cttgctttaa aaaacctccc   6000
acacctcccc ctgaacctga aacataaaat gaatgcaatt gttgttgtta acttgtttat   6060
tgcagcttat aatggttaca aataaagcaa tagcatcaca aatttcacaa ataaagcatt   6120 ttttttcactg cattctagtt gtggtttgtc caaactcatc aatgtatctt atcatgtctg   6180
gatctgatca ctgcttgagc ctaggagatc cgaaccagat aagtgaaatc tagttccaaa   6240
ctattttgtc attttttaatt ttcgtattag cttacgacgc tacacccagt tcccatctat   6300
tttgtcactc ttccctaaat aatccttaaa aactccattt ccaccctcc cagttcccaa    6360 ctattttgtc cgcccacagc ggggcatttt tcttcctgtt atgtttttaa tcaaacatcc   6420
tgccaactcc atgtgacaaa ccgtcatctt cggctacttt ttctctgtca cagaatgaaa   6480 attttttctgt catctcttcg ttattaatgt ttgtaattga ctgaatatca acgcttattt   6540
gcagcctgaa tggcgaatgg gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta atcgggggc    6720 tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgttt acaatttcag   7020
gtggcacttt tcggggaaat gtgcgcggaa cccctatttg tttatttttc taaatacatt   7080
caaatatgta tccgctcatg agacaataac cctgataaat gcttcaataa tattgaaaaa   7140
ggaagagtat gagtattcaa catttccgtg tcgcccttat tcccttttt gcggcatttt    7200 gccttcctgt ttttgctcac ccagaaacgc tggtgaaagt aaaagatgct gaagatcagt   7260
tgggtgcacg agtgggttac atcgaactgg atctcaacag cggtaagatc cttgagagtt   7320
ttcgccccga agaacgtttt ccaatgatga gcactttaa agttctgcta tgtggcgcgg     7380
```

-continued

```
tattatcccg tattgacgcc gggcaagagc aactcggtcg ccgcatacac tattctcaga    7440
atgacttggt tgagtactca ccagtcacag aaaagcatct tacggatggc atgacagtaa    7500
gagaattatg cagtgctgcc ataaccatga gtgataacac tgcggccaac ttacttctga    7560
caacgatcgg aggaccgaag gagctaaccg cttttttgca caacatgggg gatcatgtaa    7620
ctcgccttga tcgttgggaa ccggagctga atgaagccat accaaacgac gagcgtgaca    7680
ccacgatgcc tgtagcaatg gcaacaacgt tgcgcaaact attaactggc gaactactta    7740
ctctagcttc ccggcaacaa ttaatagact ggatggaggc ggataaagtt gcaggaccac    7800
ttctgcgctc ggcccttccg gctggctggt ttattgctga taaatctgga gccggtgagc    7860
gtgggtctcg cggtatcatt gcagcactgg ggccagatgg taagccctcc cgtatcgtag    7920
ttatctacac gacggggagt caggcaacta tggatgaacg aaatagacag atcgctgaga    7980
taggtgcctc actgattaag cattggtaac tgtcagacca agtttactca tatatacttt    8040
agattgattt aaaacttcat ttttaattta aaaggatcta ggtgaagatc cttttttgata    8100 atctcatgac caaaatccct taacgtgagt tttcgttcca ctgagcgtca gaccgcgggg    8160
catgactaac atgagaatta caacttatat cgtatggggc tgacttcagg tgctacattt    8220
gaagagataa attgcactga aatctagaaa tattttatct gattaataag atgatcttct    8280
tgagatcgtt ttggtctgcg cgtaatctct tgctctgaaa acggaaaaaa ccgccttgca    8340
gggcggtttt tcgaaggttc tctgagctac caactctttg aaccgaggta actggcttgg    8400
aggagcgcag tcaccaaaac ttgtcctttc agtttagcct taaccggcgc atgacttcaa    8460
gactaactcc tctaaatcaa ttaccagtgg ctgctgccag tggtgctttt gcatgtcttt    8520
ccgggttgga ctcaagacga tagttaccgg ataaggcgca gcggtcggac tgaacggggg    8580
gttcgtgcat acagtccagc ttggagcgaa ctgcctaccc ggaactgagt gtcaggcgtg    8640
gaatgagaca aacgcggcca taacagcgga atgacaccgg taaaccgaaa ggcaggaaca    8700
ggagagcgca cgagggagcc gccaggggaa acgcctggta tctttatagt cctgtcgggt    8760
ttcgccacca ctgatttgag cgtcagattt cgtgatgctt gtcaggggggg cggagcctat    8820 ggaaaaacgg ctttgccgcg ccctctcac ttccctgtta agtatcttcc tggcatcttc     8880
caggaaatct ccgccccgtt cgtaagccat ttccgctcgc cgcagtcgaa cgaccgagcg    8940
tagcgagtca gtgagcgagg aagcggaata tatcctgtat cacatattct gctgacgcac    9000
cggtgcagcc tttttctcc tgccacatga agcacttcac tgacaccctc atcagtgcca     9060
acatagtaag ccagtataca ctccgctagc gctgatgtcc ggcggtgctt ttgccgttac    9120
gcaccacccc gtcagtagct gaacaggagg gacagctgat agaaacagaa gccagttctt    9180
tcctgcgtta tccccctgatt ctgtggataa ccgtattacc gcctttgagt gagctgatac    9240
cgctcgccgc agccgaacga ccgagcgcag cgagtcagtg agcgaggaag cggaagagcg    9300
cctgatgcgg tattttctcc ttacgcatct gtgcggtatt tcacaccgca tagaccagcc    9360
gcgtaacctg gcaaaatcgg ttacggttga gtaataaatg                           9400
```

<210> SEQ ID NO 10
<211> LENGTH: 10077
<212> TYPE: DNA
<213> ORGANISM: Artificial Sequence
<220> FEATURE:
<223> OTHER INFORMATION: Synthesized
<400> SEQUENCE: 10

-continued

```
gatgccctgc gtaagcgggt gtgggcggac aataaagtct taaactgaac aaaatagatc        60
taaactatga caataaagtc ttaaactaga cagaatagtt gtaaactgaa atcagtccag       120
ttatgctgtg aaaaagcata ctggactttt gttatggcta aagcaaactc ttcattttct       180
gaagtgcaaa ttgcccgtcg tattaaagag gggcgtggcc aagggcatgt aaagactata       240
ttcgcggcgt tgtgacaatt taccgaacaa ctccgcggcc gggaagccga tctcggcttg       300
aacgaattgt taggtggcgg tacttgggtc gatatcaaag tgcatcactt cttcccgtat       360
gcccaacttt gtatagagag ccactgcggg atcgtcaccg taatctgctt gcacgtagat       420
cacataagca ccaagcgcgt tggcctcatg cttgaggaga ttgatgagcg cggtggcaat       480
gccctgcctc cggtgctcgc cggagactgc gagatcatag atatagatct cactacgcgg       540
ctgctcaaac ttgggcagaa cgtaagccgc gagagcgcca acaaccgctt cttggtcgaa       600
ggcagcaagc gcgatgaatg tcttactacg gagcaagttc ccgaggtaat cggagtccgg       660
ctgatgttgg gagtaggtgg ctacgtctcc gaactcacga ccgaaaagat caagagcagc       720
ccgcatggat ttgacttggt cagggccgag cctacatgtg cgaatgatgc ccatacttga       780
gccacctaac tttgttttag ggcgactgcc ctgctgcgta acatcgttgc tgctgcgtaa       840
catcgttgct gctccataac atcaaacatc gacccacggc gtaacgcgct tgctgcttgg       900
atgcccgagg catagactgt acaaaaaaac agtcataaca agccatgaaa accgccactg       960
cgccgttacc accgctgcgt tcggtcaagg ttctggacca gttgcgtgag cgcatacgct      1020
acttgcatta cagtttacga accgaacagg cttatgtcaa ctgggttcgt gccttcatcc      1080
gtttccacgg tgtgcgtcac ccggcaacct tgggcagcag cgaagtcgcc ataacttcgt      1140
atagcataca ttatacgaag ttatctgtaa ctataacggt cctaaggtag cgagtttaaa      1200
cgacgtccta gattggttac tgggcgatga aggtttagtc ggcaaatcgt ccaacgttag      1260
tgacagcgtc agcggcaagt taatgcctat cattttgttg ataggcgcgg tcttgttttt      1320
aggtttaata ttttattta tctacagata catgatgaaa ggagggaagg gaggtggtgt      1380
tggcgcagca acgtcgccaa ctcccattgt tatttctatg caaaaccca caccaacaac      1440 ggcccctcga taataaaaga caaaaataat ataaaatata tgtataatta attaaattca      1500
aaatatatgt ataaggccgg ccttagtcag ttacttgtac agctcgtcca tgccgagagt      1560
gatcccggcg gcggtcacga actccagcag gaccatgtga tcgcgcttct cgttggggtc      1620
tttgctcagg gcggactggg tgctcaggta gtggttgtcg ggcagcagca cggggccgtc      1680
gccgatgggg gtgttctgct ggtagtggtc ggcgagctgc acgctgccgt cctcgatgtt      1740
gtggcggatc ttgaagttca ccttgatgcc gttcttctgc ttgtcggcca tgatatagac      1800
gttgtggctg ttgtagttgt actccagctt gtgccccagg atgttgccgt cctccttgaa      1860
gtcgatgccc ttcagctcga tgcggttcac cagggtgtcg ccctcgaact tcacctcggc      1920
gcgggtcttg tagttgccgt cgtccttgaa gaagatggtg cgctcctgga cgtagccttc      1980
gggcatggcg gacttgaaga agtcgtgctg cttcatgtgg tcggggtagc ggctgaagca      2040
ctgcacgccg taggtcaggg tggtcacgag ggtgggccag ggcacgggca gcttgccggt      2100
ggtgcagatg aacttcaggg tcagcttgcc gtaggtggca tcgccctcgc cctcgccgga      2160
cacgctgaac ttgtggccgt ttacgtcgcc gtccagctcg accaggatgg gcaccacccc      2220
ggtgaacagc tcctcgccct tgctcatccc gggtgactgg aagtacaggt tttcttgcga      2280
gtacaccaat tcattcatga gttgagtcgc ttccttaact ggctgaaaag gctcttcagg      2340
tttcaccatg aaaactttat ggccccccca caatactgag tcagcattta atcgccaacc      2400
```

-continued

```
actaacccac tgctgcgcct cctgatttgt caacaattcc atgaagtttt tcggcacgct    2460
tgtgaaataa ttgtttgtgt tggtgaaatt cgatgctgag tgtataccaa caatgaaccc    2520
atctctagtt gatactaatg gactgccaca ctgcccatcc ttggtttgaa tccaatgctt    2580
ccagaatatg ccatcagatg aagggaatgt gcaagaagtg tctgacacca tgctagacat    2640
gctcttagtt tggaagttgg ttgtcacaag acatattctc tcttcccttt gtggctctct    2700
aaatttcagc ttttgaggaa atggtgggaa atccttaggc atgcgaataa ttatcatgtc    2760
cctcccatca atgaggtgtt gttgcaaagt cgtggtgttc ttgaccttga atacaccatg    2820
tagtgattgg accaacagtg ttccattatt tcttctaaac aagtgcttgt ttgtaatgat    2880
gaagggacca aatccaatac catacaacga tgttgtgtgc ccatcagatt cattcgtcaa    2940
atgacaaatg gtgctcgata tagggttgta atcacgcggc cccttaaaca agctctctcc    3000
ggcgtagtca ggcacgtcgt aaggataagc catatttaaa tatatgcttg cttgtgtgtt    3060
ccttattgaa gccttggtgt gactgattta ctagtagcgt tgaggcgtct tatatacccg    3120
accgttatct ggcctacgtg acacaaggca cgttgttaga ttaataatct tatcttttta    3180
tcttaattga taagattatt tttatctggc tgttataaaa acgggatcat gaacacggac    3240
gctcagtcga cagatctgtc gacggtttaa acactagttc gcgacctact ccggaatatt    3300
aataggttgc tgatatcggg agttcagtcg tcgaatgcaa agcgtaaaaa atattaataa    3360
ggtaaaaatt acagctacat aaattacaca atttaaacgg atcgatgagc tccatatggc    3420
ctggagccat ccgcaatttg aaaaaggtgg cgggtccggc ggaggtagcg gcggaggttc    3480
ttggtctcac cctcagttcg agaaggatga cgatgataaa accatgggat ccctaggtac    3540
cgcggccgcg gaagcagctg gtgggaaata cagaagcaca gtcagcaaaa gcaaagaccc    3600
ctcggggctg ctcatctctg tgatcaggac tctgtctact agtgacgatg tcgaagacag    3660
ggaaaatgaa aagggtcgcc ttgaagaagc ctacgagaaa tgtgaccgtg acctggatga    3720
attgattgta cagcactaca cagaattgac gacagccatt cgcacatacc agagcatcac    3780
agagcgcatc actaactccc gaaataaaat aaagcaggta aaagagaacc tgctttcatg    3840
caagatgctg ctgcactgca aacgggatga gcttcggaaa ctgtggattg aaggaattga    3900
gcataagcat gtcctgaact tgttggatga aattgagaat atcaagcaag tgcctcaaaa    3960
gctggaacag tgcatggcca gcaagcacta tctcagtgcc actgacatgt tggtgtcagc    4020
agttgagtct ttggagggcc ccctgctcca ggtggaagga ctgagtgacc ttcgactaga    4080
gcttcacagc aagaagatga accttcactt ggttctcata gatgaactac accggcacct    4140
gtacatcaaa tcgactagcc gagttgtgca gcgtaacaag gaaaaaggga aaatcagctc    4200
cctcgtgaaa gatgcttctg ttcctctgat tgatgttaca aacctcccta ctcctcgaaa    4260
attccttgat acctctcact attctactgc tggaagctca agtgtgaggg agataaatct    4320
gcaggacatc aaggaagatt tagaattgga tccagaggaa aacagcaccc tgtttatggg    4380
tatcctcatt aagggcttgg cgaaactgaa gaagatccca gaaacagtta aggcaatcat    4440
agagcgcttg gagcaggagt tgaagcaaat tgtgaagagg tctacaaccc aggtggcaga    4500
cagtggctat cagcggggggg agaacgttac tgtggagaac caaccaaggt tgcttctaga    4560
actgctggag ttactgtttg acaagtttaa tgctgtagcc gctgcacact ctgtggtcct    4620
gggatacctg caggacactg tagtgactcc actgactcag caggaagata tcaaactgta    4680
tgatatggca gatgtatggg tgaagatcca agatgttcta cagatgctat taactgagta    4740
```

```
cttggatatg aaaaatactc gtacggcctc tgaaccatca gctcaactaa gctatgccag   4800
cactggacga gagtttgcag cctttttttgc caagaagaaa cctcaaaggc caaaaaattc   4860
tcttttcaag ttcgaatcgt cctcccatgc catcagtatg agcgcctatc tgcgagaaca   4920
gagaagggag ctctatagtc ggagtggaga actgcaaggg ggtcctgatg acaacttaat   4980
tgaaggtgga ggaacaaaat ttgtctgcaa acctggagcc agaaacatta ccgtcatatt   5040
ccacccatta ctaagattta ttcaggagat tgagcatgct ctgggtcttg gcccagccaa   5100
acagtgtcct cttcgagagt ttctcaccgt gtacatcaaa aacatctttc tcaatcaagt   5160
cttggctgag atcaacaagg agattgaagg agtcactaaa acatctgacc ctttgaagat   5220
tctggccaac gcagacacca tgaaggtgct gggagtgcag cggcctctcc tacagagcac   5280
aatcattgtg gagaagacag ttcaagacct cctgaacctg atgcatgact tgagtgcata   5340
ttcagatcaa ttcctcaaca tggtgtgcgt gaagctccag gagtacaagg acacctgcac   5400
tgcagcttac aggggtattg tccagtcaga agaaaaactt gtcatcagtg catcctgggc   5460
aaaagatgat gatatcagca gactcttgaa atctctacca aactggatga atatggctca   5520
acccaaacag ctgaggccaa aaagagagga ggaagaagat ttcataaggg cagcttttgg   5580
caaggagtct gaagttctta ttgggaacct gggtgataaa ttaatccctc cacaagacat   5640
ccttcgtgac gtcagtgacc tcaaagcctt ggccaacatg catgaaagcc tggaatggtt   5700
ggcaagtcga acaaagtcag ctttctccaa tctttctaca tcccagatgc tttctcctgc   5760
tcaagacagc cacacgaaca cggatctccc cccagtgtca gagcagatca tgcagactct   5820
cagtgaactt gccaaatcgt tccaggatat ggctgaccgc tgcttgcttg tcttacatct   5880
ggaagtgagg gttcactgtt tccactatct tatccctctt gcaaaggagg ggaactatgc   5940
cattgtggct aatgtggaaa gtatggatta tgaccccctg gtggtcaagc tcaacaaaga   6000
tatcagcgcc attgaagagg ccatgagcgc cagccttcag cagcacaagt tccagtatat   6060
cttcgaaggc ctgggccacc tgatctcctg catcctcatt aatggtgccc agtacttcag   6120
gcgcatcagt gagtctggca tcaagaaaat gtgtaggaac atttttgttc ttcagcagaa   6180
tttgaccaac atcaccatgt cgcgggaggc agacctggac tttgcaaggc agtactacga   6240
gatgctttac aacacagctg acgagctcct gaacctggtg gtggaccagg gtgtgaagta   6300
cacggagctg gagtacatcc acgctctgac cctgctgcac cgcagccaga ctggggtggg   6360
ggaactgacc acccagaaca cgaggctgca gaggctcaaa gagatcatct gcgagcaggc   6420
tgccatcaag caagccacca aggacaagaa gataactacc gttggctcga gttaactgac   6480
taaaagcttc gaaaggaagc tgagttggct gctgccaccg ctgagcaata actagcataa   6540
ccccttgggg cctctaaacg ggtcttgagg ggttttttgc tgaaaggagg aactatcctc   6600
agggtcgaga agtactagag gatcataatc agccatacca catttgtaga ggttttactt   6660
gctttaaaaa acctcccaca cctccccctg aacctgaaac ataaaatgaa tgcaattgtt   6720
gttgttaact tgtttattgc agcttataat ggttacaaat aaagcaatag catcacaaat   6780
ttcacaaata aagcattttt ttcactgcat tctagttgtg gtttgtccaa actcatcaat   6840
gtatcttatc atgtctggat ctgatcactg cttgagccta ggagatccga accagataag   6900
tgaaatctag ttccaaacta ttttgtcatt tttaattttc gtattagctt acgacgctac   6960
acccagttcc catctatttt gtcactcttc cctaaataat ccttaaaaac tccatttcca   7020
cccctcccag ttcccaacta ttttgtccgc ccacagcggg gcattttttct tcctgttatg   7080 tttttaatca aacatcctgc caactccatg tgacaaaccg tcatcttcgg ctacttttttc   7140
```

-continued

```
tctgtcacag aatgaaaatt tttctgtcat ctcttcgtta ttaatgtttg taattgactg    7200
aatatcaacg cttatttgca gcctgaatgg cgaatgggac gcgccctgta gcggcgcatt    7260
aagcgcggcg ggtgtggtgg ttacgcgcag cgtgaccgct acacttgcca gcgccctagc    7320
gcccgctcct ttcgctttct tcccttcctt tctcgccacg ttcgccggct ttccccgtca    7380
agctctaaat cggggggctcc ctttaggggtt ccgatttagt gctttacggc acctcgaccc    7440
caaaaaactt gattagggtg atggttcacg tagtgggcca tcgccctgat agacggtttt    7500
tcgccctttg acgttggagt ccacgttctt taatagtgga ctcttgttcc aaactggaac    7560
aacactcaac cctatctcgg tctattcttt tgatttataa gggattttgc cgatttcggc    7620
ctattggtta aaaaatgagc tgatttaaca aaaatttaac gcgaatttta acaaaatatt    7680
aacgtttaca atttcaggtg gcacttttcg gggaaatgtg cgcggaaccc ctatttgttt    7740 attttttctaa atacattcaa atatgtatcc gctcatgaga caataaccct gataaatgct    7800
tcaataatat tgaaaaagga agagtatgag tattcaacat ttccgtgtcg cccttattcc    7860
cttttttgcg gcattttgcc ttcctgtttt tgctcaccca gaaacgctgg tgaaagtaaa    7920
agatgctgaa gatcagttgg gtgcacgagt gggttacatc gaactggatc tcaacagcgg    7980
taagatcctt gagagttttc gccccgaaga acgttttcca atgatgagca cttttaaagt    8040
tctgctatgt ggcgcggtat tatcccgtat tgacgccggg caagagcaac tcggtcgccg    8100
catacactat tctcagaatg acttggttga gtactcacca gtcacagaaa agcatcttac    8160
ggatggcatg acagtaagag aattatgcag tgctgccata accatgagtg ataacactgc    8220
ggccaactta cttctgacaa cgatcggagg accgaaggag ctaaccgctt ttttgcacaa    8280 catggggat catgtaactc gccttgatcg ttgggaaccg gagctgaatg aagccatacc    8340
aaacgacgag cgtgacacca cgatgcctgt agcaatggca acaacgttgc gcaaactatt    8400
aactggcgaa ctacttactc tagcttcccg gcaacaatta atagactgga tggaggcgga    8460
taaagttgca ggaccacttc tgcgctcggc ccttccggct ggctggttta ttgctgataa    8520
atctggagcc ggtgagcgtg ggtctcgcgg tatcattgca gcactggggc cagatggtaa    8580
gccctcccgt atcgtagtta tctacacgac ggggagtcag gcaactatgg atgaacgaaa    8640
tagacagatc gctgagatag gtgcctcact gattaagcat tggtaactgt cagaccaagt    8700
ttactcatat atactttaga ttgatttaaa acttcatttt taatttaaaa ggatctaggt    8760
gaagatcctt tttgataatc tcatgaccaa atcccttaa cgtgagtttt cgttccactg    8820
agcgtcagac cgcggggcat gactaacatg agaattacaa cttatatcgt atggggctga    8880
cttcaggtgc tacatttgaa gagataaatt gcactgaaat ctagaaatat tttatctgat    8940
taataagatg atcttcttga gatcgttttg gtctgcgcgt aatctcttgc tctgaaaacg    9000
gaaaaaaccg ccttgcaggg cggttttttcg aaggttctct gagctaccaa ctctttgaac    9060
cgaggtaact ggcttggagg agcgcagtca ccaaaacttg tcctttcagt ttagccttaa    9120
ccggcgcatg acttcaagac taactcctct aaatcaatta ccagtggctg ctgccagtgg    9180
tgcttttgca tgtctttccg ggttggactc aagacgatag ttaccggata aggcgcagcg    9240
gtcggactga acggggggtt cgtgcataca gtccagcttg gagcgaactg cctacccgga    9300
actgagtgtc aggcgtggaa tgagacaaac gcggccataa cagcggaatg acaccggtaa    9360
accgaaaggc aggaacagga gagcgcacga gggagccgcc aggggaaacg cctggtatct    9420
ttatagtcct gtcgggtttc gccaccactg atttgagcgt cagatttcgt gatgcttgtc    9480
```

```
agggggggcgg agcctatgga aaaacggctt tgccgcggcc ctctcacttc cctgttaagt    9540
atcttcctgg catcttccag gaaatctccg ccccgttcgt aagccatttc cgctcgccgc    9600
agtcgaacga ccgagcgtag cgagtcagtg agcgaggaag cggaatatat cctgtatcac    9660
atattctgct gacgcaccgg tgcagccttt tttctcctgc cacatgaagc acttcactga    9720
caccctcatc agtgccaaca tagtaagcca gtatacactc cgctagcgct gatgtccggc    9780
ggtgcttttg ccgttacgca ccaccccgtc agtagctgaa caggagggac agctgataga    9840
aacagaagcc agttctttcc tgcgttatcc cctgattctg tggataaccg tattaccgcc    9900
tttgagtgag ctgataccgc tcgccgcagc cgaacgaccg agcgcagcga gtcagtgagc    9960
gaggaagcgg aagagcgcct gatgcggtat tttctcctta cgcatctgtg cggtatttca   10020
caccgcatag accagccgcg taacctggca aaatcggtta cggttgagta ataaatg      10077
```

```
<210> SEQ ID NO 11
<211> LENGTH: 9283
<212> TYPE: DNA
<213> ORGANISM: Artificial Sequence
<220> FEATURE:
<223> OTHER INFORMATION: Synthesized

<400> SEQUENCE: 11
```

```
gatgccctgc gtaagcgggt gtgggcggac aataaagtct taaactgaac aaaatagatc      60
taaactatga caataaagtc ttaaactaga cagaatagtt gtaaactgaa atcagtccag     120
ttatgctgtg aaaaagcata ctggactttt gttatggcta aagcaaactc ttcattttct     180
gaagtgcaaa ttgcccgtcg tattaaagag gggcgtggcc aagggcatgt aaagactata     240
ttcgcggcgt tgtgacaatt taccgaacaa ctccgcggcc gggaagccga tctcggcttg     300
aacgaattgt taggtggcgg tacttgggtc gatatcaaag tgcatcactt cttccccgtat     360 gcccaacttt gtatagagag ccactgcggg atcgtcaccg taatctgctt gcacgtagat     420
cacataagca ccaagcgcgt tggcctcatg cttgaggaga ttgatgagcg cggtggcaat     480
gccctgcctc cggtgctcgc cggagactgc gagatcatag atatagatct cactacgcgg     540
ctgctcaaac ttgggcagaa cgtaagccgc gagagcgcca acaaccgctt cttggtcgaa     600
ggcagcaagc gcgatgaatg tcttactacg gagcaagttc ccgaggtaat cggagtccgg     660
ctgatgttgg gagtaggtgg ctacgtctcc gaactcacga ccgaaaagat caagagcagc     720
ccgcatggat ttgacttggt cagggccgag cctacatgtg cgaatgatgc ccatacttga     780
gccacctaac tttgttttag ggcgactgcc ctgctgcgta acatcgttgc tgctgcgtaa     840
catcgttgct gctccataac atcaaacatc gacccacggc gtaacgcgct tgctgcttgg     900
atgcccgagg catagactgt acaaaaaaac agtcataaca agccatgaaa accgccactg     960
cgccgttacc accgctgcgt tcggtcaagg ttctggacca gttgcgtgag cgcatacgct    1020
acttgcatta cagtttacga accgaacagg cttatgtcaa ctgggttcgt gccttcatcc    1080
gtttccacgg tgtgcgtcac ccggcaacct tgggcagcag cgaagtcgcc ataacttcgt    1140
atagcataca ttatacgaag ttatctgtaa ctataacggt cctaaggtag cgagtttaaa    1200
cgacgtccta gattggttac tgggcgatga aggtttagtc ggcaaatcgt ccaacgttag    1260
tgacagcgtc agcggcaagt taatgcctat cattttgttg ataggcgcgg tcttgttttt    1320
aggtttaata ttttattttta tctacagata catgatgaaa ggaggggaagg gaggtggtgt    1380 tggcgcagca acgtcgccaa ctcccattgt tatttctatg caaaaccccca caccaacaac    1440 ggcccctcga taataaaaga caaaaataat ataaaatata tgtataatta attaaattca    1500
```

```
aaatatatgt ataaggccgg ccttagtcag ttacttgtac agctcgtcca tgccgagagt   1560
gatcccggcg gcggtcacga actccagcag gaccatgtga tcgcgcttct cgttggggtc   1620
tttgctcagg gcggactggg tgctcaggta gtggttgtcg ggcagcagca cggggccgtc   1680
gccgatgggg gtgttctgct ggtagtggtc ggcgagctgc acgctgccgt cctcgatgtt   1740
gtggcggatc ttgaagttca ccttgatgcc gttcttctgc ttgtcggcca tgatatagac   1800
gttgtggctg ttgtagttgt actccagctt gtgcccagg atgttgccgt cctccttgaa    1860
gtcgatgccc ttcagctcga tgcggttcac cagggtgtcg ccctcgaact tcacctcggc   1920
gcgggtcttg tagttgccgt cgtccttgaa gaagatggtg cgctcctgga cgtagccttc   1980
gggcatggcg gacttgaaga agtcgtgctg cttcatgtgg tcggggtagc ggctgaagca   2040
ctgcacgccg taggtcaggg tggtcacgag ggtgggccag ggcacgggca gcttgccggt   2100
ggtgcagatg aacttcaggg tcagcttgcc gtaggtggca tcgccctcgc cctcgccgga   2160
cacgctgaac ttgtggccgt ttacgtcgcc gtccagctcg accaggatgg gcaccacccc   2220
ggtgaacagc tcctcgccct tgctcatccc gggtgactgg aagtacaggt tttcttgcga   2280
gtacaccaat tcattcatga gttgagtcgc ttccttaact ggctgaaaag gctcttcagg   2340
tttcaccatg aaaactttat ggccccccca caatactgag tcagcattta atcgccaacc   2400
actaacccac tgctgcgcct cctgatttgt caacaattcc atgaagtttt tcggcacgct   2460
tgtgaaataa ttgtttgtgt tggtgaaatt cgatgctgag tgtataccaa caatgaaccc   2520
atctctagtt gatactaatg gactgccaca ctgcccatcc ttggtttgaa tccaatgctt   2580
ccagaatatg ccatcagatg aagggaatgt gcaagaagtg tctgacacca tgctagacat   2640
gctcttagtt tggaagttgg ttgtcacaag acatattctc tcttcccttt gtggctctct   2700
aaatttcagc ttttgaggaa atggtgggaa atccttaggc atgcgaataa ttatcatgtc   2760
cctcccatca atgaggtgtt gttgcaaagt cgtggtgttc ttgaccttga atacaccatg   2820
tagtgattgg accaacagtg ttccattatt tcttctaaac aagtgcttgt ttgtaatgat   2880
gaagggacca aatccaatac catacaacga tgttgtgtgc ccatcagatt cattcgtcaa   2940
atgacaaatg gtgctcgata tagggttgta atcacgcggc cccttaaaca agctctctcc   3000
ggcgtagtca ggcacgtcgt aaggataagc catatttaaa tatatgcttg cttgtgtgtt   3060
ccttattgaa gccttggtgt gactgattta ctagtagcgt tgaggcgtct tatatacccg   3120
accgttatct ggcctacgtg acacaaggca cgttgttaga ttaataatct tatctttta    3180 tcttaattga taagattatt tttatctggc tgttataaaa acgggatcat gaacacggac   3240
gctcagtcga cagatctgtc gacggtttaa acactagttc gcgacctact ccggaatatt   3300
aataggttgc tgatatcggg agttcagtcg tcgaatgcaa agcgtaaaaa atattaataa   3360
ggtaaaaatt acagctacat aaattacaca atttaaacgg atcgatgagc tccatatggc   3420
ctggagccat ccgcaatttg aaaaaggtgg cgggtccggc ggaggtagcg gcggaggttc   3480
ttggtctcac cctcagttcg agaaggatga cgatgataaa accatgggat ccctaggtac   3540
cgcggccgcg accacggccg agttgttcga ggagcctttt gtggcagatg aatatattga   3600
acgtcttgta tggagaaccc caggaggagg ctctagaggt ggacctgaag cttttgatcc   3660
taaaagatta ttagaagaat ttgtaaatca tattcaggaa ctccagataa tggatgaaag   3720
gattcagagg aaagtagaga aactagagca acaatgtcag aaagaagcca aggaatttgc   3780
caagaaggta caagagctgc agaaaagcaa tcaggttgcc ttccaacatt ccaagaact    3840
```

-continued

```
agatgagcac attagctatg tagcaactaa agtctgtcac cttggagacc agttagaggg    3900
ggtaaacaca cccagacaac gggcagtgga ggctcagaaa ttgatgaaat actttaatga    3960
gtttctagat ggagaattga aatctgatgt ttttacaaat tctgaaaaga taaaggaagc    4020
agcagacatc attcagaagt tgcacctaat tgcccaagag ttaccttttg atagattttc    4080
agaagttaaa tccaaaattg caagtaaata ccatgattta gaatgccagc tgattcagga    4140
gtttaccagt gctcaaagaa gaggtgaaat ctccagaatg agagaagtag cagcagtttt    4200
acttcatttt aagggttatt cccattgtgt tgatgtttat ataaagcagt gccaggaggg    4260
tgcttatttg agaaatgata tatttgaaga cgctggaata ctctgtcaaa gagtgaacaa    4320
acaagttgga gatatcttca gtaatccaga aacagtcctg gctaaactta ttcaaaatgt    4380
atttgaaatc aaactacaga gttttgtgaa agagcagtta gaagaatgta ggaagtccga    4440
tgcagagcaa tatctcaaaa atctctatga tctgtataca agaaccacca atctttccag    4500
caagctgatg gagtttaatt taggtactga taaacagact ttcttgtcta agcttatcaa    4560
atccattttc atttcctatt tggagaacta tattgaggtg gagactggat atttgaaaag    4620
cagaagtgct atgatcctac agcgctatta tgattcgaaa aaccatcaaa agagatccat    4680
tggcacagga ggtattcaag atttgaagga aagaattaga cagcgtacca acttaccact    4740
tgggccaagt atcgatactc atggggagac ttttctatcc caagaagtgg tggttaatct    4800
tttacaagaa accaaacaag cctttgaaag atgtcatagg ctctctgatc cttctgactt    4860
accaaggaat gccttcagaa ttttttaccat tcttgtggaa tttttatgta ttgagcatat    4920
tgattatgct ttggaaacag gacttgctgg aattccctct tcagattcta ggaatgcaaa    4980
tctttatttt ttggacgttg tgcaacaggc caatactatt tttcatcttt ttgacaaaca    5040
gtttaatgat caccttatgc cactaataag ctcttctcct aagttatctg aatgccttca    5100
gaagaaaaaa gaaataattg aacaaatgga gatgaaattg gatactggca ttgataggac    5160
attaaattgt atgattggac agatgaagca tattttggct gcagaacaga agaaaacaga    5220 tttttaagcca gaagatgaaa acaatgtttt gattcaatat actaatgcct gtgtaaaagt    5280
ctgtgcttac gtaagaaaac aagtggagaa gattaaaaat tccatggatg ggaagaatgt    5340
ggatacagtt ttgatggaac ttggagtacg ttttcatcga cttatctatg agcatcttca    5400
acaatattcc tacagttgta tggggtggcat gttggcaatt tgtgatgtag ccgaatatag    5460
gaagtgtgcc aaagacttca agattccaat ggtattacat cttttttgata ctctgcatgc    5520 tctttgcaat cttctggtag ttgccccaga taatttaaag caagtctgct caggagaaca    5580
acttgctaat ctggacaaga atatacttca ctccttcgta caacttcgtg ctgattatag    5640
atctgcccgc cttgctcgac acttcagcta actcgagtta actgactaaa agcttcgaaa    5700
ggaagctgag ttggctgctg ccaccgctga gcaataacta gcataacccc ttggggcctc    5760
taaacgggtc ttgaggggtt ttttgctgaa aggaggaact atcctcaggg tcgagaagta    5820
ctagaggatc ataatcagcc ataccacatt tgtagaggtt ttacttgctt taaaaaacct    5880
cccacacctc cccctgaacc tgaaacataa aatgaatgca attgttgttg ttaacttgtt    5940
tattgcagct tataatggtt acaaataaag caatagcatc acaaatttca caaataaagc    6000 attttttttca ctgcattcta gttgtggttt gtccaaactc atcaatgtat cttatcatgt    6060
ctggatctga tcactgcttg agcctaggag atccgaacca gataagtgaa atctagttcc    6120
aaactatttt gtcattttta attttcgtat tagcttacga cgctacaccc agttcccatc    6180
tattttgtca ctcttcccta aataatcctt aaaaactcca tttccacccc tcccagttcc    6240
```

-continued

```
caactatttt gtccgcccac agcggggcat ttttcttcct gttatgtttt taatcaaaca    6300
tcctgccaac tccatgtgac aaaccgtcat cttcggctac tttttctctg tcacagaatg    6360
aaaatttttc tgtcatctct tcgttattaa tgtttgtaat tgactgaata tcaacgctta    6420
tttgcagcct gaatggcgaa tgggacgcgc cctgtagcgg cgcattaagc gcggcgggtg    6480
tggtggttac gcgcagcgtg accgctacac ttgccagcgc cctagcgccc gctcctttcg    6540
ctttcttccc ttcctttctc gccacgttcg ccggctttcc ccgtcaagct ctaaatcggg    6600
ggctcccttt agggttccga tttagtgctt tacggcacct cgaccccaaa aaacttgatt    6660
agggtgatgg ttcacgtagt gggccatcgc cctgatagac ggtttttcgc cctttgacgt    6720
tggagtccac gttctttaat agtggactct tgttccaaac tggaacaaca ctcaacccta    6780
tctcggtcta ttcttttgat ttataaggga ttttgccgat ttcggcctat tggttaaaaa    6840
atgagctgat ttaacaaaaa tttaacgcga attttaacaa aatattaacg tttacaattt    6900
caggtggcac ttttcgggga aatgtgcgcg gaacccctat ttgtttattt ttctaaatac    6960
attcaaatat gtatccgctc atgagacaat aaccctgata aatgcttcaa taatattgaa    7020
aaaggaagag tatgagtatt caacatttcc gtgtcgccct tattcccttt tttgcggcat    7080
tttgccttcc tgttttttgct cacccagaaa cgctggtgaa agtaaaagat gctgaagatc    7140
agttgggtgc acgagtgggt tacatcgaac tggatctcaa cagcggtaag atccttgaga    7200
gttttcgccc cgaagaacgt tttccaatga tgagcacttt taaagttctg ctatgtggcg    7260
cggtattatc ccgtattgac gccgggcaag agcaactcgg tcgccgcata cactattctc    7320
agaatgactt ggttgagtac tcaccagtca cagaaaagca tcttacggat ggcatgacag    7380
taagagaatt atgcagtgct gccataacca tgagtgataa cactgcggcc aacttacttc    7440
tgacaacgat cggaggaccg aaggagctaa ccgctttttt gcacaacatg ggggatcatg    7500
taactcgcct tgatcgttgg gaaccggagc tgaatgaagc cataccaaac gacgagcgtg    7560
acaccacgat gcctgtagca atggcaacaa cgttgcgcaa actattaact ggcgaactac    7620
ttactctagc ttcccggcaa caattaatag actggatgga ggcggataaa gttgcaggac    7680
cacttctgcg ctcggccctt ccggctggct ggtttattgc tgataaatct ggagccggtg    7740
agcgtgggtc tcgcggtatc attgcagcac tggggccaga tggtaagccc tcccgtatcg    7800
tagttatcta cacgacgggg agtcaggcaa ctatggatga acgaaataga cagatcgctg    7860
agataggtgc ctcactgatt aagcattggt aactgtcaga ccaagtttac tcatatatac    7920
tttagattga tttaaaactt catttttaat ttaaaaggat ctaggtgaag atcctttttg    7980
ataatctcat gaccaaaatc ccttaacgtg agttttcgtt ccactgagcg tcagaccgcg    8040
gggcatgact aacatgagaa ttacaactta tatcgtatgg ggctgacttc aggtgctaca    8100
tttgaagaga taaattgcac tgaaatctag aaatatttta tctgattaat aagatgatct    8160
tcttgagatc gttttggtct gcgcgtaatc tcttgctctg aaaacggaaa aaaccgcctt    8220
gcagggcggt ttttcgaagg ttctctgagc taccaactct ttgaaccgag gtaactggct    8280
tggaggagcg cagtcaccaa aacttgtcct ttcagtttag ccttaaccgg cgcatgactt    8340
caagactaac tcctctaaat caattaccag tggctgctgc cagtggtgct tttgcatgtc    8400
tttccgggtt ggactcaaga cgatagttac cggataaggc gcagcggtcg gactgaacgg    8460
ggggttcgtg catacagtcc agcttggagc gaactgccta cccggaactg agtgtcaggc    8520
gtggaatgag acaaacgcgg ccataacagc ggaatgacac cggtaaaccg aaaggcagga    8580
```

-continued

```
acaggagagc gcacgaggga gccgccaggg gaaacgcctg gtatctttat agtcctgtcg    8640
ggtttcgcca ccactgattt gagcgtcaga tttcgtgatg cttgtcaggg gggcggagcc    8700
tatggaaaaa cggctttgcc gcggccctct cacttccctg ttaagtatct tcctggcatc    8760
ttccaggaaa tctccgcccc gttcgtaagc catttccgct cgccgcagtc gaacgaccga    8820
gcgtagcgag tcagtgagcg aggaagcgga atatatcctg tatcacatat tctgctgacg    8880
caccggtgca gccttttttc tcctgccaca tgaagcactt cactgacacc ctcatcagtg    8940
ccaacatagt aagccagtat acactccgct agcgctgatg tccggcggtg cttttgccgt    9000
tacgcaccac cccgtcagta gctgaacagg agggacagct gatagaaaca gaagccagtt    9060
ctttcctgcg ttatcccctg attctgtgga taaccgtatt accgcctttg agtgagctga    9120
taccgctcgc cgcagccgaa cgaccgagcg cagcgagtca gtgagcgagg aagcggaaga    9180
gcgcctgatg cggtattttc tccttacgca tctgtgcggt atttcacacc gcatagacca    9240
gccgcgtaac ctggcaaaat cggttacggt tgagtaataa atg                       9283
```

```
<210> SEQ ID NO 12
<211> LENGTH: 9555
<212> TYPE: DNA
<213> ORGANISM: Artificial Sequence
<220> FEATURE:
<223> OTHER INFORMATION: Synthesized

<400> SEQUENCE: 12
```

```
gatgccctgc gtaagcgggt gtgggcggac aataaagtct taaactgaac aaaatagatc      60
taaactatga caataaagtc ttaaactaga cagaatagtt gtaaactgaa atcagtccag     120
ttatgctgtg aaaaagcata ctggactttt gttatggcta aagcaaactc ttcattttct     180
gaagtgcaaa ttgccccgtcg tattaaagag gggcgtggcc aagggcatgt aaagactata     240
ttcgcggcgt tgtgacaatt taccgaacaa ctccgcggcc gggaagccga tctcggcttg     300
aacgaattgt taggtggcgg tacttgggtc gatatcaaag tgcatcactt cttcccgtat     360
gcccaacttt gtatagagag ccactgcggg atcgtcaccg taatctgctt gcacgtagat     420
cacataagca ccaagcgcgt tggcctcatg cttgaggaga ttgatgagcg cggtggcaat     480
gccctgcctc cggtgctcgc cggagactgc gagatcatag atatagatct cactacgcgg     540
ctgctcaaac ttgggcagaa cgtaagccgc gagagcgcca acaaccgctt cttggtcgaa     600
ggcagcaagc gcgatgaatg tcttactacg gagcaagttc ccgaggtaat cggagtccgg     660
ctgatgttgg gagtaggtgg ctacgtctcc gaactcacga ccgaaaagat caagagcagc     720
ccgcatggat ttgacttggt cagggccgag cctacatgtg cgaatgatgc ccatacttga     780
gccacctaac tttgttttag ggcgactgcc ctgctgcgta acatcgttgc tgctgcgtaa     840
catcgttgct gctccataac atcaaacatc gacccacggc gtaacgcgct tgctgcttgg     900
atgcccgagg catagactgt acaaaaaaac agtcataaca agccatgaaa accgccactg     960
cgccgttacc accgctgcgt tcggtcaagg ttctggacca gttgcgtgag cgcatacgct    1020
acttgcatta cagtttacga accgaacagg cttatgtcaa ctgggttcgt gccttcatcc    1080
gtttccacgg tgtgcgtcac ccggcaacct gggcagcag cgaagtcgcc ataacttcgt     1140
atagcataca ttatacgaag ttatctgtaa ctataacggt cctaaggtag cgagtttaaa    1200
cgacgtccta gattggttac tgggcgatga aggtttagtc ggcaaatcgt ccaacgttag    1260
tgacagcgtc agcggcaagt taatgcctat cattttgttg ataggcgcgg tcttgttttt    1320
aggtttaata ttttattttta tctacagata catgatgaaa ggaggggaagg gaggtggtgt    1380
```

-continued

```
tggcgcagca acgtcgccaa ctcccattgt tatttctatg caaaacccca caccaacaac    1440
ggcccctcga taataaaaga caaaaataat ataaaatata tgtataatta attaaattca    1500
aaatatatgt ataaggccgg ccttagtcag ttacttgtac agctcgtcca tgccgagagt    1560
gatcccggcg gcggtcacga actccagcag gaccatgtga tcgcgcttct cgttggggtc    1620
tttgctcagg gcggactggg tgctcaggta gtggttgtcg ggcagcagca cggggccgtc    1680
gccgatgggg gtgttctgct ggtagtggtc ggcgagctgc acgctgccgt cctcgatgtt    1740
gtggcggatc ttgaagttca ccttgatgcc gttcttctgc ttgtcggcca tgatatagac    1800 gttgtgggctg ttgtagttgt actccagctt gtgccccagg atgttgccgt cctccttgaa    1860
gtcgatgccc ttcagctcga tgcggttcac caggttgtcg ccctcgaact tcacctcggc    1920
gcgggtcttg tagttgccgt cgtccttgaa gaagatggtg cgctcctgga cgtagccttc    1980
gggcatggcg gacttgaaga agtcgtgctg cttcatgtgg tcggggtagc ggctgaagca    2040
ctgcacgccg taggtcaggg tggtcacgag ggtgggccag ggcacgggca gcttgccggt    2100
ggtgcagatg aacttcaggg tcagcttgcc gtaggtggca tcgccctcgc cctcgccgga    2160
cacgctgaac ttgtggccgt ttacgtcgcc gtccagctcg accaggatgg gcaccacccc    2220
ggtgaacagc tcctcgccct tgctcatccc gggtgactgg aagtacaggt tttcttgcga    2280
gtacaccaat tcattcatga gttgagtcgc ttccttaact ggctgaaaag gctcttcagg    2340
tttcaccatg aaaactttat ggcccccca caatactgag tcagcattta atcgccaacc    2400
actaacccac tgctgcgcct cctgatttgt caacaattcc atgaagtttt tcggcacgct    2460
tgtgaaataa ttgtttgtgt tggtgaaatt cgatgctgag tgtataccaa caatgaaccc    2520
atctctagtt gatactaatg gactgccaca ctgcccatcc ttggtttgaa tccaatgctt    2580
ccagaatatg ccatcagatg aagggaatgt gcaagaagtg tctgacacca tgctagacat    2640
gctcttagtt tggaagttgg ttgtcacaag acatattctc tcttcccttt gtggctctct    2700
aaatttcagc ttttgaggaa atggtgggaa atccttaggc atgcgaataa ttatcatgtc    2760
cctcccatca atgaggtgtt gttgcaaagt cgtggtgttc ttgaccttga atacaccatg    2820
tagtgattgg accaacagtg ttccattatt tcttctaaac aagtgcttgt ttgtaatgat    2880
gaagggacca aatccaatac catacaacga tgttgtgtgc ccatcagatt cattcgtcaa    2940
atgacaaatg gtgctcgata tagggttgta atcacgcggc cccttaaaca agctctctcc    3000
ggcgtagtca ggcacgtcgt aaggataagc catatttaaa tatatgcttg cttgtgtgtt    3060
ccttattgaa gccttggtgt gactgattta ctagtagcgt tgaggcgtct tatataccccg    3120 accgttatct ggcctacgtg acacaaggca cgttgttaga ttaataatct tatctttta    3180 tcttaattga taagattatt tttatctggc tgttataaaa acgggatcat gaacacggac    3240
gctcagtcga cagatctgtc gacggtttaa acactagttc gcgacctact ccggaatatt    3300
aataggttgc tgtatcgggg agttcagtcg tcgaatgcaa agcgtaaaaa atattaataa    3360
ggtaaaaatt acagctacat aaattacaca atttaaacgg atcgatgagc tccatatggc    3420
ctggagccat ccgcaatttg aaaaaggtgg cgggtccggc ggaggtagcg gcggaggttc    3480
ttggtctcac cctcagttcg agaaggatga cgatgataaa accatgggat ccgcggagaa    3540
cagcgagagt ctgggcaccg tccccgagca cgagcggatc ttgcaggaga tcgagagcac    3600
cgacaccgcc tgtgtgggggc ccaccctccg gtctgtgtat gatgaccaac caaatgcgca    3660
caagaagttt atggaaaagt tagatgcttg tatccgtaat catgacaagg aaattgaaaa    3720
```

-continued

```
gatgtgtaat tttcatcatc agggttttgt agatgctatt acagaactcc ttaaagtaag   3780
gactgatgca gaaaaactga aggtgcaagt tactgatacc aaccgaaggt ttcaagatgc   3840
tggaaaagag gtgatagtcc acacagaaga tatcattcga tgtagaattc agcagagaaa   3900
tattacaact gtagtagaaa aattgcagtt atgccttcct gtgctagaaa tgtacagtaa   3960
gctgaaagaa cagatgagtg ccaaaaggta ctattctgcc ctaaaaacta tggaacaatt   4020
agagaatgtg tactttccct gggttagtca ataccggttt tgtcagctca tgatagaaaa   4080
tcttcccaaa ctccgtgagg atattaaaga aatctccatg tctgatctca aagacttttt   4140
ggaaagtatt cgaaacatt ctgacaaaat aggtgaaaca gcaatgaaac aggcacagca   4200
tcagaaaacc ttcagtgttt ctctgcagaa acaaaataaa atgaaatttg ggaaaaatat   4260
gtatataaat cgtgatagaa ttccagagga aaggaatgaa actgtattga aacattcact   4320
tgaagaagag gatgagaatg aagaagagat cttaactgtt caggatcttg ttgattttc   4380 ccctgtttat cgatgtttgc acatttattc tgttttgggt gacgaggaaa catttgaaaa   4440
ctattatcga aaacaaagaa agaaacaagc aagactggta ttgcaacccc agtcgaatat   4500
gcatgaaaca gttgatggct atagaagata tttcactcaa attgtagggt tctttgtggt   4560
agaagatcac atttacatg tgacccaagg attagtaacc agggcataca ctgatgaact   4620
ttggaacatg gccctctcaa agataattgc tgtccttaga gctcattcat cctattgcac   4680
tgatcctgat cttgttctgg agctgaagaa tcttattgta atatttgcag atactttaca   4740
gggttatggt tttccagtga accgactttt tgaccttta tttgaaataa gagaccaata   4800
caatgaaaca ctgcttaaga aatgggctgg agttttcagg gacattttg aagaagataa   4860 ttacagcccc atccctgttg tcaatgaaga agaatataaa attgtcatca gcaaatttcc   4920
ctttcaagat ccagaccttg aaaagcagtc tttcccaaag aaattcccca tgtctcagtc   4980
agtgcctcat atttacattc aagttaaaga atttatttat gccagcctta aattttcaga   5040
gtcactacac cggagctcaa cagaaataga cgatatgctt agaaaatcaa caaatctgct   5100
gctgaccaga actttgagta gctgtttact gaaccttatt agaaaacctc atataggttt   5160
gacagagctg gtacaaatca tcataaacac aacacacctg gagcaagctt gtaaatatct   5220
tgaggacttt ataactaaca ttacaaatat ttcccaagaa actgttcata ctacaagact   5280
ttatggactt tctactttca aggatgctcg acatgcagca gaaggagaaa tatataccaa   5340
actgaatcaa aaaattgatg aatttgttca gcttgctgat tatgactgga caatgtctga   5400
gccagatgga agagctagtg gttatttaat ggaccttata aattttttga gaagcatctt   5460
tcaagtgttt actcatttgc ctgggaaagt tgctcagaca gcttgcatgt cagcctgcca   5520
gcatctgtca acatccttaa tgcagatgct actggacagt gagttaaaac aaataagcat   5580
gggagctgtt cagcagttta acttagatgt catacagtgt gaattgtttg ccagctctga   5640
gcctgtgcca ggattccagg gggataccct gcagctagca ttcattgacc tcagacaact   5700
ccttgacctg tttatggttt gggattggtc tacttaccta gctgattatg ggcagccagc   5760
ttctaagtac cttcgggtga atccaaacac agcccttact cttttggaga agatgaagga   5820
tactagcaaa aagaacaata tatttgctca gttcaggaag aatgatcgag acaaacagaa   5880
gttgatagag acagtcgtga aacagctgag aagtttggtg aatggtatgt cccagcacat   5940
gggctcgagt taactgacta aaagcttcga aaggaagctg agttggctgc tgccaccgct   6000
gagcaataac tagcataacc ccttggggcc tctaaacggg tcttgagggg ttttttgctg   6060
aaaggaggaa ctatcctcag ggtcgagaag tactagagga tcataatcag ccataccaca   6120
```

```
tttgtagagg ttttacttgc tttaaaaaac ctcccacacc tcccctgaa cctgaaacat    6180 aaaatgaatg caattgttgt tgttaacttg tttattgcag cttataatgg ttacaaataa    6240
agcaatagca tcacaaattt cacaaataaa gcatttttt cactgcattc tagttgtggt    6300
ttgtccaaac tcatcaatgt atcttatcat gtctggatct gatcactgct tgagcctagg    6360
agatccgaac cagataagtg aaatctagtt ccaaactatt ttgtcatttt taattttcgt    6420
attagcttac gacgctacac ccagttccca tctattttgt cactcttccc taaataatcc    6480
ttaaaaactc catttccacc cctcccagtt cccaactatt ttgtccgccc acagcggggc    6540 attttcttc ctgttatgtt tttaatcaaa catcctgcca actccatgtg acaaccgtc    6600 atcttcggct acttttctc tgtcacagaa tgaaaatttt tctgtcatct cttcgttatt    6660
aatgtttgta attgactgaa tatcaacgct tatttgcagc ctgaatggcg aatgggacgc    6720
gccctgtagc ggcgcattaa gcgcggcggg tgtggtggtt acgcgcagcg tgaccgctac    6780
acttgccagc gccctagcgc ccgctccttt cgctttcttc ccttcctttc tcgccacgtt    6840
cgccggcttt ccccgtcaag ctctaaatcg ggggctccct ttagggttcc gatttagtgc    6900
tttacggcac ctcgacccca aaaaacttga ttagggtgat ggttcacgta gtgggccatc    6960
gccctgatag acggtttttc gccctttgac gttggagtcc acgttcttta atagtggact    7020
cttgttccaa actggaacaa cactcaaccc tatctcggtc tattcttttg atttataagg    7080
gattttgccg atttcggcct attggttaaa aaatgagctg atttaacaaa aatttaacgc    7140
gaattttaac aaaatattaa cgtttacaat ttcaggtggc actttcggg gaaatgtgcg    7200 cggaacccct atttgtttat ttttctaaat acattcaaat atgtatccgc tcatgagaca    7260
ataaccctga taaatgcttc aataatattg aaaaaggaag agtatgagta ttcaacattt    7320
ccgtgtcgcc cttattccct tttttgcggc attttgcctt cctgtttttg ctcacccaga    7380
aacgctggtg aaagtaaaag atgctgaaga tcagttgggt gcacgagtgg gttacatcga    7440
actggatctc aacagcggta agatccttga gagttttcgc cccgaagaac gttttccaat    7500
gatgagcact tttaaagttc tgctatgtgg cgcggtatta tcccgtattg acgccgggca    7560
agagcaactc ggtcgccgca tacactattc tcagaatgac ttggttgagt actcaccagt    7620
cacagaaaag catcttacgg atggcatgac agtaagagaa ttatgcagtg ctgccataac    7680
catgagtgat aacactgcgg ccaacttact tctgacaacg atcggaggac cgaaggagct    7740
aaccgctttt ttgcacaaca tggggggatca tgtaactcgc cttgatcgtt gggaaccgga    7800
gctgaatgaa gccataccaa acgacgagcg tgacaccacg atgcctgtag caatggcaac    7860
aacgttgcgc aaactattaa ctggcgaact acttactcta gcttcccggc aacaattaat    7920
agactggatg gaggcggata aagttgcagg accacttctg cgctcggccc ttccggctgg    7980
ctggtttatt gctgataaat ctggagccgg tgagcgtggg tctcgcggta tcattgcagc    8040
actggggcca gatggtaagc cctcccgtat cgtagttatc tacacgacgg ggagtcaggc    8100
aactatggat gaacgaaata gacagatcgc tgagataggt gcctcactga ttaagcattg    8160
gtaactgtca gaccaagttt actcatatat actttagatt gatttaaaac ttcattttta    8220
atttaaaagg atctaggtga agatcctttt tgataatctc atgaccaaaa tcccttaacg    8280
tgagttttcg ttccactgag cgtcagaccg cggggcatga ctaacatgag aattacaact    8340
tatatcgtat ggggctgact tcaggtgcta catttgaaga gataaattgc actgaaatct    8400
agaaatattt tatctgatta ataagatgat cttcttgaga tcgttttggt ctgcgcgtaa    8460
```

```
tctcttgctc tgaaaacgga aaaaaccgcc ttgcagggcg gttttttcgaa ggttctctga      8520 gctaccaact ctttgaaccg aggtaactgg cttggaggag cgcagtcacc aaaacttgtc      8580
ctttcagttt agccttaacc ggcgcatgac ttcaagacta actcctctaa atcaattacc      8640
agtggctgct gccagtggtg cttttgcatg tctttccggg ttggactcaa gacgatagtt      8700
accggataag gcgcagcggt cggactgaac gggggggttcg tgcatacagt ccagcttgga      8760
gcgaactgcc tacccggaac tgagtgtcag gcgtggaatg agacaaacgc ggccataaca      8820
gcggaatgac accggtaaac cgaaaggcag gaacaggaga gcgcacgagg gagccgccag      8880
gggaaacgcc tggtatcttt atagtcctgt cgggtttcgc caccactgat ttgagcgtca      8940
gatttcgtga tgcttgtcag ggggcggag cctatggaaa aacggctttg ccgcggccct      9000
ctcacttccc tgttaagtat cttcctggca tcttccagga aatctccgcc ccgttcgtaa      9060
gccatttccg ctcgccgcag tcgaacgacc gagcgtagcg agtcagtgag cgaggaagcg      9120
gaatatatcc tgtatcacat attctgctga cgcaccggtg cagcctttt tctcctgcca      9180 catgaagcac ttcactgaca ccctcatcag tgccaacata gtaagccagt atacactccg      9240
ctagcgctga tgtccggcgg tgcttttgcc gttacgcacc accccgtcag tagctgaaca      9300
ggagggacag ctgatagaaa cagaagccag ttctttcctg cgttatcccc tgattctgtg      9360
gataaccgta ttaccgcctt tgagtgagct gataccgctc gccgcagccg aacgaccgag      9420
cgcagcgagt cagtgagcga ggaagcggaa gagcgcctga tgcggtattt tctccttacg      9480
catctgtgcg gtatttcaca ccgcatagac cagccgcgta acctggcaaa atcggttacg      9540
gttgagtaat aaatg                                                      9555
```

```
<210> SEQ ID NO 13
<211> LENGTH: 9208
<212> TYPE: DNA
<213> ORGANISM: Artificial Sequence
<220> FEATURE:
<223> OTHER INFORMATION: Synthesized

<400> SEQUENCE: 13
gatgccctgc gtaagcgggt gtgggcggac aataaagtct taaactgaac aaaatagatc        60
taaactatga caataaagtc ttaaactaga cagaatagtt gtaaactgaa atcagtccag       120
ttatgctgtg aaaaagcata ctggactttt gttatggcta aagcaaactc ttcattttct       180
gaagtgcaaa ttgcccgtcg tattaaagag gggcgtggcc aagggcatgt aaagactata       240
ttcgcggcgt tgtgacaatt taccgaacaa ctccgcggcc gggaagccga tctcggcttg       300
aacgaattgt taggtggcgg tacttgggtc gatatcaaag tgcatcactt cttcccgtat       360
gcccaacttt gtatagagag ccactgcggg atcgtcaccg taatctgctt gcacgtagat       420
cacataagca ccaagcgcgt tggcctcatg cttgaggaga ttgatgagcg cggtggcaat       480
gccctgcctc cggtgctcgc cggagactgc gagatcatag atatagatct cactacgcgg       540
ctgctcaaac ttgggcagaa cgtaagccgc gagagcgcca acaaccgctt cttggtcgaa       600
ggcagcaagc gcgatgaatg tcttactacg gagcaagttc ccgaggtaat cggagtccgg       660
ctgatgttgg gagtaggtgg ctacgtctcc gaactcacga ccgaaaagat caagagcagc       720
ccgcatggat ttgacttggt cagggccgag cctacatgtg cgaatgatgc ccatacttga       780
gccacctaac tttgtttttag ggcgactgcc ctgctgcgta acatcgttgc tgctgcgtaa       840
catcgttgct gctccataac atcaaacatc gacccacggc gtaacgcgct tgctgcttgg       900
atgcccgagg catagactgt acaaaaaaac agtcataaca agccatgaaa accgccactg       960
```

```
cgccgttacc accgctgcgt tcggtcaagg ttctggacca gttgcgtgag cgcatacgct   1020
acttgcatta cagtttacga accgaacagg cttatgtcaa ctgggttcgt gccttcatcc   1080
gtttccacgg tgtgcgtcac ccggcaacct tgggcagcag cgaagtcgcc ataacttcgt   1140
atagcataca ttatacgaag ttatctgtaa ctataacggt cctaaggtag cgagtttaaa   1200
cgacgtccta gattggttac tgggcgatga aggtttagtc ggcaaatcgt ccaacgttag   1260
tgacagcgtc agcggcaagt taatgcctat cattttgttg ataggcgcgg tcttgttttt   1320
aggtttaata ttttatttta tctacagata catgatgaaa ggagggaagg gaggtggtgt   1380
tggcgcagca acgtcgccaa ctcccattgt tatttctatg caaaacccca caccaacaac   1440
ggcccctcga taataaaaga caaaaataat ataaaatata tgtataatta attaaattca   1500
aaatatatgt ataaggccgg ccttagtcag ttacttgtac agctcgtcca tgccgagagt   1560
gatcccggcg gcggtcacga actccagcag gaccatgtga tcgcgcttct cgttggggtc   1620
tttgctcagg gcggactggg tgctcaggta gtggttgtcg ggcagcagca cggggccgtc   1680
gccgatgggg gtgttctgct ggtagtggtc ggcgagctgc acgctgccgt cctcgatgtt   1740
gtggcggatc ttgaagttca ccttgatgcc gttcttctgc ttgtcggcca tgatatagac   1800
gttgtggctg ttgtagttgt actccagctt gtgccccagg atgttgccgt cctccttgaa   1860
gtcgatgccc ttcagctcga tgcggttcac cagggtgtcg ccctcgaact tcacctcggc   1920
gcgggtcttg tagttgccgt cgtccttgaa gaagatggtg cgctcctgga cgtagccttc   1980
gggcatggcg gacttgaaga agtcgtgctg cttcatgtgg tcggggtagc ggctgaagca   2040
ctgcacgccg taggtcaggg tggtcacgag ggtgggccag ggcacgggca gcttgccggt   2100
ggtgcagatg aacttcaggg tcagcttgcc gtaggtggca tcgccctcgc cctcgccgga   2160
cacgctgaac ttgtggccgt ttacgtcgcc gtccagctcg accaggatgg gcaccacccc   2220
ggtgaacagc tcctcgccct tgctcatccc gggtgactgg aagtacaggt tttcttgcga   2280
gtacaccaat tcattcatga gttgagtcgc ttccttaact ggctgaaaag gctcttcagg   2340
tttcaccatg aaaactttat ggccccccca caatactgag tcagcattta atcgccaacc   2400
actaacccac tgctgcgcct cctgatttgt caacaattcc atgaagtttt tcggcacgct   2460
tgtgaaataa ttgtttgtgt tggtgaaatt cgatgctgag tgtataccaa caatgaaccc   2520
atctctagtt gatactaatg gactgccaca ctgcccatcc ttggtttgaa tccaatgctt   2580
ccagaatatg ccatcagatg aagggaatgt gcaagaagtg tctgacacca tgctagacat   2640
gctcttagtt tggaagttgg ttgtcacaag acatattctc tcttcccttt gtggctctct   2700
aaatttcagc ttttgaggaa atggtgggaa atccttaggc atgcgaataa ttatcatgtc   2760
cctcccatca atgaggtgtt gttgcaaagt cgtggtgttc ttgaccttga atacaccatg   2820
tagtgattgg accaacagtg ttccattatt tcttctaaac aagtgcttgt ttgtaatgat   2880
gaagggacca aatccaatac catacaacga tgttgtgtgc ccatcagatt cattcgtcaa   2940
atgacaaatg gtgctcgata tagggttgta atcacgcggc cccttaaaca agctctctcc   3000
ggcgtagtca ggcacgtcgt aaggataagc catatttaaa tatatgcttg cttgtgtgtt   3060
ccttattgaa gccttggtgt gactgattta ctagtagcgt tgaggcgtct tatatacccg   3120
accgttatct ggcctacgtg acacaaggca cgttgttaga ttaataatct tatctttta   3180 tcttaattga taagattatt tttatctggc tgttataaaa acgggatcat gaacacggac   3240
gctcagtcga cagatctgtc gacggtttaa acactagttc gcgacctact ccggaatatt   3300
```

-continued

```
aataggttgc tgatatcggg agttcagtcg tcgaatgcaa agcgtaaaaa atattaataa   3360
ggtaaaaatt acagctacat aaattacaca atttaaacgg atcgatgagc tccatatggc   3420
ctggagccat ccgcaatttg aaaaaggtgg cgggtccggc ggaggtagcg gcggaggttc   3480
ttggtctcac cctcagttcg agaaggatga cgatgataaa accatgggat ccctaggtac   3540
catgattccc ccacaggagg catccgctcg acggcgggag attgaggaca agctgaagca   3600
ggaggaggag actctgtcct tcatccgaga cagcctggag aagagcgacc agctcactaa   3660
gaacatggtg tctatcttat catcctttga gagccgcctt atgaagctgg agaactccat   3720
catccctgtg cacaagcaga cggagaatct gcagcggctg caggagaatg ttgagaagac   3780
gctgtcctgc ctggaccatg tcatcagcta ctaccatgtg gccagtgaca ctgagaagat   3840
catcagagag ggccccacag gtaggctgga agagtacctg ggaagcatgg ccaagattca   3900
gaaggcagtg gagtatttcc aggacaacag cccagacagc ccggaactca acaaagtgaa   3960
actgctcttt gagcgcggga aggaggccct ggagtccgaa tttcgcagcc tgatgacgcg   4020
gcacagtaag gtcgtctcgc ccgtgctcat cttggatctg atcagtggtg acgatgatct   4080
ggaggcccag gaggacgtga ccctggagca cctgcccgag agcgtgctcc aggatgtcat   4140
tcgcatctcc cgctggctgg tggaatatgg ccgcaaccaa gatttcatga cgtctacta   4200 ccagatacgc tccagccagc tggaccgctc catcaaagga ctgaaggagc atttccataa   4260
gagcagttct tcctctgggg ttccctactc ccctgctatc cccaacaaga ggaaagacac   4320
acctaccaag aagccagtca agcggccagg gacgatccgt aaggctcaga accttctgaa   4380
acagtattcc cagcatggtc tagatgggaa aaaggggggc tctaacctca ttcctctgga   4440
agggagagat gacatgctgg acgtggagac cgatgcctac atccactgcg tcagtgcctt   4500
cgtcaagctg gcgcagagcg agtaccagct gctggccgac atcatccccg agcaccacca   4560
gaagaagacc ttcgactccc tgatacagga tgccctggat gggctgatgc ttgaaggga   4620 gaacatcgtg tctgctgccc ggaaggccat tgtgcgacac gacttctcca cggtgctcac   4680
cgtcttcccc atcctgcgac acctcaagca gaccaagcct gagtttgacc aggtgctcca   4740
gggcacggct gccagcacaa agaacaagct gcctggcctc atcacatcca tggagaccat   4800
cggtgccaaa gcgctggagg acttcgcaga caacatcaag aatgacccgg acaaggagta   4860
caacatgccg aaggacggca ccgtacacga gctcaccagc aatgccatcc tcttcctgca   4920
gcagcttttg gacttccagg agacggcagg cgccatgctg gcctcccaag agaccagctc   4980
ttcggccacc agctacagct ctgagttcag caagcggctg ctaagcacct atatctgtaa   5040
agtgctgggc aacctgcagt tgaacttgct gagcaagtcc aaggtgtacg aggacccagc   5100
tctgagcgcc atcttcctgc acaacaacta caattacatc ctcaagtccc tggagaagtc   5160
tgaactgatc cagctggtgg cagtgacaca gaagactgct gagcgctcct accgggagca   5220
cattgagcag cagatccaga cctaccagcg cagctggtta aaggtgactg attacatcgc   5280
agagaagaat ctacctgtgt ccagcccggg agtcaagctc cgggacaagg agcggcagat   5340
tatcaaggag cgttttaagg gcttcaatga tggcctcgaa gaactgtgca aaatccagaa   5400
ggcctgggct attccagaca cagagcagag ggacaggatt cgccaggccc agaagaccat   5460
tgtcaaggag acctacgggg cctttctaca gaagtttggc agcgtgccct tcaccaagaa   5520
cccggagaag tacatcaagt acggggtgga gcaggtgggc gacatgatcg atcgcctttt   5580
cgacacctct gcctaactcg agttaactga ctaaaagctt cgaaaggaag ctgagttggc   5640
tgctgccacc gctgagcaat aactagcata accccttggg gcctctaaac gggtcttgag   5700
```

-continued

```
gggttttttg ctgaaaggag gaactatcct cagggtcgag aagtactaga ggatcataat   5760
cagccatacc acatttgtag aggttttact tgctttaaaa aacctcccac acctcccct    5820 gaacctgaaa cataaaatga atgcaattgt tgttgttaac ttgtttattg cagcttataa   5880
tggttacaaa taaagcaata gcatcacaaa tttcacaaat aaagcatttt tttcactgca   5940
ttctagttgt ggtttgtcca aactcatcaa tgtatcttat catgtctgga tctgatcact   6000
gcttgagcct aggagatccg aaccagataa gtgaaatcta gttccaaact attttgtcat   6060
ttttaatttt cgtattagct tacgacgcta cacccagttc ccatctattt tgtcactctt   6120
ccctaaataa tccttaaaaa ctccatttcc acccctccca gttcccaact attttgtccg   6180
cccacagcgg ggcattttc ttcctgttat gttttaatc aaacatcctg ccaactccat      6240
gtgacaaacc gtcatcttcg ctacttttt ctctgtcaca gaatgaaaat ttttctgtca     6300
tctcttcgtt attaatgttt gtaattgact gaatatcaac gcttatttgc agcctgaatg   6360
gcgaatggga cgcgccctgt agcggcgcat taagcgcggc gggtgtggtg gttacgcgca   6420
gcgtgaccgc tacacttgcc agcgccctag cgcccgctcc tttcgctttc ttcccttcct   6480
ttctcgccac gttcgccggc tttccccgtc aagctctaaa tcggggggctc cctttagggt    6540 tccgatttag tgctttacgg cacctcgacc ccaaaaaact tgattagggt gatggttcac   6600
gtagtgggcc atcgccctga tagacggttt ttcgcccttt gacgttggag tccacgttct   6660
ttaatagtgg actcttgttc caaactggaa caacactcaa ccctatctcg gtctattctt   6720
ttgatttata agggattttg ccgatttcgg cctattggtt aaaaaatgag ctgatttaac   6780
aaaaatttaa cgcgaatttt aacaaaatat taacgtttac aatttcaggt ggcacttttc   6840
ggggaaatgt gcgcggaacc cctatttgtt tattttcta aatacattca aatatgtatc     6900
cgctcatgag acaataaccc tgataaatgc ttcaataata ttgaaaaagg aagagtatga   6960
gtattcaaca tttccgtgtc gcccttattc ccttttttgc ggcattttgc cttcctgttt   7020
ttgctcaccc agaaacgctg gtgaaagtaa aagatgctga agatcagttg ggtgcacgag   7080
tgggttacat cgaactggat ctcaacagcg gtaagatcct tgagagtttt cgccccgaag   7140
aacgttttcc aatgatgagc actttttaaag ttctgctatg tggcgcggta ttatcccgta    7200
ttgacgccgg gcaagagcaa ctcggtcgcc gcatacacta ttctcagaat gacttggttg   7260
agtactcacc agtcacagaa aagcatctta cggatggcat gacagtaaga gaattatgca   7320
gtgctgccat aaccatgagt gataacactg cggccaactt acttctgaca acgatcggag   7380
gaccgaagga gctaaccgct tttttgcaca acatggggga tcatgtaact cgccttgatc   7440
gttgggaacc ggagctgaat gaagccatac caaacgacga gcgtgacacc acgatgcctg   7500
tagcaatggc aacaacgttg cgcaaactat taactggcga actacttact ctagcttccc   7560
ggcaacaatt aatagactgg atggaggcgg ataaagttgc aggaccactt ctgcgctcgg   7620
cccttccggc tggctggttt attgctgata atctggagc cggtgagcgt gggtctcgcg     7680
gtatcattgc agcactgggg ccagatggta agccctcccg tatcgtagtt atctacacga   7740
cggggagtca ggcaactatg gatgaacgaa atagacagat cgctgagata ggtgcctcac   7800
tgattaagca ttggtaactg tcagaccaag tttactcata tatactttag attgatttaa   7860
aacttcattt ttaatttaaa aggatctagg tgaagatcct ttttgataat ctcatgacca   7920
aaatccctta acgtgagttt tcgttccact gagcgtcaga ccgcggggca tgactaacat   7980
gagaattaca acttatatcg tatggggctg acttcaggtg ctacatttga agagataaat   8040
```

-continued

```
tgcactgaaa tctagaaata ttttatctga ttaataagat gatcttcttg agatcgtttt    8100
ggtctgcgcg taatctcttg ctctgaaaac ggaaaaaacc gccttgcagg gcggtttttc    8160
gaaggttctc tgagctacca actctttgaa ccgaggtaac tggcttggag gagcgcagtc    8220
accaaaactt gtcctttcag tttagcctta accggcgcat gacttcaaga ctaactcctc    8280
taaatcaatt accagtggct gctgccagtg gtgctttgc atgtctttcc gggttggact     8340
caagacgata gttaccggat aaggcgcagc ggtcggactg aacggggggt tcgtgcatac    8400
agtccagctt ggagcgaact gcctacccgg aactgagtgt caggcgtgga atgagacaaa    8460
cgcggccata acagcggaat gacaccggta aaccgaaagg caggaacagg agagcgcacg    8520
agggagccgc caggggaaac gcctggtatc tttatagtcc tgtcgggttt cgccaccact    8580
gatttgagcg tcagatttcg tgatgcttgt caggggggcg gagcctatgg aaaaacggct    8640
ttgccgcggc cctctcactt ccctgttaag tatcttcctg gcatcttcca ggaaatctcc    8700
gccccgttcg taagccattt ccgctcgccg cagtcgaacg accgagcgta gcgagtcagt    8760
gagcgaggaa gcggaatata tcctgtatca catattctgc tgacgcaccg gtgcagcctt    8820
ttttctcctg ccacatgaag cacttcactg acaccctcat cagtgccaac atagtaagcc    8880
agtatacact ccgctagcgc tgatgtccgg cggtgctttt gccgttacgc accacccgt      8940 cagtagctga acaggaggga cagctgatag aaacagaagc cagttctttc ctgcgttatc    9000
ccctgattct gtggataacc gtattaccgc ctttgagtga gctgataccg ctcgccgcag    9060
ccgaacgacc gagcgcagcg agtcagtgag cgaggaagcg gaagagcgcc tgatgcggta    9120
ttttctcctt acgcatctgt gcggtatttc acaccgcata gaccagccgc gtaacctggc    9180
aaaatcggtt acggttgagt aataaatg                                       9208
```

```
<210> SEQ ID NO 14
<211> LENGTH: 9364
<212> TYPE: DNA
<213> ORGANISM: Artificial Sequence
<220> FEATURE:
<223> OTHER INFORMATION: Synthesized

<400> SEQUENCE: 14
```

```
gatgccctgc gtaagcgggt gtgggcggac aataaagtct taaactgaac aaaatagatc      60
taaactatga caataaagtc ttaaactaga cagaatagtt gtaaactgaa atcagtccag     120
ttatgctgtg aaaaagcata ctggactttt gttatggcta aagcaaactc ttcattttct     180
gaagtgcaaa ttgcccgtcg tattaaagag gggcgtggcc aagggcatgt aaagactata     240
ttcgcggcgt tgtgacaatt taccgaacaa ctccgcggcc gggaagccga tctcggcttg     300
aacgaattgt taggtggcgg tacttgggtc gatatcaaag tgcatcactt cttcccgtat     360
gcccaacttt gtatagagag ccactgcggg atcgtcaccg taatctgctt gcacgtagat     420
cacataagca ccaagcgcgt tggcctcatg cttgaggaga ttgatgagcg cggtggcaat     480
gccctgcctc cggtgctcgc cggagactgc gagatcatag atatagatct cactacgcgg     540
ctgctcaaac ttgggcagaa cgtaagccgc gagagcgcca acaaccgctt cttggtcgaa     600
ggcagcaagc gcgatgaatg tcttactacg gagcaagttc ccgaggtaat cggagtccgg     660
ctgatgttgg gagtaggtgg ctacgtctcc gaactcacga ccgaaaagat caagagcagc     720
ccgcatggat ttgacttggt cagggccgag cctacatgtg cgaatgatgc ccatacttga     780
gccacctaac tttgttttag gcgactgccc tgctgcgta acatcgttgc tgctgcgtaa      840
catcgttgct gctccataac atcaaacatc gacccacggc gtaacgcgct tgctgcttgg     900
```

```
atgcccgagg catagactgt acaaaaaaac agtcataaca agccatgaaa accgccactg      960
cgccgttacc accgctgcgt tcggtcaagg ttctggacca gttgcgtgag cgcatacgct     1020
acttgcatta cagtttacga accgaacagg cttatgtcaa ctgggttcgt gccttcatcc     1080
gtttccacgg tgtgcgtcac ccggcaacct tgggcagcag cgaagtcgcc ataacttcgt     1140
atagcataca ttatacgaag ttatctgtaa ctataacggt cctaaggtag cgagtttaaa     1200
cgacgtccta gattggttac tgggcgatga aggtttagtc ggcaaatcgt ccaacgttag     1260
tgacagcgtc agcggcaagt taatgcctat cattttgttg ataggcgcgg tcttgttttt     1320
aggtttaata ttttatttta tctacagata catgatgaaa ggagggaagg gaggtggtgt     1380
tggcgcagca acgtcgccaa ctcccattgt tatttctatg caaaacccca caccaacaac     1440
ggcccctcga taataaaaga caaaaataat ataaaatata tgtataatta attaaattca     1500
aaatatatgt ataaggccgg ccttagtcag ttacttgtac agctcgtcca tgccgagagt     1560
gatcccggcg gcggtcacga actccagcag gaccatgtga tcgcgcttct cgttggggtc     1620
tttgctcagg gcggactggg tgctcaggta gtggttgtcg ggcagcagca cggggccgtc     1680
gccgatgggg gtgttctgct ggtagtggtc ggcgagctgc acgctgccgt cctcgatgtt     1740
gtggcggatc ttgaagttca ccttgatgcc gttcttctgc ttgtcggcca tgatatagac     1800
gttgtggctg ttgtagttgt actccagctt gtgccccagg atgttgccgt cctccttgaa     1860
gtcgatgccc ttcagctcga tgcggttcac cagggtgtcg ccctcgaact tcacctcggc     1920
gcgggtcttg tagttgccgt cgtccttgaa gaagatggtg cgctcctgga cgtagccttc     1980
gggcatggcg gacttgaaga agtcgtgctg cttcatgtgg tcggggtagc ggctgaagca     2040
ctgcacgccg taggtcaggg tggtcacgag ggtgggccag ggcacgggca gcttgccggt     2100
ggtgcagatg aacttcaggg tcagcttgcc gtaggtggca tcgccctcgc cctcgccgga     2160
cacgctgaac ttgtggccgt ttacgtcgcc gtccagctcg accaggatgg gcaccacccc     2220
ggtgaacagc tcctcgccct tgctcatccc gggtgactgg aagtacaggt tttcttgcga     2280
gtacaccaat tcattcatga gttgagtcgc ttccttaact ggctgaaaag gctcttcagg     2340
tttcaccatg aaaactttat ggcccccca caatactgag tcagcattta atcgccaacc       2400
actaacccac tgctgcgcct cctgatttgt caacaattcc atgaagtttt tcggcacgct     2460
tgtgaaataa ttgtttgtgt tggtgaaatt cgatgctgag tgtataccaa caatgaaccc     2520
atctctagtt gatactaatg gactgccaca ctgcccatcc ttggtttgaa tccaatgctt     2580
ccagaatatg ccatcagatg aagggaatgt gcaagaagtg tctgacacca tgctagacat     2640
gctcttagtt tggaagttgg ttgtcacaag acatattctc tcttcccttt gtggctctct     2700
aaatttcagc ttttgaggaa atggtgggaa atccttaggc atgcgaataa ttatcatgtc     2760
cctcccatca atgaggtgtt gttgcaaagt cgtggtgttc ttgaccttga atacaccatg     2820
tagtgattgg accaacagtg ttccattatt tcttctaaac aagtgcttgt ttgtaatgat     2880
gaagggacca aatccaatac catacaacga tgttgtgtgc ccatcagatt cattcgtcaa     2940
atgacaaatg gtgctcgata tagggttgta atcacgcggc cccttaaaca agctctctcc     3000
ggcgtagtca ggcacgtcgt aaggataagc catatttaaa tatatgcttg cttgtgtgtt     3060
ccttattgaa gccttggtgt gactgattta ctagtagcgt tgaggcgtct tatatacccg     3120
accgttatct ggcctacgtg acacaaggca cgttgttaga ttaataatct tatctttta      3180 tcttaattga taagattatt tttatctggc tgttataaaa acgggatcat gaacacggac     3240
```

-continued

```
gctcagtcga cagatctgtc gacggtttaa acactagttc gcgacctact ccggaatatt   3300
aataggttgc tgatatcggg agttcagtcg tcgaatgcaa agcgtaaaaa atattaataa   3360
ggtaaaaatt acagctacat aaattacaca atttaaacgg atcgatgagc tccatatggc   3420
ctggagccat ccgcaatttg aaaaaggtgg cgggtccggc ggaggtagcg gcggaggttc   3480
ttggtctcac cctcagttcg agaaggatga cgatgataaa accatgggat ccctaggtac   3540
ccttaagatg gcgatggcga tgtcggacag tggggcgagc cgcctgcgtc ggcagctgga   3600
gtcagggggt tttgaggcgc ggctgtacgt gaagcagctc tcgcagcagt cggatgggga   3660
ccgggacctc caggagcacc ggcagcgcat ccaggcgctg gcggaggaga cggcgcagaa   3720
cctgaagcgc aacgtctacc agaactaccg gcagttcata gagacggccc gcgagatctc   3780
ctacctggag agcgagatgt accagctcag ccatttgctg accgagcaga aaagcagcct   3840
ggagagcatc ccgcttacgt tgctgcctgc cgctgctgcc gccggagccg ccgccgcctc   3900
tggaggggag gagggagtcg gtgggcgggg gggccgagac cacctccgag gccaggccgg   3960 cttttttctcc accccggggg gtgcctcccg cgacggctcc ggtccaggcg aggaaggaaa   4020
gcagcgcact ctcaccaccc tgcttgagaa ggtggaaggc tgcaggcatc tgctggagac   4080
gccgggacag tacttggtgt acaatgggga cctagtggaa tacgatgcgg accacatggc   4140
ccaactgcag cgggtgcacg gctttctcat gaacgattgc ttgttggtgg ctacctggct   4200
gcctcagcgg cgtgggatgt atcgctacaa cgctctctat tccctagatg gtttggccgt   4260
agtcaatgtc aaggacaacc cgcccatgaa ggacatgttc aagctgctta tgttccccga   4320
gagccgtatt ttccaggccg aaaatgctaa aatcaaacga gagtggctgg aagtgctgga   4380
ggacaccaag agggccctca gtgagaaaag gcgaagggag caggaggagg cagcggcccc   4440
tcgagggcca ccccaagtga cttccaaggc cactaaccca tttgaggatg acgaagaaga   4500
agaaccagct gttcctgagg tagaggaaga gaaggtggac ctctccatgg aatggatcca   4560
ggagttacct gaagacctgg atgtctgcat tgcgcagaga gactttgaag gggcggttga   4620
cctgctggat aaattgaacc attacctgga agataaacct agcccacctc ctgtaaaaga   4680
actaagggcc aaagtggagg agcgagttcg acagctcact gaggtgctag ttttcgaact   4740
ctccccagat cgttccctga gaggtggtcc gaaggctact cgcagagcag tttcgcaact   4800
gatccggctg ggccagtgca cgaaggcctg tgagctattt ttgagaaaca gggcagccgc   4860
tgttcatact gcaattcgtc agcttcgcat cgaaggtgcc actttactct atattcataa   4920
gctgtgccat gtcttctta ccagccttct cgagactgca agagaatttg agatcgattt   4980
tgcaggcact gacagcggct gctactctgc ctttgtggtc tgggcaagat cagccatggg   5040
catgttcgtg gatgctttta gcaagcaggt gtttgatagt aaggagagcc tctctacagc   5100
agctgagtgt gtaaaagtgg ctaaggagca ttgccagcaa ctgggtgata tcggactgga   5160
tctcaccttc atcatccatg cccttctggt gaaagacatc caaggggcct tgcacagtta   5220
caaagaaatc atcattgaag ccactaaaca tcgcaactct gaagagatgt ggaggaggat   5280
gaacttgatg acgccagaag ccctgggtaa gctcaaagaa gagatgaaaa gttgtgggt   5340 aagtaacttt gagcagtaca caggggatga ctgctgggtg aacctaagtt acacagtggt   5400
tgctttcacc aaacagacca tgggcttctt ggaagaggcc ctgaagctgt atttcccaga   5460
gctgcacatg gtacttttgg agagcctggt ggaaatcatt ttggttgctg ttcagcatgt   5520
ggattatagt cttcgatgtg agcaggatcc agagaagaaa gctttatca gacagaatgc   5580 atccttttta tatgaaacag tcctccctgt ggtggagaaa aggtttgaag aaggtgtggg   5640
```

```
gaaacctgcc aagcaactcc aagatctgag gaatgcatct agacttattc gtgtgaatcc    5700
tgaaagtaca acatcagtgg tctaagaatt ccttaagcgg aggcctgcag ggctcgagtt    5760
aactgactaa aagcttcgaa aggaagctga gttggctgct gccaccgctg agcaataact    5820
agcataaccc cttggggcct ctaaacgggt cttgaggggg tttttgctga aaggaggaac    5880
tatcctcagg gtcgagaagt actagaggat cataatcagc cataccacat ttgtagaggt    5940
tttacttgct ttaaaaaacc tcccacacct cccctgaac ctgaaacata aaatgaatgc    6000
aattgttgtt gttaacttgt ttattgcagc ttataatggt tacaaataaa gcaatagcat    6060
cacaaatttc acaaataaag catttttttc actgcattct agttgtggtt tgtccaaact    6120
catcaatgta tcttatcatg tctggatctg atcactgctt gagcctagga gatccgaacc    6180
agataagtga aatctagttc caaactattt tgtcattttt aattttcgta ttagcttacg    6240
acgctacacc cagttcccat ctattttgtc actcttccct aaataatcct taaaaactcc    6300
atttccaccc ctcccagttc ccaactattt tgtccgccca cagcggggca ttttttcttcc    6360 tgttatgttt ttaatcaaac atcctgccaa ctccatgtga caaaccgtca tcttcggcta    6420 cttttttctct gtcacagaat gaaaattttt ctgtcatctc ttcgttatta atgtttgtaa    6480
ttgactgaat atcaacgctt atttgcagcc tgaatggcga atgggacgcg ccctgtagcg    6540
gcgcattaag cgcggcgggt gtggtggtta cgcgcagcgt gaccgctaca cttgccagcg    6600
ccctagcgcc cgctcctttc gctttcttcc cttcctttct cgccacgttc gccggctttc    6660
cccgtcaagc tctaaatcgg gggctccctt tagggttccg atttagtgct ttacggcacc    6720
tcgaccccaa aaaacttgat tagggtgatg gttcacgtag tgggccatcg ccctgataga    6780
cggtttttcg ccctttgacg ttggagtcca cgttctttaa tagtggactc ttgttccaaa    6840
ctggaacaac actcaaccct atctcggtct attctttga tttataaggg attttgccga    6900
tttcggccta ttggttaaaa aatgagctga tttaacaaaa atttaacgcg aattttaaca    6960
aaatattaac gtttacaatt tcaggtggca cttttcgggg aaatgtgcgc ggaacccta    7020 tttgtttatt tttctaaata cattcaaata tgtatccgct catgagacaa taaccctgat    7080
aaatgcttca ataatattga aaaaggaaga gtatgagtat tcaacatttc cgtgtcgccc    7140
ttattcccct ttttgcggca tttttgcctt cctgtttttgc tcacccagaa acgctggtga    7200
aagtaaaaga tgctgaagat cagttgggtg cacgagtggg ttacatcgaa ctggatctca    7260
acagcggtaa gatccttgag agttttcgcc ccgaagaacg ttttccaatg atgagcactt    7320
ttaaagttct gctatgtggc gcggtattat cccgtattga cgccgggcaa gagcaactcg    7380
gtcgccgcat acactattct cagaatgact tggttgagta ctcaccagtc acagaaaagc    7440
atcttacgga tggcatgaca gtaagagaat tatgcagtgc tgccataacc atgagtgata    7500
acactgcggc caacttactt ctgacaacga tcggaggacc gaaggagcta accgcttttt    7560
tgcacaacat gggggatcat gtaactcgcc ttgatcgttg ggaaccggag ctgaatgaag    7620
ccataccaaa cgacgagcgt gacaccacga tgcctgtagc aatggcaaca acgttgcgca    7680
aactattaac tggcgaacta cttactctag cttcccggca acaattaata gactggatgg    7740
aggcggataa agttgcagga ccacttctgc gctcggccct tccggctggc tggtttattg    7800
ctgataaatc tggagccggt gagcgtgggt ctcgcggtat cattgcagca ctggggccag    7860
atggtaagcc ctcccgtatc gtagttatct acacgacggg gagtcaggca actatggatg    7920
aacgaaatag acagatcgct gagataggtg cctcactgat taagcattgg taactgtcag    7980
```

-continued

```
accaagttta ctcatatata ctttagattg atttaaaact tcatttttaa tttaaaagga    8040
tctaggtgaa gatccttttt gataatctca tgaccaaaat cccttaacgt gagttttcgt    8100
tccactgagc gtcagaccgc ggggcatgac taacatgaga attacaactt atatcgtatg    8160
gggctgactt caggtgctac atttgaagag ataaattgca ctgaaatcta gaaatatttt    8220
atctgattaa taagatgatc ttcttgagat cgttttggtc tgcgcgtaat ctcttgctct    8280
gaaaacggaa aaaaccgcct tgcagggcgg tttttcgaag gttctctgag ctaccaactc    8340
tttgaaccga ggtaactggc ttggaggagc gcagtcacca aaacttgtcc tttcagttta    8400
gccttaaccg gcgcatgact tcaagactaa ctcctctaaa tcaattacca gtggctgctg    8460
ccagtggtgc ttttgcatgt ctttccgggt tggactcaag acgatagtta ccggataagg    8520
cgcagcggtc ggactgaacg gggggttcgt gcatacagtc cagcttggag cgaactgcct    8580
acccggaact gagtgtcagg cgtggaatga gacaaacgcg gccataacag cggaatgaca    8640
ccggtaaacc gaaaggcagg aacaggagag cgcacgaggg agccgccagg ggaaacgcct    8700
ggtatcttta tagtcctgtc gggtttcgcc accactgatt tgagcgtcag atttcgtgat    8760
gcttgtcagg ggggcggagc ctatggaaaa acggctttgc cgcggccctc tcacttccct    8820
gttaagtatc ttcctggcat cttccaggaa atctccgccc cgttcgtaag ccatttccgc    8880
tcgccgcagt cgaacgaccg agcgtagcga gtcagtgagc gaggaagcgg aatatatcct    8940
gtatcacata ttctgctgac gcaccggtgc agcctttttt ctcctgccac atgaagcact    9000
tcactgacac cctcatcagt gccaacatag taagccagta tacactccgc tagcgctgat    9060
gtccggcggt gcttttgccg ttacgcacca ccccgtcagt agctgaacag gagggacagc    9120
tgatagaaac agaagccagt tctttcctgc gttatcccct gattctgtgg ataaccgtat    9180
taccgccttt gagtgagctg ataccgctcg ccgcagccga acgaccgagc gcagcgagtc    9240
agtgagcgag gaagcggaag agcgcctgat gcggtatttt ctccttacgc atctgtgcgg    9300
tatttcacac cgcatagacc agccgcgtaa cctggcaaaa tcggttacgg ttgagtaata    9360
aatg                                                                 9364
```

<210> SEQ ID NO 15
<211> LENGTH: 11728
<212> TYPE: DNA
<213> ORGANISM: Artificial Sequence
<220> FEATURE:
<223> OTHER INFORMATION: Synthesized

<400> SEQUENCE: 15

```
gatgccctgc gtaagcgggt gtgggcggac aataaagtct taaactgaac aaaatagatc      60
taaactatga caataaagtc ttaaactaga cagaatagtt gtaaactgaa atcagtccag     120
ttatgctgtg aaaaagcata ctggactttt gttatggcta aagcaaactc ttcattttct     180
gaagtgcaaa ttgcccgtcg tattaaagag gggcgtggcc aagggcatgt aaagactata     240
ttcgcggcgt tgtgacaatt taccgaacaa ctccgcggcc gggaagccga tctcggcttg     300
aacgaattgt taggtggcgg tacttgggtc gatatcaaag tgcatcactt cttcccgtat     360
gcccaacttt gtatagagag ccactgcggg atcgtcaccg taatctgctt gcacgtagat     420
cacataagca ccaagcgcgt tggcctcatg cttgaggaga ttgatgagcg cggtggcaat     480
gccctgcctc cggtgctcgc cggagactgc gagatcatag atatagatct cactacgcgg     540
ctgctcaaac ttgggcagaa cgtaagccgc gagagcgcca caaccgctt cttggtcgaa     600 ggcagcaagc gcgatgaatg tcttactacg gagcaagttc ccgaggtaat cggagtccgg     660
```

```
ctgatgttgg gagtaggtgg ctacgtctcc gaactcacga ccgaaaagat caagagcagc      720
ccgcatggat ttgacttggt cagggccgag cctacatgtg cgaatgatgc ccatacttga      780
gccacctaac tttgtttttag ggcgactgcc ctgctgcgta acatcgttgc tgctgcgtaa     840
catcgttgct gctccataac atcaaacatc gacccacggc gtaacgcgct tgctgcttgg      900
atgcccgagg catagactgt acaaaaaaac agtcataaca agccatgaaa accgccactg      960
cgccgttacc accgctgcgt tcggtcaagg ttctggacca gttgcgtgag cgcatacgct     1020
acttgcatta cagtttacga accgaacagg cttatgtcaa ctgggttcgt gccttcatcc     1080
gtttccacgg tgtgcgtcac ccggcaacct tgggcagcag cgaagtcgcc ataacttcgt     1140
atagcataca ttatacgaag ttatctgtaa ctataacggt cctaaggtag cgagtttaaa     1200
cgacgtccta gattggttac tgggcgatga aggtttagtc ggcaaatcgt ccaacgttag     1260
tgacagcgtc agcggcaagt taatgcctat cattttgttg ataggcgcgg tcttgttttt     1320
aggtttaata ttttattta tctacagata catgatgaaa ggagggaagg gaggtggtgt      1380
tggcgcagca acgtcgccaa ctcccattgt tatttctatg caaaaccccca caccaacaac     1440 ggcccctcga taataaaaga caaaaataat ataaaatata tgtataatta attaaattca     1500
aaatatatgt ataaggccgg ccttagtcag ttacttgtac agctcgtcca tgccgagagt     1560
gatcccggcg gcggtcacga actccagcag gaccatgtga tcgcgcttct cgttggggtc     1620
tttgctcagg gcggactggg tgctcaggta gtggttgtcg ggcagcagca cggggccgtc     1680
gccgatgggg gtgttctgct ggtagtggtc ggcgagctgc acgctgccgt cctcgatgtt     1740
gtggcggatc ttgaagttca ccttgatgcc gttcttctgc ttgtcggcca tgatatagac     1800
gttgtggctg ttgtagttgt actccagctt gtgccccagg atgttgccgt cctccttgaa     1860
gtcgatgccc ttcagctcga tgcggttcac cagggtgtcg ccctcgaact tcacctcggc     1920
gcgggtcttg tagttgccgt cgtccttgaa gaagatggtg cgctcctgga cgtagccttc     1980
gggcatggcg gacttgaaga agtcgtgctg cttcatgtgg tcggggtagc ggctgaagca     2040
ctgcacgccg taggtcaggg tggtcacgag ggtgggccag ggcacgggca gcttgccggt     2100
ggtgcagatg aacttcaggg tcagcttgcc gtaggtggca tcgccctcgc cctcgccgga     2160
cacgctgaac ttgtggccgt ttacgtcgcc gtccagctcg accaggatgg gcaccacccc     2220
ggtgaacagc tcctcgccct tgctcatccc gggtgactgg aagtacaggt tttcttgcga     2280
gtacaccaat tcattcatga gttgagtcgc ttccttaact ggctgaaaag gctcttcagg     2340
tttcaccatg aaaactttat ggccccccca caatactgag tcagcattta atcgccaacc     2400
actaacccac tgctgcgcct cctgatttgt caacaattcc atgaagtttt tcggcacgct     2460
tgtgaaataa ttgtttgtgt tggtgaaatt cgatgctgag tgtataccaa caatgaaccc     2520
atctctagtt gatactaatg gactgccaca ctgcccatcc ttggtttgaa tccaatgctt     2580
ccagaatatg ccatcagatg aagggaatgt gcaagaagtg tctgacacca tgctagacat     2640
gctcttagtt tggaagttgg ttgtcacaag acatattctc tcttcccttt gtggctctct     2700
aaatttcagc tttttgaggaa atggtgggaa atccttaggc atgcgaataa ttatcatgtc     2760
cctcccatca atgaggtgtt gttgcaaagt cgtggtgttc ttgaccttga atacaccatg     2820
tagtgattgg accaacagtg ttccattatt tcttctaaac aagtgcttgt ttgtaatgat     2880
gaagggacca aatccaatac catacaacga tgttgtgtgc ccatcagatt cattcgtcaa     2940
atgacaaatg gtgctcgata tagggttgta atcacgcggc cccttaaaca agctctctcc     3000
```

-continued

```
ggcgtagtca ggcacgtcgt aaggataagc catatttaaa tatatgcttg cttgtgtgtt   3060
ccttattgaa gccttggtgt gactgattta ctagtagcgt tgaggcgtct tatatacccg   3120
accgttatct ggcctacgtg acacaaggca cgttgttaga ttaataatct tatctttta    3180 tcttaattga taagattatt tttatctggc tgttataaaa acgggatcat gaacacggac   3240
gctcagtcga cagatctgtc gacggtttaa acactagttc gcgacctact ccggaatatt   3300
aataggttgc tgatatcggg agttcagtcg tcgaatgcaa agcgtaaaaa atattaataa   3360
ggtaaaaatt acagctacat aaattacaca atttaaacgg atcgatgagc tccatatggg   3420
atccgcggag aacagcgaga gtctgggcac cgtccccgag cacgagcgga tcttgcagga   3480
gatcgagagc accgacaccg cctgtgtggg gcccaccctc cggtctgtgt atgatgacca   3540
accaaatgcg cacaagaagt ttatggaaaa gttagatgct tgtatccgta atcatgacaa   3600
ggaaattgaa aagatgtgta attttcatca tcagggtttt gtagatgcta ttacagaact   3660
ccttaaagta aggactgatg cagaaaaact gaaggtgcaa gttactgata ccaaccgaag   3720
gtttcaagat gctggaaaag aggtgatagt ccacacagaa gatatcattc gatgtagaat   3780
tcagcagaga aatattacaa ctgtagtaga aaaattgcag ttatgccttc ctgtgctaga   3840
aatgtacagt aagctgaaag aacagatgag tgccaaaagg tactattctg ccctaaaaac   3900
tatggaacaa ttagagaatg tgtactttcc ctgggttagt caataccggt tttgtcagct   3960
catgatagaa aatcttccca aactccgtga ggatattaaa gaaatctcca tgtctgatct   4020
caaagacttt ttggaaagta ttcgaaaaca ttctgacaaa ataggtgaaa cagcaatgaa   4080
acaggcacag catcagaaaa ccttcagtgt ttctctgcag aaacaaaata aaatgaaatt   4140
tgggaaaaat atgtatataa atcgtgatag aattccagag gaaaggaatg aaactgtatt   4200
gaaacattca cttgaagaag aggatgagaa tgaagaagac atcttaactg ttcaggatct   4260
tgttgatttt tcccctgttt atcgatgttt gcacatttat tctgttttgg gtgacgagga   4320
aacatttgaa aactattatc gaaaacaaag aaagaaacaa gcaagactgg tattgcaacc   4380
ccagtcgaat atgcatgaaa cagttgatgg ctatagaaga tatttcactc aaattgtagg   4440
gttctttgtg gtagaagatc acattttaca tgtgacccaa ggattagtaa ccagggcata   4500
cactgatgaa ctttggaaca tggccctctc aaagataatt gctgtcctta gagctcattc   4560
atcctattgc actgatcctg atcttgttct ggagctgaag aatcttattg taatatttgc   4620 agatactta cagggttatg gttttccagt gaaccgactt tttgaccttt tatttgaaat    4680
aagagaccaa tacaatgaaa cactgcttaa gaaatgggct ggagttttca gggacatttt   4740
tgaagaagat aattacagcc ccatccctgt tgtcaatgaa gaagaatata aaattgtcat   4800
cagcaaattt cccttttcaag atccagacct tgaaaagcag tctttcccaa agaaattccc   4860
catgtctcag tcagtgcctc atatttacat tcaagttaaa gaatttattt atgccagcct   4920
taaattttca gagtcactac accggagctc aacagaaata gacgatatgc ttagaaaatc   4980
aacaaatctg ctgctgacca gaactttgag tagctgttta ctgaacctta ttagaaaacc   5040
tcatataggt ttgacagagc tggtacaaat catcataaac acaacacacc tggagcaagc   5100
ttgtaaatat cttgaggact ttataactaa cattacaaat atttcccaag aaactgttca   5160
tactacaaga ctttatggac tttctacttt caaggatgct cgacatgcag cagaaggaga   5220
aatatatacc aaactgaatc aaaaaattga tgaatttgtt cagcttgctg attatgactg   5280
gacaatgtct gagccagatg gaagagctag tggttattta atggacctta taaattttt    5340 gagaagcatc tttcaagtgt ttactcattt gcctgggaaa gttgctcaga cagcttgcat   5400
```

-continued

```
gtcagcctgc cagcatctgt caacatcctt aatgcagatg ctactggaca gtgagttaaa    5460
acaaataagc atgggagctg ttcagcagtt taacttagat gtcatacagt gtgaattgtt    5520
tgccagctct gagcctgtgc caggattcca gggggatacc ctgcagctag cattcattga    5580
cctcagacaa ctccttgacc tgtttatggt ttgggattgg tctacttacc tagctgatta    5640
tgggcagcca gcttctaagt accttcgggt gaatccaaac acagcccta ctcttttgga     5700 gaagatgaag gatactagca aaaagaacaa tatatttgct cagttcagga agaatgatcg    5760
agacaaacag aagttgatag agacagtcgt gaaacagctg agaagtttgg tgaatggtat    5820
gtcccagcac atgggctcga gtgagaatct gtatttccag agcggtaccg cggccgcgat    5880
gaaggagaca gaccgggagg ccgttgcgac agcagtgcaa agggttgctg ggatgctcca    5940
gcgcccggac cagctggaca aggtggagca gtatcgcagg agagaagcgc ggaagaaggc    6000
ctccgtggag gccagattga aggccgccat ccagtcacag ttggacgggg tgcgcacagg    6060
cctcagccag ctccacaacg ccctgaatga cgtcaaagac atccagcagt cgctggcaga    6120
cgtcagcaag gactggaggc agagcatcaa caccattgag agcctcaagg acgtcaaaga    6180
cgccgtggtg cagcacagcc agctcgccgc agccgtggag aacctcaaga acatcttctc    6240
agtgcctgag attgtgaggg agacccagga cctaattgaa caagggcac tcctgcaagc      6300 ccaccggaag ctgatggacc tggaatgctc ccgggacggg ctgatgtacg agcagtaccg    6360
catggacagt gggaacacgc gtgacatgac cctcatccat ggctactttg gcagcacgca    6420
ggggctctct gatgagctgg ctaagcagct gtggatggtg ctgcagaggt cactggtcac    6480
tgtccgccgt gaccccacct tgctggtctc agttgtcagg atcattgaaa gggaagagaa    6540
aattgacagg cgcatacttg accggaaaaa gcaaactggc tttgttcctc ctgggaggcc    6600
caagaattgg aaggagaaaa tgttcaccat cttggagagg actgtgacca ccagaattga    6660
gggcacacag gcagatacca gagagtctga caagatgtgg cttgtccgcc acctggaaat    6720
tataaggaag tacgtcctgg atgacctcat tgtcgccaaa aacctgatgg ttcagtgctt    6780
tcctccccac tatgagatct ttaagaacct cctgaacatg taccaccaag ccctgagcac    6840
gcggatgcag gacctcgcat cggaagacct ggaagccaat gagatcgtga gcctcttgac    6900
gtgggtctta aacacctaca caagtactga gatgatgagg aacgtggagc tggccccgga    6960
agtggatgtc ggcaccctgg agccattgct ttctccacac gtggtctctg agctgcttga    7020
cacgtacatg tccacgctca cttcaaacat catcgcctgg ctgcggaaag cgctggagac    7080
agacaagaaa gactgggtca aagagacaga gccagaagcc gaccaggacg ggtactacca    7140
gaccacactc cctgccattg tcttccagat gtttgaacag aatcttcaag ttgctgctca    7200
gataagtgaa gatttgaaaa caaaggtact agttttatgt cttcagcaga tgaattcttt    7260
cctaagcaga tataaagatg aagcgcagct gtataaagaa gagcacctga ggaatcggca    7320
gcaccctcac tgctacgttc agtacatgat cgccatcatc aacaactgcc agaccttcaa    7380
ggaatccata gtcagtttaa aaagaaagta tttaaagaat gaagtggaag agggtgtgtc    7440
tccgagccag cccagcatgg acgggatttt agacgccatc gcgaaggagg ctgcagcgg     7500 tttgctggag gaggtcttcc tggacctgga gcaacatctg aatgaattga tgacgaagaa    7560
gtggctatta gggtcaaacg ctgtagacat tatctgtgtc accgtggaag actatttcaa    7620
cgattttgcc aaaattaaaa agccgtataa gaagaggatg acggccgagg cgcaccggcg    7680
cgtggtggtg gagtacctgc gggcggtcat gcagaagcgc atttccttcc ggagcccgga    7740
```

```
ggagcgcaag gagggtgccg agaagatggt tagggaggca gagcagctgc gcttcctgtt   7800
ccggaagctg gcgtccggtt tcggggaaga cgtggacgga tactgcgaca ccatcgtggc   7860
tgtggccgaa gtgatcaagc tgacagaccc ttctctgctc tacctggagg tctccactct   7920
ggtcagcaag tatccagaca tcagggatga ccacatcggt gcgctgctgg ctgtgcgtgg   7980
ggacgccagc cgtgacatga agcagaccat catggagacc ctggagcagg gcccagcaca   8040
ggccagcccc agctacgtgc ccctcttcaa ggacattgtg gtgcccagcc tgaacgtggc   8100
caagctgctc aagtaactcg agttaactga ctaaaagctt cgaaaggaag ctgagttggc   8160
tgctgccacc gctgagcaat aactagcata accccttggg gcctctaaac gggtcttgag   8220
gggttttttg ctgaaaggag gaactatcct cagggtcgag aagtactaga ggatcataat   8280
cagccatacc acatttgtag aggttttact tgctttaaaa aacctcccac acctccccct   8340
gaacctgaaa cataaaatga atgcaattgt tgttgttaac ttgtttattg cagcttataa   8400
tggttacaaa taaagcaata gcatcacaaa tttcacaaat aaagcatttt tttcactgca   8460
ttctagttgt ggtttgtcca aactcatcaa tgtatcttat catgtctgga tctgatcact   8520
gcttgagcct aggagatccg aaccagataa gtgaaatcta gttccaaact attttgtcat   8580
ttttaatttt cgtattagct tacgacgcta cacccagttc ccatctattt tgtcactctt   8640
ccctaaataa tccttaaaaa ctccatttcc acccctccca gttcccaact attttgtccg   8700
cccacagcgg ggcatttttc ttcctgttat gtttttaatc aaacatcctg ccaactccat   8760
gtgacaaacc gtcatcttcg gctacttttt ctctgtcaca gaatgaaaat ttttctgtca   8820
tctcttcgtt attaatgttt gtaattgact gaatatcaac gcttatttgc agcctgaatg   8880
gcgaatggga cgcgccctgt agcggcgcat taagcgcggc gggtgtggtg gttacgcgca   8940
gcgtgaccgc tacacttgcc agcgccctag cgcccgctcc tttcgctttc ttcccttcct   9000
ttctcgccac gttcgccggc tttccccgtc aagctctaaa tcggggggctc cctttagggt   9060 tccgatttag tgctttacgg cacctcgacc ccaaaaaact tgattagggt gatggttcac   9120
gtagtgggcc atcgccctga tagacggttt ttcgcccttt gacgttggag tccacgttct   9180
ttaatagtgg actcttgttc caaactggaa caacactcaa ccctatctcg gtctattctt   9240
ttgatttata agggattttg ccgatttcgg cctattggtt aaaaaatgag ctgatttaac   9300
aaaaatttaa cgcgaatttt aacaaaatat taacgtttac aatttcaggt ggcacttttc   9360
ggggaaatgt gcgcggaacc cctatttgtt tattttttcta aatacattca aatatgtatc   9420
cgctcatgag acaataaccc tgataaatgc ttcaataata ttgaaaaagg aagagtatga   9480
gtattcaaca tttccgtgtc gcccttattc ccttttttgc ggcattttgc cttcctgttt   9540
ttgctcaccc agaaacgctg gtgaaagtaa aagatgctga agatcagttg ggtgcacgag   9600
tgggttacat cgaactggat ctcaacagcg gtaagatcct tgagagtttt cgccccgaag   9660
aacgttttcc aatgatgagc acttttaaag ttctgctatg tggcgcggta ttatcccgta   9720
ttgacgccgg gcaagagcaa ctcggtcgcc gcatacacta ttctcagaat gacttggttg   9780
agtactcacc agtcacagaa aagcatctta cggatggcat gacagtaaga gaattatgca   9840
gtgctgccat aaccatgagt gataacactg cggccaactt acttctgaca acgatcggag   9900
gaccgaagga gctaaccgct tttttgcaca acatggggga tcatgtaact cgccttgatc   9960
gttgggaacc ggagctgaat gaagccatac caaacgacga gcgtgacacc acgatgcctg  10020
tagcaatggc aacaacgttg cgcaaactat taactggcga actacttact ctagcttccc  10080
ggcaacaatt aatagactgg atggaggcgg ataaagttgc aggaccactt ctgcgctcgg  10140
```

```
cccttccggc tggctggttt attgctgata aatctggagc cggtgagcgt gggtctcgcg      10200
gtatcattgc agcactgggg ccagatggta agccctcccg tatcgtagtt atctacacga      10260
cggggagtca ggcaactatg atgaacgaa atagacagat cgctgagata ggtgcctcac       10320
tgattaagca ttggtaactg tcagaccaag tttactcata tatactttag attgattaa       10380 aacttcattt ttaatttaaa aggatctagg tgaagatcct ttttgataat ctcatgacca      10440
aaatccctta acgtgagttt tcgttccact gagcgtcaga ccgcggggca tgactaacat      10500
gagaattaca acttatatcg tatggggctg acttcaggtg ctacatttga agagataaat      10560
tgcactgaaa tctagaaata ttttatctga ttaataagat gatcttcttg agatcgtttt      10620
ggtctgcgcg taatctcttg ctctgaaaac ggaaaaaacc gccttgcagg gcggttttc       10680 gaaggttctc tgagctacca actctttgaa ccgaggtaac tggcttggag gagcgcagtc      10740
accaaaactt gtcctttcag tttagcctta accggcgcat gacttcaaga ctaactcctc      10800
taaatcaatt accagtggct gctgccagtg gtgcttttgc atgtctttcc gggttggact      10860
caagacgata gttaccggat aaggcgcagc ggtcggactg aacggggggt tcgtgcatac      10920
agtccagctt ggagcgaact gcctacccgg aactgagtgt caggcgtgga atgagacaaa      10980
cgcggccata acagcggaat gacaccggta aaccgaaagg caggaacagg agagcgcacg      11040
agggagccgc caggggaaac gcctggtatc tttatagtcc tgtcgggttt cgccaccact      11100
gatttgagcg tcagatttcg tgatgcttgt caggggggcg gagcctatgg aaaaacggct      11160
ttgccgcggc cctctcactt ccctgttaag tatcttcctg gcatcttcca ggaaatctcc      11220
gccccgttcg taagccattt ccgctcgccg cagtcgaacg accgagcgta gcgagtcagt      11280
gagcgaggaa gcggaatata tcctgtatca catattctgc tgacgcaccg gtgcagcctt      11340
ttttctcctg ccacatgaag cacttcactg acaccctcat cagtgccaac atagtaagcc      11400
agtatacact ccgctagcgc tgatgtccgg cggtgctttt gccgttacgc accaccccgt      11460
cagtagctga acaggaggga cagctgatag aaacagaagc cagttctttc ctgcgttatc      11520
ccctgattct gtggataacc gtattaccgc ctttgagtga gctgataccg ctcgccgcag      11580
ccgaacgacc gagcgcagcg agtcagtgag cgaggaagcg gaagagcgcc tgatgcggta      11640
ttttctcctt acgcatctgt gcggtatttc acaccgcata gaccagccgc gtaacctggc      11700
aaaatcggtt acggttgagt aataaatg                                         11728
```

<210> SEQ ID NO 16
<211> LENGTH: 12046
<212> TYPE: DNA
<213> ORGANISM: Artificial Sequence
<220> FEATURE:
<223> OTHER INFORMATION: Synthesized

<400> SEQUENCE: 16

```
gatgccctgc gtaagcgggt gtgggcggac aataaagtct taaactgaac aaaatagatc         60
taaactatga caataaagtc ttaaactaga cagaatagtt gtaaactgaa atcagtccag        120
ttatgctgtg aaaaagcata ctggactttt gttatggcta aagcaaactc ttcattttct        180
gaagtgcaaa ttgcccgtcg tattaaagag gggcgtggcc aagggcatgt aaagactata        240
ttcgcggcgt tgtgacaatt taccgaacaa ctccgcggcc gggaagccga tctcggcttg        300
aacgaattgt taggtggcgg tacttgggtc gatatcaaag tgcatcactt cttcccgtat        360
gcccaacttt gtatagagag ccactgcggg atcgtcaccg taatctgctt gcacgtagat        420
```

```
cacataagca ccaagcgcgt tggcctcatg cttgaggaga ttgatgagcg cggtggcaat      480
gccctgcctc cggtgctcgc cggagactgc gagatcatag atatagatct cactacgcgg      540
ctgctcaaac ttgggcagaa cgtaagccgc gagagcgcca acaaccgctt cttggtcgaa      600
ggcagcaagc gcgatgaatg tcttactacg gagcaagttc ccgaggtaat cggagtccgg      660
ctgatgttgg gagtaggtgg ctacgtctcc gaactcacga ccgaaaagat caagagcagc      720
ccgcatggat ttgacttggt cagggccgag cctacatgtg cgaatgatgc ccatacttga      780
gccacctaac tttgttttag ggcgactgcc ctgctgcgta acatcgttgc tgctgcgtaa      840
catcgttgct gctccataac atcaaacatc gacccacggc gtaacgcgct tgctgcttgg      900
atgcccgagg catagactgt acaaaaaaac agtcataaca agccatgaaa accgccactg      960
cgccgttacc accgctgcgt tcggtcaagg ttctggacca gttgcgtgag cgcatacgct     1020
acttgcatta cagtttacga accgaacagg cttatgtcaa ctgggttcgt gccttcatcc     1080
gtttccacgg tgtgcgtcac ccggcaacct tgggcagcag cgaagtcgcc ataacttcgt     1140
atagcataca ttatacgaag ttatctgtaa ctataacggt cctaaggtag cgagtttaaa     1200
cgacgtccta gattggttac tgggcgatga aggtttagtc ggcaaatcgt ccaacgttag     1260
tgacagcgtc agcggcaagt taatgcctat cattttgttg ataggcgcgg tcttgttttt     1320
aggtttaata ttttatttta tctacagata catgatgaaa ggagggaagg gaggtggtgt     1380
tggcgcagca acgtcgccaa ctcccattgt tatttctatg caaaacccca caccaacaac     1440
ggcccctcga taataaaaga caaaaataat ataaaatata tgtataatta attaaattca     1500
aaatatatgt ataaggccgg ccttagtcag ttaattaagt ttgtgcccca gtttgctagg     1560
gaggtcgcag tatctggcca cagccacctc gtgctgctcg acgtaggtct ctttgtcggc     1620
ctccttgatt ctttccagtc tgtggtccac atagtagacg ccgggcatct tgaggttctt     1680
agcgggtttc ttggatctgt atgtggtctt gaagttgcag atcaggtggc ccccgcccac     1740
gagcttcagg gccatgtcgc ttctgccttc caggccgccg tcagcggggt acagcatctc     1800
ggtgttggcc tcccagccga gtgttttctt ctgcatcaca gggccgttgg atgggaagtt     1860
cacccctctg atcttgacgt tgtagatgag gcagccgtcc tggaggctgg tgtcctgggt     1920
agcggtcagc acgcccccgt cttcgtatgt ggtgactctc tcccatgtga gccctcagg      1980 gaaggactgc ttaaagaagt cggggatgcc ctgggtgtgg ttgatgaagg ttctgctgcc     2040
gtacatgaag ctggtagcca ggatgtcgaa ggcgaagggg agagggccgc cctcgaccac     2100
cttgattctc atggtctggg tgccctcgta gggcttgcct tcgccctcgg atgtgcactt     2160
gaagtggtgg ttgttcacgg tgccctccat gtacagcttc atgtgcatgt tctccttaat     2220
cagctcttcg cccttagaca ccatcccggg tgactggaag tacaggtttt cttgcgagta     2280
caccaattca ttcatgagtt gagtcgcttc cttaactggc tgaaaaggct cttcaggttt     2340
caccatgaaa actttatggc ccccccacaa tactgagtca gcatttaatc gccaaccact     2400
aacccactgc tgcgcctcct gatttgtcaa caattccatg aagttttttcg gcacgcttgt     2460 gaaataattg tttgtgttgg tgaaattcga tgctgagtgt ataccaacaa tgaacccatc     2520
tctagttgat actaatggac tgccacactg cccatccttg gtttgaatcc aatgcttcca     2580
gaatatgcca tcagatgaag ggaatgtgca agaagtgtct gacaccatgc tagacatgct     2640
cttagtttgg aagttggttg tcacaagaca tattctctct tcccctttgtg gctctctaaa     2700 tttcagcttt tgaggaaatg gtgggaaatc cttaggcatg cgaataatta tcatgtccct     2760
cccatcaatg aggtgttgtt gcaaagtcgt ggtgttcttg accttgaata caccatgtag     2820
```

-continued

```
tgattggacc aacagtgttc cattatttct tctaaacaag tgcttgtttg taatgatgaa    2880
gggaccaaat ccaataccat acaacgatgt tgtgtgccca tcagattcat tcgtcaaatg    2940
acaaatggtg ctcgatatag ggttgtaatc acgcggcccc ttaaacaagc tctctccggc    3000
gtagtcaggc acgtcgtaag gataagccat atttaaatat atgcttgctt gtgtgttcct    3060
tattgaagcc ttggtgtgac tgatttacta gtagcgttga ggcgtcttat atacccgacc    3120
gttatctggc ctacgtgaca caaggcacgt tgttagatta ataatcttat cttttttatct   3180 taattgataa gattattttt atctggctgt tataaaaacg ggatcatgaa cacggacgct    3240
cagtcgacag atctgtcgac ggtttaaaca ctagttcgcg acctactccg gaatattaat    3300
aggttgctga tatcgggagt tcagtcgtcg aatgcaaagc gtaaaaaata ttaataaggt    3360
aaaaattaca gctacataaa ttacacaatt taaacggatc gatgagctcc atatggcggc    3420
cgcggaagca gctggtggga aatacagaag cacagtcagc aaaagcaaag acccctcggg    3480
gctgctcatc tctgtgatca ggactctgtc tactagtgac gatgtcgaag acagggaaaa    3540
tgaaaagggt cgccttgaag aagcctacga gaaatgtgac cgtgacctgg atgaattgat    3600
tgtacagcac tacacagaat tgacgacagc cattcgcaca taccagagca tcacagagcg    3660
catcactaac tcccgaaata aaataaagca ggtaaaagag aacctgcttt catgcaagat    3720
gctgctgcac tgcaaacggg atgagcttcg gaaactgtgg attgaaggaa ttgagcataa    3780
gcatgtcctg aacttgttgg atgaaattga gaatatcaag caagtgcctc aaaagctgga    3840
acagtgcatg gccagcaagc actatctcag tgccactgac atgttggtgt cagcagttga    3900
gtctttggag ggccccctgc tccaggtgga aggactgagt gaccttcgac tagagcttca    3960
cagcaagaag atgaaccttc acttggttct catagatgaa ctacaccggc acctgtacat    4020
caaatcgact agccgagttg tgcagcgtaa caaggaaaaa gggaaaatca gctccctcgt    4080
gaaagatgct tctgttcctc tgattgatgt tacaaacctc cctactcctc gaaaattcct    4140
tgatacctct cactattcta ctgctggaag ctcaagtgtg agggagataa atctgcagga    4200
catcaaggaa gatttagaat tggatccaga ggaaaacagc accctgttta tgggtatcct    4260
cattaagggc ttggcgaaac tgaagaagat cccagaaaca gttaaggcaa tcatagagcg    4320
cttggagcag gagttgaagc aaattgtgaa gaggtctaca acccaggtgg cagacagtgg    4380
ctatcagcgg ggggagaacg ttactgtgga gaaccaacca aggttgcttc tagaactgct    4440
ggagttactg tttgacaagt ttaatgctgt agccgctgca cactctgtgg tcctgggata    4500
cctgcaggac actgtagtga ctccactgac tcagcaggaa gatatcaaac tgtatgatat    4560
ggcagatgta tgggtgaaga tccaagatgt tctacagatg ctattaactg agtacttgga    4620
tatgaaaaat actcgtacgg cctctgaacc atcagctcaa ctaagctatg ccagcactgg    4680
acgagagttt gcagcctttt ttgccaagaa gaaacctcaa aggccaaaaa attctctttt    4740
caagttcgaa tcgtcctccc atgccatcag tatgagcgcc tatctgcgag aacagagaag    4800
ggagctctat agtcggagtg gagaactgca aggggggtcct gatgacaact taattgaagg    4860
tggaggaaca aaatttgtct gcaaacctgg agccagaaac attaccgtca tattccaccc    4920
attactaaga tttattcagg agattgagca tgctctgggt cttggcccag ccaaacagtg    4980
tcctcttcga gagtttctca ccgtgtacat caaaaacatc tttctcaatc aagtcttggc    5040
tgagatcaac aaggagattg aaggagtcac taaaacatct gacccttttga agattctggc    5100 caacgcagac accatgaagg tgctgggagt gcagcggcct ctcctacaga gcacaatcat    5160
```

-continued

```
tgtggagaag acagttcaag acctcctgaa cctgatgcat gacttgagtg catattcaga   5220
tcaattcctc aacatggtgt gcgtgaagct ccaggagtac aaggacacct gcactgcagc   5280
ttacaggggt attgtccagt cagaagaaaa acttgtcatc agtgcatcct gggcaaaaga   5340
tgatgatatc agcagactct tgaaatctct accaaactgg atgaatatgg ctcaacccaa   5400
acagctgagg ccaaaaagag aggaggaaga agatttcata agggcagctt ttggcaagga   5460
gtctgaagtt cttattggga acctgggtga taaattaatc cctccacaag acatccttcg   5520
tgacgtcagt gacctcaaag ccttggccaa catgcatgaa agcctggaat ggttggcaag   5580
tcgaacaaag tcagctttct ccaatctttc tacatcccag atgctttctc ctgctcaaga   5640
cagccacacg aacacggatc tccccccagt gtcagagcag atcatgcaga ctctcagtga   5700
acttgccaaa tcgttccagg atatggctga ccgctgcttg cttgtcttac atctggaagt   5760
gagggttcac tgtttccact atcttatccc tcttgcaaag gaggggaact atgccattgt   5820
ggctaatgtg gaaagtatgg attatgaccc cctggtggtc aagctcaaca aagatatcag   5880
cgccattgaa gaggccatga gcgccagcct tcagcagcac aagttccagt atatcttcga   5940
aggcctgggc cacctgatct cctgcatcct cattaatggt gcccagtact tcaggcgcat   6000
cagtgagtct ggcatcaaga aaatgtgtag gaacattttt gttcttcagc agaatttgac   6060
caacatcacc atgtcgcggg aggcagacct ggactttgca aggcagtact acgagatgct   6120
ttacaacaca gctgacgagc tcctgaacct ggtggtggac cagggtgtga agtacacgga   6180
gctggagtac atccacgctc tgaccctgct gcaccgcagc cagactgggg tgggggaact   6240
gaccacccag aacacgaggc tgcagaggct caaagagatc atctgcgagc aggctgccat   6300
caagcaagcc accaaggaca agaagataac taccgttggc tcgagtgaga acttgtactt   6360
tcagtcctta agcggtacca tgattccccc acaggaggca tccgctcgac ggcgggagat   6420
tgaggacaag ctgaagcagg aggaggagac tctgtccttc atccgagaca gcctggagaa   6480
gagcgaccag ctcactaaga acatggtgtc tatcttatca tcctttgaga gccgccttat   6540
gaagctggag aactccatca tccctgtgca caagcagacg gagaatctgc agcggctgca   6600
ggagaatgtt gagaagacgc tgtcctgcct ggaccatgtc atcagctact accatgtggc   6660
cagtgacact gagaagatca tcagagaggg ccccacaggt aggctggaag agtacctggg   6720
aagcatggcc aagattcaga aggcagtgga gtatttccag gacaacagcc agacagccc   6780 ggaactcaac aaagtgaaac tgctctttga gcgcgggaag gaggccctgg agtccgaatt   6840
tcgcagcctg atgacgcggc acagtaaggt cgtctcgccc gtgctcatct tggatctgat   6900
cagtggtgac gatgatctgg aggcccagga ggacgtgacc ctggagcacc tgcccgagag   6960
cgtgctccag gatgtcattc gcatctcccg ctggctggtg aatatggcc gcaaccaaga   7020 tttcatgaac gtctactacc agatacgctc cagccagctg gaccgctcca tcaaaggact   7080
gaaggagcat ttccataaga gcagttcttc tctctggggtt ccctactccc ctgctatccc   7140
caacaagagg aaagacacac ctaccaagaa gccagtcaag cggccaggga cgatccgtaa   7200
ggctcagaac cttctgaaac agtattccca gcatggtcta gatgggaaaa aggggggctc   7260
taacctcatt cctctggaag ggagagatga catgctggac gtggagaccg atgcctacat   7320
ccactgcgtc agtgccttcg tcaagctggc gcagagcgag taccagctgc tggccgacat   7380
catccccgag caccaccaga agaagacctt cgactccctg atacaggatg ccctggatgg   7440
gctgatgctt gaagggggaga acatcgtgtc tgctgcccgg aaggccattg tgcgacacga   7500
cttctccacg gtgctcaccg tcttcccat cctgcgacac ctcaagcaga ccaagcctga   7560
```

-continued

```
gtttgaccag gtgctccagg gcacggctgc cagcacaaag aacaagctgc ctggcctcat   7620
cacatccatg gagaccatcg gtgccaaagc gctggaggac ttcgcagaca acatcaagaa   7680
tgacccggac aaggagtaca acatgccgaa ggacggcacc gtacacgagc tcaccagcaa   7740
tgccatcctc ttcctgcagc agcttttgga cttccaggag acggcaggcg ccatgctggc   7800
ctcccaagag accagctctt cggccaccag ctacagctct gagttcagca agcggctgct   7860
aagcacctat atctgtaaag tgctgggcaa cctgcagttg aacttgctga gcaagtccaa   7920
ggtgtacgag gacccagctc tgagcgccat cttcctgcac aacaactaca attacatcct   7980
caagtccctg gagaagtctg aactgatcca gctggtggca gtgacacaga agactgctga   8040
gcgctcctac cgggagcaca ttgagcagca gatccagacc taccagcgca gctggttaaa   8100
ggtgactgat tacatcgcag agaagaatct acctgtgttc cagccgggag tcaagctccg   8160
ggacaaggag cggcagatta tcaaggagcg ttttaagggc ttcaatgatg gcctcgaaga   8220
actgtgcaaa atccagaagg cctgggctat tccagacaca gagcagaggg acaggattcg   8280
ccaggcccag aagaccattg tcaaggagac ctacggggcc tttctacaga agtttggcag   8340
cgtgcccttc accaagaacc cggagaagta catcaagtac ggggtggagc aggtgggcga   8400
catgatcgat cgccttttcg acacctctgc ctaactcgag ttaactgact aaaagcttcg   8460
aaaggaagct gagttggctg ctgccaccgc tgagcaataa ctagcataac cccttggggc   8520
ctctaaacgg gtcttgaggg gttttttgct gaaaggagga actatcctca gggtcgagaa   8580
gtactagagg atcataatca gccataccac atttgtagag gttttacttg ctttaaaaaa   8640
cctcccacac ctccccctga acctgaaaca taaaatgaat gcaattgttg ttgttaactt   8700
gtttattgca gcttataatg gttacaaata aagcaatagc atcacaaatt tcacaaataa   8760
agcatttttt tcactgcatt ctagttgtgg tttgtccaaa ctcatcaatg tatcttatca   8820
tgtctggatc tgatcactgc ttgagcctag gagatccgaa ccagataagt gaaatctagt   8880
tccaaactat tttgtcattt ttaattttcg tattagctta cgacgctaca cccagttccc   8940
atctattttg tcactcttcc ctaaataatc cttaaaaact ccatttccac ccctcccagt   9000
tcccaactat tttgtccgcc cacagcgggg catttttctt cctgttatgt ttttaatcaa   9060
acatcctgcc aactccatgt gacaaaccgt catcttcggc tacttttct ctgtcacaga    9120 atgaaaattt ttctgtcatc tcttcgttat taatgtttgt aattgactga atatcaacgc   9180
ttatttgcag cctgaatggc gaatgggacg cgccctgtag cggcgcatta agcgcggcgg   9240
gtgtggtggt tacgcgcagc gtgaccgcta cacttgccag cgccctagcg cccgctcctt   9300
tcgctttctt cccttccttt ctcgccacgt tcgccggctt tccccgtcaa gctctaaatc   9360
gggggctccc tttagggttc cgatttagtg ctttacggca cctcgacccc aaaaaacttg   9420
attagggtga tggttcacgt agtgggccat cgccctgata gacggttttt cgccctttga   9480
cgttggagtc cacgttcttt aatagtggac tcttgttcca aactggaaca cactcaacc    9540 ctatctcggt ctattctttt gatttataag ggattttgcc gatttcggcc tattggttaa   9600
aaaatgagct gatttaacaa aaatttaacg cgaattttaa caaaatatta cgtttacaa    9660 tttcaggtgg cacttttcgg ggaaatgtgc gcggaacccc tatttgttta tttttctaaa   9720
tacattcaaa tatgtatccg ctcatgagac aataaccctg ataaatgctt caataatatt   9780
gaaaaaggaa gagtatgagt attcaacatt tccgtgtcgc ccttattccc ttttttgcgg   9840
cattttgcct tcctgttttt gctcacccag aaacgctggt gaaagtaaaa gatgctgaag   9900
```

-continued

```
atcagttggg tgcacgagtg ggttacatcg aactggatct caacagcggt aagatccttg   9960
agagttttcg ccccgaagaa cgtttttccaa tgatgagcac tttttaaagtt ctgctatgtg  10020 gcgcggtatt atcccgtatt gacgccgggc aagagcaact cggtcgccgc atacactatt   10080
ctcagaatga cttggttgag tactcaccag tcacagaaaa gcatcttacg gatggcatga   10140
cagtaagaga attatgcagt gctgccataa ccatgagtga taacactgcg gccaacttac   10200
ttctgacaac gatcggagga ccgaaggagc taaccgcttt tttgcacaac atggggggatc  10260 atgtaactcg ccttgatcgt tgggaaccgg agctgaatga agccatacca aacgacgagc   10320
gtgacaccac gatgcctgta gcaatggcaa caacgttgcg caaactatta actggcgaac   10380
tacttactct agcttcccgg caacaattaa tagactggat ggaggcggat aaagttgcag   10440
gaccacttct gcgctcggcc cttccggctg gctggtttat tgctgataaa tctggagccg   10500
gtgagcgtgg gtctcgcggt atcattgcag cactggggcc agatggtaag ccctcccgta   10560
tcgtagttat ctacacgacg gggagtcagg caactatgga tgaacgaaat agacagatcg   10620
ctgagatagg tgcctcactg attaagcatt ggtaactgtc agaccaagtt tactcatata   10680
tactttagat tgatttaaaa cttcattttt aatttaaaag gatctaggtg aagatccttt   10740
ttgataatct catgaccaaa atcccttaac gtgagttttc gttccactga gcgtcagacc   10800
gcggggcatg actaacatga gaattacaac ttatatcgta tggggctgac ttcaggtgct   10860
acatttgaag agataaattg cactgaaatc tagaaatatt ttatctgatt aataagatga   10920
tcttcttgag atcgttttgg tctgcgcgta atctcttgct ctgaaaacgg aaaaaaccgc   10980
cttgcagggc ggtttttcga aggttctctg agctaccaac tctttgaacc gaggtaactg   11040
gcttggagga gcgcagtcac caaaacttgt cctttcagtt tagccttaac cggcgcatga   11100
cttcaagact aactcctcta aatcaattac cagtggctgc tgccagtggt gcttttgcat   11160
gtctttccgg gttggactca agacgatagt taccggataa ggcgcagcgg tcggactgaa   11220
cggggggttc gtgcatacag tccagcttgg agcgaactgc ctacccggaa ctgagtgtca   11280
ggcgtggaat gagacaaacg cggccataac agcggaatga caccggtaaa ccgaaaggca   11340
ggaacaggag agcgcacgag ggagccgcca ggggaaacgc ctggtatctt tatagtcctg   11400
tcgggtttcg ccaccactga tttgagcgtc agatttcgtg atgcttgtca ggggggcgga   11460
gcctatggaa aaacggcttt gccgcggccc tctcacttcc ctgttaagta tcttcctggc   11520
atcttccagg aaatctccgc cccgttcgta agccatttcc gctcgccgca gtcgaacgac   11580
cgagcgtagc gagtcagtga gcgaggaagc ggaatatatc ctgtatcaca tattctgctg   11640
acgcaccggt gcagcctttt ttctcctgcc acatgaagca cttcactgac accctcatca   11700
gtgccaacat agtaagccag tatacactcc gctagcgctg atgtccggcg gtgcttttgc   11760
cgttacgcac caccccgtca gtagctgaac aggagggaca gctgatagaa acagaagcca   11820
gttctttcct gcgttatccc ctgattctgt ggataaccgt attaccgcct ttgagtgagc   11880
tgataccgct cgccgcagcc gaacgaccga gcgcagcgag tcagtgagcg aggaagcgga   11940
agagcgcctg atgcggtatt ttctccttac gcatctgtgc ggtatttcac accgcataga   12000
ccagccgcgt aacctggcaa aatcggttac ggttgagtaa taaatg            12046
```

<210> SEQ ID NO 17
<211> LENGTH: 7406
<212> TYPE: DNA
<213> ORGANISM: Artificial Sequence
<220> FEATURE:
<223> OTHER INFORMATION: Synthesized -continued

<400> SEQUENCE: 17

```
cgcgccggta tgtacaggaa gaggtttata ctaaactgtt acattgcaaa cgtggtttcg      60
tgtgccaagt gtgaaaaccg atgtttaatc aaggctctga cgcatttcta caaccacgac     120
tccaagtgtg tgggtgaagt cagatgttta aacccatgtg cctggcagat aacttcgtat     180
aatgtatgct atacgaagtt atggtacgcg gccgcgtaga ggatctgttg atcagcagtt     240
caacctgttg ataatacgga cctttaattc aacccaacac aatatattat agttaaataa     300
gaattattat caaatcattt gtatattaat taaaatacta tactgtaaat tacattttat     360
ttacaatcac tcgacaccgg tgatatccat atgggatcca cagcaatcaa gcatgcatta     420
caaagagaca tttttacacc aaatgatgaa cgcctgctga gcattgtgaa tgtctgcaaa     480
gcaggaaaaa agaaaaagaa ctgttttttta tgtgccacag tgacaactga acgccctgtg     540
caggttaagg tggtcaaagt caagaaatcc gataagggag atttctacaa aaggcagatt     600
gcatgggccc ttcgagatct tgctgtggta gatgccaaag atgctatcaa agaaaatcct     660
gaatttgatt tacactttga aaaaatatat aaatgggttg ccagcagcac tgctgaaaag     720
aatgcattta tttcatgcat ttggaaattg aatcagcgat atctccggaa gaaaattgat     780
tttgtcaatg ttagctcaca gcttttggaa gaactgccta aagttacaga agaatctgtt     840
ccaagtggag aaaatcagag tgtgacagga ggtgatgaag aagtagtaga tgaataccaa     900
gagttaaatg caagagaaga acaggatatc gaaataatga tggaaggctg tgaatatgca     960
atctcgaatg cggaagcctt tgcagaaaaa ttgtccagag agctgcaggt gctagatggg    1020
gctaacatcc agtcaatcat ggcatctgaa aaacaagtca acatcctgat gaaattgcta    1080
gatgaggctc taaaggaggt agatcagatt gaattgaaac tgagcagtta tgaggaaatg    1140
ctccaaagtg taaaagaaca aatggatcag atctctgaaa gcaaccacct aattcatctt    1200
agtaacacta ataatgtaaa actcctatct gagatagagt tccttgtgaa ccacatggac    1260
ttggccaaag gtcatataaa ggcccttcag gaaggagatc ttgcttcttc cagaggcatt    1320
gaggcctgca ccaatgctgc tgatgccctt ctgcagtgca tgaatgtagc tcttcgacca    1380
ggccatgact tgcttctggc agtcaaacag caacagcagc gattcagtga tttgcgagag    1440
ctttttgccc ggagactggc cagtcacctc aacaatgttt ttgttcaaca gggtcatgat    1500
cagagttcga ctcttgccca acactctgtt gaactgactt tacccaatca tcatccattt    1560
catagagatt tgctccgata tgccaagctg atggagtggc taaagagtac agattatgga    1620
aaatatgaag gactaacaaa gaattacatg gattatttat cccgactata tgaaagagaa    1680
atcaaagatt tctttgaagt tgcaaagatc aagatgactg gcacaactaa agaaagcaag    1740
aagtttgcta cactgcctcg aaaagaaagt gctgtcaaac aggaaacaga gagtcttcat    1800
ggaagttcgg ggaaattaac tggatctact tctagtctaa ataagctcag tgttcagagt    1860
tcagggaatc gcagatctca gtcatcttcc ctgttggata tgggaaacat gtctgcctct    1920
gatctcgatg ttgctgacag gaccaaattt gataagatct ttgaacaggt actaagtgaa    1980
ctggagcccc tatgtctggc agaacaggac ttcataagta aattttttcaa actacagcaa    2040 catcaaagta tgcctggaac tatggctgaa gcagaggacc tggatggagg aacattatca    2100
cggcaacata attgtggcac accactgcct gtttcatctg agaaagatat gatccgccaa    2160
atgatgatta aaatatttcg ctgcattgag ccagagctga caacctaat tgcattagga    2220 gacaaaattg atagctttaa ctctctttat atgttagtca aaatgagtca tcatgtgtgg    2280
```

-continued

```
actgcacaaa atgtggaccc tgcttctttc ctaagtacta cattgggaaa tgttttggtg     2340
actgtcaaaa ggaactttga caaatgcatt agtaaccaaa taaggcaaat ggaagaagta     2400
aagatctcaa aaaagagtaa agttggaatt cttccatttg ttgctgaatt tgaagaattt     2460
gctggacttg cagaatcaat cttcaaaaat gctgagcgtc gtggagacct ggataaagca     2520
tacaccaaac ttatcagagg agtatttgtt aatgtggaga aagtagcaaa tgaaagccag     2580
aagaccccca gggatgtggt tatgatggaa aactttcacc atattttttgc aactctttct     2640 cgattgaaaa tctcatgtct agaagcagaa aaaaagaag ccaaacaaaa atacacagat      2700
caccttcagt cttatgtcat ttactcttta ggacaacctc ttgaaaaact aaatcatttc     2760
tttgaaggtg ttgaagctcg cgtggcacag ggcataaggg aggaggaagt aagttaccaa     2820
cttgcattta acaaacaaga acttcgtaaa gtcattaagg agtaccctgg aaaggaagta     2880
aaaaaaggtc tagataacct ctacaagaaa gttgataaac atttatgtga agaagagaac     2940
ttacttcagg tggtgtggca ctccatgcaa gatgaattta tacgccagta taagcacttt     3000
gaaggtttga tagctcgctg ttatcctgga tctggtgtta caatggaatt cactattcag     3060
gacattctgg attattgttc cagcattgca cagtcccacg gctcgagtga aaacctgtac     3120
ttccagagct ctagcttaag cgcggccgcg accacggccg agttgttcga ggagcctttt     3180
gtggcagatg aatatattga acgtcttgta tggagaaccc caggaggagg ctctagaggt     3240
ggacctgaag cttttgatcc taaaagatta ttagaagaat ttgtaaatca tattcaggaa     3300
ctccagataa tggatgaaag gattcagagg aaagtagaga aactagagca acaatgtcag     3360
aaagaagcca aggaatttgc caagaaggta caagagctgc agaaaagcaa tcaggttgcc     3420
ttccaacatt tccaagaact agatgagcac attagctatg tagcaactaa agtctgtcac     3480
cttggagacc agttagaggg ggtaaacaca cccagacaac gggcagtgga ggctcagaaa     3540
ttgatgaaat actttaatga gtttctagat ggagaattga aatctgatgt ttttacaaat     3600
tctgaaaaga taaaggaagc agcagacatc attcagaagt tgcacctaat tgcccaagag     3660
ttaccttttg atagattttc agaagttaaa tccaaaattg caagtaaata ccatgattta     3720
gaatgccagc tgattcagga gtttaccagt gctcaaagaa gaggtgaaat ctccagaatg     3780
agagaagtag cagcagtttt acttcatttt aagggttatt cccattgtgt tgatgtttat     3840
ataaagcagt gccaggaggg tgcttatttg agaaatgata tatttgaaga cgctggaata     3900
ctctgtcaaa gagtgaacaa acaagttgga gatatcttca gtaatccaga aacagtcctg     3960
gctaaactta ttcaaaatgt atttgaaatc aaactacaga gttttgtgaa agagcagtta     4020
gaagaatgta ggaagtccga tgcagagcaa tatctcaaaa atctctatga tctgtataca     4080
agaaccacca atctttccag caagctgatg gagtttaatt taggtactga taaacagact     4140
ttcttgtcta agcttatcaa atccatttttc atttcctatt tggagaacta tattgaggtg     4200
gagactggat atttgaaaag cagaagtgct atgatcctac agcgctatta tgattcgaaa     4260
aaccatcaaa agagatccat tggcacagga ggtattcaag atttgaagga aagaattaga     4320
cagcgtacca acttaccact tgggccaagt atcgatactc atggggagac ttttctatcc     4380
caagaagtgg tggttaatct tttacaagaa accaaacaag cctttgaaag atgtgcatagg    4440 ctctctgatc cttctgactt accaaggaat gccttcagaa ttttttaccat tcttgtggaa     4500 ttttttatgta ttgagcatat tgattatgct ttggaaacag gacttgctgg aattccctct     4560
tcagattcta ggatgcaaa tctttatttt ttggacgttg tgcaacaggc caatactatt       4620
tttcatcttt ttgacaaaca gtttaatgat cacctttatgc cactaataag ctcttctcct     4680
```

```
aagttatctg aatgccttca gaagaaaaaa gaaataattg aacaaatgga gatgaaattg    4740
gatactggca ttgataggac attaaattgt atgattggac agatgaagca tattttggct    4800
gcagaacaga agaaaacaga ttttaagcca gaagatgaaa acaatgtttt gattcaatat    4860
actaatgcct gtgtaaaagt ctgtgcttac gtaagaaaac aagtggagaa gattaaaaat    4920
tccatggatg ggaagaatgt ggatacagtt ttgatggaac ttggagtacg ttttcatcga    4980
cttatctatg agcatcttca acaatattcc tacagttgta tgggtggcat gttggcaatt    5040
tgtgatgtag ccgaatatag gaagtgtgcc aaagacttca agattccaat ggtattacat    5100 cttttgata ctctgcatgc tctttgcaat cttctggtag ttgccccaga taatttaaag    5160
caagtctgct caggagaaca acttgctaat ctggacaaga atatacttca ctccttcgta    5220
caacttcgtg ctgattatag atctgcccgc cttgctcgac acttcagcta actcgagggt    5280
acccgaaagg aagctgagtt ggctgctgcc accgctgagc aataactagc ataacccctt    5340
ggggcctcta aacgggtctt gaggggtttt ttgctgaaag gaggaactat cctcaggggg    5400
agatggggga ggctaactga aacacggaag gagacaatac cggaaggaac ccgcgctatg    5460
acggcaataa aaagacagaa taaaacgcac gggtgttggg tcgtttgttc ataaacgcgg    5520
ggttcggtcc cagggctggc actctgtcga taccccaccg agaccccatt gggaccaata    5580
cgcccgcgtt tcttcctttt ccccacccca accccaagt tcgggtgaag cccagggct    5640 cgcagccaac gtcggggcgg caagccctgc catagccact acgggtacgt ctgaaagcat    5700
gcctttttgg aatttacgta ctaagctctc atgtttcacg tactaagctc tcatgtttaa    5760
cgtactaagc tctcatgttt aacgaactaa accctcatgg ctaacgtact aagctctcat    5820
ggctaacgta ctaagctctc atgtttcacg tactaagctc tcatgtttga acaataaaat    5880
taatataaat cagcaactta aatagcctct aaggttttaa gttttataag aaaaaaaaga    5940
atatataagg cttttaaagc ttttaaggtt taacggttgt ggacaacaag ccagggatgt    6000
aacgcactga gaagccctta gagcctctca aagcaatttt cagtgacaca ggaacactta    6060
acggctgaca gaattagctt cacgctgccg caagcactca gggcgcaagg ctgctaaag    6120 gaagcggaac acgtagaaag ccagtccgca gaaacggtgc tgaccccgga tgaatgtcag    6180
ctactgggct atctggacaa gggaaaacgc aagcgcaaag agaaagcagg tagcttgcag    6240
tgggcttaca tggcgatagc tagactgggc ggttttatgg acagcaagcg aaccggaatt    6300
gccagctggg gcgccctctg gtaaggttgg gaagccctgc aaagtaaact ggatggcttt    6360
cttgccgcca aggatctgat ggcgcagggg atcaagatct gatcaagaga caggatgagg    6420
atcgtttcgc atgattgaac aagatggatt gcacgcaggt tctccggccg cttgggtgga    6480
gaggctattc ggctatgact gggcacaaca gacaatcggc tgctctgatg ccgccgtgtt    6540
ccggctgtca gcgcaggggc gcccggttct ttttgtcaag accgacctgt ccggtgccct    6600
gaatgaactg caggacgagg cagcgcggct atcgtggctg gccacgacgg gcgttccttg    6660
cgcagctgtg ctcgacgttg tcactgaagc gggaagggac tggctgctat tgggcgaagt    6720
gccggggcag gatctcctgt catctcacct tgctcctgcc gagaaagtat ccatcatggc    6780
tgatgcaatg cggcggctgc atacgcttga tccggctacc tgcccattcg accaccaagc    6840
gaaacatcgc atcgagcgag cacgtactcg atggaagcc ggtcttgtcg atcaggatga    6900
tctggacgaa gagcatcagg ggctcgcgcc agccgaactg ttcgccaggc tcaaggcgcg    6960
catgcccgac ggcgaggatc tcgtcgtgac acatggcgat gcctgcttgc cgaatatcat    7020
```

-continued

```
ggtggaaaat ggccgctttt ctggattcat cgactgtggc cggctgggtg tggcggaccg    7080
ctatcaggac atagcgttgg ctacccgtga tattgctgaa gagcttggcg gcgaatgggc    7140
tgaccgcttc ctcgtgcttt acggtatcgc cgctcccgat tcgcagcgca tcgccttcta    7200
tcgccttctt gacgagttct tctgagcggg actctggggt tcgaaatgac cgaccaagcg    7260
acgcccaacc tgccatcacg agatttcgat tccaccgccg ccttctatga aaggttgggc    7320
ttcggaatcg ttttccggga cgccggctgg atgatcctcc agcgcgggga tctcatgctg    7380
gagttcttcg cccacatcat atcgat                                        7406
```

<210> SEQ ID NO 18
<211> LENGTH: 7532
<212> TYPE: DNA
<213> ORGANISM: Artificial Sequence
<220> FEATURE:
<223> OTHER INFORMATION: Synthesized

<400> SEQUENCE: 18

```
cgcgccggta tgtacaggaa gaggtttata ctaaactgtt acattgcaaa cgtggtttcg      60
tgtgccaagt gtgaaaaccg atgtttaatc aaggctctga cgcatttcta caaccacgac     120
tccaagtgtg tgggtgaagt cagatgttta aacccatgtg cctggcagat aacttcgtat     180
aatgtatgct atacgaagtt atggtacgcg gccgcgtaga ggatctgttg atcagcagtt     240
caacctgttg ataatacgga cctttaattc aacccaacac aatatattat agttaaataa     300
gaattattat caaatcattt gtatattaat taaaatacta tactgtaaat tacattttat     360
ttacaatcac tcgacaccgg tgatatccat atggcggccg ctagccgatc acgacaaccc     420
ccccttgtga ccggcatctc tccaaatgaa gggataccat ggacgaaggt cacaatcagg     480
ggagaaaatc tggggactgg ccccaccgac ctcataggct tgaccatttg tggacataat     540
tgcctcctga cggcagaatg gatgtctgca agtaaaatag tatgtcgagt gggacaagcc     600
aaaaatgaca aaggagacat tattgtcacc actaagtcag gtggcagagg aacctcaaca     660
gtctctttca agctactcaa acctgagaaa ataggcattt tggatcagtc tgctgtgtgg     720
gttgatgaaa tgaattatta tgatatgcgc actgacagga acaaaggaat ccgcccttg     780 tccttacgtc ctgctaaccc gcttggcatt gagattgaaa aaagtaaatt ttcgcagaag     840
gacttagaaa tgctattcca tggaatgagt gctgatttta caagtgagaa tttctcagca     900
gcctggtatc ttatagagaa tcactcaaac accagttttg agcagctcaa aatggcagtc     960
accaacctaa agagacaggc taacaagaag agtgagggca gcctggccta tgtgaaaggc    1020
ggtctcagta cattcttcga agcacaggat gccctctcag ccatccatca aaaactagaa    1080
gcagatggaa cggaaaaagt agaaggatcc atgacgcaga aactggagaa tgttctgaac    1140
agagcaagta atactgcaga cacattgttt caagaagtat taggtcggaa agacaaggca    1200
gattccacta gaaatgcact caatgtgctt cagcgattta gtttctttt caaccttcct    1260 ctaaatattg aaaggaatat tcaaaagggt gattatgatg tggttattaa tgattatgaa    1320
aaggccaagt cactttttgg gaaaacggag gtgcaagttt caagaaaata ttatgctgaa    1380
gtagaaacaa ggattgaagc tttaagagaa ttacttctgg ataaaattgct tgagacacca    1440 tcaactttac atgaccaaaa acgttacata aggtacctgt ctgaccttca tgcgtctggt    1500
gaccctgctt ggcaatgcat tggagcccaa cacaagtgga tccttcagct catgcacagt    1560
tgcaaagagg gctacgtgaa agatctgaaa ggtaacccag gcctgcacag tcccatgttg    1620
gatcttgata atgatacacg tccctcagtg ttgggccatc tcagtcagac agcgtccctg    1680
```

-continued

```
aagaggggca gcagctttca gtctggtcga gacgacacgt ggagatacaa aactccccac    1740
agggtggcct ttgttgaaaa attgacaaaa ctcgtcttga gccagctgcc taacttctgg    1800
aaactctgga tctcctacgt taatggaagc ctcttcagtg agactgctga gaagtcaggc    1860
cagattgaaa gatcaaagaa tgtaaggcaa agacaaaatg attttaagaa aatgattcag    1920
gaagtaatgc actccctggt gaagcttacc cgcggagccc tgcttcccct cagcatccgg    1980 gatgggaag ccaagcagta cggaggctgg gaggtgaagt gcgagctctc cggacagtgg    2040
ctcgctcacg ccatccagac tgtaagactt actcacgaat cgttgactgc ccttgaaatt    2100
cctaatgacc tgttacagac tatccaggat ctcatcttgg atctccgagt acgttgcgta    2160
atggccacgt tgcagcacac ggcggaagaa ataaagagat tagctgaaaa agaagactgg    2220
attgttgaca atgaaggact gacttctcta ccatgtcagt ttgaacagtg catcgtgtgt    2280
tctctgcagt cactgaaggg ggttctggag tgcaagccgg gagaggccag tgtcttccaa    2340
caacctaaaa cacaggagga ggtttgccag ctaagcatca atataatgca ggttttttata    2400 tactgtctgg aacagttgag caccaagcct gatgcagata tagatactac acatctctct    2460
gttgatgttt cttcccctga cttgtttgga agtatccatg aagacttcag cttgacctca    2520
gaacagcgcc ttttgatagt cctaagtaat tgctgctatc tagaacgtca caccttccta    2580
aatatcgcag aacattttga aaagcacaac ttccagggaa tagaaaaaat cacacaggtt    2640
agcatggcct cattgaaaga actagatcaa agactctttg aaaattacat cgagttgaaa    2700
gcagatccca tcgttggctc cttagaacct ggaatttatg caggatattt tgattggaag    2760
gactgcctgc ctccaacagg tgtcagaaac tatttaaaag aagcactggt gaatataatt    2820
gccgtgcatg cagaggtgtt caccatttcc aaagaactgg tccctcgggt actatccaag    2880
gtgatagaag cagtttctga agagctcagt cgactgatgc agtgtgtttc atccttcagc    2940
aaaaatggag ctttacaggc gagacttgaa atctgtgctt tgagggacac tgtggctgtt    3000
tacctgacac ccgaaagcaa gtcaagtttt aagcaggctt tggaagccct gccccagctt    3060
tccagtggag cagataaaaa gttactggaa gagctcctga acaagttcaa gagtagcatg    3120
cacttgcagc tcacctgttt ccaagcagct tcttcaacca tgatgaaaac aggctcgagt    3180
gaaaatttgt attttcaaag cactagtggt acccttaaga tggcgatggc gatgtcggac    3240
agtggggcga gccgcctgcg tcggcagctg gagtcagggg gttttgaggc gcggctgtac    3300
gtgaagcagc tctcgcagca gtcggatggg gaccgggacc tccaggagca ccggcagcgc    3360
atccaggcgc tggcggagga gacggcgcag aacctgaagc gcaacgtcta ccagaactac    3420
cggcagttca tagagacggc ccgcgagatc tcctacctgg agagcgagat gtaccagctc    3480
agccatttgc tgaccgagca gaaaagcagc ctggagagca tcccgcttac gttgctgcct    3540
gccgctgctg ccgccggagc cgccgccgcc tctggagggg aggagggagt cggtggggcg    3600
gggggccgag accacctccg aggccaggcc ggcttttttct ccaccccggg gggtgcctcc    3660
cgcgacggct ccggtccagg cgaggaagga aagcagcgca ctctcaccac cctgcttgag    3720
aaggtggaag gctgcaggca tctgctggag acgccgggac agtacttggt gtacaatggg    3780
gacctagtgg aatacgatgc ggaccacatg gcccaactgc agcgggtgca cggctttctc    3840
atgaacgatt gcttgttggt ggctacctgg ctgcctcagc ggcgtgggat gtatcgctac    3900
aacgctctct attccctaga tggtttggcc gtagtcaatg tcaaggacaa cccgcccatg    3960
aaggacatgt tcaagctgct tatgttcccc gagagccgta ttttccaggc cgaaaatgct    4020
```

-continued

```
aaaatcaaac gagagtggct ggaagtgctg gaggacacca agagggccct cagtgagaaa   4080
aggcgaaggg agcaggagga ggcagcggcc cctcgagggc caccccaagt gacttccaag   4140
gccactaacc catttgagga tgacgaagaa gaagaaccag ctgttcctga ggtagaggaa   4200
gagaaggtgg acctctccat ggaatggatc caggagttac ctgaagacct ggatgtctgc   4260
attgcgcaga gagactttga aggggcggtt gacctgctgg ataaaattgaa ccattacctg  4320 gaagataaac ctagcccacc tcctgtaaaa gaactaaggg ccaaagtgga ggagcgagtt   4380
cgacagctca ctgaggtgct agttttcgaa ctctccccag atcgttccct gagaggtggt   4440
ccgaaggcta ctcgcagagc agtttcgcaa ctgatccggc tgggccagtg cacgaaggcc   4500
tgtgagctat ttttgagaaa cagggcagcc gctgttcata ctgcaattcg tcagcttcgc   4560
atcgaaggtg ccactttact ctatattcat aagctgtgcc atgtcttctt taccagcctt   4620
ctcgagactg caagagaatt tgagatcgat tttgcaggca ctgacagcgg ctgctactct   4680
gcctttgtgg tctgggcaag atcagccatg ggcatgttcg tggatgcttt tagcaagcag   4740
gtgtttgata gtaaggagag cctctctaca gcagctgagt gtgtaaaagt ggctaaggag   4800
cattgccagc aactgggtga tatcggactg gatctcacct tcatcatcca tgcccttctg   4860
gtgaaagaca tccaaggggc cttgcacagt tacaaagaaa tcatcattga agccactaaa   4920
catcgcaact ctgaagagat gtggaggagg atgaacttga tgacgccaga gccctgggt    4980 aagctcaaag aagagatgaa aagttgtggg gtaagtaact ttgagcagta cacaggggat   5040
gactgctggg tgaacctaag ttacacagtg gttgctttca ccaaacagac catgggcttc   5100
ttggaagagg ccctgaagct gtatttccca gagctgcaca tggtacttt ggagagcctg    5160 gtggaaatca tttttggttgc tgttcagcat gtggattata gtcttcgatg tgagcaggat   5220
ccagagaaga aagcttttat cagacagaat gcatcctttt tatatgaaac agtcctccct   5280
gtggtggaga aaaggtttga agaaggtgtg gggaaacctg ccaagcaact ccaagatctg   5340
aggaatgcat ctagacttat tcgtgtgaat cctgaaagta caacatcagt ggtctaagaa   5400
ttcggtaccc gaaaggaagc tgagttggct gctgccaccg ctgagcaata actagcataa   5460
cccccttggg cctctaaacg ggtcttgagg ggtttttttgc tgaaaggagg aactatcctc   5520
agggggagat gggggaggct aactgaaaca cggaaggaga caataccgga aggaacccgc   5580
gctatgacga caataaaaag acagaataaa acgcacgggt gttgggtcgt ttgttcataa   5640
acgcggggtt cggtcccagg gctggcactc tgtcgatacc ccaccgagac cccattggga   5700
ccaatacgcc cgcgtttctt ccttttcccc accccaaccc ccaagttcgg gtgaaggccc   5760
agggctcgca gccaacgtcg gggcggcaag ccctgccata gccactacgg gtacgtctga   5820
aagcatgcct ttttggaatt tacgtactaa gctctcatgt ttcacgtact aagctctcat   5880
gtttaacgta ctaagctctc atgtttaacg aactaaaccc tcatggctaa cgtactaagc   5940
tctcatggct aacgtactaa gctctcatgt ttcacgtact aagctctcat gtttgaacaa   6000
taaaattaat ataaatcagc aacttaaata gcctctaagg ttttaagtttt tataagaaaa   6060 aaaagaatat ataaggcttt taaagctttt aaggtttaac ggttgtggac aacaagccag   6120
ggatgtaacg cactgagaag cccttagagc ctctcaaagc aattttcagt gacacaggaa   6180
cacttaacgg ctgacagaat tagcttcacg ctgccgcaag cactcagggc gcaagggctg   6240
ctaaaggaag cggaacacgt agaaagccag tccgcagaaa cggtgctgac cccggatgaa   6300
tgtcagctac tgggctatct ggacaaggga aaacgcaagc gcaaagagaa agcaggtagc   6360
ttgcagtggg cttacatggc gatagctaga ctgggcggtt ttatggacag caagcgaacc   6420
```

-continued

```
ggaattgcca gctggggcgc cctctggtaa ggttgggaag ccctgcaaag taaactggat      6480
ggctttcttg ccgccaagga tctgatggcg caggggatca agatctgatc aagagacagg      6540
atgaggatcg tttcgcatga ttgaacaaga tggattgcac gcaggttctc cggccgcttg      6600
ggtggagagg ctattcggct atgactgggc acaacagaca atcggctgct ctgatgccgc      6660
cgtgttccgg ctgtcagcgc aggggcgccc ggttcttttt gtcaagaccg acctgtccgg      6720
tgccctgaat gaactgcagg acgaggcagc gcggctatcg tggctggcca cgacgggcgt      6780
tccttgcgca gctgtgctcg acgttgtcac tgaagcggga agggactggc tgctattggg      6840
cgaagtgccg gggcaggatc tcctgtcatc tcaccttgct cctgccgaga aagtatccat      6900
catggctgat gcaatgcggc ggctgcatac gcttgatccg gctacctgcc cattcgacca      6960
ccaagcgaaa catcgcatcg agcgagcacg tactcggatg gaagccggtc ttgtcgatca      7020
ggatgatctg gacgaagagc atcaggggct cgcgccagcc gaactgttcg ccaggctcaa      7080
ggcgcgcatg cccgacggcg aggatctcgt cgtgacacat ggcgatgcct gcttgccgaa      7140
tatcatggtg gaaaatggcc gcttttctgg attcatcgac tgtggccggc tgggtgtggc      7200
ggaccgctat caggacatag cgttggctac ccgtgatatt gctgaagagc ttggcggcga      7260
atgggctgac cgcttcctcg tgctttacgg tatcgccgct cccgattcgc agcgcatcgc      7320
cttctatcgc cttcttgacg agttcttctg agcgggactc tggggttcga aatgaccgac      7380
caagcgacgc ccaacctgcc atcacgagat ttcgattcca ccgccgcctt ctatgaaagg      7440
ttgggcttcg gaatcgtttt ccgggacgcc ggctggatga tcctccagcg cggggatctc      7500
atgctggagt tcttcgccca catcatatcg at                                    7532
```

```
<210> SEQ ID NO 19
<211> LENGTH: 7526
<212> TYPE: DNA
<213> ORGANISM: Artificial Sequence
<220> FEATURE:
<223> OTHER INFORMATION: Synthesized

<400> SEQUENCE: 19
```

```
cgcgccggta tgtacaggaa gaggtttata ctaaactgtt acattgcaaa cgtggtttcg        60
tgtgccaagt gtgaaaaccg atgtttaatc aaggctctga cgcatttcta caaccacgac       120
tccaagtgtg tgggtgaagt cagatgttta aacccatgtg cctggcagat aacttcgtat       180
aatgtatgct atacgaagtt atggtacgcg ccgcgtaga ggatctgttg atcagcagtt       240
caacctgttg ataatacgga cctttaattc aacccaacac aatatattat agttaaataa       300
gaattattat caaatcattt gtatattaat taaaatacta tactgtaaat tacattttat       360
ttacaatcac tcgacaccgg tgatatccat atgggatcca cagcaatcaa gcatgcatta       420
caaagagaca tttttacacc aaatgatgaa cgcctgctga gcattgtgaa tgtctgcaaa       480
gcaggaaaaa agaaaaagaa ctgttttta tgtgccacag tgacaactga acgccctgtg       540
caggttaagg tggtcaaagt caagaaatcc gataagggag atttctacaa aaggcagatt       600
gcatgggccc ttcgagatct tgctgtggta gatgccaaag atgctatcaa agaaaatcct       660
gaatttgatt tacactttga aaaaatatat aaatgggttg ccagcagcac tgctgaaaag       720
aatgcattta tttcatgcat ttggaaattg aatcagcgat atctccggaa gaaaattgat       780
tttgtcaatg ttagctcaca gcttttggaa gaactgccta aagttacaga agaatctgtt       840
ccaagtggag aaaatcagag tgtgacagga ggtgatgaag aagtagtaga tgaataccaa       900
```

-continued

```
gagttaaatg caagagaaga acaggatatc gaaataatga tggaaggctg tgaatatgca      960
atctcgaatg cggaagcctt tgcagaaaaa ttgtccagag agctgcaggt gctagatggg     1020
gctaacatcc agtcaatcat ggcatctgaa aaacaagtca acatcctgat gaaattgcta     1080
gatgaggctc taaaggaggt agatcagatt gaattgaaac tgagcagtta tgaggaaatg     1140
ctccaaagtg taaaagaaca aatggatcag atctctgaaa gcaaccacct aattcatctt     1200
agtaacacta ataatgtaaa actcctatct gagatagagt tccttgtgaa ccacatggac     1260
ttggccaaag gtcatataaa ggcccttcag gaaggagatc ttgcttcttc cagaggcatt     1320
gaggcctgca ccaatgctgc tgatgccctt ctgcagtgca tgaatgtagc tcttcgacca     1380
ggccatgact tgcttctggc agtcaaacag caacagcagc gattcagtga tttgcgagag     1440 cttttttgccc ggagactggc cagtcacctc aacaatgttt ttgttcaaca gggtcatgat     1500
cagagttcga ctcttgccca acactctgtt gaactgactt tacccaatca tcatccattt     1560
catagagatt tgctccgata tgccaagctg atggagtggc taaagagtac agattatgga     1620
aaatatgaag gactaacaaa gaattacatg gattatttat cccgactata tgaaagagaa     1680
atcaaagatt tctttgaagt tgcaaagatc aagatgactg gcacaactaa agaaagcaag     1740
aagtttgcta cactgcctcg aaaagaaagt gctgtcaaac aggaaacaga gagtcttcat     1800
ggaagttcgg ggaaattaac tggatctact tctagtctaa ataagctcag tgttcagagt     1860
tcagggaatc gcagatctca gtcatcttcc ctgttggata tggaaacat gtctgcctct     1920 gatctcgatg ttgctgacag gaccaaattt gataagatct ttgaacaggt actaagtgaa     1980
ctggagcccc tatgtctggc agaacaggac ttcataagta aatttttcaa actacagcaa     2040
catcaaagta tgcctggaac tatggctgaa gcagaggacc tggatggagg aacattatca     2100
cggcaacata attgtggcac accactgcct gtttcatctg agaaagatat gatccgccaa     2160
atgatgatta aaatatttcg ctgcattgag ccagagctga caacctaat tgcattagga     2220 gacaaaattg atagctttaa ctctctttat atgttagtca aaatgagtca tcatgtgtgg     2280
actgcacaaa atgtggaccc tgcttctttc ctaagtacta cattgggaaa tgttttggtg     2340
actgtcaaaa ggaactttga caaatgcatt agtaaccaaa taaggcaaat ggaagaagta     2400
aagatctcaa aaaagagtaa agttggaatt cttccatttg ttgctgaatt tgaagaattt     2460
gctggacttg cagaatcaat cttcaaaaat gctgagcgtc gtggagacct ggataaagca     2520
tacaccaaac ttatcagagg agtatttgtt aatgtggaga aagtagcaaa tgaaagccag     2580 aagacccccca gggatgtggt tatgatggaa aactttcacc atattttgc aactctttct     2640 cgattgaaaa tctcatgtct agaagcagaa aaaaagaag ccaaacaaaa atacacagat     2700
caccttcagt cttatgtcat ttactcttta ggacaacctc ttgaaaaact aaatcatttc     2760
tttgaaggtg ttgaagctcg cgtggcacag ggcataaggg aggaggaagt aagttaccaa     2820
cttgcattta acaaacaaga acttcgtaaa gtcattaagg agtaccctgg aaaggaagta     2880
aaaaaaggtc tagataacct ctacaagaaa gttgataaac atttatgtga agaagagaac     2940
ttacttcagg tggtgtggca ctccatgcaa gatgaattta tacgccagta taagcacttt     3000
gaaggtttga tagctcgctg ttatcctgga tctggtgtta caatggaatt cactattcag     3060
gacattctgg attattgttc cagcattgca cagtcccacg gctcgagtga aaacctgtac     3120
ttccagagct ctagcttaag catggcctgg agccatccgc aatttgaaaa aggtggcggg     3180
tccggcggag gtagcggcgg aggttcttgg tctcaccctc agttcgagaa ggatgacgat     3240
gataaaacca tgggatccct aggtaccgcg gccgcgacca cggccgagtt gttcgaggag     3300
```

```
ccttttgtgg cagatgaata tattgaacgt cttgtatgga gaacccagg aggaggctct   3360 agaggtggac ctgaagcttt tgatcctaaa agattattag aagaatttgt aaatcatatt   3420
caggaactcc agataatgga tgaaaggatt cagaggaaag tagagaaact agagcaacaa   3480
tgtcagaaag aagccaagga atttgccaag aaggtacaag agctgcagaa aagcaatcag   3540
gttgccttcc aacatttcca agaactagat gagcacatta gctatgtagc aactaaagtc   3600
tgtcaccttg gagaccagtt agaggggta aacacaccca gacaacgggc agtggaggct   3660
cagaaattga tgaaatactt taatgagttt ctagatggag aattgaaatc tgatgttttt   3720
acaaattctg aaaagataaa ggaagcagca gacatcattc agaagttgca cctaattgcc   3780
caagagttac cttttgatag attttcagaa gttaaatcca aaattgcaag taaataccat   3840
gatttagaat gccagctgat tcaggagttt accagtgctc aaagaagagg tgaaatctcc   3900
agaatgagag aagtagcagc agttttactt cattttaagg gttattccca ttgtgttgat   3960
gtttatataa agcagtgcca ggagggtgct tatttgagaa atgatatatt tgaagacgct   4020
ggaatactct gtcaaagagt gaacaaacaa gttggagata tcttcagtaa tccagaaaca   4080
gtcctggcta aacttattca aaatgtattt gaaatcaaac tacagagttt tgtgaaagag   4140
cagttagaag aatgtaggaa gtccgatgca gagcaatatc tcaaaaatct ctatgatctg   4200
tatacaagaa ccaccaatct ttccagcaag ctgatggagt ttaatttagg tactgataaa   4260
cagactttct tgtctaagct tatcaaatcc attttcattt cctatttgga gaactatatt   4320
gaggtggaga ctggatattt gaaaagcaga agtgctatga tcctacagcg ctattatgat   4380
tcgaaaaacc atcaaaagag atccattggc acaggaggta ttcaagattt gaaggaaaga   4440
attagacagc gtaccaactt accacttggg ccaagtatcg atactcatgg ggagactttt   4500
ctatcccaag aagtggtggt taatcttta caagaaacca aacaagcctt tgaaagatgt   4560
cataggctct ctgatccttc tgacttacca aggaatgcct tcagaatttt taccattctt   4620
gtggaatttt tatgtattga gcatattgat tatgctttgg aaacaggact tgctggaatt   4680
ccctcttcag attctaggaa tgcaaatctt tattttttgg acgttgtgca acaggccaat   4740
actatttttc atcttttga caaacagttt aatgatcacc ttatgccact aataagctct   4800
tctcctaagt tatctgaatg ccttcagaag aaaaaagaaa taattgaaca aatggagatg   4860
aaattggata ctggcattga taggacatta aattgtatga ttggacagat gaagcatatt   4920
ttggctgcag aacagaagaa aacagatttt aagccagaag atgaaaacaa tgttttgatt   4980
caatatacta atgcctgtgt aaaagtctgt gcttacgtaa gaaaacaagt ggagaagatt   5040
aaaaattcca tggatgggaa gaatgtggat acagttttga tggaacttgg agtacgtttt   5100
catcgactta tctatgagca tcttcaacaa tattcctaca gttgtatggg tggcatgttg   5160
gcaatttgtg atgtagccga atataggaag tgtgccaaag acttcaagat tccaatggta   5220
ttacatcttt ttgatactct gcatgctctt tgcaatcttc tggtagttgc cccagataat   5280
ttaaagcaag tctgctcagg agaacaactt gctaatctgg acaagaatat acttcactcc   5340
ttcgtacaac ttcgtgctga ttatagatct gcccgccttg ctcgacactt cagctaaggt   5400
acccgaaagg aagctgagtt ggctgctgcc accgctgagc aataactagc ataacccctt   5460
ggggcctcta acgggtctt gaggggtttt ttgctgaaag gaggaactat cctcaggggg   5520
agatggggga ggctaactga aacacggaag gagacaatac cggaaggaac ccgcgctatg   5580
acggcaataa aaagacagaa taaaacgcac gggtgttggg tcgtttgttc ataaacgcgg   5640
```

-continued

```
ggttcggtcc cagggctggc actctgtcga tacccaccg agaccccatt gggaccaata      5700
cgcccgcgtt tcttccttt ccccacccca acccccaagt tcgggtgaag gcccaggct       5760 cgcagccaac gtcggggcgg caagccctgc catagccact acgggtacgt ctgaaagcat     5820
gcctttttgg aatttacgta ctaagctctc atgtttcacg tactaagctc tcatgtttaa     5880
cgtactaagc tctcatgttt aacgaactaa accctcatgg ctaacgtact aagctctcat     5940
ggctaacgta ctaagctctc atgtttcacg tactaagctc tcatgtttga acaataaaat     6000
taatataaat cagcaactta aatagcctct aaggttttaa gttttataag aaaaaaaga      6060 atatataagg cttttaaagc ttttaaggtt taacggttgt ggacaacaag ccagggatgt     6120
aacgcactga gaagcccta gagcctctca aagcaatttt cagtgacaca ggaacactta      6180
acggctgaca gaattagctt cacgctgccg caagcactca gggcgcaagg ctgctaaag     6240 gaagcggaac acgtagaaag ccagtccgca gaaacggtgc tgaccccgga tgaatgtcag     6300
ctactgggct atctggacaa gggaaaacgc aagcgcaaag agaaagcagg tagcttgcag    6360
tgggcttaca tggcgatagc tagactgggc ggttttatgg acagcaagcg aaccggaatt    6420
gccagctggg gcgccctctg gtaaggttgg gaagccctgc aaagtaaact ggatggcttt    6480
cttgccgcca aggatctgat ggcgcagggg atcaagatct gatcaagaga caggatgagg    6540
atcgtttcgc atgattgaac aagatggatt gcacgcaggt tctccggccg cttgggtgga    6600
gaggctattc ggctatgact gggcacaaca gacaatcggc tgctctgatg ccgccgtgtt    6660
ccggctgtca gcgcagggc gcccggttct ttttgtcaag accgacctgt ccggtgccct    6720
gaatgaactg caggacgagg cagcgcggct atcgtggctg gccacgacgg cgttccttg    6780 cgcagctgtg ctcgacgttg tcactgaagc gggaagggac tggctgctat tgggcgaagt    6840
gccggggcag gatctcctgt catctcacct tgctcctgcc gagaaagtat ccatcatggc     6900
tgatgcaatg cggcggctgc atacgcttga tccggctacc tgcccattcg accaccaagc    6960
gaaacatcgc atcgagcgag cacgtactcg gatggaagcc ggtcttgtcg atcaggatga    7020
tctggacgaa gagcatcagg ggctcgcgcc agccgaactg ttcgccaggc tcaaggcgcg    7080
catgcccgac ggcgaggatc tcgtcgtgac acatggcgat gcctgcttgc cgaatatcat    7140
ggtggaaaat ggccgctttt ctggattcat cgactgtggc cggctgggtg tggcggaccg    7200
ctatcaggac atagcgttgg ctacccgtga tattgctgaa gagcttggcg gcgaatgggc    7260
tgaccgcttc ctcgtgcttt acggtatcgc cgctcccgat tcgcagcgca tcgccttcta    7320
tcgccttctt gacgagttct tctgagcggg actctgggt tcgaaatgac cgaccaagcg    7380
acgcccaacc tgccatcacg agatttcgat tccaccgccg ccttctatga aaggttgggc    7440
ttcggaatcg ttttccggga cgccggctgg atgatcctcc agcgcgggga tctcatgctg    7500
gagttcttcg cccacatcat atcgat                                         7526
```

<210> SEQ ID NO 20
<211> LENGTH: 5911
<212> TYPE: DNA
<213> ORGANISM: Artificial Sequence
<220> FEATURE:
<223> OTHER INFORMATION: Synthesized

<400> SEQUENCE: 20

```
tggcgaatgg gacgcgccct gtagcggcgc attaagcgcg gcgggtgtgg tggttacgcg       60
cagcgtgacc gctacacttg ccagcgccct agcgcccgct cctttcgctt tcttcccttc      120
ctttctcgcc acgttcgccg gctttccccg tcaagctcta aatcggggc tccctttagg     180
```

-continued

```
gttccgattt agtgctttac ggcacctcga ccccaaaaaa cttgattagg gtgatggttc      240
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttatttttc taaatacatt caaatatgta      540
tccgctcatg agacaataac cctgataaat gcttcaataa tattgaaaaa ggaagagtat      600
gagtattcaa catttccgtg tcgcccttat tccctttttt gcggcatttt gccttcctgt      660
ttttgctcac ccagaaacgc tggtgaaagt aaaagatgct gaagatcagt tgggtgcacg      720
agtgggttac atcgaactgg atctcaacag cggtaagatc cttgagagtt ttcgccccga      780
agaacgtttt ccaatgatga gcacttttaa agttctgcta tgtggcgcgg tattatcccg      840
tattgacgcc gggcaagagc aactcggtcg ccgcatacac tattctcaga atgacttggt      900
tgagtactca ccagtcacag aaaagcatct tacggatggc atgacagtaa gagaattatg      960
cagtgctgcc ataaccatga gtgataacac tgcggccaac ttacttctga caacgatcgg     1020
aggaccgaag gagctaaccg cttttttgca caacatgggg gatcatgtaa ctcgccttga     1080
tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380
gacggggagt caggcaacta tggatgaacg aaatagacag atcgctgaga taggtgcctc     1440
actgattaag cattggtaac tgtcagacca agtttactca tatatacttt agattgattt     1500
aaaacttcat ttttaattta aaaggatcta ggtgaagatc ctttttgata atctcatgac     1560
caaaatccct taacgtgagt tttcgttcca ctgagcgtca gaccccgtag aaaagatcaa     1620
aggatcttct tgagatcctt ttttttctgcg cgtaatctgc tgcttgcaaa caaaaaaacc     1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agtggctgct gccagtggcg ataagtcgtg tcttaccggg ttggactcaa gacgatagtt     1920
accggataag gcgcagcggt cgggctgaac ggggggttcg tgcacacagc ccagcttgga     1980
gcgaacgacc tacaccgaac tgagatacct acagcgtgag ctatgagaaa gcgccacgct     2040
tcccgaaggg agaaaggcgg acaggtatcc ggtaagcggc agggtcggaa caggagagcg     2100
cacgagggag cttccagggg gaaacgcctg gtatctttat agtcctgtcg ggtttcgcca     2160
cctctgactt gagcgtcgat ttttgtgatg ctcgtcaggg gggcggagcc tatggaaaaa     2220
cgccagcaac gcggcctttt tacggttcct ggccttttgc tggccttttg ctcacatgtt     2280
ctttcctgcg ttatcccctg attctgtgga taaccgtatt accgcctttg agtgagctga     2340
taccgctcgc cgcagccgaa cgaccgagcg cagcgagtca gtgagcgagg aagcggaaga     2400
gcgcctgatg cggtatttttc tccttacgca tctgtgcggt atttcacacc gcatatatgg     2460
tgcactctca gtacaatctg ctctgatgcc gcatagttaa gccagtatac actccgctat     2520
```

-continued

```
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga ataacgccg gaacattagt gcaggcagct     4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
```

```
gcccaacagt cccccggcca cggggcctgc caccataccc acgccgaaac aagcgctcat      4980
gagcccgaag tggcgagccc gatcttcccc atcggtgatg tcggcgatat aggcgccagc      5040
aaccgcacct gtggcgccgg tgatgccggc cacgatgcgt ccggcgtaga ggatcgagat      5100
ctcgatcccg cgaaattaat acgactcact atagggggaat tgtgagcgga taacaattcc      5160
cctctagaaa taattttgtt taactttaag aaggagatat acatatgggc acccgtgacg      5220
acgagtacga ctacctgttc aaggtggtgc tgatcggtga cagcggcgtg ggtaaatcca      5280
acctgctgtc ccgcttcacc cgtaacgagt caacctgga gtccaagtcc accatcggcg       5340
tggagttcgc cacccgttcc atccaggtgg acggtaagac catcaaggct cagatctggg      5400
acaccgctgg tctggagcgc taccgcgcca tcacctccgc ttactaccgc ggtgccgtgg      5460
gtgctctcct ggtgtacgac atcgctaagc acctgaccta cgagaacgtg gagcgctggc      5520
tgaaggagct gcgcgaccac gctgactcca acatcgtcat catgctggtg ggcaacaagt      5580
ccgacctgcg ccacctgcgt gctgtgccta ctgacgaagc tcgcgctttc gctgagaaga      5640
acggcctgtc cttcatcgag accagcgctc tggactccac caacgtggag gccgctttcc      5700
agaccatcct caccgagatc tacggctcga gtgggagctc tggaggccac catcaccatc      5760
atcaccatca ctaagtaacc ggctgctaac aaagcccgaa aggaagctga gttggctgct      5820
gccaccgctg agcaataact agcataaccc cttggggcct ctaaacgggt cttgaggggt      5880
tttttgctga aaggaggaac tatatccgga t                                     5911
```

```
<210> SEQ ID NO 21
<211> LENGTH: 42
<212> TYPE: DNA
<213> ORGANISM: Artificial Sequence
<220> FEATURE:
<223> OTHER INFORMATION: Synthesized

<400> SEQUENCE: 21
tatccatatg ggatccacag caatcaagca tgcattacaa ag                         42

<210> SEQ ID NO 22
<211> LENGTH: 46
<212> TYPE: DNA
<213> ORGANISM: Artificial Sequence
<220> FEATURE:
<223> OTHER INFORMATION: Synthesized

<400> SEQUENCE: 22
atcactcgac accggtgata tccatatggg atccacagca atcaag                     46

<210> SEQ ID NO 23
<211> LENGTH: 48
<212> TYPE: DNA
<213> ORGANISM: Artificial Sequence
<220> FEATURE:
<223> OTHER INFORMATION: Synthesized

<400> SEQUENCE: 23
caggttttca ctcgagccgt gggactgtgc aatgctggaa caataatc                   48

<210> SEQ ID NO 24
<211> LENGTH: 48
<212> TYPE: DNA
<213> ORGANISM: Artificial Sequence
<220> FEATURE:
<223> OTHER INFORMATION: Synthesized
```

-continued

```
<400> SEQUENCE: 24
taagctagag ctctggaagt acaggttttc actcgagccg tgggactg                       48

<210> SEQ ID NO 25
<211> LENGTH: 48
<212> TYPE: DNA
<213> ORGANISM: Artificial Sequence
<220> FEATURE:
<223> OTHER INFORMATION: Synthesized

<400> SEQUENCE: 25
gcttaagcgc ggccgcgacc acggccgagt tgttcgagga gccttttg                       48

<210> SEQ ID NO 26
<211> LENGTH: 48
<212> TYPE: DNA
<213> ORGANISM: Artificial Sequence
<220> FEATURE:
<223> OTHER INFORMATION: Synthesized

<400> SEQUENCE: 26
acctgtactt ccagagctct agcttaagcg cggccgcgac cacggccg                       48

<210> SEQ ID NO 27
<211> LENGTH: 48
<212> TYPE: DNA
<213> ORGANISM: Artificial Sequence
<220> FEATURE:
<223> OTHER INFORMATION: Synthesized

<400> SEQUENCE: 27
cctttcgggt accctcgagt tagctgaagt gtcgagcaag gcgggcag                       48

<210> SEQ ID NO 28
<211> LENGTH: 44
<212> TYPE: DNA
<213> ORGANISM: Artificial Sequence
<220> FEATURE:
<223> OTHER INFORMATION: Synthesized

<400> SEQUENCE: 28
cagcagccaa ctcagcttcc tttcgggtac cctcgagtta gctg                           44

<210> SEQ ID NO 29
<211> LENGTH: 44
<212> TYPE: DNA
<213> ORGANISM: Artificial Sequence
<220> FEATURE:
<223> OTHER INFORMATION: Synthesized

<400> SEQUENCE: 29
tatccatatg gcggccgcta gccgatcacg acaacccccc cttg                           44

<210> SEQ ID NO 30
<211> LENGTH: 45
<212> TYPE: DNA
<213> ORGANISM: Artificial Sequence
<220> FEATURE:
<223> OTHER INFORMATION: Synthesized

<400> SEQUENCE: 30
atcactcgac accggtgata tccatatggc ggccgctagc cgatc                          45

<210> SEQ ID NO 31
<211> LENGTH: 48
```

-continued

```
<212> TYPE: DNA
<213> ORGANISM: Artificial Sequence
<220> FEATURE:
<223> OTHER INFORMATION: Synthesized

<400> SEQUENCE: 31
atacaaattt tcactcgagc ctgttttcat catggttgaa gaagctgc                   48

<210> SEQ ID NO 32
<211> LENGTH: 48
<212> TYPE: DNA
<213> ORGANISM: Artificial Sequence
<220> FEATURE:
<223> OTHER INFORMATION: Synthesized

<400> SEQUENCE: 32
gtaccactag tgctttgaaa atacaaattt tcactcgagc ctgttttc                   48

<210> SEQ ID NO 33
<211> LENGTH: 48
<212> TYPE: DNA
<213> ORGANISM: Artificial Sequence
<220> FEATURE:
<223> OTHER INFORMATION: Synthesized

<400> SEQUENCE: 33
agcactagtg gtacccttaa gatggcgatg gcgatgtcgg acagtggg                   48

<210> SEQ ID NO 34
<211> LENGTH: 48
<212> TYPE: DNA
<213> ORGANISM: Artificial Sequence
<220> FEATURE:
<223> OTHER INFORMATION: Synthesized

<400> SEQUENCE: 34
agtgaaaatt tgtattttca aagcactagt ggtaccctta agatggcg                   48

<210> SEQ ID NO 35
<211> LENGTH: 45
<212> TYPE: DNA
<213> ORGANISM: Artificial Sequence
<220> FEATURE:
<223> OTHER INFORMATION: Synthesized

<400> SEQUENCE: 35
ctttcgggta ccgaattctt agaccactga tgttgtactt tcagg                      45

<210> SEQ ID NO 36
<211> LENGTH: 46
<212> TYPE: DNA
<213> ORGANISM: Artificial Sequence
<220> FEATURE:
<223> OTHER INFORMATION: Synthesized

<400> SEQUENCE: 36
cagcagccaa ctcagcttcc tttcgggtac cgaattctta gaccac                     46

<210> SEQ ID NO 37
<211> LENGTH: 48
<212> TYPE: DNA
<213> ORGANISM: Artificial Sequence
<220> FEATURE:
<223> OTHER INFORMATION: Synthesized

<400> SEQUENCE: 37
```
agagcggtac cgcggccgcg atgaaggaga cagaccggga ggccgttg                48

<210> SEQ ID NO 38
<211> LENGTH: 48
<212> TYPE: DNA
<213> ORGANISM: Artificial Sequence
<220> FEATURE:
<223> OTHER INFORMATION: Synthesized

<400> SEQUENCE: 38
cgagtgagaa tctgtatttc cagagcggta ccgcggccgc gatgaagg                48

<210> SEQ ID NO 39
<211> LENGTH: 42
<212> TYPE: DNA
<213> ORGANISM: Artificial Sequence
<220> FEATURE:
<223> OTHER INFORMATION: Synthesized

<400> SEQUENCE: 39
gtcagttaac tcgagttact tgagcagctt ggccacgttc ag                42

<210> SEQ ID NO 40
<211> LENGTH: 43
<212> TYPE: DNA
<213> ORGANISM: Artificial Sequence
<220> FEATURE:
<223> OTHER INFORMATION: Synthesized

<400> SEQUENCE: 40
cctttcgaag cttttagtca gttaactcga gttacttgag cag                43

<210> SEQ ID NO 41
<211> LENGTH: 43
<212> TYPE: DNA
<213> ORGANISM: Artificial Sequence
<220> FEATURE:
<223> OTHER INFORMATION: Synthesized

<400> SEQUENCE: 41
agctccatat gggatccgcg gagaacagcg agagtctggg cac                43

<210> SEQ ID NO 42
<211> LENGTH: 43
<212> TYPE: DNA
<213> ORGANISM: Artificial Sequence
<220> FEATURE:
<223> OTHER INFORMATION: Synthesized

<400> SEQUENCE: 42
atttaaacgg atcgatgagc tccatatggg atccgcggag aac                43

<210> SEQ ID NO 43
<211> LENGTH: 48
<212> TYPE: DNA
<213> ORGANISM: Artificial Sequence
<220> FEATURE:
<223> OTHER INFORMATION: Synthesized

<400> SEQUENCE: 43
acagattctc actcgagccc atgtgctggg acataccatt caccaaac                48

<210> SEQ ID NO 44
<211> LENGTH: 48
<212> TYPE: DNA
<213> ORGANISM: Artificial Sequence -continued
<220> FEATURE:
<223> OTHER INFORMATION: Synthesized

<400> SEQUENCE: 44
cgcggtaccg ctctggaaat acagattctc actcgagccc atgtgctg                          48

<210> SEQ ID NO 45
<211> LENGTH: 45
<212> TYPE: DNA
<213> ORGANISM: Artificial Sequence
<220> FEATURE:
<223> OTHER INFORMATION: Synthesized

<400> SEQUENCE: 45
gctccatatg gcggccgcgg aagcagctgg tgggaaatac agaag                            45

<210> SEQ ID NO 46
<211> LENGTH: 45
<212> TYPE: DNA
<213> ORGANISM: Artificial Sequence
<220> FEATURE:
<223> OTHER INFORMATION: Synthesized

<400> SEQUENCE: 46
atttaaacgg atcgatgagc tccatatggc ggccgcggaa gcagc                            45

<210> SEQ ID NO 47
<211> LENGTH: 48
<212> TYPE: DNA
<213> ORGANISM: Artificial Sequence
<220> FEATURE:
<223> OTHER INFORMATION: Synthesized

<400> SEQUENCE: 47
agtacaagtt ctcactcgag ccaacggtag ttatcttctt gtccttgg                          48

<210> SEQ ID NO 48
<211> LENGTH: 46
<212> TYPE: DNA
<213> ORGANISM: Artificial Sequence
<220> FEATURE:
<223> OTHER INFORMATION: Synthesized

<400> SEQUENCE: 48
gtaccgctta aggactgaaa gtacaagttc tcactcgagc caacgg                           46

<210> SEQ ID NO 49
<211> LENGTH: 47
<212> TYPE: DNA
<213> ORGANISM: Artificial Sequence
<220> FEATURE:
<223> OTHER INFORMATION: Synthesized

<400> SEQUENCE: 49
tcagtcctta agcggtacca tgattccccc acaggaggca tccgctc                           47

<210> SEQ ID NO 50
<211> LENGTH: 44
<212> TYPE: DNA
<213> ORGANISM: Artificial Sequence
<220> FEATURE:
<223> OTHER INFORMATION: Synthesized

<400> SEQUENCE: 50
agtgagaact tgtactttca gtccttaagc ggtaccatga ttcc                             44

-continued

<210> SEQ ID NO 51
<211> LENGTH: 42
<212> TYPE: DNA
<213> ORGANISM: Artificial Sequence
<220> FEATURE:
<223> OTHER INFORMATION: Synthesized

<400> SEQUENCE: 51
tcagttaact cgagttaggc agaggtgtca aaaaggcgat cg                          42

<210> SEQ ID NO 52
<211> LENGTH: 44
<212> TYPE: DNA
<213> ORGANISM: Artificial Sequence
<220> FEATURE:
<223> OTHER INFORMATION: Synthesized

<400> SEQUENCE: 52
cctttcgaag cttttagtca gttaactcga gttaggcaga ggtg                       44

<210> SEQ ID NO 53
<211> LENGTH: 49
<212> TYPE: DNA
<213> ORGANISM: Artificial Sequence
<220> FEATURE:
<223> OTHER INFORMATION: Synthesized

<400> SEQUENCE: 53
tacttccaga gctctagctt aagcatggcc tggagccatc cgcaatttg                  49

<210> SEQ ID NO 54
<211> LENGTH: 49
<212> TYPE: DNA
<213> ORGANISM: Artificial Sequence
<220> FEATURE:
<223> OTHER INFORMATION: Synthesized

<400> SEQUENCE: 54
caactcagct tcctttcggg taccttagct gaagtgtcga gcaaggcgg                  49

<210> SEQ ID NO 55
<211> LENGTH: 30
<212> TYPE: DNA
<213> ORGANISM: Artificial Sequence
<220> FEATURE:
<223> OTHER INFORMATION: Synthesized

<400> SEQUENCE: 55
aaaacatatg ggcacccgtg acgacgagta                                       30

<210> SEQ ID NO 56
<211> LENGTH: 34
<212> TYPE: DNA
<213> ORGANISM: Artificial Sequence
<220> FEATURE:
<223> OTHER INFORMATION: Synthesized

<400> SEQUENCE: 56
atttctcgag ccgtagatct cggtgaggat ggtc                                  34

SMARTBAC BACULOVIRUS EXPRESSION SYSTEM AND APPLICATION THEREOF

RELATED APPLICATION

The present application is a National Phase of International Application Number PCT/CN2018/079510, filed Mar. 20, 2018, and claims the priority of China Application No. 201810028508.0, filed Jan. 12, 2018.

TECHNICAL FIELD

The present invention belongs to the field of biotechnology, and relates to a baculovirus expression system and its application, in particular to the SmartBac system, a novel baculovirus expression system that simultaneously expresses multiple proteins in insect cells and its application in the expression of supramolecular complexes.

BACKGROUND ART

Baculovirus Expression System (BVES) is a powerful tool for efficiently expressing foreign proteins in insect cells, which has the advantages of good safety, high expression level, and being able to perform post-translational processing. Because the baculovirus genome is huge, clones of foreign genes cannot be directly inserted by enzyme digestion and ligation, the baculovirus genome was modified and a matching transfer vector was constructed to recombine the two into a recombinant baculovirus with foreign genes capable of infecting insect cells. Currently, in the widely used Bac to Bac system, the baculovirus shuttle vector (Bacmid) can not only replicate in *E. coli*, but also infect lepidopteran insect cells, and in *E. coli*, the vector can undergo Tn7 site-specific recombination with the matching transfer vector containing foreign genes. The recombinant baculovirus shuttle vector can efficiently replicate in *E. coli* and after purification, it can be used to transfect insect cells.

The baculovirus genome has a large capacity, and multiple open reading frames (ORFs) can be inserted into the transfer vector, and then the resulting recombinant baculovirus shuttle vector can simultaneously express multiple proteins in insect cells. This is also the general idea to achieve the co-expression of multiple proteins in insect cells at present. For example, the plasmid pFastBac-Dual contains two open reading frames (ORFs) placed head to head, one ORF starts with the p10 promoter, and ends with the HSV tk polyadenylation (HSV tk pA for short) signal sequence; the other ORF starts with the polyhedrin promoter and ends with the SV40 polyadenylation (SV40 pA for short) signal sequence. The plasmid pFastBac-Dual can be used as a transfer vector, but it can only express two proteins at the same time. If more than two proteins are to be expressed, other transfer vectors need to be constructed. For example, to express a protein complex composed of four different subunits, the following steps are required: (1) constructing recombinant plasmid pFastBac-Dual-A-B (plasmid pFastBac-Dual containing gene A and gene B) and recombinant plasmid pFastBac-Dual-C-D (plasmid pFastBac-Dual containing gene C and gene D); (2) performing recombination of the recombinant plasmids constructed in step (1) with Bacmid, respectively, to obtain two recombinant Bacmids; (3) transfecting the two recombinant Bacmids obtained in step (2) into insect cells, respectively, to obtain two viruses; (4) infecting insect cells simultaneously with the two viruses obtained in step (3) to achieve co-expression of the four subunits. The protein expression level of this multi-virus co-infection method is usually lower than that of cells infected with a single virus.

In recent years, the popular MultiBac system takes this into consideration and only uses one recombinant Bacmid to infect cells and then express protein complexes. The expression strategy of the system is also using one ORF to express one protein. Through the recombination mediated by the LoxP sites on the acceptor plasmid and the donor plasmid, the fusion of the plasmids is achieved, the ORFs of different sources are integrated into one transfer vector, and then the transfer vector is recombined with Bacmid to achieve the co-expression of multiple proteins. The limitation of this method is that it is necessary to construct a variety of donor plasmids and acceptor plasmids containing target genes. The donor plasmids and the acceptor plasmids need to be integrated and screened many times to obtain the final transfer vector for expression, which is time and labor consuming.

In addition to the cumbersome molecular cloning operation, the above two methods also have the following disadvantages: one is that it is impossible to control the copy number of each subunit during the expression, and the protein complex with more uniform properties cannot be purified at last; the other is that it is impossible to determine whether the target protein is expressed during viral infection.

In order to solve the above problems, the team of the inventors of the present invention has developed a new method for simultaneously expressing multiple proteins in insect cells (hereinafter referred to as Method 1) and filed a patent application (Application No.: 201610248592.8). In Method 1, the genes encoding the TEV enzyme and the genes encoding each protein are strung together in one ORF: firstly they are expressed as a polypeptide chain; then, the TEV enzyme located at the N-terminus of the polypeptide chain will cleaves each protein from the polypeptide chain through the TEV enzyme cleavage site(s) (TCS(s)) between the proteins to achieve simultaneous expression and in vivo assembly of multiple proteins. In order to monitor the expression of these ORFs in insect cells, the genes encoding fluorescent proteins of different colors are connected behind the polyprotein gene via TCS, and expressed together with multiple proteins in a long polypeptide chain. This idea was realized in the pFBD-mCEG vector constructed by the inventors. Using the above method and vectors, the inventors constructed a recombinant plasmid pFBD-mCEG-COPI, and successfully expressed in insect cells an active human COPI protein composed of 7 different subunits.

But Method 1 still has certain limitations. Firstly, Method 1 requires that all genes encoding protein subunits are strung together and inserted into one vector for protein expression. For protein complexes with larger molecular weights, the corresponding DNA sequences are also longer. It is difficult and time-consuming to construct a vector containing a relatively long gene fragment (the size of the vector is about 20 kb), either through the method of gene synthesis or the method of classical molecular cloning in the laboratory. Secondly, the expression of the polypeptide chain can be well monitored by fusing the fluorescent protein at the end of the polypeptide chain for expression, but occasionally, the incomplete cleavage between the fluorescent protein and the polypeptide chain may occur. This will inevitably affect the normal assembly of protein complexes in expressing cells. Thirdly, the replication origin of the pFBD-mCEG vector in *E. coli* is a high copy replication origin. When the larger plasmid constructed using this vector is replicated in *E. coli*, due to its high copy replication, it will bring greater pressure to the bacteria, and the bacteria may start other metabolic pathways to combat this pressure. The final result is poor plasmid stability, which is very likely to cause gene loss.

In addition, recombinant expression of a protein complex containing multiple subunits in vitro often requires screening of a subunit most suitable for adding a purification tag. When a protein complex is recombinantly expressed, a purification tag is usually added to a certain subunit, and the subunit containing this tag is purified by affinity chromatography. Due to the relatively tight interaction between this subunit and the other subunits that make up the complex, the entire protein complex can be purified. However, the addition of purification tags to different subunits often has different effects on the purification of the entire complex. If an effective cloning strategy is not adopted, it will take a lot of time and effort to construct expression vectors. Assuming that the pFBD-mCEG vector is to be used to express a protein complex with 8 subunits and a molecular weight of about 600 kDa, if a trial and error method is simply used, 8 expression vectors with a size of about 25 kb need to be constructed, wherein the difference between the expression vectors is that the subunits with purification tags are different. This is not a very easy job for any molecular biology laboratory.

SUMMARY OF THE INVENTION

In order to effectively solve the above problems, the present invention provides a novel SmartBac baculovirus expression system, and three cloning strategies to achieve the expression of protein complexes with molecular weights of less than 600 kDa and the expression of protein complexes with molecular weights of no less than 600 kDa and efficient screening of a subunit most suitable for adding a purification tag.

The SmartBac baculovirus expression system provided by the present invention is any one of the following (A)-(D):

(A) SmartBac baculovirus expression system A, comprising a acceptor plasmid and a donor plasmid; the acceptor plasmid and the donor plasmid can be recombined and fused into one plasmid;

the acceptor plasmid is acceptor plasmid A and/or acceptor plasmid B;

the acceptor plasmid A contains a DNA fragment A; in order from upstream to downstream, the DNA fragment A comprises a promoter A, a gene sequence encoding a protease, a recognition sequence for the cleavage site of the protease, an insertion region of a gene encoding a target object to be expressed, and a termination sequence A; the acceptor plasmid B contains a DNA fragment B and a DNA fragment C; in order from upstream to downstream, the DNA fragment B comprises a promoter B, a gene sequence encoding the protease, and a termination sequence B; in order from upstream to downstream, the DNA fragment C comprises a promoter C, an insertion region of a gene encoding a target object to be expressed, and a termination sequence C;

the donor plasmid contains a DNA fragment D; in order from upstream to downstream, the DNA fragment D comprises a promoter D, an insertion region of a gene encoding a target object to be expressed, and a termination sequence D;

the target object is a protein or a protein subunit or a protein fragment or a polypeptide or a polypeptide fragment;

(B) SmartBac baculovirus expression system B, comprising a acceptor plasmid and a donor plasmid; the acceptor plasmid and the donor plasmid can be recombined and fused into one plasmid;

the acceptor plasmid contains a DNA fragment A; in order from upstream to downstream, the DNA fragment A comprises a promoter A, an insertion region of a gene encoding a target object to be expressed, and a termination sequence A;

the donor plasmid is donor plasmid A and/or donor plasmid B;

the donor plasmid A contains a DNA fragment B; in order from upstream to downstream, the DNA fragment B comprises a promoter B, a gene sequence encoding a protease, a recognition sequence for the cleavage site of the protease, an insertion region of a gene encoding a target object to be expressed, and a termination sequence B;

the donor plasmid B contains a DNA fragment C and a DNA fragment D; in order from upstream to downstream, the DNA fragment C comprises a promoter C, a gene sequence encoding the protease, and a termination sequence C; in order from upstream to downstream, the DNA fragment D comprises a promoter D, an insertion region of a gene encoding a target object to be expressed, and a termination sequence D;

the target object is a protein or a protein subunit or a protein fragment or a polypeptide or a polypeptide fragment;

(C) SmartBac baculovirus expression system C, comprising the acceptor plasmid in the SmartBac baculovirus expression system A or the SmartBac baculovirus expression system B; it does not comprise any donor plasmids;

(D) SmartBac baculovirus expression system D, which is different from the SmartBac baculovirus expression system A or the SmartBac baculovirus expression system B or the SmartBac baculovirus expression system C only in that: the insertion region of a gene encoding a target object to be expressed is replaced by several insertion regions spaced from each other by the recognition sequence for the cleavage site of the protease, and each insertion region is used to insert the gene encoding a target object to be expressed.

The acceptor plasmid further contains a small Tn7 element flank for production of recombinant baculoviruses.

Further, for the SmartBac baculovirus expression system A, in order from upstream to downstream, the DNA fragment A further contains the recognition sequence for the cleavage site of the protease and a gene sequence encoding a fluorescent protein between the insertion region of a gene encoding a target object to be expressed and the termination sequence A.

Further, for the SmartBac baculovirus expression system A, in order from upstream to downstream, the DNA fragment B further contains the recognition sequence for the cleavage site of the protease and a gene sequence encoding a fluorescent protein between the gene sequence encoding the protease and the termination sequence B.

Further, for the SmartBac baculovirus expression system A, in order from upstream to downstream, the DNA fragment D further contains the recognition sequence for the cleavage site of the protease and a gene sequence encoding a fluorescent protein between the insertion region of a gene encoding a target object to be expressed and the termination sequence D.

In the present invention, both the acceptor plasmid and the donor plasmid contain a recognition sequence for a site-specific recombinase; depending on the recognition sequence for a site-specific recombinase, the acceptor plasmid and the donor plasmid can be fused into one large plasmid.

Further, the site-specific recombinase is specifically Cre recombinase; correspondingly, the recognition sequence for a site-specific recombinase is a loxP site sequence. Of course, the site-specific recombinase can also be other recombinases with the same or similar functions.

Further, the acceptor plasmid contains an unconditional replication origin; the donor plasmid contains a conditional replication origin.

More specifically, in the present invention, the unconditional replication origin is specifically a p15A replication origin (the p15A replication origin allows the plasmid to be propagated in ordinary *E. coli* clone strains with a low copy, which better maintains the stability of the large plasmid); the conditional replication origin is specifically a R6Kγ replication origin (the plasmid can only be propagated in bacterial hosts containing the pir gene).

Further, the acceptor plasmid and the donor plasmid contain different resistance selection marker genes.

More specifically, in the present invention, the acceptor plasmid carries an ampicillin resistance gene and a gentamicin resistance gene; the donor plasmid carries a kanamycin resistance gene.

Further, in the present invention, for the SmartBac baculovirus expression system A, the promoter A is a p6.9 promoter; the promoter B is a GP64 promoter; the promoter C is p6.9 promoter; and the promoter D is a p10 promoter.

Among them, the p6.9 promoter drives expression in the early stage of infection compared to the conventionally used very late polyhedrin promoter, and the cell state at this stage is better than that in the late stage of viral infection, which can avoid the aggregation of the expressed foreign proteins.

Further, in the present invention, for the SmartBac baculovirus expression system A, the termination sequence A is an SV40 pA signal sequence; the termination sequence B is an IE1 ter signal sequence; the termination sequence C is an SV40 pA signal sequence; and the termination sequence D is an HSV tk pA signal sequence.

Further, for the SmartBac baculovirus expression system A, in order from upstream to downstream, the insertion region of a gene encoding a target object to be expressed contains a multiple cloning site 1, a LacZ-α expression cassette and a multiple cloning site 2.

Among them, for the SmartBac baculovirus expression system A, the DNA fragment D further contains a PUC replication origin between the multiple cloning site 1 and the multiple cloning site 2 in the insertion region of a gene encoding a target object to be expressed.

In the present invention, the protease is specifically TEV protease. Of course, the protease can also be other proteases having the same or similar functions.

Still further, for the SmartBac baculovirus expression system A, in order from upstream to downstream, the DNA fragment A is obtained by connecting a p6.9 promoter (set forth in positions 1235-1329 of SEQ ID NO: 1 or positions 1235-1329 of SEQ ID NO: 2), a gene sequence encoding TEV protease with an N-terminal HA tag (set forth in positions 1339-2097 of SEQ ID NO: 1 or positions 1339-2097 of SEQ ID NO: 2), a recognition sequence for a TEV protease cleavage site (ICS) (set forth in positions 2098-2118 of SEQ ID NO: 1 or positions 2098-2118 of SEQ ID NO: 2), a sequence encoding a Twin-Strep tag (set forth in positions 2119-2205 of SEQ ID NO: 1 or positions 2119-2205 of SEQ ID NO: 2), a recognition sequence for an enterokinase cleavage site (set forth in positions 2206-2220 of SEQ ID NO: 1 or positions 2206-2220 of SEQ ID NO: 2), a multiple cloning site 1 (set forth in positions 2222-2249 of SEQ ID NO: 1 or positions 2222-2249 of SEQ ID NO: 2), a LacZ-α expression cassette (set forth in positions 2250-2790 of SEQ ID NO: 1 or positions 2250-2790 of SEQ ID NO: 2), a multiple cloning site 2 (set forth in positions 2799-2837 of SEQ ID NO: 1 or positions 2799-2843 of SEQ ID NO: 2), a recognition sequence for a TEV protease cleavage site (TCS) (set forth in positions 2839-2859 of SEQ ID NO: 1 or positions 2845-2865 of SEQ ID NO: 2), a gene sequence encoding a fluorescent protein (EGFP set forth in positions 2869-3585 of SEQ ID NO: 1 or TagRFP set forth in positions 2875-3585 of SEQ ID NO: 2) and an SV40 pA signal sequence (set forth in positions 3731-3971 of SEQ ID NO: 1 or positions 3731-3971 of SEQ ID NO: 2).

Still further, for the SmartBac baculovirus expression system A, in order from upstream to downstream, the DNA fragment B is obtained by connecting a GP64 promoter (set forth in positions 3047-3252 of SEQ ID NO: 3 or positions 3044-3249 of SEQ ID NO: 4), a gene sequence encoding TEV protease with an N-terminal ETA tag (set forth in positions 2275-3033 of SEQ ID NO: 3 or positions 2272-3030 of SEQ ID NO:4), a recognition sequence for a TEV protease cleavage site (TCS) (set forth in positions 2254-2274 of SEQ ID NO: 3 or positions 2251-2271 of SEQ ID NO: 4), a gene sequence encoding a fluorescent protein (EGFP set forth in positions 1531-2247 of SEQ ID NO: 3 or TagRFP set forth in positions 1531-2244 of SEQ ID NO: 4) and an IE1ter signal sequence (set forth in positions 1208-1514 of SEQ ID NO: 3 or positions 1208-1514 of SEQ ID NO: 4).

Still further, for the SmartBac baculovirus expression system A, in order from upstream to downstream, the DNA fragment C is obtained by connecting a p6.9 promoter (set forth in positions 3306-3400 of SEQ ID NO: 3 or positions 3303-3397 of SEQ ID NO: 4), a sequence encoding a Twin-Strep tag (set forth in positions 3419-3505 of SEQ ID NO: 3 or positions 3416-3502 of SEQ ID NO: 4), a recognition sequence for an enterokinase cleavage site (set forth in positions 3506-3520 of SEQ ID NO: 3 or positions 3503-3517 of SEQ ID NO: 4), a multiple cloning site 1 (set forth in positions 3522-3549 of SEQ ID NO: 3 or positions 3519-3546 of SEQ ID NO: 4), a LacZ-α expression cassette (set forth in positions 3550-4090 of SEQ ID NO: 3 or positions 3547-4087 of SEQ ID NO: 4), a multiple cloning site 2 (set forth in positions 4099-4149 of SEQ ID NO: 3 or positions 4096-4146 of SEQ ID NO: 4) and an SV40 pA signal sequence (set forth in positions 4281-4521 of SEQ ID NO: 3 or positions 4278-4528 of SEQ ID NO: 4).

Still further, for the SmartBac baculovirus expression system A, in order from upstream to downstream, the DNA fragment D is obtained by connecting a p10 promoter (set forth in positions 259-368 of SEQ ID NO: 5 or positions 259-368 of SEQ ID NO: 6), a sequence encoding a 10× His tag (set forth in positions 397-426 of SEQ ID NO: 5 or positions 397-426 of SEQ ID NO: 6), a recognition sequence for an enterokinase cleavage site (set forth in positions 436-450 of SEQ ID NO: 5 or positions 436-450 of SEQ ID NO: 6), a multiple cloning site 1 (set forth in positions 452-473 of SEQ ID NO: 5 or positions 452-473 of SEQ ID NO: 6), a PUC replication origin (set forth in positions 644-1232 of SEQ ID NO: 5 or positions 644-1232 of SEQ ID NO: 6), a LacZ-α expression cassette (set forth in positions 1443-1983 of SEQ ID NO: 5 or positions 1443-1983 of SEQ ID NO: 6), a multiple cloning site 2 (set forth in positions 1992-2030 of SEQ ID NO: 5 or positions 1992-2036 of SEQ ID NO: 6), a recognition sequence for a TEV protease cleavage site (TCS) (set forth in positions 2032-2052 of SEQ ID NO: 5 or positions 2038-2058 of SEQ ID NO: 6), a gene sequence encoding a fluorescent protein (EGFP set forth in positions 2062-2778 of SEQ ID NO: 5 or TagRFP set forth in positions 2068-2778 of SEQ ID NO: 6) and an HSVtk pA signal sequence (set forth in positions 2907-3188 of SEQ ID NO: 5 or positions 2907-3188 of SEQ ID NO: 6).

Among them, in the present invention, the fluorescent protein is specifically a green fluorescent protein or a red fluorescent protein.

More specifically, for the SmartBac baculovirus expression system A, the sequence of the DNA fragment A is specifically set forth in positions 1235-3971 of SEQ ID NO: 1 or positions 1235-3971 of SEQ ID NO: 2.

More specifically, for the SmartBac baculovirus expression system A, the sequence of the DNA fragment B is set forth in positions 1208-3252 of SEQ ID NO: 3 or positions 1208-3249 of SEQ ID NO: 4.

More specifically, for the SmartBac baculovirus expression system A, the sequence of the DNA fragment C is set forth in positions 3306-4521 of SEQ ID NO: 3 or positions 3303-4518 of SEQ ID NO: 4.

More specifically, for the SmartBac baculovirus expression system A, the sequence of the DNA fragment D is set forth in positions 259-3188 of SEQ ID NO: 5 or positions 259-3188 of SEQ ID NO: 6.

In addition, for the SmartBac baculovirus expression system A, there are several single restriction sites on both sides of the p6.9 promoter and p10 promoter regions in the acceptor plasmid and the donor plasmid, respectively, so that when needed, the existing promoter can be cut off and replaced with other promoters that can initiate protein expression in insect cells.

In a specific embodiment of the present invention, for the SmartBac baculovirus expression system A, the acceptor plasmid A is a 4V1G plasmid and/or a 4V1R plasmid; the complete sequence of the 4V1G plasmid is SEQ ID NO: 1; the complete sequence of the 4V1R plasmid is SEQ ID NO: 2. The acceptor plasmid B is a 5V1TG plasmid and/or a 5V1TR plasmid; the complete sequence of the 5V1TG plasmid is SEQ ID NO: 3; the complete sequence of the 5V1TR plasmid is SEQ ID NO: 4. The donor plasmid is a 4V2G plasmid and/or a 4V2R plasmid; the complete sequence of the 4V2G plasmid is SEQ ID NO: 5; the complete sequence of the 4V2R plasmid is SEQ ID NO: 6.

Among them, in SEQ ID NO: 1, the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1224 is a multiple cloning site BP; the sequence set forth in positions 1235-1329 is a p6.9 promoter, the sequence set forth in positions 1339-2097 is a gene sequence encoding TEV protease with an N-terminal HA tag, the sequence set forth in positions 2098-2118 is a recognition sequence for a TEV protease cleavage site (TCS), the sequence set forth in positions 2119-2205 is a sequence encoding a Twin-Strep tag, the sequence set forth in positions 2206-2220 is a recognition sequence for an enterokinase cleavage site, the sequence set forth in positions 2222-2249 is a multiple cloning site 1, the sequence set forth in positions 2250-2790 is a LacZ-α expression cassette, the sequence set forth in positions 2799-2837 is a multiple cloning site 2, the sequence set forth in positions 2839-2859 is a recognition sequence for a TEV protease cleavage site (TCS), the sequence set forth in positions 2862-2867 is a SalI recognition site, the sequence set forth in positions 2869-3585 is a gene sequence encoding a fluorescent protein EGFP, the sequence set forth in positions 3731-3971 is an SV40pA signal sequence, the sequence set forth in positions 4000-4165 is a Tn7L element, the sequence set forth in positions 4349-4804 is a f1 replication origin, the sequence set forth in positions 4936-5796 is a gene sequence encoding an ampicillin resistance protein and the sequence set forth in positions 6067-6612 is a p15A replication origin.

In SEQ ID NO:2, the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1224 is a multiple cloning site BP, the sequence set forth in positions 1235-1329 is a p6.9 promoter, the sequence set forth in positions 1339-2097 is a gene sequence encoding TEV protease with an N-terminal HA tag, the sequence set forth in positions 2098-2118 is a recognition sequence for a TEV protease cleavage site (TCS), the sequence set forth in positions 2119-2205 is a sequence encoding a Twin-Strep tag, the sequence set forth in positions 2206-2220 is a recognition sequence for an enterokinase cleavage site, the sequence set forth in positions 2222-2249 is a multiple cloning site 1, the sequence set forth in positions 2250-2790 is a LacZ-α expression cassette, the sequence set forth in positions 2799-2843 is a multiple cloning site 2, the sequence set forth in positions 2845-2865 is a recognition sequence for a TEV protease cleavage site (TCS), the sequence set forth in positions 2868-2873 is a SalI recognition site, the sequence set forth in positions 2875-3585 is a gene sequence encoding a fluorescent protein TagRFP, the sequence set forth in positions 3731-3971 is an SV40 pA signal sequence, the sequence set forth in positions 4000-4165 is a Tn7L element, the sequence set forth in positions 4349-4804 is a f1 replication origin, the sequence set forth in positions 4831-4935 is an Amp promoter, the sequence set forth in positions 4936-5796 is a gene sequence encoding an ampicillin resistance protein, and the sequence set forth in positions 6067-6612 is a p15A replication origin.

In SEQ ID NO: 3, the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1193 is an I-CeuI cleavage site, the sequence set forth in positions 1202-1207 is an AatII cleavage site, the sequence set forth in positions 1208-1514 is an 1E1ter signal sequence, the sequence set forth in positions 1515-1522 is a FseI cleavage site, the sequence set forth in positions 1531-2247 is a gene sequence encoding a fluorescent protein EGFP, the sequence set forth in positions 2248-2253 is a SmaI cleavage site, the sequence set forth in positions 2254-2274 is a recognition sequence for a TEV protease cleavage site (TCS), the sequence set forth in positions 2275-3033 is a gene sequence encoding TEV protease with an N-terminal HA tag, the sequence set forth in positions 3034-3041 is a SwaI cleavage site, the sequence set forth in positions 3047-3252 is a GP64 promoter, the sequence set forth in positions 3290-3295 is a BspEI cleavage site, the sequence set forth in positions 3306-3400 is a P6.9 promoter, the sequence set forth in positions 3407-3418 is a multiple cloning site AP, the sequence set forth in positions 3419-3505 is a sequence encoding a Twin-Strep tag, the sequence set forth in positions 3506-3520 is a recognition sequence for an enterokinase cleavage site, the sequence set forth in positions 3522-3549 is a multiple cloning site 1, the sequence set forth in positions 3550-4090 is a LacZ-α expression cassette, the sequence set forth in positions 4099-4149 is a multiple cloning site 2, the sequence set forth in positions 4281-4521 is an SV40 pA signal sequence, the sequence set forth in positions 4550-4715 is a Tn7L element, the sequence set forth in positions 4899-5354 is a f1 replication origin, the sequence set forth in positions 5486-6346 is a gene sequence encoding an ampicillin resistance protein, and the sequence set forth in positions 6617-7162 is a p15A replication origin.

In SEQ ID NO: 4, the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1193 is an I-CeuI cleavage site, the sequence set forth in positions 1202-1207 is an AatII cleavage site, the sequence set forth in positions 1208-1514 is an 1E1 ter signal sequence, the sequence set forth in positions 1515-1522 is a FseI cleavage site, the sequence set forth in positions 1531-2244 is a gene sequence encoding a fluorescent protein TagRFP, the sequence set forth in positions 2245-2250 is a SmaI cleavage site, the sequence set forth in positions 2251-2271 is a recognition sequence for a TEV protease cleavage site, the sequence set forth in positions 2272-3030 is a gene sequence encoding TEV protease with an N-terminal HA tag, the sequence set forth in positions 3031-3038 is a SwaI cleavage site, the sequence set forth in positions 3044-3249 is a GP64 promoter, the sequence set forth in positions 3287-3292 is a BspEI cleavage site, the sequence set forth in positions 3303-3397 is a P6.9 promoter, the sequence set forth in positions 3404-3415 is a multiple cloning site AP, the sequence set forth in positions 3416-3502 is a sequence encoding a Twin-Strep tag, the sequence set forth in positions 3503-3517 is the recognition sequence for an enterokinase cleavage site, the sequence set forth in positions 3519-3546 is a multiple cloning site 1, the sequence set forth in positions 3547-4087 is a LacZ-α expression cassette, the sequence set forth in positions 4096-4146 is a multiple cloning site 2, the sequence set forth in positions 4278-4518 is an SV40pA signal sequence, the sequence set forth in positions 4547-4712 is a Tn7L element, the sequence set forth in positions 4896-5351 is a f1 replication origin, the sequence set forth in positions 5483-6343 is a gene sequence encoding an ampicillin resistance protein, and the sequence set forth in positions 6614-7159 is a p15A replication origin.

In SEQ ID NO: 5, the sequence set forth in positions 169-202 is a LoxP site, the sequence set forth in positions 208-215 is a NotI cleavage site, the sequence set forth in positions 259-368 is a p10 promoter, the sequence set forth in positions 376-393 is a multiple cloning site AP, the sequence set forth in positions 397-426 is a sequence encoding a 10× His tag, the sequence set forth in positions 436-450 is a recognition sequence for an enterokinase cleavage site, the sequence set forth in positions 452-473 is a multiple cloning site 1, the sequence set forth in positions 644-1232 is a PUC replication origin, the sequence set forth in positions 1443-1983 is a LacZ-α expression cassette, the sequence set forth in positions 1992-2030 is a multiple cloning site 2, the sequence set forth in positions 2032-2052 is a recognition sequence for a TEN protease cleavage site, the sequence set forth in positions 2055-2060 is a SacI recognition site, the sequence set forth in positions 2062-2778 is a gene sequence encoding a fluorescent protein EGEFP, the sequence set forth in positions 2907-3188 is an HSV-tk pA signal sequence, the sequence set forth in positions 3224-3579 is a R6Kγ replication origin, and the sequence set forth in positions 3940-4734 is a sequence encoding a kanamycin resistance protein.

In SEQ ID NO: 6, the sequence set forth in positions 169-202 is a LoxP site, the sequence set forth in positions 208-215 is a NotI cleavage site, the sequence set forth in positions 259-368 is a p10 promoter, the sequence set forth in positions 376-393 is a multiple cloning site AP, the sequence set forth in positions 397-426 is a sequence encoding a 10× His tag, the sequence set forth in positions 436-450 is a recognition sequence for an enterokinase cleavage site, the sequence set forth in positions 452-473 is a multiple cloning site 1, the sequence set forth in positions 644-1232 is a PUC replication origin, the sequence set forth in positions 1443-1983 is a LacZ-α expression cassette, the sequence set forth in positions 1992-2036 is a multiple cloning site 2, the sequence set forth in positions 2038-2058 is a recognition sequence for a TEV protease cleavage site, the sequence set forth in positions 2061-2066 is a SacI recognition site, the sequence set forth in positions 2068-2778 is a gene sequence encoding a fluorescent protein TagRFP, the sequence set forth in positions 2907-3188 is an HSV-tk pA signal sequence, the sequence set forth in positions 3224-3579 is a R6Kγ replication origin, and the sequence set forth in positions 3940-4734 is a sequence encoding a kanamycin resistance protein.

The SmartBac baculovirus expression system can specifically be composed of the 4V1G plasmid, the 4V1R plasmid, the 5V1TG plasmid, the 5V1TR plasmid, the 4V2G plasmid and the 4V2R plasmid.

Of course, a DNA fragment group consisting of all or part of the DNA fragment A, the DNA fragment B, the DNA fragment C and the DNA fragment D described above also falls within the protection scope of the present invention.

A Mammalian cell expression system obtained by replacing the promoters and the termination sequences that are recognized by insect cells for expressing a target protein of the acceptor plasmid and the donor plasmid in the SmartBac baculovirus expression system with promoters and termination sequences that can be recognized by mammalian cells, and a DNA fragment group consisting of all or part of the DNA fragment A, the DNA fragment B, the DNA fragment C and the DNA fragment D in the mammalian cell expression system also fall within the protection scope of the present invention.

Use of the DNA fragment group or the SmartBac baculovirus expression system described above in the simultaneous expression of n target objects also falls within the protection scope of the present invention, wherein the target object is a protein or a protein subunit or a protein fragment or a polypeptide or a polypeptide fragment; and n is a natural number of greater than or equal to 2.

The present invention also protects a method for expressing a protein complex using the SmartBac baculovirus expression system described above.

The method for expressing a protein complex using the SmartBac baculovirus expression system described above provided by the present invention can be specifically the following (1) or (2):

(1) if the molecular weight of the protein complex to be expressed is less than 600 kDa, the method comprises the following steps:

(a1) the encoding genes of all the subunits that make up the protein complex are divided into two groups with a similar total length, and the genes encoding the subunits in each group are fused into a long fusion gene spaced by the recognition sequence for the cleavage site of the protease, two fusion genes are obtained from the two groups;

(a2) one of the two fusion genes is cloned into the insertion region of a gene encoding a target object to be expressed in the acceptor plasmid to obtain a recombinant acceptor plasmid; the other of the two fusion genes is cloned into the insertion region of a gene encoding a target object to be expressed in the donor plasmid to obtain a recombinant donor plasmid; the acceptor plasmid and the donor plasmid used in this step can be selected from plasmids carrying genes encoding fluorescent proteins of different colors, so that the expression of different proteins can be monitored;

(a3) under the action of the site-specific recombinase, the recombinant acceptor plasmid and the recombinant donor plasmid are fused into one large plasmid, which is a transfer plasmid;

(a4) the transfer plasmid is transformed into receptor bacteria containing a baculovirus shuttle plasmid to obtain a recombinant baculovirus shuttle plasmid;

(a5) insect cells are infected with the recombinant baculovirus shuttle plasmid to obtain a recombinant baculovirus;

(a6) insect cells are infected with the recombinant baculovirus to achieve the expression of the protein complex;

in this method, the acceptor plasmid can be either the acceptor plasmid A (specifically the 4V1G plasmid or the 4V1R plasmid) or the acceptor plasmid B (specifically the 5V1TG plasmid or the 5V1TR plasmid);

(2) if the molecular weight of the protein complex to be expressed is no less than 600 kDa, the method is the following (B) or (C):

(B) the method comprises the following steps:

(b1) the encoding genes of all the subunits that make up the protein complex are divided into M groups, and the genes encoding the subunits in each group are fused into a long fusion gene spaced by the recognition sequence for the cleavage site of the protease, M fusion genes are obtained from the M groups; wherein $M=2m$ and m is a natural number of greater than or equal to 2;

(b2) the first one of the M fusion genes is cloned into the insertion region of a gene encoding a target object to be expressed in the acceptor plasmid to obtain a recombinant acceptor plasmid 1; the second one of the M fusion genes is cloned into the insertion region of a gene encoding a target object to be expressed in the donor plasmid to obtain a recombinant donor plasmid 1; the third one of the M fusion genes is cloned into the insertion region of a gene encoding a target object to be expressed in the acceptor plasmid to obtain a recombinant acceptor plasmid 2; the fourth one of the M fusion genes is cloned into the insertion region of a gene encoding a target object to be expressed in the donor plasmid to obtain a recombinant donor plasmid 2; the rest can be done in the same manner; the M−1th one of the M fusion genes is cloned into the insertion region of a gene encoding a target object to be expressed in the acceptor plasmid to obtain a recombinant acceptor plasmid m; the Mth one of the M fusion genes is cloned into the insertion region of a gene encoding a target object to be expressed in the donor plasmid to obtain a recombinant donor plasmid m; in this step, the acceptor plasmids used for the M fusion genes are preferably plasmids carrying genes encoding fluorescent proteins of different colors, so that the expression of different proteins can be monitored; in addition, each fusion gene cloned into the insertion region of a gene encoding a target object to be expressed in the donor plasmid preferably has a stop codon, so as to ensure that the single transfer plasmid obtained subsequently has a single color of fluorescence;

(b3) under the action of the site-specific recombinase, the recombinant acceptor plasmid 1 and the recombinant donor plasmid 1 are fused into one large plasmid, which is a transfer plasmid 1; under the action of the site-specific recombinase, the recombinant acceptor plasmid 2 and the recombinant donor plasmid 2 are fused into one large plasmid, which is a transfer plasmid 2; the rest can be done in the same manner; under the action of the site-specific recombinase, the recombinant acceptor plasmid m and the recombinant donor plasmid m are fused into one large plasmid, which is a transfer plasmid m;

(b4) the transfer plasmid 1 is transformed into receptor bacteria containing a baculovirus shuttle plasmid to obtain a recombinant baculovirus shuttle plasmid 1; the transfer plasmid 2 is transformed into receptor bacteria containing a baculovirus shuttle plasmid to obtain a recombinant baculovirus shuttle plasmid 2; the rest can be done in the same manner; the transfer plasmid m is transformed into receptor bacteria containing a baculovirus shuttle plasmid to obtain a recombinant baculovirus shuttle plasmid m;

(b5) insect cells are infected with the recombinant baculovirus shuttle plasmid 1 to obtain a recombinant baculovirus 1; insect cells are infected with the recombinant baculovirus shuttle plasmid 2 to obtain a recombinant baculovirus 2; the rest can be done in the same manner; insect cells are infected with the recombinant baculovirus shuttle plasmid m to obtain a recombinant baculovirus m;

(b6) insect cells are infected with the recombinant baculovirus 1, the recombinant baculovirus 2 . . . , the recombinant baculovirus m together to achieve the expression of the protein complex;

(C) the method comprises the following steps:

(c1) the encoding genes of all the subunits that make up the protein complex are divided into M groups, and the genes encoding the subunits in each group are fused into a long fusion gene spaced by the recognition sequence for the cleavage site of the protease, M fusion genes are obtained from the M groups; wherein $M=2m-1$ and m is a natural number of greater than or equal to 2;

(c2) the first one of the M fusion genes is cloned into the insertion region of a gene encoding a target object to be expressed in the acceptor plasmid to obtain a recombinant acceptor plasmid 1; the second one of the M fusion genes is cloned into the insertion region of a gene encoding a target object to be expressed in the donor plasmid to obtain a recombinant donor plasmid 1; the third one of the M fusion genes is cloned into the insertion region of a gene encoding a target object to be expressed in the acceptor plasmid to obtain a recombinant acceptor plasmid 2; the fourth one of the M fusion genes is cloned into the insertion region of a gene encoding a target object to be expressed in the donor plasmid to obtain a recombinant donor plasmid 2; the rest can be done in the same manner; the M−2th one of the M fusion genes is cloned into the insertion region of a gene encoding a target object to be expressed in the acceptor plasmid to obtain a recombinant acceptor plasmid (M−1)/2; the M−1th one of the M fusion genes is cloned into the insertion region of a gene encoding a target object to be expressed in the donor plasmid to obtain a recombinant donor plasmid (M−1)/2; the kith one of the M fusion genes is cloned into the insertion region of a gene encoding a target object to be expressed in the acceptor plasmid to obtain a recombinant acceptor plasmid m; in this step, the acceptor plasmids used for the M fusion genes are preferably plasmids carrying genes encoding fluorescent proteins of different colors, so that the expression of different proteins can be monitored; in addition, each fusion gene cloned into the insertion region of a gene encoding a target object to be expressed in the donor plasmid preferably has a stop codon, so as to ensure that the single transfer plasmid obtained subsequently has a single color of fluorescence;

(c3) under the action of the site-specific recombinase, the recombinant acceptor plasmid 1 and the recombinant donor plasmid 1 are fused into one large plasmid, which is a transfer plasmid 1; under the action of the site-specific recombinase, the recombinant acceptor plasmid 2 and the recombinant donor plasmid 2 are fused into one large plasmid, which is a transfer plasmid 2; the rest can be done in the same manner; under the action of the site-specific recombinase, the recombinant acceptor plasmid (M−1)/2 and the recombinant donor plasmid (M−1)/2 are fused into one large plasmid, which is a transfer plasmid (M−1)/2; the recombinant acceptor plasmid m is a transfer plasmid m;

(c4) the transfer plasmid 1 is transformed into receptor bacteria containing a baculovirus shuttle plasmid to obtain a recombinant baculovirus shuttle plasmid 1; the transfer plasmid 2 is transformed into receptor bacteria containing a baculovirus shuttle plasmid to obtain a recombinant baculovirus shuttle plasmid 2; the rest can be done in the same manner; the transfer plasmid (M−1)/2 is transformed into receptor bacteria containing a baculovirus shuttle plasmid to obtain a recombinant baculovirus shuttle plasmid (M−1)/2; the transfer plasmid m is transformed into receptor bacteria containing a baculovirus shuttle plasmid to obtain a recombinant baculovirus shuttle plasmid m;

(c5) insect cells are infected with the recombinant baculovirus shuttle plasmid 1 to obtain a recombinant baculovirus 1; insect cells are infected with the recombinant baculovirus shuttle plasmid 2 to obtain a recombinant baculovirus 2; the rest can be done in the same manner; insect cells are infected with the recombinant baculovirus shuttle plasmid m to obtain a recombinant baculovirus m;

(c6) insect cells are infected with the recombinant baculovirus 1, the recombinant baculovirus 2 . . . , the recombinant baculovirus m together to achieve the expression of the protein complex;

In methods (B) and (C), the acceptor plasmid is preferably the acceptor plasmid B (specifically, the 5V1TG plasmid or the 5V1TR plasmid).

The present invention also protects a method for screening a subunit suitable for adding a purification tag in a protein complex to be expressed using the SmartBac baculovirus expression system described above.

The method for screening a subunit suitable for adding a purification tag in a protein complex to be expressed using the SmartBac baculovirus expression system described above provided by the present invention can be specifically the following (3) or (4):

(3) if the molecular weight of the protein complex to be expressed is less than 600 kDa, the method comprises the following steps:

(a1) one transfer plasmid is constructed according the steps (a1)-(a3); the transfer plasmid does not contain the sequence encoding the purification tag;

(a'2) the encoding genes of all the subunits of the protein complex to be expressed are cloned into the insertion regions of a gene encoding a target object to be expressed in the acceptor plasmids, respectively, and each of the encoding gene is able to be fused with the sequence encoding the purification tag to express, one recombinant acceptor plasmid is obtained for each subunit, and the recombinant acceptor plasmid is a transfer plasmid;

(a'3) all the transfer plasmids in steps (a'1) and (a'2) are transformed into receptor bacteria containing a baculovirus shuttle plasmid, respectively, and one recombinant baculovirus shuttle plasmid is obtained for each transfer plasmid;

(a'4) all the recombinant baculovirus shuttle plasmids in step (a'3) are used to infect insect cells, respectively, to obtain their corresponding recombinant baculoviruses;

(a'5) each of all the recombinant baculoviruses corresponding to the transfer plasmids in step (a'2) and the recombinant baculovirus corresponding to the transfer plasmid in step (a'1) are combined, respectively, to infect insect cells together, and then the protein complex expressed by each group of cells after infection is purified according to the purification tag, so as to determine the subunit suitable for adding the purification tag in the protein complex;

Among them, after purifying the protein complex expressed by each group of cells after infection according to the purification tag, SDS-PAGE can be performed, and then according to the SDS-PAGE result, the subunit suitable for adding the purification tag in the protein complex is determined as follows: if a certain subunit A added with the purification tag can capture all other subunits that make up the complex, and except for the subunit A with the purification tag, the ratio among the other subunits is also relatively uniform, the subunit A can be determined to be a subunit suitable for adding the purification tag in the protein complex;

(4) if the molecular weight of the protein complex to be expressed is no less than 600 kDa, the method comprises the following steps:

(b'1) m transfer plasmids are constructed according to the steps (b1)-(b3) or the steps (c1)-(c3); the transfer plasmids do not contain the sequence encoding the purification tag;

(b'2) the encoding genes of all the subunits of the protein complex to be expressed are cloned into the insertion regions of a gene encoding a target object to be expressed in the acceptor plasmids, respectively, and each of the encoding gene is able to be fused with the sequence encoding the purification tag to express, one recombinant acceptor plasmid is obtained for each subunit, and the recombinant acceptor plasmid is a transfer plasmid;

(b'3) all the transfer plasmids in steps (B'1) and (b'2) are transformed into receptor bacteria containing a baculovirus shuttle plasmid, respectively, and one recombinant baculovirus shuttle plasmid is obtained for each transfer plasmid;

(b'4) all the recombinant baculovirus shuttle plasmids in step (b'3) are used to infect insect cells, respectively, to obtain their corresponding recombinant baculoviruses;

(b'5) each of all the recombinant baculoviruses corresponding to the transfer plasmids in step (b'2) and the m recombinant baculoviruses corresponding to the m transfer plasmids in step (b'1) are combined, respectively, to infect insect cells together, and then the protein complex expressed by each group of cells after infection is purified according to the purification tag, so as to determine the subunit suitable for adding the purification tag in the protein complex;

Among them, after purifying the protein complex expressed by each group of cells after infection according to the purification tag, SDS-PAGE can be performed, and then according to the SDS-PAGE result, the subunit suitable for adding the purification tag in the protein complex is determined as follows: if a certain subunit A added with the purification tag can capture all other subunits that make up the complex, and except for the subunit A with the purification tag, the ratio among the other subunits is also relatively uniform, the subunit A can be determined to be a subunit suitable for adding the purification tag in the protein complex.

Further, in the present invention, the purification tag is a Twin-Strep tag. Correspondingly, Strep affinity medium can be used for purification of the protein complex to be expressed.

In an embodiment of the present invention, in is specifically 2.

In a specific embodiment of the present invention, the protein complex to be expressed is specifically a human exocyst complex. The human exocyst complex is composed of the following 8 protein subunits: EXOC1 (102 kDa), EXOC2 (104 kDa), EXOC3 (86 kDa), EXOC4 (110 kDa), EXOO5 (82 kDa), EXOC6 (94 kDa), EXOC7 (78 kDa) and EXOC8 (82 kDa).

Correspondingly, the method for expressing the human exocyst complex provided by the present invention specifically comprises the following, steps:

(1) under the action of Cre recombinase, a recombinant acceptor plasmid 5V1TR-E47 (whose complete sequence is set forth in SEQ ID NO: 16) and a recombinant donor plasmid 4V2-E155 (whose complete sequence is set forth in SEQ ID NO: 19) are fused into one large plasmid, i.e., transfer plasmid E1S547; under the action of Cre recombinase, a recombinant acceptor plasmid 5V1TG-E63 (whose complete sequence is set forth in SEQ ID NO: 15) and a recombinant donor plasmid 4V2-E28 (whose complete sequence is set forth in SEQ ID NO: 18) are fused into one large plasmid, i.e., transfer plasmid E2863;

(2) the transfer plasmid E1S547 is transformed into receptor bacteria containing a baculovirus shuttle plasmid to obtain a recombinant baculovirus shuttle plasmid BC-E1S547; the transfer plasmid E2863 is transformed into receptor bacteria containing a baculovirus shuttle plasmid to obtain a recombinant baculovirus shuttle plasmid BC-E2863;

(3) insect cells are infected with the recombinant baculovirus shuttle plasmid BC-E1S547 to obtain a recombinant baculovirus BV-E1S547; insect cells are infected with the recombinant baculovirus shuttle plasmid BC-E2863 to obtain a recombinant baculovirus BV-E2863;

(4) insect cells are infected with the recombinant baculovirus BV-E1S547 and the recombinant baculovirus BV-E2863 together to achieve the expression of the human exocyst complex.

In the present invention, the insect cells are specifically Sf9 cells.

Finally, the present invention also protects a method for expressing a protein complex using the mammalian cell expression system described above. Compared with the method for expressing a protein complex using the Smart-Bac baculovirus expression system described above provided by the present invention, the difference of the method only lies in that the SmartBac baculovirus expression system is replaced with the mammalian cell expression system and insect cells are replaced with mammalian cells.

DESCRIPTION OF THE DRAWINGS

FIG. 1A shows the plasmid maps of acceptor plasmid 4V1G;

FIG. 1B shows the plasmid maps of acceptor plasmid 4V1R;

FIG. 1C shows the plasmid maps of acceptor plasmid 5V1TG;

FIG. 1D shows the plasmid maps of acceptor plasmid 5V1TR;

FIG. 1E shows the plasmid maps of donor plasmid 4V2G;

FIG. 1F shows the plasmid maps of donor plasmid 4V2R.

DETAILED DESCRIPTION OF THE INVENTION

Figure 1A:
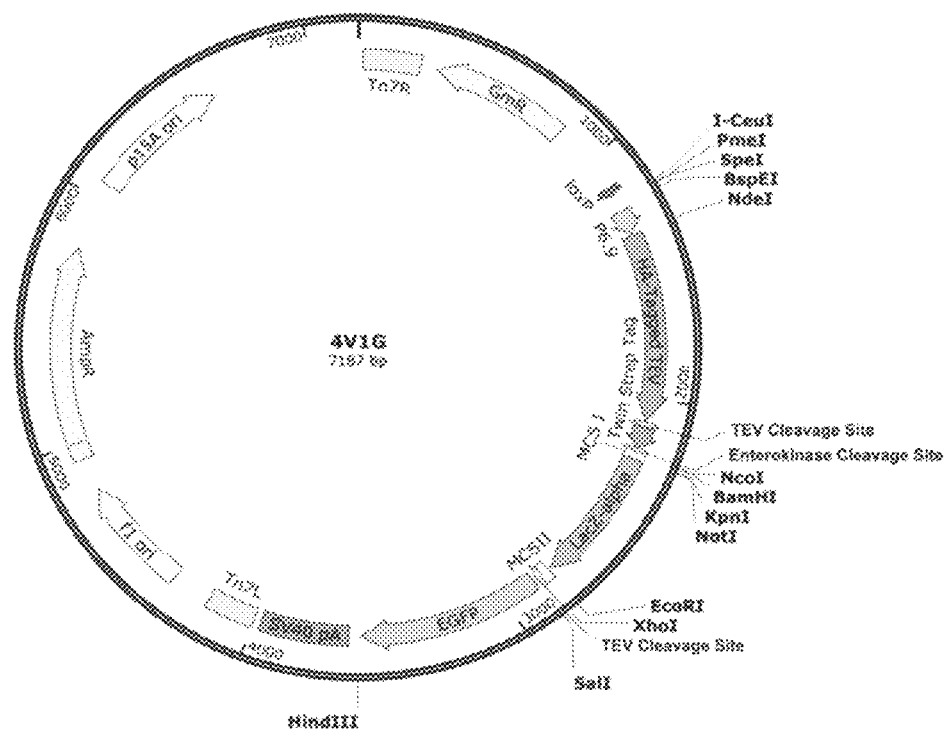
FIG. 1A-1F show the plasmid maps of the six vectors contained in the SmartBac system.
Figure 1B:
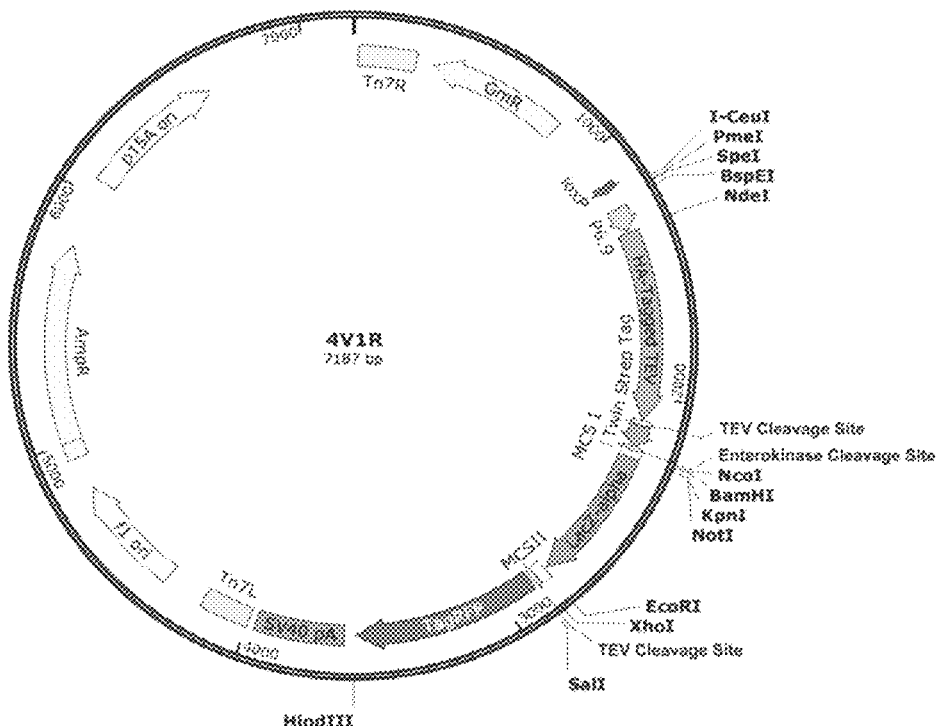
Figures 1C, 1D:
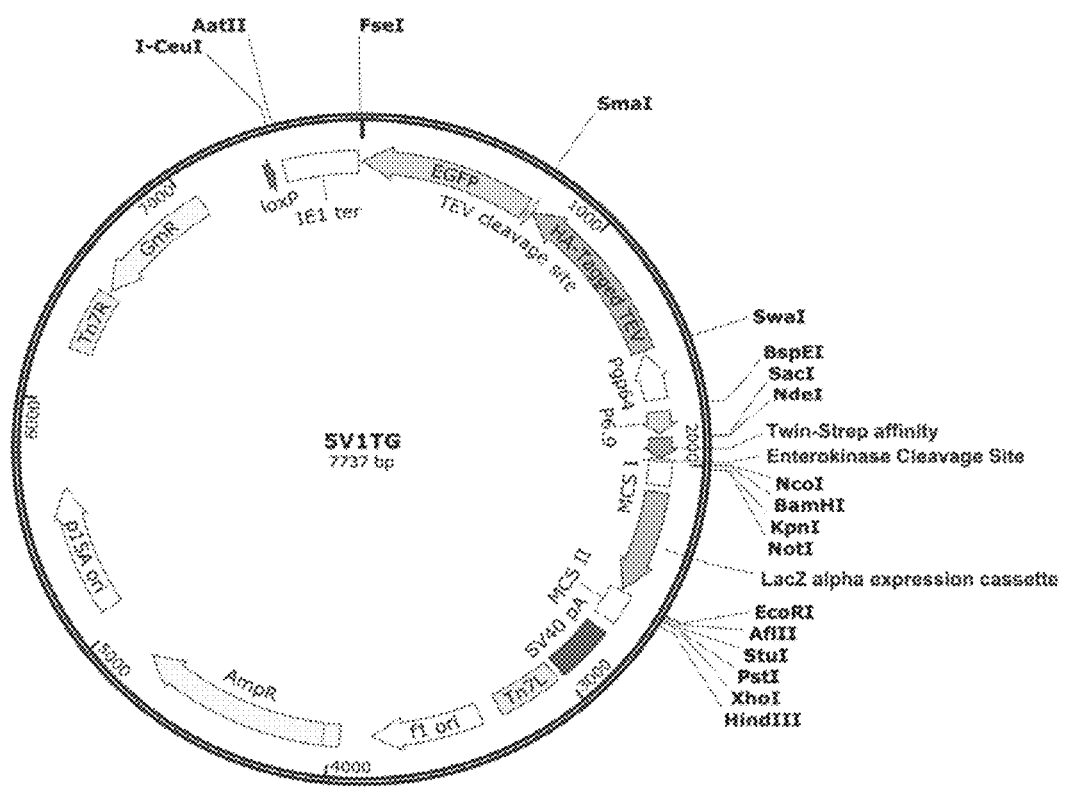
Figures 1E, 1F:
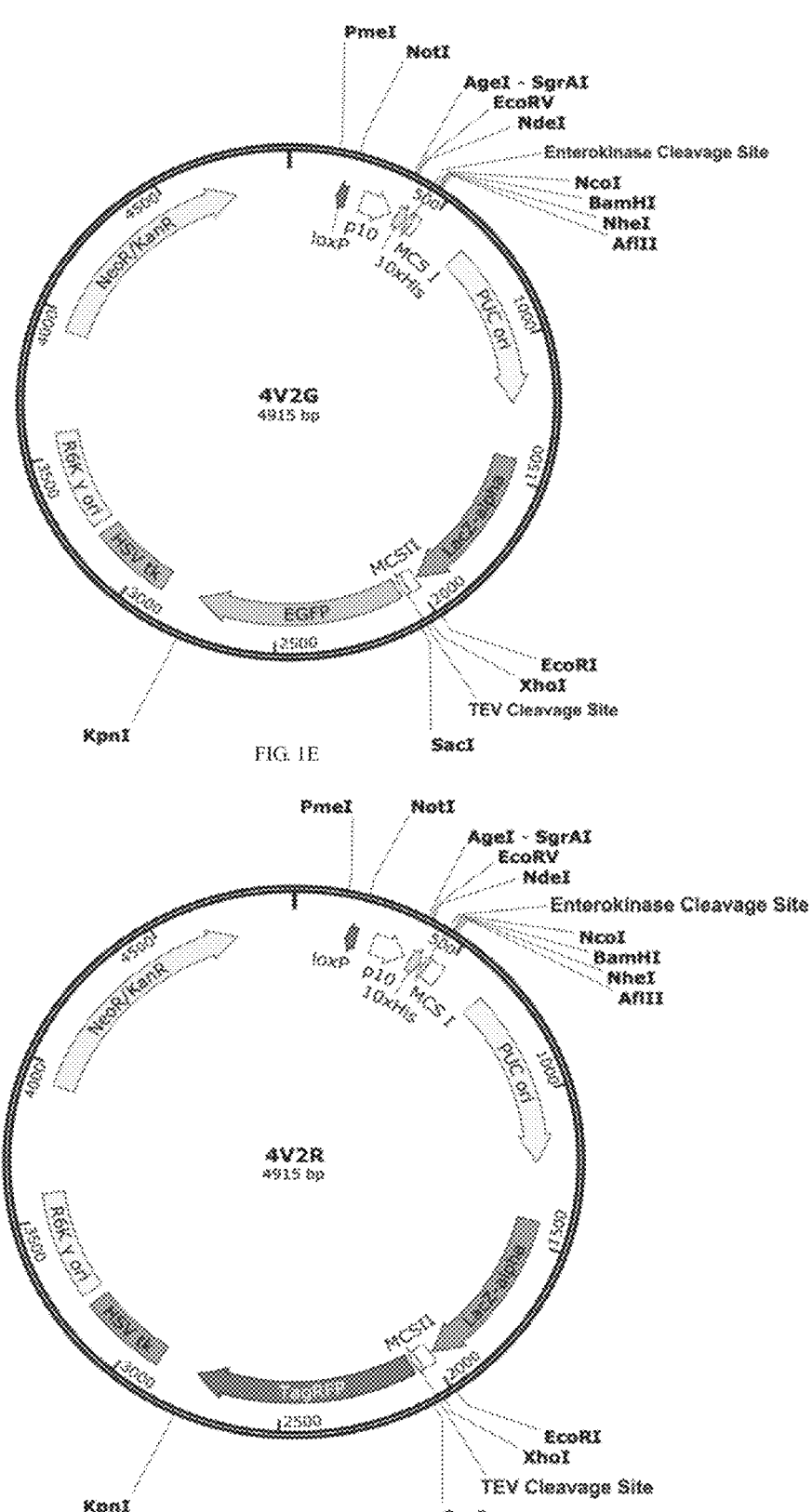

The following examples facilitate a better understanding of the present invention, but do not limit the present invention. Unless otherwise specified, the experimental methods in the following examples are conventional methods. Unless otherwise specified, the test materials used in the following examples were purchased from conventional biochemical reagent stores. In the following examples, each quantitative experiment was repeated three times, and the results were averaged.

1. Description of the SmartBac Vector System

The SmartBac system comprises 6 vectors, 4 of which are acceptor plasmids and 2 of which are donor plasmids (FIG. 1). The present invention adopts a widely applicable UPS (univector plasmid-fusion system) strategy to overcome the difficulty of constructing large plasmids with conventional cloning methods. This strategy uses Cre-loxP site-specific recombination to catalyze the fusion between a donor plasmid and a acceptor plasmid. The donor plasmid with kanamycin resistance (K$^+$) carries a conditional R6Kγ replication origin and can only be propagated in bacterial hosts containing the pir gene. The acceptor plasmid with ampicillin resistance (A$^+$) carries an unconditional replication origin and can be propagated in all strains. Both donor and acceptor plasmids have a LoxP site that can be recognized by Cre recombinase to undergo intermolecular recombination. After the donor plasmid and the acceptor plasmid undergo a fusion reaction, the reaction product is transformed into a strain that does not contain the pir gene (pir strain), and can be screened with A$^+$K$^+$ double antibiotic plate to obtain a colony containing a fusion plasmid. Using this strategy, the present invention can first prepare donor and acceptor plasmids containing several target genes, and then fuse the donor and acceptor plasmids to obtain larger plasmids.

The four acceptor plasmids are 4V1G (FIG. 1A), 4V1R (FIG. 1B), 5V1TG (FIG. 1C) and 5V1TR (FIG. 1D), respectively, and the two donor plasmids are 4V2G (FIG. 1E) and 4V2R (FIG. 1F), respectively. Each acceptor plasmid contains a p15A replication origin, which allows the plasmid to propagate in ordinary E. coli cloning strains in a low copy and can better maintain the stability of the large plasmid. Each acceptor plasmid also contains resistance markers for ampicillin and gentamicin, as well as a small Tn7 element flank for the production of recombinant baculoviruses. In the acceptor plasmids, it is the p6.9 promoter that initiates expression of transgenic sequences in insect cells. The p6.9 promoter drives expression in the early stage of infection compared to the conventionally used very late polyhedrin promoter, and the cell state at this stage is better than that in the late stage of viral infection, which can avoid the aggregation of the expressed foreign proteins.

The 4V1G and 4V1R acceptor plasmids carry a sequence encoding TEV protease with an N-terminal HA tag, followed by a TEV protease cleavage site (TCS) and a sequence encoding a Twin-Strep tag and then a recognition sequence for an enterokinase cleavage site. Between a multiple cloning site (MCS) 1 and a multiple cloning site (MCS) 2, there is a LacZ-α expression cassette, which allows blue-white selection of recombinant clones. Another TCS and a sequence encoding EGFP (4V1G) or TagRFP (4V1R) is downstream of MCS2. The fluorescent protein and the target protein can be expressed as a single ORF. By observing the fluorescence of infected cells, it is easy to determine whether the target protein has been expressed.

In the 5V1TG and 5V1TR acceptor plasmids (unlike 4V1G and 4V1R acceptor plasmids), the encoding sequences of TEV protease and EGFP (5V1TG) or TagRFP (5V1TR) were fused and expressed as a GP64 promoter driven ORF. This can completely avoid the incomplete cleavage between the fluorescent protein and the polypeptide chain that may occur in 4V1G and 4V1R.

The 4V2G and 4V2R donor plasmids carry a sequence encoding an N-terminal 10× His tag, followed by a recognition sequence for an enterokinase cleavage site. Both vectors contain kanamycin resistance markers. The screening region consists of a high-copy PUC replication origin and a LacZ-α expression cassette flanked by MCS1 and MCS2. Downstream of MCS2, there are sequences encoding a TCS and a fluorescent protein (EGFP in 4V2G and TagRFP in 4V2R). The expression of the target protein is driven by a very late p10 promoter. The 4V2 vector also contains a conditional replication origin R6Kγ. Once the screening region is replaced by a foreign gene, the donor vector contains only the R6Kγ origin and can only be propagated in E. coli strains with pir$^+$ genotype.

There are several single restriction sites on both sides of the p6.9 and p10 promoter regions in the 4V1/5V1 acceptor plasmids and 4V2 donor plasmids, respectively, so that when needed, the existing promoter can be cut off and replaced with other promoters that can initiate protein expression in insect cells.

2. Application Strategy of SmartBac Vector System

Large protein complexes can be expressed more easily and quickly in insect cells using the Smartbac vector system. A variety of experimental schemes can be used to generate transfer plasmids from Smartbac vectors that are ultimately used to express protein complexes. The present invention only provides two classic schemes to illustrate how to use Smartbac series of vectors.

Figure 2:
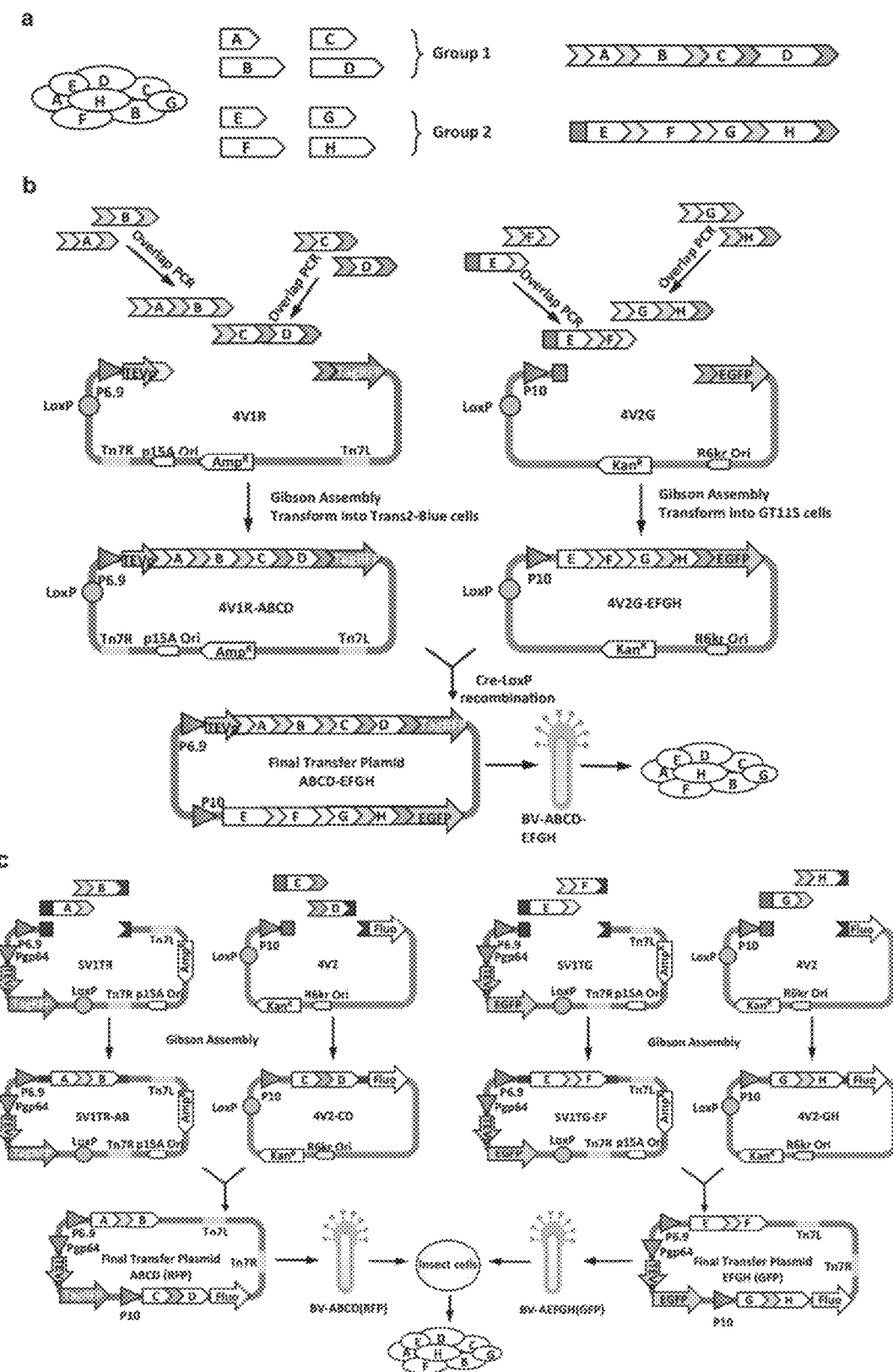
FIG. 2 shows the cloning strategies for expressing protein complexes (Scheme 1 and Scheme 2). a and b are cloning strategies for expressing a protein complex with a molecular weight of less than 600 kDa (Scheme 1). a shows the genes encoding the 8 subunits are divided into two groups with a similar total length. b is a specific schematic diagram illustrating the cloning process for expressing a protein complex with a molecular weight of less than 600 kDa. c is a cloning strategy for expressing a protein complex with a molecular weight of no less than 600 kDa (Scheme 2).

Scheme 1. Cloning Strategy for Expressing Protein Complexes with Molecular Weights of less than 600 kDa If a protein complex composed of 8 different subunits A, B, C, D, E, F, G and H is to be expressed in insect cells and the molecular weight of the complex is less than 600 kDa, scheme 1 can be used. As shown in panel a of FIG. 2, the genes encoding the 8 subunits are divided into two groups with a similar total length, wherein group 1 comprises genes A, B, C and D and group 2 comprises genes E, F, G and H. The four genes in each group are spliced into a long fusion gene spaced by a site encoding a TCS. The fused DNA fragment of group 1 is ABCD, and the fused DNA fragment of group 2 is EFGH. Next, the long ABCD fragment is further divided into two short DNA fragments AB and CD; and the long EFGH fragment is divided into two short DNA fragments EF and GH. Next, the corresponding primers are designed and A and B fragments are fused into AB, C and D fragments are fused into CD, E and F fragments are fused into EF, and G and H fragments are fused into GH using the overlap PCR. Then through the Gibson assembly reaction, the fragments AB and CD are fused with the linearized Smartbac RFP expression acceptor plasmid. Similarly, the fragments EF and GH are also fused with the linearized Smartbac GFP expression donor plasmid (4V2G). Using SmartBac series of vectors, recombinant bacteria containing positive recombinant plasmids 4V1R-ABCD and 4V2G-EFGH can be easily selected by blue-white screening. Finally, the two plasmids 4V1R-ABCD and 4V2G-EFGH were extracted, and they were fused into a final transfer plasmid ABCD-EFGH by Cre-LoxP site-specific recombination. After this plasmid is transformed into DH10Bac competent cells, a recombinant Bacmid will be obtained. Transfecting this Bacmid into insect cells will produce high-titer baculovirus BV-ABCD-EFGH for expressing the target complex. By monitoring the red fluorescence of TagRFP, the expression of ABCD fusion protein can be known; and by monitoring the green fluorescence of EGFP, the expression of EFGF fusion protein can be determined. Panel b of FIG. 2 shows the use of 4V1R and 4V2G, but 5V1TR and 4V2G, or 4V1G and 4V2R, or 5V1TG and 4V2R can also be used.

Scheme 2. Cloning Strategy for Expressing Protein Complexes with Molecular Weights of no less than 600 kDa If the molecular weight of the protein complex to be expressed is no less than 600 kDa, using Scheme 1 requires the construction of a final transfer plasmid with a size greater than 25 kb. It is often difficult to construct such a large plasmid without experience. Even if the construction is successful, the multi-protein complex may not be expressed in insect cells. This is because recombinant baculoviruses produced by large transfer plasmids tend to exhibit inherent genetic instability. The loss of foreign genes may occur during the amplification of the P2 generation virus. In this case, scheme 2 is more appropriate. As shown in panel c of FIG. 2, fragments A and B are assembled with linearized 5V1TR to form 5V1TR-AB plasmid, and fragments C and D are fused with linearized 4V2 vector to form 4V2-CD plasmid. A stop codon is added to the 3' end of gene D, so that the fluorescent proteins present on the 4V2G and 4V2R vectors will not be expressed. 5V1TR-AB and 4V2-CD will be fused into a final transfer plasmid. ABCD (RFP) by Cre-LoxP site-specific recombination. After this plasmid is transformed into DH10Bac, recombinant Bacmid-ABCD will be obtained. Similarly, 5V1TG-EF plasmid carrying fragments E and F and 4V2-GH plasmid carrying fragments G and H can be fused into another final transfer plasmid EFGH (GFP), and can be transformed into DH10Bac to produce recombinant Bacmid-EFGH. The two recombinant baculoviruses BV-ABCD and BV-EFGH can be obtained by infecting insect cells with these two recombinant Bacmids, respectively. BV-ABCD will express subunits A, B, C and D and TagRFP, while BV-EFGH will express subunits E, F, G and H and EGFP. Therefore, insect cells infected with these two baculoviruses at the same time will produce a complete protein complex, and the presence of TagRFP and EGFP fluorescence indicates that each subunit has been successfully expressed. Panel c of FIG. 2 shows the use of two acceptor plasmids, 5V1TG and 5V1TR, but the following acceptor plasmid combinations can also be used: 4V1G and 4V1R, 5V1TG and 4V1R, 5V1TR and 4V1G.

Scheme 3. Strategy for Screening the Best Subunit with the Purification Tag

Figures 3, 4:
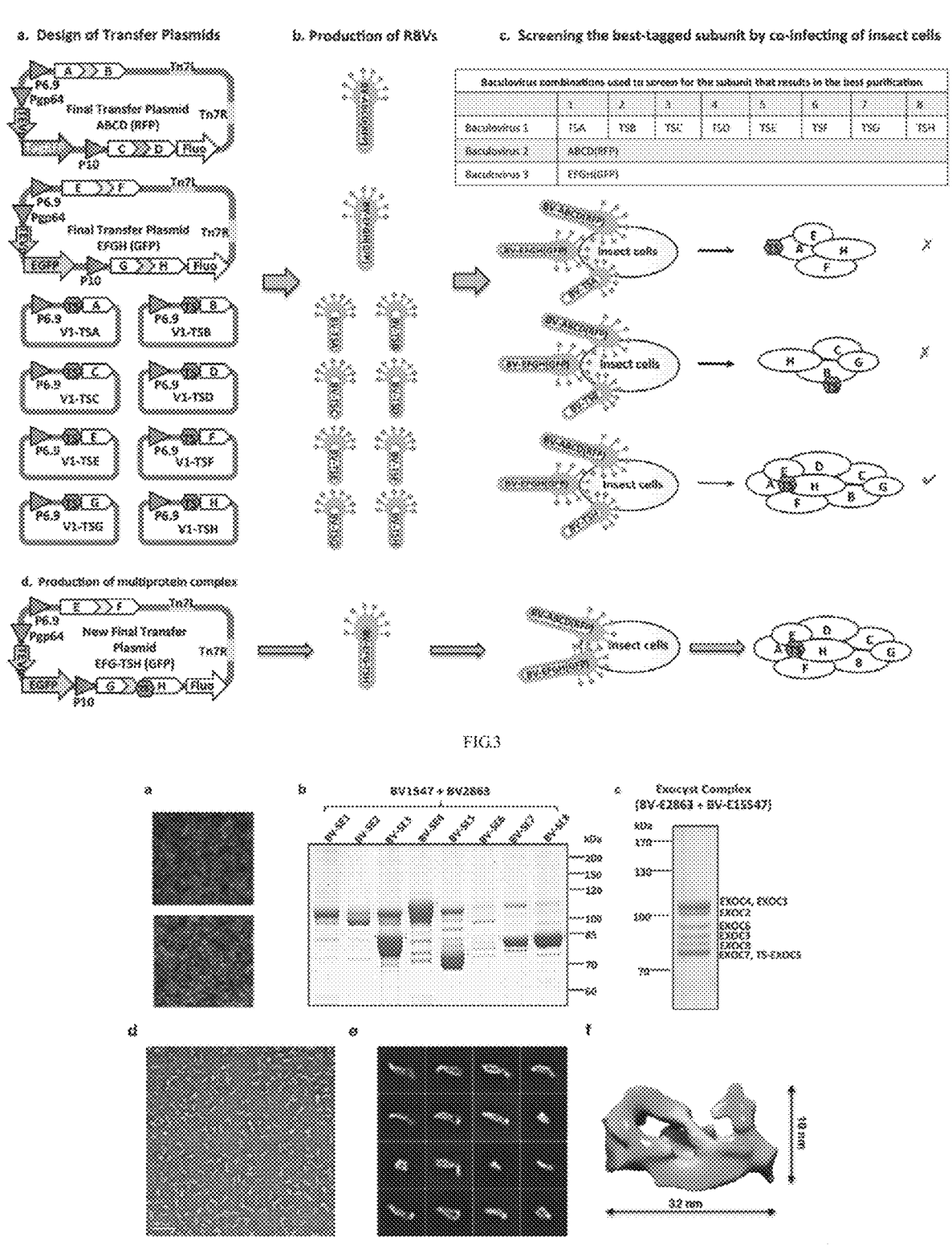
FIG. 3 shows the strategy for screening the best subunit with the purification tag (Scheme 3). a shows the constructed 10 transfer plasmids; b shows the packaged 10 recombinant baculoviruses; c shows the 8 virus combinations that infect insect cells (each combination comprises 3 viruses); d is a flow chart for continued expression of a protein complex after identification of the subunits suitable for adding the purification tag.
FIG. 4 shows the identification of the expression effect of human exocyst complex expressed by the SmartBac baculovirus expression system. a shows the preliminary determination of the expression of the protein subunits based on the expression of fluorescent proteins; b shows SDS-PAGE analysis to identify which protein subunit is suitable for Twin-strep tag for purification of the entire exocyst complex; c shows SDS-PAGE identification of the purified exocyst complex; d is the electron microscope negative staining image of the exocyst complex; e shows the result of further two-dimensional classification using RELION 2 in the electron microscope image shown in d; f shows the initial model of the exocyst complex produced by EMAN2.

The four acceptor plasmids of the Smartbac system all carry N-terminal Twin-Strep tags, and the two donor plasmids carry N-terminal 10× His tags. Each tag can be fused with the target subunit and expressed to purify the entire complex. If a protein complex with a molecular weight of no less than 600 kDa and containing, 8 different subunits A, B, C, D, E, F, G, and H is to be expressed, due to the lack of prior knowledge, it is unknown which subunit the purification tag is added to is more advantageous to purification of the entire complex. The present invention adopts the following cloning construction scheme to screen out the subunit most suitable for the addition of the purification tag for the purification of the entire complex. First, two large final transfer plasmids ABCD (TagRFP) and EFGH (EGFP) are constructed according to scheme 2, and none of the subunits expressed on these two large plasmids contain a purification tag (FIG. 3, panel a). Then any one of the acceptor plasmids (4V1G, 4V1R, 5V1TG or 5V1TR) is used to construct 8 smaller transfer plasmids (from V1-TSA to V1-TSH), each of which expresses a subunit with an N-terminal Twin-Strep tag. This will eventually result in 10 recombinant baculoviruses, including BV-ABCD (TagRFP), BV-EFGH (EGFP) and BV-TSn (wherein n is from A to H) (FIG. 3, panel b). Next, three baculoviruses BV-ABCD (TagRFP), BV-EFGH (EGFP) and a BV-TSn are used to co-infect insect cells. In this way, there are a total of 8 virus combinations (each combination comprises 3 viruses) to try (FIG. 3, panel c). After the cells infected with 8 virus combinations are lysed and purified with Strep affinity medium, the subunit H with the affinity tag is determined to be the most effective in purifying the entire complex. At this time, in order to increase the yield and obtain a more uniform sample, it is necessary to construct a new intermediate vector G-TSH, in which the subunit H carries the Twin-Strep affinity tag. The new vector G-TSH and the original intermediate vector EF are fused produce a new transfer vector, EFG-TSH (EGFP), this new transfer vector will produce a new recombinant baculovirus BV-EFG-TSH (GFP). Infecting insect cells with it and the existing recombinant baculovirus BV-ABCD (TagRFP) will achieve the expression of the target protein complex (FIG. 3, panel d). Viral infection and protein expression can be monitored by the fluorescence distribution and intensity of EGFP and TagRFP in infected cells.

Example 1. Expression of Human Exocyst Complex Using SmartBac Baculovirus Expression System Unless otherwise specified, the experimental methods used in this example are conventional methods.

Unless otherwise specified, the materials and reagents used in this example are commercially available.

1. The present invention first constructed six vectors of the SmartBac system. These six vectors were synthesized by GENEWIZ.

Four Acceptor Plasmids:

(1) 4V1G Plasmid

The complete sequence of the 4V1 G plasmid is set forth in SEQ ID NO: 1, wherein the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1224 is a multiple cloning site BP, the sequence set forth in positions 1235-1329 is a p6.9 promoter, the sequence set forth in positions 1339-2097 is a gene sequence encoding TEV protease with an N-terminal HA tag, the sequence set forth in positions 2098-2118 is a recognition sequence for a TEV protease cleavage site (TCS), the sequence set forth in positions 2119-2205 is a sequence encoding a Twin-Strep tag, the sequence set forth in positions 2206-2220 is a recognition sequence for an enterokinase cleavage site, the sequence set forth in positions 2222-2249 is a multiple cloning site 1, the sequence set forth in positions 2250-2790 is a LacZ-α expression cassette, the sequence set forth in positions 2799-2837 is a multiple cloning site 2, the sequence set forth in positions 2839-2859 is a recognition sequence for a TEV protease cleavage site (TCS), the sequence set forth in positions 2862-2867 is a SalI recognition site, the sequence set forth in positions 2869-3585 is a gene sequence encoding a fluorescent protein EGFP, the sequence set forth in positions 3731-3971 is an SV40pA signal sequence, the sequence set forth in positions 4000-4165 is a Tn7L element, the sequence set forth in positions 4349-4804 is a f1 replication origin, the sequence set forth in positions 4936-5796 is a gene sequence encoding an ampicillin resistance protein and the sequence set forth in positions 6067-6612 is a p15A replication origin.

(2) 4V1R Plasmid

The complete sequence of the 4V1R plasmid is set forth in SEQ ID NO: 2, wherein the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1224 is a multiple cloning site BP, the sequence set forth in positions 1235-1329 is a p6.9 promoter, the sequence set forth in positions 1339-2097 is a gene sequence encoding TEV protease with an N-terminal HA tag, the sequence set forth in positions 2098-2118 is a recognition sequence for a TEV protease cleavage site (TCS), the sequence set forth in positions 2119-2205 is a sequence encoding a Twin-Strep tag, the sequence set forth in positions 2206-2220 is a recognition sequence for an enterokinase cleavage site, the sequence set forth in positions 2222-2249 is a multiple cloning site 1, the sequence set forth in positions 2250-2790 is a LacZ-α expression cassette, the sequence set forth in positions 2799-2843 is a multiple cloning site 2, the sequence set forth in positions 2845-2865 is a recognition sequence for a TEV protease cleavage site (TCS), the sequence set forth in positions 2868-2873 is a SalI recognition site, the sequence set forth in positions 2875-3585 is a gene sequence encoding a fluorescent protein TagRFP, the sequence set forth in positions 3731-3971 is an SV40pA signal sequence, the sequence set forth in positions 4000-4165 is a Tn7L element, the sequence set forth in positions 4349-4804 is a f1 replication origin, the sequence set forth in positions 4831-4935 is an Amp promoter, the sequence set forth in positions 4936-5796 is a gene sequence encoding an ampicillin resistance protein, and the sequence set forth in positions 6067-6612 is a p15A replication origin.

(3) 5V1TG Plasmid

The complete sequence of the 5V1TG plasmid is set forth in SEQ ID NO: 3, wherein the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1193 is an 1-CeuI cleavage site, the sequence set forth in positions 1202-1207 is an AatII cleavage site, the sequence set forth in positions 1208-1514 is an IE1 ter signal sequence, the sequence set forth in positions 1515-1522 is a FseI cleavage site, the sequence set forth in positions 1531-2247 is a gene sequence encoding a fluorescent protein EGFP, the sequence set forth in positions 2248-2253 is a SmaI cleavage site, the sequence set forth in positions 2254-2274 is a recognition sequence for a TEV protease cleavage site (TCS), the sequence set forth in positions 2275-3033 is a gene sequence encoding TEV protease with an N-terminal HA tag, the sequence set forth in positions 3034-3041 is a SwaI site, the sequence set forth in positions 3047-3252 is a GP64 promoter, the sequence set forth in positions 3290-3295 is a BspEI cleavage site, the sequence set forth in positions 3306-3400 is a P6.9 promoter, the sequence set forth in positions 3407-3418 is a multiple cloning site AP, the sequence set forth in positions 3419-3505 is a sequence encoding a Twin-Strep tag, the sequence set forth in positions 3506-3520 is a recognition sequence for an enterokinase cleavage site, the sequence set forth in positions 3522-3549 is a multiple cloning site 1, the sequence set forth in positions 3550-4090 is a LacZ-α expression cassette, the sequence set forth in positions 4099-4149 is a multiple cloning site 2, the sequence set forth in positions 4281-4521 is an SV40 pA signal sequence, the sequence set forth in positions 4550-4715 is a Tn7L element, the sequence set forth in positions 4899-5354 is a f1 replication origin, the sequence set forth in positions 5486-6346 is a gene sequence encoding an ampicillin resistance protein, and the sequence set forth in positions 6617-7162 is a p15A replication origin.

(4) 5V1TR Plasmid

The complete sequence of the 5V1TR plasmid is set forth in SEQ ID NO: 4, wherein the sequence set forth in positions 20-243 is a Tn7R element, the sequence set forth in positions 310-843 is a gene sequence encoding a gentamicin resistance protein, the sequence set forth in positions 1131-1164 is a loxP site, the sequence set forth in positions 1168-1193 is an I-CeuI cleavage site, the sequence set forth in positions 1202-1207 is an AatII cleavage site, the sequence set forth in positions 1208-1514 is an IE1 ter signal sequence, the sequence set forth in positions 1515-1522 is a FseI cleavage site, the sequence set forth in positions 1531-2244 is a gene sequence encoding a fluorescent protein TagRFP, the sequence set forth in positions 2245-2250 is a SmaI cleavage site, the sequence set forth in positions 2251-2271 is a recognition sequence for a TEV protease cleavage site (TCS), the sequence set forth in positions 2272-3030 is a gene sequence encoding TEV protease with an N-terminal HA tag, the sequence set forth in positions 3031-3038 is a SwaI cleavage site, the sequence set forth in positions 3044-3249 is a GP64 promoter, the sequence set forth in positions 3287-3292 is a BspEI cleavage site, the sequence set forth in positions 3303-3397 is a P6.9 promoter, the sequence set forth in positions 3404-3415 is a multiple cloning site AP, the sequence set forth in positions 3416-3502 is a sequence encoding a Twin-Strep tag, the sequence set forth in positions 3503-3517 is a recognition sequence for an enterokinase cleavage site, the sequence set forth in positions 3519-3546 is a multiple cloning site 1, the sequence set forth in positions 3547-4087 is a LacZ-α expression cassette, the sequence set forth in positions 4096-4146 is a multiple cloning site 2, the sequence set forth in positions 4278-4518 is an SV40 pA signal sequence, the sequence set forth in positions 4547-4712 is a Tn7L element, the sequence set forth in positions 4896-5351 is a f1 replication origin, the sequence set forth in positions 5483-6343 is a gene sequence encoding an ampicillin resistance protein, and the sequence set forth in positions 6614-7159 is a p15A replication origin.

Two Donor Plasmids:

(1) 4V2G Plasmid

The complete sequence of the 4V2G plasmid is set forth in SEQ ID NO: 5, wherein the sequence set forth in positions 169-202 is a LoxP site, the sequence set forth in positions 208-215 is a NotI cleavage site, the sequence set forth in positions 259-368 is a p10 promoter, the sequence set forth in positions 376-393 is a multiple cloning site AP, the sequence set forth in positions 397-426 is a sequence encoding a 10× His tag, the sequence set forth in positions 436-450 is a recognition sequence for an enterokinase cleavage site, the sequence set forth in positions 452-473 is a multiple cloning site 1, the sequence set forth in positions 644-1232 is a PUC replication origin, the sequence set forth in positions 1443-1983 is a LacZ-α expression cassette, the sequence set forth in positions 1992-2030 is a multiple cloning site 2, the sequence set forth in positions 2032-2052 is a recognition sequence for a TEV protease cleavage site, the sequence set forth in positions 2055-2060 is a SacI recognition site, the sequence set forth in positions 2062-2778 is a gene sequence encoding a fluorescent protein EGFP, the sequence set forth in positions 2907-3188 is an HSV-tk pA signal sequence, the sequence set forth in positions 3224-3579 is a R6Kγ replication origin, and the sequence set forth in positions 3940-4734 is a sequence encoding a kanamycin resistance protein.

(2) 4V2R Plasmid

The complete sequence of the 4V2R plasmid is set forth in SEQ ID NO: 6, wherein the sequence set forth in positions 169-202 is a LoxP site, the sequence set forth in positions 208-215 is a NotI cleavage site, the sequence set forth in positions 259-368 is a p10 promoter, the sequence set forth in positions 376-393 is a multiple cloning site AP, the sequence set forth in positions 397-426 is a sequence encoding a 10× His tag, the sequence set forth in positions 436-450 is a recognition sequence for an enterokinase cleavage site, the sequence set forth in positions 452-473 is a multiple cloning site 1, the sequence set forth in positions 644-1232 is a PUC replication origin, the sequence set forth in positions 1443-1983 is a LacZ-α expression cassette, the sequence set forth in positions 1992-2036 is a multiple cloning site 2, the sequence set forth in positions 2038-2058 is a recognition sequence for a TEV protease cleavage site, the sequence set forth in positions 2061-2066 is a SacI recognition site, the sequence set forth in positions 2068-2778 is a gene sequence encoding a fluorescent protein TagRFP, the sequence set forth in positions 2907-3188 is an HSV-tk pA signal sequence, the sequence set forth in positions 3224-3579 is a R6Kγ replication origin, and the sequence set forth in positions 3940-4734 is a sequence encoding a kanamycin resistance protein.

2. Using scheme 3 of the present invention, the human exocyst complex was expressed in insect cells for the first time, and the subunit most suitable for purification of the complex was selected. Using the purification tag on this subunit, a more uniform and biologically active exocyst complex was successfully purified. The purified sample was observed by negative staining under electron microscope, and it was found that the shape of the sample was similar to that of the exocyst complex naturally extracted from *Saccharomyces cerevisiae*.

The exocyst complex is responsible for binding secretory vesicles to the plasma membrane in preparation for membrane fusion mediated by soluble N-ethylmaleimide-sensitive factor (NSF) attachment protein receptor (SNARE). The human exocyst complex comprises eight evolutionarily conserved subunits EXOC1 (102 kDa), EXOC2 (104 kDa), EXOC3 (86 kDa), EXOC4 (110 kDa), EXOC5 (82 kDa), EXOC6 (94 kDa), EXOC7 (78 kDa) and EXOC8 (82 kDa). Because the complex has not been recombinantly expressed, it is unknown which subunit the purification tag is added to is most suitable for purification of the entire exocyst complex. In order to determine the subunit most suitable for purification of the entire complex, the present invention adopts scheme 3 for vector construction. Table 1 lists all vectors constructed by the present invention for the recombinant expression of exocyst in insect cells.

TABLE 1

Vectors constructed using the SmartBac system for recombinant expression of human exocyst complex and viruses used

| Subunit | Intermediate vector | Final transfer vector | Recombinant baculovirus |
|---|---|---|---|
| TS-tagged EXOCn | | 5V1TG-SEn | BV-SEn |
| EXOC2, EXOC8 | 4V2-E28 | E2863 | BV-E2863 |
| EXOC6, EXOC3 | 5V1TG-E63 | | |
| EXOC1, EXOC5 | 4V2-E15 | E1547 | BV-E1547 |
| EXOC4, EXOC7 | 5V1TR-E47 | | |
| EXOC1, TS-tagged EXOC5 | 4V2-E1SE5 | E1S547 | BV-E1S547 |

The encoding genes of all the subunits of exocyst were from Origene (EXOC1-SC126966, EXOC2-SC111916, EXOC3-RC209413, EXOC4-SC 102359, EXOC5-SC127665, EXOC6-SC100885, EXOC7-RC227511, EXOC8-RC207859). Rab11(1-173)Q70L gene was synthesized by GENEWIZ. The primers used were synthesized by Invitrogen. All clones were sequenced at Beijing Boshang Company. Restriction enzymes BamHI-HF, EcoRI-HF, KpnI-HF, NdeI, NotI-HF, XhoI, alkaline phosphatase CIP, DNA polymerase Q5 Premix, Cre recombinase and Gibson assembly kit NEBuilder® HiFi DNA Assembly Master Mix were purchased from NEB. Gel recovery kit was purchased from Qiagen. DNA polymerase KOD-FX was purchased from Toyoba. GT115 competent cells were purchased from Invivogen. Trans2-blue competent cells were purchased from TransGen. DNA Ligation Kit was purchased from Takara. Competent cells DH10Bac, insect cells sf9, transfection reagents cellfectin II and Grace's Insect Cell Culture Medium, Unsupplemented medium were all purchased from Invitrogen, and their product catalog numbers are 10361012, B82501, 10362100 and 11595030, respectively. Phospholipid Rhod B-DHPE for activity assay was also purchased from Invitrogen, and various other phospholipids and Extruder device used to prepare liposomes were all purchased from Avanti Lipids Polar, ESF921 insect cell culture medium was purchased from Expression System. Strep Affinity Medium was purchased from IBA. Protease inhibitor (Complete-EDTA Free) and Ni-NTA medium were purchased from Roche. Molecular sieve Superdex 200 (10/300 GL) was purchased from GE. GTP was purchased from Sigma. Other reagent materials are commercially available.

Lysis buffer 1: 50 mM HEPES pH 8.0, 150 mM NaCl, 10% (v/v) glycerol and 1 mM DTT (supplemented with Roche protease inhibitor).

Elution buffer 1: 50 mM HEPES pH 8.0, 150 mM NaCl, 10% (v/v) glycerol, 1 mM DTT and 10 mM desthiobiotin.

Lysis buffer 2: 20 mM Tris-HCl pH 8.0, 500 mM NaCl, 20 mM imidazole and 0.1 mM PMSF.

Elution buffer 2: 20 mM Tris-HCl pH 8.0, 500 mM NaCl, 150 mM imidazole and 0.1 mM PMSF.

Molecular sieve buffer: 20 mM Tris-HCl pH 8.0, 150 mM NaCl, 0.1 mM PMSF.

Assay buffer: 50 mM Hepes pH 7.4, 150 mM NaCl.

2.1 Construction of Dual Gene Intermediate Vectors

The primers used in the construction of the dual gene intermediate vectors are shown in Table 2.

TABLE 2

Primers used in the construction of the dual gene intermediate vectors

| Primer name | Primer Sequence (5'-3') |
| --- | --- |
| E1F1 | TATCCATATGGGATCCACAGCAATCAAGCATGCATTACAAAG |
| E1F2 | ATCACTCGACACCGGTGATATCCATATGGGATCCACAGCAATCAAG |
| E1R1 | CAGGTTTTCACTCGAGCCGTGGGACTGTGCAATGCTGGAACAATAATC |
| E1R2 | TAAGCTAGAGCTCTGGAAGTACAGGTTTTCACTCGAGCCGTGGGACTG |
| E5F1 | GCTTAAGCGCGGCCGCGACCACGGCCGAGTTGTTCGAGGAGCCTTTTG |
| E5F2 | ACCTGTACTTCCAGAGCTCTAGCTTAAGCGCGGCCGCGACCACGGCCG |
| E5R1 | CCTTTCGGGTACCCTCGAGTTAGCTGAAGTGTCGAGCAAGGCGGGCAG |
| E5R2 | CAGCAGCCAACTCAGCTTCCTTTCGGGTACCCTCGAGTTAGCTG |
| E2F1 | TATCCATATGGCGGCCGCTAGCCGATCACGACAACCCCCCCTTG |
| E2F2 | ATCACTCGACACCGGTGATATCCATATGGCGGCCGCTAGCCGATC |
| E2R1 | ATACAAATTTTCACTCGAGCCTGTTTTCATCATGGTTGAAGAAGCTGC |
| E2R2 | GTACCACTAGTGCTTTGAAAATACAAATTTTCACTCGAGCCTGTTTTC |
| E8F1 | AGCACTAGTGGTACCCTTAAGATGGCGATGGCGATGTCGGACAGTGGG |
| E8F2 | AGTGAAAATTTGTATTTTCAAAGCACTAGTGGTACCCTTAAGATGGCG |
| E8R1 | CTTTCGGGTACCGAATTCTTAGACCACTGATGTTGTACTTTCAGG |
| E8R2 | CAGCAGCCAACTCAGCTTCCTTTCGGGTACCGAATTCTTAGACCAC |
| E3F1 | AGAGCGGTACCGCGGCCGCGATGAAGGAGACAGACCGGGAGGCCGTTG |
| E3F2 | CGAGTGAGAATCTGTATTTCCAGAGCGGTACCGCGGCCGCGATGAAGG |
| E3R1 | GTCAGTTAACTCGAGTTACTTGAGCAGCTTGGCCACGTTCAG |
| E3R2 | CCTTTCGAAGCTTTTAGTCAGTTAACTCGAGTTACTTGAGCAG |
| E6F1 | AGCTCCATATGGGATCCGCGGAGAACAGCGAGAGTCTGGGCAC |
| E6F2 | ATTTAAACGGATCGATGAGCTCCATATGGGATCCGCGGAGAAC |
| E6R1 | ACAGATTCTCACTCGAGCCCATGTGCTGGGACATACCATTCACCAAAC |
| E6R2 | CGCGGTACCGCTCTGGAAATACAGATTCTCACTCGAGCCCATGTGCTG |
| E4F1 | GCTCCATATGGCGGCCGCGGAAGCAGCTGGTGGGAAATACAGAAG |
| E4F2 | ATTTAAACGGATCGATGAGCTCCATATGGCGGCCGCGGAAGCAGC |
| E4R1 | AGTACAAGTTCTCACTCGAGCCAACGGTAGTTATCTTCTTGTCCTTGG |
| E4R2 | GTACCGCTTAAGGACTGAAAGTACAAGTTCTCACTCGAGCCAACGG |
| E7F1 | TCAGTCCTTAAGCGGTACCATGATTCCCCCACAGGAGGCATCCGCTC |
| E7F2 | AGTGAGAACTTGTACTTTCAGTCCTTAAGCGGTACCATGATTCC |
| E7R1 | TCAGTTAACTCGAGTTAGGCAGAGGTGTCAAAAAGGCGATCG |
| E7R2 | CCTTTCGAAGCTTTTAGTCAGTTAACTCGAGTTAGGCAGAGGTG |
| S5-F | TACTTCCAGAGCTCTAGCTTAAGCATGGCCTGGAGCCATCCGCAATTTG |
| S5-R | CAACTCAGCTTCCTTTCGGGTACCTTAGCTGAAGTGTCGAGCAAGGCGG |

(1) PCR Reaction of Each Subunit Fragment

The PCR reactions of the eight subunit genes of exocyst are shown in Table 3.

TABLE 3

PCR reactions of eight subunit genes of exocyst

| Template | Primers used in the first round of PCR | Primers used in the second round of PCR |
|---|---|---|
| EXOC1 gene | E1F1 and E1R1 | E1F2 and E1R2 |
| EXOC2 gene | E2F1 and E2R1 | E2F2 and E2R2 |
| EXOC3 gene | E3F1 and E3R1 | E3F2 and E3R2 |
| EXOC4 gene | E4F1 and E4R1 | E4F2 and E4R2 |
| EXOC5 gene | E5F1 and E5R1 | E5F2 and E5R2 |
| EXOC6 gene | E6F1 and E6R1 | E6F2 and E6R2 |
| EXOC7 gene | E7F1 and E7R1 | E7F2 and E7R2 |
| EXOC8 gene | E8F1 and E8R1 | E8F2 and E8R2 |

Using the plasmids containing the target genes as templates, the PCR reactions in Table 3 were performed. The first round of PCR was completed with NEB's Q5 Premix. The reaction procedure was as follows: 98° C. for 30 s; 30 cycles of (98° C. for 10 s, 72° C. for 3 min); 72° C. for 10 min. After the products of the first round of PCR were recovered, they were used as the templates as the second round of PCR reaction. The reaction procedure was as follows: 98° C. for 30 s; 30 cycles of (98° C. for 10 s, 72° C. for 3 min); 72° C. for 10 min. The PCR products were recovered.

(2) Linearization of Vectors

The plasmid 4V2G was digested with restriction enzymes NdeI, KpnI-HF and EcoRI-HF, and treated at 37° C. for 1 h; then CIP was added and the resulting mixture was treated at 37° C. for 1 h; finally, about 2.5 kb of vector backbone 4V2 was recovered using the gel recovery kit.

The plasmid 5V1TG was digested with restriction enzymes NdeI and XhoI and treated at 37° C. for 1 h; then CIP was added and the resulting mixture was treated at 37° C. for 1 h; finally, about 7 kb of vector backbone was recovered using the gel recovery kit.

The plasmid 5V1TR was digested with restriction enzymes NdeI and XhoI and treated at 37° C. for 1 h; then CIP was added and the resulting mixture was treated at 37° C. for 1 h; finally, about 7 kb of vector backbone was recovered using the gel recovery kit.

(3) Gibson Assembly Reaction of PCR Products and Linearized Vectors

According to the instruction of NEBuilder® HiFi DNA Assembly Master Mix, the linearized 4V2 vector backbone and the second round PCR products of EXOC1 and EXOC5 were subjected to Gibson recombination to obtain the recombinant plasmid 4V2-E15; the linearized 4V2 vector backbone and the second round PCR products of EXOC2 and EXOC8 were recombined to obtain the recombinant plasmid 4V2-E28. The recombinant products were transformed into GT115 competent cells, and the white recombinant colonies were picked by antibiotic screening and blue-white screening for PCR identification. Plasmids were extracted from the positive colonies and sequenced. The clones that were proved correct by sequencing were kept.

Similarly, the linearized 5V1TG vector and the second round PCR products of EXOC6 and EXOC3 were subjected to Gibson assembly to obtain the recombinant plasmid 5V1TG-E63; the linearized 5V1TR vector and the second round PCR products of EXOC4 and EXOC7 were subjected to Gibson assembly to obtain the recombinant plasmid 5V1TR-E47. The two assembled products were transformed into Trans2-blue competent cells, respectively, and the white recombinant colonies were picked by antibiotic screening and blue-white screening for PCR identification. Plasmids were extracted from the positive colonies and sequenced. The clones that were proved correct by sequencing were kept.

The complete sequence of the recombinant plasmid 4V2-E15 is set forth in SEQ ID NO: 17; the complete sequence of the recombinant plasmid 4V2-E28 is set forth in SEQ ID NO: 18; the complete sequence of the recombinant plasmid 5V1TG-E63 is set forth in SEQ ID NO: 15; the complete sequence of the recombinant plasmid 5V1TR-E47 is set forth in SEQ ID NO: 16. These four recombinant plasmids do not express the Twin-Strep tag.

2.2 Construction of Single Gene Intermediate Vectors (1) PCR Reaction and Digestion Treatment of Each Subunit Fragment Using the plasmids containing the target genes as templates, the first round of PCR reactions in Table 3 was performed. The first round of PCR was completed with NEB's Q5 Premix. The reaction procedure was as follows: 98° C. for 30 s; 30 cycles of (98° C. for 10 s, 72° C. for 3 min); 72° C. for 10 min. The PCR products were recovered. The PCR products of EXOC1 and EXOC6 were double digested with BamHI-HF and XhoI, PCR products of EXOC7 were double digested with KpnI-HF and XhoI; the PCR products of EXOC2, EXOC3, EXOC4, EXOC5 were double digested with NotI and XhoI; the PCR product of EXOC8 was double digested with EcoRI-HF and KpnI-HF.

(2) Linearization of Vectors

The plasmid 5V1TG was double-digested with restriction enzymes BamHI-HF and XhoI and treated at 37° C. for 1 h; then CIP was added and the resulting mixture was treated at 37° C. for 1 h;

the plasmid 5V1TG was double-digested with restriction enzymes KpnI-HF and XhoI and treated at 37° C. for 1 h; then CIP was added and the resulting mixture was treated at 37° C. forth;

the plasmid 5V1TG was double-digested with restriction enzymes NotI and XhoI and treated at 37° C. for 1 h; then CIP was added and the resulting mixture was treated at 37° C. forth;

the plasmid 5V1TG was double-digested with restriction enzymes EcoRI-HF and KpnI-HF and treated at 37° C. for 1 h; then CIP was added and the resulting mixture was treated at 37° C. for 1 h;

the above four vector backbones of about 7 kb were recovered using the gel recovery kit.

(3) Ligation Reactions Between Target Fragments and Vector Backbones

The ligation reactions between the digested PCR fragments and the linearized vectors were performed according to the instruction of the Takara. DNA ligation Kit to generate 5V1TG-SEn series of plasmids (n is a natural number from 1 to 8, corresponding to EXOC1 to EXOC8). The transformation of the products of the ligation reactions was conducted by transforming these two assembled products into Trans2-blue competent cells, respectively, and the white recombinant colonies were picked by antibiotic screening and blue-white screening for PCR identification. Plasmids were extracted from the positive colonies and sequenced. The clones that were proved correct by sequencing were kept.

The complete sequence of the recombinant plasmid 5V1TG-SE1 is set forth in SEQ ID NO: 7; the complete sequence of the recombinant plasmid 5V1TG-SE2 is set forth in SEQ ID NO: 8; the complete sequence of the recombinant plasmid 5V1TG-SE3 is set forth in SEQ ID NO: 9; the complete sequence of the recombinant plasmid 5V1TG-SE4 is set forth in SEQ ID NO: 10; the complete sequence of the recombinant plasmid 5V1TG-SE5 is set forth in SEQ NO: 11; the complete sequence of the recombinant plasmid 5V1TG-SE6 is set forth in SEQ ID NO: 12; the complete sequence of the recombinant plasmid 5V1TG-SE7 is set forth in SEQ ID NO: 13; the complete sequence of the recombinant plasmid 5V1TG-SE8 is set forth in SEQ ID NO: 14. The N-terminus of EXOC protein in each of these eight recombinant plasmids was fused and expressed with an Twin-Strep tag.

2.3 Construction of Final Transfer Vectors E1547 and E2863

(1) 0.1 pmol of the recombinant plasmids 5V1TR-E47 and 4V2-E15 and 1 μl of Cre recombinase were mixed in a 20 μl reaction system and incubated at 30° C. for 1 h. 10 μl of the reaction mixture was used to transform 100 μl of Trans2-blue competent cells. After heat shock at 42° C. for 30 s, 500 μl of SOC medium was added and the resulting mixture was incubated at 30° C. with shaking for 4 h. The cell suspension was spread on LB agar plates containing 50 μg/ml kanamycin and 100 μg/ml ampicillin, and cultured upside down at 30° C. for 24 h. PCR identification of recombinant colonies was performed using the primers Loxp-F (5'-CCACTGCGCCGTTACCAC-3') and Loxp-R (5'-GCCGGTATGTACAGGAAG-3'). A 375 bp PCR product can be amplified from positive colonies. The final transfer plasmid E1547 was extracted from the positive clones.

(2) The process of constructing the final transfer plasmid E2863 from the recombinant plasmids 5V1TG-E63 and 4V2-E28 was completed with reference to step (1).

2.4 Pilot Plant Test of Expression of Human Exocyst Complex in Insect Cells and Screening for Subunit Most Suitable For Purification of Entire Complex (1) The eight recombinant plasmids 5V1TG-SEn and the two final transfer plasmids E1547 and E2863 were transformed into DH10Bac competent cells, and the recombinant colonies were obtained through antibiotic screening and blue-white screening. (Note: E1547 and E2863 were large plasmids larger than 19 kb, so their transformed bacteria were cultured at 30° C. to avoid gene loss.)

(2) After completing step (1), the recombinant Bacmid DNA of the recombinant colonies was extracted and subjected to PCR identification. Each recombinant Bacmid of 5V1TG-SEn was identified by the classic identification method (see Invitrogen Bac to Bac manual for details). The Bacmids produced by the E1547 and E2863 plasmids were first identified by the following three primer pairs. Tn7R primer pair: 5'-GTTTTCCCAGTCACGAC-3' and 5'-AAGTTT-GAGCAGCCGCGTAG-3; Tn7L primer pair: 5'-CAG-GAAACAGCTATGAC-3' and 5'-ACCTCCCCCT-GAACCTGAAA-3'; Empty primer pair: 5'-GTTTTCCCAGTCACGAC-3' and 5'-CAG-GAAACAGCTATGAC-3'. For positive Bacmids, using the primer pair of "Tn7R" and "Tn7L", 661 bp and 521 bp PCR products were amplified. If the recombinant Bacmid was contaminated with wild-type bacmids, a 300 bp PCR product would be produced using the "Empty primer pair".

(3) After completing step (2), PCR method was further used to identify the real existence of each gene in the recombinant Bacmids.

(4) The sf9 cells in the logarithmic growth phase were diluted with Grace's Insect Cell Culture Medium, Unsupplemented insect cell culture medium to obtain a diluent and the density of sf9 cells in the diluent was $5.0 \times 10^5$ cells/mL.

(5) To a dish with a diameter of 35 min, 2 mL of the diluent obtained in step (4) was added and incubated at 28° C. for 4 h.

(6) Solution A was added to solution B and mixed well, and placed at room temperature for 25 min to obtain a mixture; wherein the preparation method of the solution A was as follows: 2.5 μg of recombinant Bacmid DNA (identified to be positive by PCR) extracted in step (2) was added to 100 μl of Grace's Insect Cell Culture Medium, Unsupplemented insect cell culture medium; the preparation method of the solution B was as follows: 8 μL of cellfectin II was added to 100 μL of Grace's Insect Cell Culture Medium, Unsupplemented insect cell culture medium.

(7) After completing step (6), the mixture obtained in step (6) was added dropwise to the dish, and then incubated at 28° C. for 4 h; the supernatant was discarded and 2 mL of Sf-900 TM II SFM medium was added and subjected to static culture at 28° C. for 144 h.

(8) After completing step (7), the dish was observed with Nikon TS100 inverted fluorescence microscope (observed with Nikon B-2A fluorescence module, excitation wavelength range: 450-490 nm; observed with Nikon-2A fluorescence module, excitation wavelength range: 510-560 nm). If both the green fluorescence and the red fluorescence were well expressed (FIG. 4, panel a), the supernatant was collected to obtain the P1 generation virus solution. The viruses finally produced by the plasmids 5V1TG-SEn, E2863 and E1547 were named BV-SEn, BV-E2863 and BV-E1547, respectively.

(9) After completing step (8), 200 μL of P1 generation virus solution was taken and inoculated into a 2 L triangular shake flask containing 180 mL of insect cell culture medium with sf9 cell concentration of $2.0 \times 10^6$ cells/mL, and incubated at 28° C. and 150 rpm for 96 h. Then the mixture was centrifuged at 4° C. and 2000 g for 5 min, and the supernatant was collected to obtain the P2 generation virus solution.

(10) 5 mL of BV-E1547 P2 generation virus solution, 5 mL of BV-E2863-P2 generation virus solution and 2.5 mL of one of BV-SEn viruses (there were eight BV-SEn viruses, so there were eight virus combinations and each of the combinations comprised three viruses were inoculated into a 2 L triangular shake flask containing 500 mL of insect cell culture medium with sf9 cell concentration of $2.0 \times 10^6$ cells/mL, and cultured at 28° C. and 150 rpm for 72 h. Then the mixture was centrifuged at 4° C. and 2000 g for 5 min, the precipitate was collected, which was the SEn infected cells. The collected cells were frozen and stored at −80° C.

(11) After completing step (10), the infected cells were taken and resuspended in lysis buffer 1, and homogenized 40 times using a Dounce homogenizer (the cells were always in an ice bath throughout the homogenization process) to obtain a cell lysate; then the lysate was centrifuged at 4° C. and 18000 rpm for 40 min to collect the supernatant.

(12) After completing step (11), the collected supernatant was loaded onto the Strep self-packing column, first eluted with 50 column volumes of lysis buffer 1 to remove impurities, and then eluted with 10 column volumes of elution buffer, the eluate collected through the column was subjected to SDS-PAGE, and the result is shown in panel b of FIG. 4. As can be seen from the SDS-PAGE results, purification with EXOC5 with a Twin-strep tag captured more subunits, and except for EXOC5 with a Twin-strep tag, the ratio among the other subunits is also relatively uniform. Therefore, judging from the experimental results, EXOC5 with a Twin-strep tag was most suitable for purification of the entire exocyst complex.

In order to obtain a more uniform exocyst sample, the present invention carried out the second round of molecular cloning design, which mainly completed the construction of 4V2-E1S5 plasmid. In this plasmid, EXOC5 contained a Twin-strep tag. The specific method was as follows:

2.5 Construction of Intermediate Transfer Vector 4V2-E1S5

(1) Using 5V1TG-SE5 plasmid as a template, PCR reaction was performed with primers S5-F and S5-R (see Table 1 for their sequences) and NEB Q5 Premix. The reaction procedure was as follows: 98° C. for 30 s; 30 cycles of (98° C. for 10 s, 72° C. for 3 min); 72° C. for 10 min. The PCR product was recovered to obtain S-EXOC5 fragment.

(2) The linearized 4V2 vector backbone and the second round PCR product of EXOC1, S-EXOC5 fragments were subjected to Gibson recombination to obtain the recombinant plasmid 4V2-E1S5.

The complete sequence of the recombinant plasmid 4V2-E1S5 is set forth in SEQ ID NO: 19.

2.6 Construction of Final Transfer Vector E1S547

0.1 pmol of the recombinant plasmids 5V1TR-E47 and 4V2-E1S5 and 1 μl of Cre recombinase were mixed in a 20 μl reaction system and incubated at 30 for 1 h. 10 μl of the reaction mixture was transform into 100 μl of Trans2-blue competent cells. After heat shock at 42° C. for 30 s, 500 μl of SOC medium was added and the resulting mixture was incubated at 30° C. with shaking for 4 h. The cell suspension was spread on LB agar plates containing 50 μg/ml kanamycin and 100 μg/ml ampicillin, and cultured upside down at 30° C. for 24 h. PCR identification of recombinant colonies was performed using the primers Loxp-F (5'-CCACTGCGCCGTTACCAC-3') and Loxp-R (5'-GCCGGTATGTACAGGAAG-3'). A 375 bp PCR product can be amplified from positive colonies. The final transfer plasmid E1S547 was extracted from the positive clones.

2.7 Expression of Human Exocyst Complex in Insect Cells and Observation by Negative Staining Under Electron Microscope (1) The final transfer plasmid E1S547 was transformed into DH10Bac competent cells, and the recombinant colonies were obtained through antibiotic screening and blue-white screening.

(2) After completing step (1), the recombinant Bacmid DNA of the recombinant colony was extracted and subjected to PCR identification. The identification method was the same as substeps (2) and (3) of step 2.4.

(3) The P2 generation virus solution of E1S547 was obtained, which was the second generation virus solution of BV-E1S547. The specific steps were the same as substeps (4) to (9) of step 2.4.

(4) After completing step (3), 5 mL of the P2 generation virus solution of BV-E1S547 and 5 mL of the P2 generation virus solution of BV-E2863 were used to co-infect 500 mL of sf9 cells cultured in a 2 L triangular shake flask with a cell density of $2.0 \times 10^6$ cells/mL. The cell culture was incubated at 28° C. and 150 rpm for 72 h and then centrifuged at 4° C. and 2000 g for 5 min. The precipitate was collected, frozen and stored at −80° C.

(5) After completing step (4), protein purification was performed. The procedures were the same as substeps (11) and (12) of step 2.4. The purified exocyst complex was subjected to SDS-PAGE. The results are shown in FIG. 4, panel c. It was shown that all 8 subunits that make up the complex were comprised, and the proportion of each subunit is equal.

(6) After completing step (5), the purified exocyst complex was diluted with lysis buffer 1 to 0.02 mg/ml, and then the sample was adsorbed for 1 min with a glow discharge treated carrier net coated with a thin carbon film (the carrier net was purchased from Life Trust). The carrier net was washed twice with lysis buffer 1 and stained with 4% (w/v) uranyl acetate for 2 min.

(7) After completing step (6), the carrier net was observed at 200 kV using a FEI Talos F200C electron microscope (ThermoFisher, USA). At 28,000× magnification, a 4K×4K DE20 camera (Direct Electron, USA) was used to capture images with a pixel size of 1.582 Angstroms (as shown in FIG. 4, panel d). Defocus values ranged from −2.5 to −3.5 μm.

(8) After completing step (7), the Gctf program was used to estimate the contrast transfer function (CTF). Using Gautomatch (http://www.mrc-lmb.cam.ac.uk/kzhang/Gautomatch/) and RELION, the particles were selected semi-automatically. A total of 379 micrographs and 18669 particles were selected. Two-dimensional classification was conducted using RELION 2 (FIG. 4, panel e). The initial model was generated using EMAN2 (FIG. 4, panel f). As can be seen from these experimental results, the recombinantly expressed human exocyst had a similar size and shape as the exocyst extracted from yeast.

2.8 In Vitro Activity Assay of Human Exocyst Complex Expressed in Insect Cells

The exocyst complex is thought to be able to anchor vesicles secreted from the Golgi apparatus to the plasma membrane. This activity depends on the GTP/GDP exchange protein Rab11 and the phospholipid PI(4,5)P2 on the plasma membrane and other protein components binding plasma membranes. Two liposomes were constructed in vitro to mimic the Golgi vesicles and phospholipid components of plasma membranes, and fluorescently labeled phospholipid NBD-PA (Ex:Es: 460/534 nm) RhodB-DHPE (Ex: Es: 560/580) were added to the two liposomes. The human Rab11(1-173)Q70L protein was obtained by recombinant expression. This protein can bind to GTP without hydrolyzing GTP, so it has been kept in a state where it can bind to exocyst. The purified human exocyst complex and Rab11 (1-173)Q70L protein and the two liposomes were incubated. If the recombinantly expressed exocyst had biological activity, the two liposomes would be pulled closer with the help of Rab11(1-173)Q70L protein. When the distance between the two liposomes was less than 10 nm and the reaction system was stimulated using NBD-PA excitation light, energy resonance transfer phenomenon would occur and there would be a clear transfer emission peak near 580 nm.

2.8.1 Cloning, Expression and Purification of Human Rab11 (1-173)Q70L Protein (1) Construction of Prokaryotic Expression Vector pEXS-DH-Rab11Q70L The synthesized human Rab11(1-173)Q70L gene was subjected to PCR reaction with primers Rab11F and Rab11R.

```
Rab11F:
5'-AAAACATATGGGCACCCGTGACGACGAGTA-3';

Rab11R:
5'-ATTTTTCGAGCCGTAGATCTCGGTGAGGATGGTC-3'.
```

The PCR reaction was completed using NEB's Q5 Premix. The reaction procedure was as follows: 98° C. for 30 s; 30 cycles of (98° C. for 10 s, 72° C. for 30 s); 72° C. for 5 min. The PCR product was recovered. The PCR product was treated with restriction enzymes NdeI and XhoI and then recovered. Prokaryotic expression vector pEXS-DH was digested with restriction enzymes NdeI and XhoI and treated at 37° C. for 1 h; then CIP was added and the resulting mixture was treated at 37° C. for 1 h; finally, a vector backbone of about 5 kb was recovered using the gel recovery kit. Referring to substep (3) of step 2.2, the ligation reaction between the target fragment and the vector was performed. The ligation product was transformed into MT competent cells, spread on ampicillin/LB plates, and incubated at 37° C. overnight. Single colonies were picked for PCR identification and sequenced. The complete sequence of the recombinant plasmid pEXS-DH-Rab11Q70L is set forth in SEQ ID NO: 20.

(2) Expression and Purification of Target Protein Rab11(1-173)Q70L

The plasmid pEXS-DH-Rab11Q70L proved correct by sequencing was transformed into *E. coli* BL21 (DE3) competent cells, and spread on ampicillin/LB plates and incubated at 37° C. overnight. Single colonies were selected and inoculated into 5 ml of LB medium with ampicillin resistance, and incubated at 37° C. with shaking overnight. The next day, 5 ml of the culture was inoculated into 800 ml of LB medium with ampicillin resistance, and cultured on a shaker at 37□ to an OD value of 0.6-0.8. IPTG was added to a final concentration of 0.25 mM and expression was induced at 16□ for 20 h.

The bacterial solution was then centrifuged at 5000 rpm and 4° C. for 10 miry to collect the bacterial cells. The bacterial cells were resuspended in lysis buffer 2 and the bacterial suspension was disrupted by ultrasound treatment. The disrupted bacterial solution was centrifuged at 18000 rpm and 4° C. for 35 min. The supernatant was loaded twice onto 1 ml of Ni-NTA medium equilibrated with lysis buffer. The medium was then washed with 20 ml of lysis buffer 2, and the target protein was eluted with elution buffer 2.

2.8.2 Activity Assay of Human Exocyst Complex Expressed in Insect Cells (1) Preparation of Liposomes Using Extruder After various phospholipid components were dissolved in chloroform and added according to the amounts and proportions in Table 4, two phospholipid mixtures A and B were obtained. The phospholipid mixture A mimicked the phospholipid component of Golgi vesicles, and the phospholipid mixture B mimicked the phospholipid component of the plasma membrane. The organic solvent was removed by using a vacuum pump to evacuate for 4 h. A certain volume of assay buffer was added to the two dried phospholipid mixtures to make the final concentration of phospholipids 5 mg/mL. Then, the phospholipid suspension was placed in a 37° C. water bath and hydrated for 30 min. After that, the phospholipid suspension was quickly frozen with liquid nitrogen, and then the phospholipid suspension was thawed in a 37° C. water bath. A total of 5 freeze-thaw cycles were repeated.

Liposome A in Table 4 was prepared with Extruder equipped with a 0.05 μm filter membrane (see the instruction for Extruder on Avanti's website for specific instrument operations); liposome B in Table 4 was prepared with Extruder equipped with a 0.2 filter membrane.

The prepared liposomes were placed at 4□ and used the same day.

TABLE 4

| Formulations of phospholipid components contained in liposome A and liposome B | | | |
|---|---|---|---|
| Liposome A | | Liposome B | |
| Phospholipid name | Phospholipid amount | Phospholipid name | Phospholipid amount |
| DOPC | 0.5 mg | DOPC | 0.5 mg |
| DOPE | 0.2 mg | DOPE | 0.2 mg |
| DOPS | 0.07 mg | DOPS | 0.07 mg |
| PI | 0.145 mg | PI | 0.145 mg |
| SM | 0.075 mg | SM | 0.075 mg |
| DOGS-NTA-Ni | 0.02 mg | PI(4,5)P2 | 0.02 mg |
| Rhod B-DHPE | 0.33 mg | NBD-PA | 0.02 mg |

(2) Determination of Activity of Exocyst Using Fluorescence Spectrophotometer

TABLE 5

| In vitro bioassay reaction system of exocyst complex | | | | |
|---|---|---|---|---|
| | Control group AB | Control group AB-Rab11 | Control group AB-EXOC | Experimental group AB-Rab11-EXOC |
| 5 mg/ml liposome A | 24 μl | 24 μl | 24 μl | 24 μl |
| 5 mg/ml liposome B | 24 μl | 2 4 μl | 24 μl | 24 μl |
| 157 mg/ml Rab11Q70L | 0 | 1 | 0 | 1 μl |
| 2 mg/ml exocyst complex | 0 | 0 | 22.5 μl | 22.5 μl |
| Assay buffer | 420.5 μl | 420.5 μl | 420.5 μl | 420.5 μl |
| 0.2M MgCl₂ | 2.5 μl | 2.5 μl | 2.5 μl | 2.5 μl |
| 0.1M GTP | 5 μl | 5 μl | 5 μl | 5 μl |
| 1M DTT | 0.5 μl | 0.5 μl | 0.5 μl | 0.5 μl |

The concentrated target protein was further purified with molecular sieve Superdex 200 (10/300GL), and the column buffer was used as the molecular sieve buffer. The protein peak was collected and concentrated for the measurement of concentration. After liquid nitrogen freezing, it was stored in a refrigerator of −80° C. until use.

Figure 5:
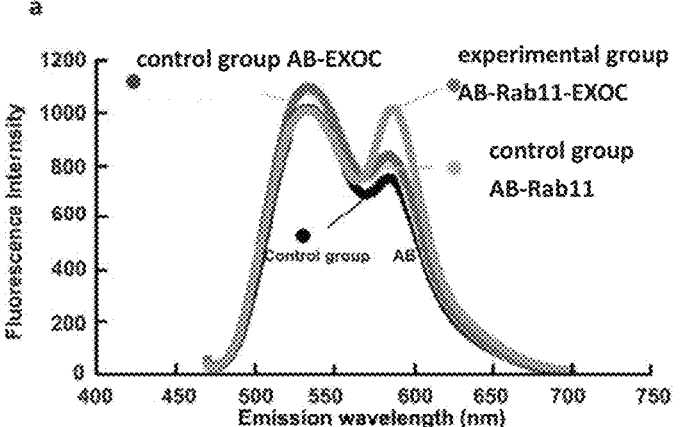
FIG. 5 shows the results of biological activity measurement of the human exocyst complex expressed by insect cells. a shows that compared with the other three control groups, the experimental group (liposome A+Rab11Q70L+ Exocyst+liposome B) has a significant fluorescence emission peak at 585 nm, while the control group that was only added with Rab11Q70L or exocyst complex has no obvious fluorescence energy resonance transfer, compared with the control group AB without adding any protein. b shows the average value and error of three independent experiments, wherein the ordinate is the ratio between the fluorescence value at 585 nm and the fluorescence value at 533 nm in the three control groups and the experimental group.
Figure 5:
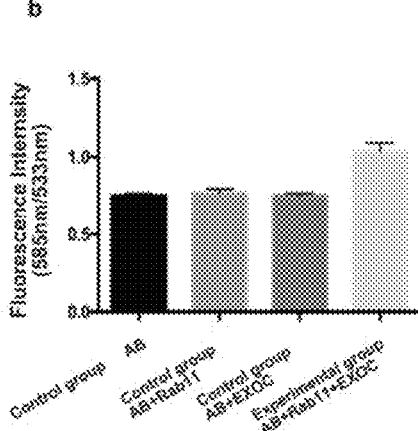

The reaction systems of the control groups and the experimental group were prepared according to the systems in Table 5. Here, taking the preparation of the reaction system of the experimental group as an example, the order of addition of the components for measuring the activity was explained. First, the assay buffer, MgCl₂, GTP and DTT were added to an EP tube and mixed well; then liposome A and Rab11Q70L protein were added to the EP tube, and incubated on ice for 1-2 h. The Hitaiki F7000 fluorescence spectrophotometer was preheated in advance, and before the measurement experiment was started, the exocyst complex and liposome B were added to the incubated mixture of liposome A and Rab11Q70L and mixed well. Immediately, the mixture was added to a 1 mL quartz cuvette and placed in the machine for measurement. The measurement mode was wavelength scanning, the excitation light was 460 nm, the emission scanning wavelength range was 470-700 nm, and the voltage was 500 V. The fluorescence intensity was measured after incubating in a 37° C. water bath for 30 min. The control groups were measured before the experimental group. The experimental results are shown in FIG. 5. It can be seen that the human exocyst complex expressed by insect cells had biological activity.

As shown in panel a of FIG. 5, compared with the other three control groups, the experimental group (liposome A+Rab11Q70L+Exocyst+liposome B) of the four groups had a significant fluorescence emission peak at 585 nm (see the arrow in panel a of FIG. 5), indicating that there was a significant fluorescence energy resonance transfer, that is, the exocyst complex drew a certain amount of A and B liposomes closer and the distance was less than 10 nm, indicating that the exocyst complex purified in vitro had the activity of anchoring the two membranes together. Compared with the control group AB without adding any protein, there was no obvious fluorescence energy resonance transfer in the control group that was only added with Rab11Q70L or exocyst complex, indicating that neither Rab11Q70L nor exocyst can bring the two liposomes closer together when they are alone, and that the functioning of exocyst depends on Rab11 which binds to GTP. FIG. 5b shows the average and error of three independent experiments, indicating that the results of the activity assay are credible. The ordinate is the ratio between the fluorescence value at 585 nm and the fluorescence value at 533 nm in the three control groups and the experimental group. The fluorescence at 533 nm is the emission wavelength of IND-PA under 460 inn excitation light.

INDUSTRIAL APPLICATIONS

In response to the three problems in Method 1, the present invention designed SmartBac series of vectors to solve, and proposed three cloning strategies to achieve the expression of protein complexes with molecular weights of less than 600 kDa and the expression of protein complexes with molecular weights of no less than 600 kDa and efficient screening of a subunit most suitable for adding a purification tag. Experiments show that the new SmartBac baculovirus expression system designed by the present invention and the specific cloning strategies can be used to express the human exocyst complex, and it is found that the EXOC5 subunit with a Twin-strep tag is most suitable for purification of the entire exocyst complex, and finally the human exocyst is expressed and purified successfully and the human exocyst has a similar size and shape as the exocyst extracted from yeast, and in vitro activity measurements shows that the recombinantly expressed exocyst complex has biological activity. The present invention is of great significance for recombinantly expressing protein complexes with complex components and large molecular weights in insect cells. In addition, in the present invention, the promoter and termination sequence recognized by insect cells on each vector for expressing the target protein can be replaced with the promoter and termination sequence that can be recognized by mammalian cells and the replaced vector system can be used for expressing complex protein complexes in mammalian cells, so the present invention also provides a method for recombinantly expressing complex protein complexes in mammalian cells.

What is claimed is:
1. A SmartBac baculovirus expression system, which is shown as follows:
SmartBac baculovirus expression system A, comprising an acceptor plasmid component and a donor plasmid component;

wherein the acceptor plasmid component and the donor plasmid component are capable of being recombined and fused into one plasmid component;

the acceptor plasmid component is the acceptor plasmid A and/or the acceptor plasmid B;

the acceptor plasmid A comprises a DNA fragment A comprising, in order from upstream to downstream, a promoter A, a gene sequence encoding a protease, a nucleotide sequence encoding a recognition sequence for a cleavage site of the protease, an insertion region of a gene encoding a target object to be expressed, and a termination sequence A;

the acceptor plasmid B comprises a DNA fragment B comprising, in order from upstream to downstream, a promoter B, a gene sequence encoding the protease, and a termination sequence B; and a DNA fragment C comprising, from upstream to downstream, a promoter C, an insertion region of a gene encoding a target object to be expressed, and a termination sequence C;

the donor plasmid component contains a DNA fragment D comprising, from upstream to downstream, a promoter D, an insertion region of a gene encoding a target object to be expressed, and a termination sequence D; wherein the target object is selected from the group consisting of proteins, protein subunits, protein fragments, polypeptides, and polypeptide fragments wherein in the SmartBac baculovirus expression system A, the sequence of the DNA fragment A is set forth in positions 1235-3971 of SEQ ID NO: 1 or positions 1235-3971 of SEQ ID NO: 2;

wherein in the SmartBac baculovirus expression system A, the sequence of the DNA fragment B is set forth in positions 1208-3252 of SEQ ID NO: 3 or positions 1208-3249 of SEQ ID NO: 4;

wherein in the SmartBac baculovirus expression system A, the sequence of the DNA fragment C is set forth in positions 3306-4521 of SEQ ID NO: 3 or positions 3303-4518 of SEQ ID NO: 4; or wherein in the SmartBac baculovirus expression system A, the sequence of the DNA fragment D is set forth in positions 259-3188 of SEQ ID NO: 5 or positions 259-3188 of SEQ ID NO: 6.

2. The SmartBac baculovirus expression system according to claim 1, wherein the acceptor plasmid component further contains a small Tn7 element flank for production of recombinant baculoviruses.

3. The SmartBac baculovirus expression system according to claim 1, wherein in the SmartBac baculovirus expression system A, in order from upstream to downstream, the DNA fragment A further contains the recognition sequence for the cleavage site of the protease and a gene sequence encoding a fluorescent protein between the insertion region of a gene encoding a target object to be expressed and the termination sequence A;

or in the SmartBac baculovirus expression system A, in order from upstream to downstream, the DNA fragment B further contains the recognition sequence for the cleavage site of the protease and a gene sequence encoding a fluorescent protein between the gene sequence encoding the protease and the termination sequence B; or in the SmartBac baculovirus expression system A, in order from upstream to downstream, the DNA fragment D further contains the recognition sequence for the cleavage site of the protease and a gene sequence encoding a fluorescent protein between the insertion region of a gene encoding a target object to be expressed and the termination sequence D.

4. The SmartBac baculovirus expression system according to claim 1, wherein both the acceptor plasmid component and the donor plasmid component contain a recognition sequence for a site-specific recombinase.

5. The SmartBac baculovirus expression system according to claim 4, wherein the site-specific recombinase is Cre recombinase.

6. The SmartBac baculovirus expression system according to claim 1, wherein the acceptor plasmid component contains an unconditional replication origin; the donor plasmid component contains a conditional replication origin.

7. The SmartBac baculovirus expression system according to claim 6, wherein:

the unconditional replication origin is a p15A replication origin; and the conditional replication origin is a R6Ky replication origin.

8. The SmartBac baculovirus expression system according to claim 1, wherein:

the acceptor plasmid component and the donor plasmid component contain different resistance selection marker genes.

9. The SmartBac baculovirus expression system according to claim 1, wherein:

in the SmartBac baculovirus expression system A, the promoter A is a p6.9 promoter; the promoter B is a GP64 promoter; the promoter C is p6.9 promoter; the promoter D is a p10 promoter; or, in the SmartBac baculovirus expression system A, the termination sequence A is an SV40 pA signal sequence; the termination sequence B is an IE1 ter signal sequence; the termination sequence C is an SV40 pA signal sequence; the termination sequence D is an HSV tk pA signal sequence.

10. The SmartBac baculovirus expression system according to claim 1, wherein, in order from upstream to downstream, any of the insertion regions of genes encoding target objects to be expressed contain a multiple cloning site 1, a LacZ-a expression cassette, and a multiple cloning site 2.

11. The SmartBac baculovirus expression system according to claim 10, wherein in the SmartBac baculovirus expression system A, the DNA fragment D further contains a PUC replication origin between the multiple cloning site 1 and the multiple cloning site 2 in the insertion region of a gene encoding a target object to be expressed.

12. The SmartBac baculovirus expression system according to claim 1, wherein the protease is TEV protease.

13. The SmartBac baculovirus expression system according to claim 12, wherein in the SmartBac baculovirus expression system A, in order from upstream to downstream, the DNA fragment A is obtained by connecting a p6.9 promoter, a gene sequence encoding TEV protease with an N-terminal HA tag, a recognition sequence for a TEV protease cleavage site, a sequence encoding a tag setting forth in positions 2119-2205 of SEQ ID NO: 1 or positions 2119-2205 of SEQ ID NO: 2, a recognition sequence for an enterokinase cleavage site, a multiple cloning site 1, a LacZ-a expression cassette,
a multiple cloning site 2,
a recognition sequence for a TEV protease cleavage
   site,
a gene sequence encoding a fluorescent protein, and
an SV40 pA signal sequence;
or, wherein in the SmartBac baculovirus expression sys-
   tem A, in order from upstream to downstream, the
   DNA fragment B is obtained by connecting
a GP64 promoter,
a gene sequence encoding TEV protease with an N-ter-
   minal HA tag,
a recognition sequence for a TEV protease cleavage
   site,
a gene sequence encoding a fluorescent protein, and
an IE1ter signal sequence;
or, wherein in the SmartBac baculovirus expression sys-
   tem A, in order from upstream to downstream, the
   DNA fragment C is obtained by connecting
a p6.9 promoter,
a sequence encoding a tag setting forth in positions
   2119-2205 of SEQ ID NO: 1 or positions 2119-2205
   of SEQ ID NO: 2,
a recognition sequence for an enterokinase cleavage
   site,
a multiple cloning site 1,
a LacZ-α expression cassette,
a multiple cloning site 2, and
an SV40 pA signal sequence;
or, wherein in the SmartBac baculovirus expression sys-
   tem A, in order from upstream to downstream, the
   DNA fragment D is obtained by connecting
a p10 promoter,
a sequence encoding a 10×His tag, a recognition sequence for an enterokinase cleavage
   site,
a multiple cloning site 1,
a PUC replication origin,
a LacZ-α expression cassette,
a multiple cloning site 2,
a recognition sequence for a TEV protease cleavage
   site,
a gene sequence encoding a fluorescent protein, and
an HSVtk pA signal sequence.

14. The SmartBac baculovirus expression system accord-
ing to claim 1, wherein:
   in the SmartBac baculovirus expression system A, the
      acceptor plasmid A is a 4V1G plasmid and/or a 4VIR
      plasmid; the complete sequence of the 4V1G plasmid is
      SEQ ID NO: 1; the complete sequence of the 4VIR
      plasmid is SEQ ID NO: 2;
   the acceptor plasmid B is a 5V1TG plasmid and/or a
      5V1TR plasmid; the complete sequence of the 5V1TG
      plasmid is SEQ ID NO: 3; the complete sequence of the
      5V1TR plasmid is SEQ ID NO: 4;
   the donor plasmid component is a 4V2G plasmid and/or
      a 4V2R plasmid; the complete sequence of the 4V2G
      plasmid is SEQ ID NO: 5; the complete sequence of the
      4V2R plasmid is SEQ ID NO: 6.

15. The SmartBac baculovirus expression system accord-
ing to claim 1, wherein:
   the promoters and the termination sequences are recog-
      nized by insect cells or by mammalian cells for
      expressing a target protein of the acceptor plasmid
      component and the donor plasmid component in the
      SmartBac baculovirus expression system.

*     *     *     *     *